US012799183B2

(12) United States Patent
Lin et al.

(10) Patent No.: US 12,799,183 B2
(45) **Date of Patent: *Nov. 17, 2026**

(54) CHIMERIC CYTOKINE RECEPTORS BEARING A PD-1 ECTODOMAIN

(71) Applicant: Allogene Therapeutics, Inc., South San Francisco, CA (US)

(72) Inventors: Regina Junhui Lin, San Mateo, CA (US); Thomas John Van Blarcom, Oakland, CA (US); Siler Panowski, Berkeley, CA (US); Barbra Johnson Sasu, San Francisco, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 657 days.

This patent is subject to a terminal disclaimer.

(21) Appl. No.: 18/365,014

(22) Filed: Aug. 3, 2023

(65) Prior Publication Data

US 2024/0016846 A1 Jan. 18, 2024

Related U.S. Application Data

(62) Division of application No. 16/804,545, filed on Feb. 28, 2020, now Pat. No. 11,786,553.

(60) Provisional application No. 62/980,737, filed on Feb. 24, 2020, provisional application No. 62/894,659, filed on Aug. 30, 2019, provisional application No. 62/812,799, filed on Mar. 1, 2019.

(51) Int. Cl.

| | |
|---|---|
| ***C07K 14/715*** | (2006.01) |
| ***A61K 38/00*** | (2006.01) |
| ***A61K 40/11*** | (2025.01) |
| ***A61K 40/31*** | (2025.01) |
| ***A61K 40/42*** | (2025.01) |
| ***C07K 16/28*** | (2006.01) |
| ***C07K 16/30*** | (2006.01) |
| ***C12N 5/0783*** | (2010.01) |
| ***C12N 5/10*** | (2006.01) |
| ***C12N 15/00*** | (2006.01) |
| ***C12N 15/67*** | (2006.01) |
| *C12N 15/62* | (2006.01) |
| *C12N 15/63* | (2006.01) |

(52) U.S. Cl.

CPC .......... *C07K 14/7155* (2013.01); *A61K 40/11* (2025.01); *A61K 40/31* (2025.01); *A61K 40/4204* (2025.01); *A61K 40/421* (2025.01); *C07K 16/2818* (2013.01); *C07K 16/30* (2013.01); *C12N 5/0636* (2013.01); *C12N 15/67* (2013.01); *A61K 38/00* (2013.01); *A61K 2239/17* (2023.05); *A61K 2239/23* (2023.05); *C07K 2319/03* (2013.01); *C07K 2319/33* (2013.01); *C07K 2319/74* (2013.01); *C12N 5/10* (2013.01); *C12N 15/62* (2013.01); *C12N 15/63* (2013.01)

(58) Field of Classification Search

CPC ...... A61K 35/17; C12N 5/0636; C12N 15/67; C12N 2510/00; C07K 2319/03; C07K 2319/33; C07K 2319/74; C07K 14/7155; C07K 14/715; C07K 2317/622

See application file for complete search history.

(56) References Cited

U.S. PATENT DOCUMENTS

| | | | | |
|---|---|---|---|---|
| 6,866,998 | B1 | 3/2005 | Kitamura et al. | |
| 8,389,282 | B2 | 3/2013 | Sadelain et al. | |
| 9,434,935 | B2 | 9/2016 | Spencer et al. | |
| 9,913,882 | B2 | 3/2018 | Slawin et al. | |
| 9,944,690 | B2 | 4/2018 | Spencer et al. | |
| 10,287,354 | B2 | 5/2019 | Brogdon et al. | |
| 10,294,304 | B2 | 5/2019 | Kuo et al. | |
| 10,336,810 | B2 | 7/2019 | Tanaka | |
| 10,548,921 | B2 | 2/2020 | Leen et al. | |
| 12,528,856 | B2 * | 1/2026 | Lin | C07K 14/71 |
| 2014/0050709 | A1 | 2/2014 | Leen et al. | |
| 2014/0087468 | A1 | 3/2014 | Spencer et al. | |
| 2015/0111294 | A1 | 4/2015 | Spencer et al. | |
| 2016/0175359 | A1 | 6/2016 | Spencer et al. | |
| 2016/0297884 | A1 | 10/2016 | Kuo et al. | |
| 2016/0297885 | A1 | 10/2016 | Kuo et al. | |
| 2018/0037630 | A1 | 2/2018 | Tanaka et al. | |
| 2019/0000881 | A1 | 1/2019 | Sadelain et al. | |
| 2019/0292533 | A1 | 9/2019 | Nager et al. | |

FOREIGN PATENT DOCUMENTS

| | | | |
|---|---|---|---|
| CA | 2842368 | A1 | 2/2013 |
| CN | 106399255 | A | 2/2017 |
| WO | 1996004389 | A1 | 2/1996 |

(Continued)

OTHER PUBLICATIONS

Babon, Jeffrey J., et al., "The molecular regulation of Janus kinase (JAK) activation", Biochem J. Aug. 15, 2014;462 (1):1-13. doi: 10.1042/BJ20140712.

Clackson, Tim , et al., "Redesigning an FKBP-ligand interface to generate chemical dimerizers with novel specificity", Proc. Natl. Acad. Sci. USA, vol. 95, Sep. 1998, pp. 10437-10442.

(Continued)

*Primary Examiner* — Hong Sang

(74) *Attorney, Agent, or Firm* — Allogene Therapeutics, Inc.

(57) ABSTRACT

Provided herein are PD-1 chimeric cytokine receptors. When present on chimeric antigen receptor (CAR)-bearing immune cells, such receptors allow for increased immune cell activation, proliferation, persistence, and/or potency, when engaged with PD-1 ligands or activation with an anti-PD-1 antibody. Also provided are methods of making and using the chimeric cytokine receptors described herein.

25 Claims, 31 Drawing Sheets

Specification includes a Sequence Listing.

(56) References Cited

FOREIGN PATENT DOCUMENTS

| | | | |
|---|---|---|---|
| WO | WO9802558 | A2 | 1/1998 |
| WO | 1999026978 | A1 | 6/1999 |
| WO | 2005031001 | A2 | 4/2005 |
| WO | WO2007075899 | A2 | 7/2007 |
| WO | WO2011069004 | A1 | 6/2011 |
| WO | 2012127464 | A2 | 9/2012 |
| WO | WO2012138858 | A1 | 10/2012 |
| WO | WO2014151960 | A2 | 9/2014 |
| WO | 2014172584 | A1 | 10/2014 |
| WO | 2014186469 | A2 | 11/2014 |
| WO | 2016061574 | A1 | 4/2016 |
| WO | WO2016055551 | A1 | 4/2016 |
| WO | 2016090312 | A1 | 6/2016 |
| WO | WO2016127257 | A1 | 8/2016 |
| WO | WO2017029512 | A1 | 2/2017 |
| WO | 2017049166 | A1 | 3/2017 |
| WO | WO2017068360 | A1 | 4/2017 |
| WO | 2017075433 | A1 | 5/2017 |
| WO | 2017108805 | A1 | 6/2017 |
| WO | WO2017103596 | A1 | 6/2017 |
| WO | 2018013918 | A2 | 1/2018 |
| WO | WO2018038945 | A1 | 3/2018 |
| WO | WO2018094244 | A1 | 5/2018 |
| WO | 2018102787 | A1 | 6/2018 |
| WO | WO2018104473 | A1 | 6/2018 |
| WO | WO2018150187 | A1 | 8/2018 |
| WO | WO2018161064 | A1 | 9/2018 |
| WO | 2018191748 | A1 | 10/2018 |
| WO | 2018208849 | A1 | 11/2018 |
| WO | 2019038368 | A1 | 2/2019 |
| WO | 2019038638 | A1 | 2/2019 |
| WO | WO2019055946 | A1 | 3/2019 |
| WO | 2019079520 | A2 | 4/2019 |
| WO | WO2019102207 | A1 | 5/2019 |
| WO | WO2019118508 | A1 | 6/2019 |
| WO | WO2019169290 | A1 | 9/2019 |
| WO | WO2019232425 | A1 | 12/2019 |
| WO | WO2019246563 | A1 | 12/2019 |
| WO | WO2020044055 | A1 | 3/2020 |
| WO | WO2020180694 | A1 | 9/2020 |
| WO | WO2016168612 | A1 | 10/2020 |
| WO | 2021173630 | A1 | 9/2021 |

OTHER PUBLICATIONS

Floss, Dorreen , et al., "Naturally occurring and synthetic constitutive-active cytokine receptors in disease and therapy", Cytokine & Growth Factor Reviews; vol. 47, Jun. 2019, pp. 1-20.

Genbank , Accession No. AAB08425; thrombopoietin receptor [*Homo sapiens*]; 2016.

Genbank , Accession No. MN366105.1Synthetic construct 11D5-3-CD8BBZ gene, complete cds; 2019.

Silvennoinen, Olli , et al., "Cytokine receptor signal transduction through Jak tyrosine kinases and Stat transcription factor", APMIS, vol. 105, Issue7-12, Jul. 1997, pp. 497-509.

Wilmes, Stephan , et al., "Mechanism of homodimeric cytokine receptor activation and dysregulation by oncogenic mutations", Science; Feb. 7, 2020;367(6478):643-652. doi: 10.1126/science.aaw3242.

Xie, et al. "Construction of an anti-programmed death-ligand 1 chimeric antigen receptor and determination of its antitumor function with transduced cells", Oncology Letter, 2018, 16:157-166.

Itaya, Miki , "Regulation of Dimerization and Activation of the Thrombopoietin Receptor", PhD Thesis, Dec. 1, 2012; Stony Brook University; https://dspace.sunyconnect.suny.edu/bitstream/handle/1951/59699/Itaya_grad.sunysb_0771E_11150.pdf?sequence=1&isAllowed=y.

Miyazaki, H., "The thrombopoietin receptor", Japanese Journal of Thrombosis and Hemostasis, 2015, vol. 26, No. 1, p. 35-41, DOI: 10.2491/jjsth.26.35.

Moraga, I., et al., "Tuning Cytokine Receptor Signaling by Re-orienting Dimer Geometry with Surrogate Ligands", Cell. 2015. vol. 160. No. 6. p. 1196-1208.

Naramura, M., et al., "Mechanisms of cellular cytotoxicity mediated by a recombinant antibody-IL2 fusion protein against human melanoma cells". Immunol Lett. Dec. 1993;39(1):91-9. doi: 10.1016/0165-2478(93)90169-3. PMID: 8144194.

Plo, Isabelle, et al., "Genetic Alterations of the Thrombopoietin/MPL/JAK2 Axis Impacting Megakaryopoiesis", Frontiers in Endocrinology; Review; Sep. 12, 2017; doi: 10.3389/fendo.2017.00234.

Saka, K., et al., "Activation of Target Signal Transducers Utilizing Chimeric Receptors With Signaling-Molecule Binding Motifs", Biotechnology and Bioengineering, Jan. 7, 2012, vol. 109, No. 6, pp. 1528-1537, DOI: 10.1002/bit.24421.

Shaposhnikov, A.V., et al., "Molecular components of JAK/STAT signaling pathway and its connection with transcription machinery", Molecular Biology, 2013, vol. 47, No. 3, p. 388-397. (Russian language article with English language abstract).

Ukai, Hideki, et al., "Formation of an active form of the interleukin-2/15 receptor beta-chain by insertion of the intracisternal a particle in a radiation-induced mouse thymic lymphoma and its role in tumorigenesis". Mol Carcinog. Jun. 2003;37(2):110-9. doi: 10.1002/mc10128. PMID: 12766910.

Wang, X. et al., Structural biology of shared cytokine receptors. Annu Rev Immunol. 2009. vol. 27. p. 29-60.

Bajgain, Pradip , "CAR T Cell Therapy for Breast Cancer: Harnessing the Tumor Milieu to Drive T Cell Activation", Research Article, J Immunother Cancer. May 10, 2018;6(1):34. doi: 10.1186/s40425-018-0347-5.

Behrmann, Iris , et al., "A single STAT recruitment module in a chimeric cytokine receptor complex is sufficient for STAT activation.", J Biol Chem.;272(8):5269-74., 1997.

Boger, Dale L., et al., "Cytokine receptor dimerization and activation: prospects for small molecule agonists.", Bioorg Med Chem. ;9(3):557-62., 2001.

Boyerinas, B. , et al., "Abstract 602: A novel TGF-B/IL-12R signal conversion platform that protects CAR T cells from TGF-B-mediated immune suppression and concurrently amplifies effector function", Proceedings of the American Association for Cancer Research Annual Meeting 2017; Apr. 1-5, 2017; Washington, DC. Philadelphia (PA): AACR; Cancer Res 2017;77(13 Suppl):Abstract 602, 4 total pages.

Cherkassky, L. , et al., "Human CAR T cells with cell-intrinsic PD-1 checkpoint blockade resist tumor-mediated inhibition", J. Clin. Invest. 126:3130-3144, 2016.

Defour, J P, et al., "Oncogenic activation of MPL/thrombopoietin receptor by 17 mutations at W515: implications for myeloproliferative neoplasms", Leukemia 30, 1214-1216; doi: 10.1038/leu.2015.271, 2016.

Defour, J P, et al., "Tryptophan at the transmembrane-cytosolic junction modulates thrombopoietin receptor dimerization and activation", PNAS 110:2540-2545, 2013.

EPO , "International Search Report & Written Opinion", mailed on May 29, 2020 for PCT Application No. PCT/US2020/020415; 17 pages.

EPO , "International Search Report and Written Opinion", mailed on Jun. 4, 2020 for PCT Application No. PCT/US2020/020340; 15 pages.

EPO , "International Search Report and Written Opinion", mailed on May 31, 2019 for PCT Application No. PCT/US2019/020340; 18 pages.

Friedmann, Michael C., et al., "Different interleukin 2 receptor beta-chain tyrosines couple to at least two signaling pathways and synergistically mediate interleukin 2-induced proliferation", Immunology; Proc. Natl. Acad. Sci. USA, vol. 93, pp. 2077-2082, Mar. 1996.

Hoyos, V. , et al., "Engineering CD19-specific T lymphocytes with interleukin-15 and a suicide gene to enhance their anti-lymphoma/leukemia effects and safety", Leukemia 24:1160-1170, 2010.

Hurton, L. V., et al., "Tethered IL-15 augments antitumor activity and promotes a stem-cell memory subset in tumor-specific T cells", PNAS E7788-E7797, 2016.

Johnson, L.A. , et al., "Rational development and characterization of humanized anti-EGFR variant III chimeric antigen receptor T cells for glioblastoma", Science Translational Medicine, vol. 7, No.

(56) References Cited

OTHER PUBLICATIONS

275, Feb. 18, 2015, pp. 1-16, XP055362795, US ISSN: 1946-6234, DOI: 10.1126/scitranslmed.aaa4963.
Kagoya, Yuki , et al., "A Novel Chimeric Antigen Receptor Containing a JAK-STAT Signaling Domain Mediates Superior Antitumor Effects", Nat Med. Feb. 2018; 24(3): 352-359; doi: 10.1038/nm.4478, Feb. 5, 2018.
Kloss, C. , "TGFBeta signaling blockade within PSMA targeted CAR human T cells for the eradication of metastatic prostate cancer", Abstract 638, Molucular Therapy vol. 24, Supplement 1, 2 total pages, 2016.
Leen, Ann M, et al., "Reversal of Tumor Immune Inhibition Using a Chimeric Cytokine Receptor", Molecular Therapy vol. 22 No. 6, 1211-1220 Jun. 2014, Mar. 2014.
Leroy, Emilie , et al., "His 499 Regulates Dimerization and Prevents Oncogenic Activation by Asparagine Mutations of the Human Thrombopoietin Receptor", Journal of Biological Chemistry, vol. 291, No. 6, pp. 2974-2987, XP055696813, US ISSN: 0021-9258, DOI: 10.1074/jbcM115.696534, 2015.
Liu, X. , et al., "A chimeric switch-receptor targeting PD1 augments the efficacy of second-generation CAR T cells in advanced solid tumors", Cancer Res. 76:1578-1590, 2016.
Lu, Xiaohui , et al., "Dimerization by a Cytokine Receptor Is Necessary for Constitutive Activation of JAK2V617F", J Biol Chem; . Feb. 29, 2008;283(9):5258-66. doi: 10.1074/jbc.M707125200; Epub Dec. 23, 2007.
Malek, Thomas R., et al., "Interleukin-2 Receptor Signaling: At the Interface between Tolerance and Immunity", Immunity. Aug. 27, 2010; 33(2): 153-165. doi:10.1016/j.immuni.2010.08.004, 2010.
Matthews, E E, et al., "Thrombopoietin receptor activation: Transmembrane helix dimerization, rotation, and allosteric modulation", FASEB J. 25:2234-2244, 2011.
Maute, R L, "Engineering high-affinity PD-1 variants for optimized immunotherapy and immuno-PET imaging", PNAS 112:E6506-E6514, 2015.
Murray, P J, "The JAK-STAT signaling pathway: input and output integration.", J Immunol. Mar. 1, 2007;178 (5):2623-9., Feb. 2007.
Nakamura, T , et al., "A selective switch-on system for self-renewal of embryonic stem cells using chimeric cytokine receptors.", Biochem Biophys Res Commun. Jul. 9, 1998;248(1):22-7., Jul. 1998.
Shum, T, et al., "Constitutive signaling from an engineered IL7 receptor promotes durable tumor elimination by tumor-redirected T cells", Cancer Discovery 7:1-10, 2017.
Sukumaran, S. , "Enhancing the potency and specificity of engineered T cells for cancer treatment", Cancer Discovery 8:972-987, 2018.
Tokarew, Nicholas , et al., "Teaching an old dog new tricks: next-generation CAR T cells", British Journal Cancer, Nature Publishing Group; 120, 26-37. https://doi.org/10.1038/s41416-018-0325-1, Nov. 6, 2018.
Varghese, Lelia N., et al., "The Thrombopoietin Receptor: Structural Basis of Traffic and Activation by Ligand, Mutations, Agonists, and Mutated Calreticulin", Frontiers in Endocrinology, Mar. 2017, vol. 8, Article 59; doi: 10.3389/fendo.2017.00059.
Vong, Q , et al., "Inhibiting TGFbeta signaling in CAR T-cells may significantly enhance efficacy of tumor immunotherapy", Blood 130:1791, 5 total pages, 2017.
Wu, C-Y , et al., "Remote control of therapeutic T cells through a small molecule-gated chimeric receptor", Science 350:aab4077, 21 total pages, 2015.
EPO , "International Search Report & Written Opinion", mailed for PCT/US2020/048402 on Nov. 27, 2020, 23 pages.
Saur, Sebastian J., et al., "Ubiquitination and degradation of the thrombopoietin receptor c-Mpl", Blood, Feb. 11, 2010 vol. 115, No. 6, pp. 1254-1263.
EPO , "International Search Report & Written Opinion", Mailed on Jun. 21, 2021 for International Application No. PCT/US2021/019362.
Morris, Rhiannon , et al., "The molecular details of cytokine signaling via the JAK/STAT pathway", Protein Science 2018 ; vol. 27; pp. 1984-2009;, Dec. 1, 2018.
Ajina, Adam , et al., "Strategies to Address Chimeric Antigen Receptor Tonic Signaling", Mol Cancer Ther; . Sep. 2018;17(9):1795-1815. doi: 10.1158/1535-7163.MCT-17-1097.
Gacerez, Albert T., et al., "How Chimeric Antigen Receptor Design Affects Adoptive T Cell Therapy", J Cell Physiol; Dec. 2016;231(12):2590-8. doi: 10.1002/jcp.25419. Epub Jun. 2, 2016.
Grotzinger, Joachim , "Molecular mechanisms of cytokine receptor activation", Biochim Biophys Acta; Nov. 11, 2002;1592(3):215-23.
Hu, Yuan , et al., "Chimeric antigen receptor (CAR)-transduced natural killer cells in tumor immunotherapy", Acta Pharmacol Sin; Feb. 2018;39(2):167-176. doi: 10.1038/aps.2017.125. Epub Sep. 7, 2017.
Kim, Jin Hee, et al., "High cleavage efficiency of a 2A peptide derived from porcine teschovirus-1 in human cell lines, zebrafish and mice", PLoS One; 2011;6(4):e18556. doi: 10.1371/journal.pone.0018556. Epub Apr. 29, 2011.
Shao, Huang , "Structural requirements for signal transducer and activator of transcription 3 binding to phosphotyrosine ligands containing the YXXQ motif", J Biol Chem; Apr. 30, 2004;279(18):18967-73. doi: 10.1074/jbc.M314037200. Epub Feb. 13, 2004.
Shochat , "Gain-of-function mutations in interleukin-7 receptor-α (IL7R) in childhood acute lymphoblastic leukemias" Journal of Experimental Medicine; 2(2011) 208 (5): 901-908; https://doi.org/10.1084/jem.20110580.
Zenatti , "Oncogenic IL7R gain-of-function mutations in childhood T-cell acute lymphoblastic leukemia", Nature Genetics; Sep. 4, 2011;43(10):932-9. doi: 10.1038/ng.924.
Zhang, Cheng , et al., "Engineering CAR-T cells", Biomarker Research vol. 5, Article No. 22 (2017).
Behncken, Stuart N., et al., "Growth Hormone (GH)-independent Dimerization of GH Receptor by a Leucine Zipper Results in Constitutive Activation", Journal of Biological Chemistry; vol. 275 Issue 22 pp. 17000-17007 (Jun. 2000) DOI: 10.1074/jbc275.22.17000.
Ding, Jiamin , et al., "Asn 505 Mutation of the C-MPL Gene, A Cause of Familial Essential Thrombocythemia, Induces the Autonomous Homodimerizaton of the C-Mpl Independent of Ligand Stimulation.", Blood; vol. 104, Issue 11, Nov. 16, 2004, p. 738.
Metcalfe, Riley D., et al., "Structural Understanding of Interleukin 6 Family Cytokine Signaling and Targeted Therapies: Focus on Interleukin 11", Front. Immunol., Jul. 16, 2020; Sec. Cytokines and Soluble Mediators in Immunity https://doi.org/10.3389/fimmu.2020.01424.
Suthaus, Jan , et al., "Forced Homo- and Heterodimerization of All gp130-Type Receptor Complexes Leads to Constitutive Ligand-independent Signaling and Cytokine-independent Growth", Molecular Biology of the Cellvol. 21, No. 15; 2797-2807; Aug. 1, 2010; https://doi.org/10.1091/mbce10-03-0240.

* cited by examiner

FIG. 10A

Underlined: wildtype TpoR TM region
Bold: means insertion (4138 - 4302 bp)

| | | |
|---|---|---|
| Template: | SDPTRVETATETAWISLVTALHLVLGLSAVLGLLLLRWQFPAHYRRLRHALWPSL | SEQ. ID NO: 146 |
| N-1: | SDPTRVETATET-WISLVTALHLVLGLSAVLGLLLLRWQFPAHYRRLRHALWPSL | SEQ. ID NO: 147 |
| N-2: | SDPTRVETATET--ISLVTALHLVLGLSAVLGLLLLRWQFPAHYRRLRHALWPSL | SEQ. ID NO: 148 |
| N-2+1: | SDPTRVETATET-**L**ISLVTALHLVLGLSAVLGLLLLRWQFPAHYRRLRHALWPSL | SEQ. ID NO: 149 |
| N-3: | SDPTRVETATET---SLVTALHLVLGLSAVLGLLLLRWQFPAHYRRLRHALWPSL | SEQ. ID NO: 150 |
| N-4: | SDPTRVETATET----LVTALHLVLGLSAVLGLLLLRWQFPAHYRRLRHALWPSL | SEQ. ID NO: 151 |
| N-4+1: | SDPTRVETATET---**I**LVTALHLVLGLSAVLGLLLLRWQFPAHYRRLRHALWPSL | SEQ. ID NO: 152 |
| N-5: | SDPTRVETATET-----VTALHLVLGLSAVLGLLLLRWQFPAHYRRLRHALWPSL | SEQ. ID NO: 153 |
| N-6: | SDPTRVETATET------TALHLVLGLSAVLGLLLLRWQFPAHYRRLRHALWPSL | SEQ. ID NO: 154 |
| N-7: | SDPTRVETATET-------ALHLVLGLSAVLGLLLLRWQFPAHYRRLRHALWPSL | SEQ. ID NO: 155 |
| N-8: | SDPTRVETATET--------LHLVLGLSAVLGLLLLRWQFPAHYRRLRHALWPSL | SEQ. ID NO: 156 |
| N-9: | SDPTRVETATET---------HLVLGLSAVLGLLLLRWQFPAHYRRLRHALWPSL | SEQ. ID NO: 157 |

FIG. 10B (4138 - 4302 bp)

| | | |
|---|---|---|
| Template: | SDPTRVETATETAW--------ISLVTALHLVLGLSAVLGLLLLRWQFPAHYRRLRHALWPSL | SEQ. ID NO: 158 |
| N+1: | SDPTRVETATETAW-------**L**ISLVTALHLVLGLSAVLGLLLLRWQFPAHYRRLRHALWPSL | SEQ. ID NO: 159 |
| N+2: | SDPTRVETATETAW------**VL**ISLVTALHLVLGLSAVLGLLLLRWQFPAHYRRLRHALWPSL | SEQ. ID NO: 160 |
| N+3: | SDPTRVETATETAW-----**LVL**ISLVTALHLVLGLSAVLGLLLLRWQFPAHYRRLRHALWPSL | SEQ. ID NO: 161 |
| N+4: | SDPTRVETATETAW----**ILVL**ISLVTALHLVLGLSAVLGLLLLRWQFPAHYRRLRHALWPSL | SEQ. ID NO: 162 |
| N+5: | SDPTRVETATETAW---**LILVL**ISLVTALHLVLGLSAVLGLLLLRWQFPAHYRRLRHALWPSL | SEQ. ID NO: 163 |
| N+6: | SDPTRVETATETAW--**LLILVL**ISLVTALHLVLGLSAVLGLLLLRWQFPAHYRRLRHALWPSL | SEQ. ID NO: 164 |
| N+7: | SDPTRVETATETAW-**VLLILVL**ISLVTALHLVLGLSAVLGLLLLRWQFPAHYRRLRHALWPSL | SEQ. ID NO: 165 |
| N+8: | SDPTRVETATETAW**LVLLILVL**ISLVTALHLVLGLSAVLGLLLLRWQFPAHYRRLRHALWPSL | SEQ. ID NO: 166 |

SEQUENCE LISTING

```
Sequence total quantity: 224
SEQ ID NO: 1           moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 1
MALPVTALLL PLALLLHAAR P                                                21

SEQ ID NO: 2           moltype = AA  length = 187
FEATURE                Location/Qualifiers
REGION                 1..187
                       note = Description of Unknown: PD1 ectodomain sequence
source                 1..187
                       mol_type = protein
                       organism = unidentified
SEQUENCE: 2
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQ                                                            187

SEQ ID NO: 3           moltype = AA  length = 374
FEATURE                Location/Qualifiers
REGION                 1..374
                       note = Description of Artificial Sequence: Synthetic
                        polypeptide
source                 1..374
                       mol_type = protein
                       organism = synthetic construct
SEQUENCE: 3
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPGW FLDSPDRPWN PPTFSPALLV VTEGDNATFT CSFSNTSESF VLNWYRMSPS  240
NQTDKLAAFP EDRSQPGQDC RFRVTQLPNG RDFHMSVVRA RRNDSGTYLC GAISLAPKAQ  300
IKESLRAELR VTERRAEVPT AHPSPSPRPA GQFQTLVVGV VGGLLGSLVL LVWVLAVICS  360
RAARGTIGAR RTGQ                                                    374

SEQ ID NO: 4           moltype = AA  length = 561
FEATURE                Location/Qualifiers
REGION                 1..561
                       note = Description of Artificial Sequence: Synthetic
                        polypeptide
```

```
source                  1..561
                        mol_type = protein
                        organism = synthetic construct
SEQUENCE: 4
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPGW FLDSPDRPWN PPTFSPALLV VTEGDNATFT CSFSNTSESF VLNWYRMSPS  240
NQTDKLAAFP EDRSQPGQDC RFRVTQLPNG RDFHMSVVRA RRNDSGTYLC GAISLAPKAQ  300
IKESLRAELR VTERRAEVPT AHPSPSPRPA GQFQTLVVGV VGGLLGSLVL LVWVLAVICS  360
RAARGTIGAR RTGQPGWFLD SPDRPWNPPT FSPALLVVTE GDNATFTCSF SNTSESFVLN  420
WYRMSPSNQT DKLAAFPEDR SQPGQDCRFR VTQLPNGRDF HMSVVRARRN DSGTYLCGAI  480
SLAPKAQIKE SLRAELRVTE RRAEVPTAHP SPSPRPAGQF QTLVVGVVGG LLGSLVLLVW  540
VLAVICSRAA RGTIGARRTG Q                                            561

SEQ ID NO: 5            moltype = AA  length = 187
FEATURE                 Location/Qualifiers
REGION                  1..187
                        note = Description of Unknown: High-affinity (HA) PD1
                         ectodomain sequence
source                  1..187
                        mol_type = protein
                        organism = unidentified
SEQUENCE: 5
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQ                                                            187

SEQ ID NO: 6            moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 6
MGVQVETISP GDGRTFPKRG QTCVVHYTGM LEDGKKVDSS RDRNKPFKFM LGKQEVIRGW  60
EEGVAQMSVG QRAKLTISPD YAYGATGHPG IIPPHATLVF DVELLKLE               108

SEQ ID NO: 7            moltype = AA  length = 187
FEATURE                 Location/Qualifiers
REGION                  1..187
                        note = Description of Unknown: Dominant negative PD1
                         (21-207) sequence
source                  1..187
                        mol_type = protein
                        organism = unidentified
SEQUENCE: 7
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQ                                                            187

SEQ ID NO: 8            moltype = AA  length = 187
FEATURE                 Location/Qualifiers
REGION                  1..187
                        note = Description of Unknown: Dominant negative high
                         affinity PD1 sequence
source                  1..187
                        mol_type = protein
                        organism = unidentified
SEQUENCE: 8
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQ                                                            187

SEQ ID NO: 9            moltype = AA  length = 508
FEATURE                 Location/Qualifiers
source                  1..508
                        mol_type = protein
                        organism = Homo sapiens
SEQUENCE: 9
MDHLGASLWP QVGSLCLLLA GAAWAPPPNL PDPKFESKAA LLAARGPEEL LCFTERLEDL  60
VCFWEEAASA GVGPGNYSFS YQLEDEPWKL CRLHQAPTAR GAVRFWCSLP TADTSSFVPL  120
ELRVTAASGA PRYHRVIHIN EVVLLDAPVG LVARLADESG HVVLRWLPPP ETPMTSHIRY  180
EVDVSAGNGA GSVQRVEILE GRTECVLSNL RGRTRYTFAV RARMAEPSFG GFWSAWSEPV  240
```

```
SLLTPSDLDP LILTLSLILV VILVLLTVLA LLSHRRALKQ KIWPGIPSPE SEFEGLFTTH  300
KGNFQLWLYQ NDGCLWWSPC TPFTEDPPAS LEVLSERCWG TMQAVEPGTD DEGPLLEPVG  360
SEHAQDTYLV LDKWLLPRNP PSEDLPGPGG SVDIVAMDEG SEASSCSSAL ASKPSPEGAS  420
AASFEYTILD PSSQLLRPWT LCPELPPTPP HLKYLYLVVS DSGISTDYSS GDSQGAQGGL  480
SDGPYSNPYE NSLIPAAEPL PPSYVACS                                     508

SEQ ID NO: 10          moltype = AA  length = 918
FEATURE                Location/Qualifiers
source                 1..918
                       mol_type = protein
                       organism = Homo sapiens
SEQUENCE: 10
MLTLQTWLVQ ALFIFLTTES TGELLDPCGY ISPESPVVQL HSNFTAVCVL KEKCMDYFHV  60
NANYIVWKTN HFTIPKEQYT IINRTASSVT FTDIASLNIQ LTCNILTFGQ LEQNVYGITI  120
ISGLPPEKPK NLSCIVNEGK KMRCEWDRGR ETHLETNFTL KSEWATHKFA DCKAKRDTPT  180
SCTVDYSTVY FVNIEVWVEA ENALGKVTSD HINFDPVYKV KPNPPHNLSV INSEELSSIL  240
KLTWTNPSIK SVIILKYNIQ YRTKDASTWS QIPPEDTAST RSSFTVQDLK PFTEYVFRIR  300
CMKEDGKGYW SDWSEEASGI TYEDRPSKAP SFWYKIDPSH TQGYRTVQLV WKTLPPFEAN  360
GKILDYEVTL TRWKSHLQNY TVNATKLTVN LTNDRYVATL TVRNLVGKSD AAVLTIPACD  420
FQATHPVMDL KAFPKDNMLW VEWTTPRESV KKYILEWCVL SDKAPCITDW QQEDGTVHRT  480
YLRGNLAESK CYLITVTPVY ADGPGSPESI KAYLKQAPPS KGPTVRTKKV GKNEAVLEWD  540
QLPVDVQNGF IRNYTIFYRT IIGNETAVNV DSSHTEYTLS SLTSDTLYMV RMAAYTDEGG  600
KDGPEFTFTT PKFAQGEIEA IVVPVCLAFL LTTLLGVLFC FNKRDLIKKH IWPNVPDPSK  660
SHIAQWSPHT PPRHNFNSKD QMYSDGNFTD VSVVEIEAND KKPFPEDLKS LDLFKKEKIN  720
TEGHSSGIGG SSCMSSSRPS ISSSDENESS QNTSSTVQYS TVVHSGYRHQ VPSVQVFSRS  780
ESTQPLLDSE ERPEDLQLVD HVDGGDGILP RQQYFKQNCS QHESSPDISH FERSKQVSSV  840
NEEDFVRLKQ QISDHISQSC GSGQMKMFQE VSAADAFGPG TEGQVERFET VGMEAATDEG  900
MPKSYLPQTV RQGGYMPQ                                                918

SEQ ID NO: 11          moltype = AA  length = 622
FEATURE                Location/Qualifiers
source                 1..622
                       mol_type = protein
                       organism = Homo sapiens
SEQUENCE: 11
MKENVASATV FTLLLFLNTC LLNGQLPPGK PEIFKCRSPN KETFTCWWRP GTDGGLPTNY  60
SLTYHREGET LMHECPDYIT GGPNSCHFGK QYTSMWRTYI MMVNATNQMG SSFSDELYVD  120
VTYIVQPDPP LELAVEVKQP EDRKPYLWIK WSPPTLIDLK TGWFTLLYEI RLKPEKAAEW  180
EIHFAGQQTE FKILSLHPGQ KYLVQVRCKP DHGYWSAWSP ATFIQIPSDF TMNDTTVWIS  240
VAVLSAVICL IIVWAVALKG YSMVTCIFPP VPGPKIKGFD AHLLEKGKSE ELLSALGCQD  300
FPPTSDYEDL LVEYLEVDDS EDQHLMSVHS KEHPSQGMKP TYLDPDTDSG RGSCDSPSLL  360
SEKCEEPQAN PSTFYDPEVI EKPENPETTH TWDPQCISME GKIPYFHAGG SKCSTWPLPQ  420
PSQHNPRSSY HNITDVCELA VGPAGAPATL LNEAGKDALK SSQTIKSREE GKATQQREVE  480
SFHSETDQDT PWLLPQEKTP FGSAKPLDYV EIHKVNKDGA LSLLPKQREN SGKPKKPGTP  540
ENNKEYAKVS GVMDNNILVL VPDPHAKNVA CFEESAKEAP PSLEQNQAEK ALANFTATSS  600
KCRLQLGGLD YLDPACFTHS FH                                           622

SEQ ID NO: 12          moltype = AA  length = 638
FEATURE                Location/Qualifiers
source                 1..638
                       mol_type = protein
                       organism = Homo sapiens
SEQUENCE: 12
MDLWQLLLTL ALAGSSDAFS GSEATAAILS RAPWSLQSVN PGLKTNSSKE PKFTKCRSPE  60
RETFSCHWTD EVHHGTKNLG PIQLFYTRRN TQEWTQEWKE CPDYVSAGEN SCYFNSSFTS  120
IWIPYCIKLT SNGGTVDEKC FSVDEIVQPD PPIALNWTLL NVSLTGIHAD IQVRWEAPRN  180
ADIQKGWMVL EYELQYKEVN ETKWKMMDPI LTTSVPVYSL KVDKEYEVRV RSKQRNSGNY  240
GEFSEVLYVT LPQMSQFTCE EDFYFPWLLI IIFGIFGLTV MLFVFLFSKQ QRIKMLILPP  300
VPVPKIKGID PDLLKEGKLE EVNTILAIHD SYKPEFHSDD SWVEFIELDI DEPDEKTEES  360
DTDRLLSSDH EKSHSNLGVK DGDSGRTSCC EPDILETDFN ANDIHEGTSE VAQPQRLKGE  420
ADLLCLDQKN QNNSPYHDAC PATQQPSVIQ AEKNKPQPLP TEGAESTHQA AHIQLSNPSS  480
LSNIDFYAQV SDITPAGSVV LSPGQKNKAG MSQCDMHPEM VSLCQENFLM DNAYFCEADA  540
KKCIPVAPHI KVESHIQPSL NQEDIYITTE SLTTAAGRPG TGEHVPGSEM PVPDYTSIHI  600
VQSPQGLILN ATALPLPDKE FLSSCGYVST DQLNKIMP                          638

SEQ ID NO: 13          moltype = AA  length = 863
FEATURE                Location/Qualifiers
source                 1..863
                       mol_type = protein
                       organism = Homo sapiens
SEQUENCE: 13
MARLGNCSLT WAALIILLLP GSLEECGHIS VSAPIVHLGD PITASCIIKQ NCSHLDPEPQ  60
ILWRLGAELQ PGGRQQRLSD GTQESIITLP HLNHTQAFLS CCLNWGNSLQ ILDQVELRAG  120
YPPAIPHNLS CLMNLTTSSL ICQWEPGPET HLPTSFTLKS FKSRGNCQTQ GDSILDCVPK  180
DGQSHCCIPR KHLLLYQNMG IWVQAENALG TSMSPQLCLD PMDVVKLEPP MLRTMDPSPE  240
AAPPQAGCLQ LCWEPWQPGL HINQKCELRH KPQRGEASWA LVGPLPLEAL QYELCGLLPA  300
TAYTLQIRCI RWPLPGHWSD WSPSLELRTT ERAPTVRLDT WWRQRQLDPR TVQLFWKPVP  360
LEEDSGRIQG YVVSWRPSGQ AGAILPLCNT TELSCTFHLP SEAQEVALVA YNSAGTSRPT  420
PVVFSESRGP ALTRLHAMAR DPHSLWVGWE PPNPWPQGYV IEWGLGPPSA SNSNKTWRME  480
```

-continued

```
QNGRATGFLL KENIRPFQLY EIIVTPLYQD TMGPSQHVYA YSQEMAPSHA PELHLKHIGK  540
TWAQLEWVPE PPELGKSPLT HYTIFWTNAQ NQSFSAILNA SSRGFVLHGL EPASLYHIHL  600
MAASQAGATN STVLTLMTLT PEGSELHIIL GLFGLLLLLT CLCGTAWLCC SPNRKNPLWP  660
SVPDPAHSSL GSWVPTIMEE LPGPRQGQWL GQTSEMSRAL TPHPCVQDAF QLPGLGTPPI  720
TKLTVLEEDE KKPVPWESHN SSETCGLPTL VQTYVLQGDP RAVSTQPQSQ SGTSDQVLYG  780
QLLGSPTSPG PGHYLRCDST QPLLAGLTPS PKSYENLWFQ ASPLGTLVTP APSQEDDCVF  840
GPLLNFPLLQ GIRVHGMEAL GSF                                          863

SEQ ID NO: 14          moltype = AA  length = 97
FEATURE                Location/Qualifiers
REGION                 1..97
                       note = Description of Unknown: GCSFR(614-710) sequence
source                 1..97
                       mol_type = protein
                       organism = unidentified
SEQUENCE: 14
LTLMTLTPEG SELHIILGLF GLLLLLTCLC GTAWLCCSPN RKNPLWPSVP DPAHSSLGSW  60
VPTIMEEDAF QLPGLGTPPI TKLTVLEEDE KKPVPWE                           97

SEQ ID NO: 15          moltype = AA  length = 92
FEATURE                Location/Qualifiers
source                 1..92
                       mol_type = protein
                       organism = Homo sapiens
SEQUENCE: 15
TTPKFAQGEI EAIVVPVCLA FLLTTLLGVL FCFNKRDLIK KHIWPNVPDP SKSHIAQWSP  60
HTPPRHNFNS KDQMYSDGNF TDVSVVEIEA ND                                92

SEQ ID NO: 16          moltype = AA  length = 105
FEATURE                Location/Qualifiers
source                 1..105
                       mol_type = protein
                       organism = Homo sapiens
SEQUENCE: 16
SDPTRVETAT ETAWISLVTA LHLVLGLSAV LGLLLLRWQF PAHYRRLRHA LWPSLPDLHR  60
VLGQYLRDTA ALSPPKATVS DTCEEVEPSL LEILPKSSER TPLPL                  105

SEQ ID NO: 17          moltype = AA  length = 104
FEATURE                Location/Qualifiers
REGION                 1..104
                       note = Description of Artificial Sequence: Synthetic
                        polypeptide
source                 1..104
                       mol_type = protein
                       organism = synthetic construct
SEQUENCE: 17
SDPTRVETAT ETWISLVTAL HLVLGLSAVL GLLLLRWQFP AHYRRLRHAL WPSLPDLHRV  60
LGQYLRDTAA LSPPKATVSD TCEEVEPSLL EILPKSSERT PLPL                   104

SEQ ID NO: 18          moltype = AA  length = 103
FEATURE                Location/Qualifiers
REGION                 1..103
                       note = Description of Artificial Sequence: Synthetic
                        polypeptide
source                 1..103
                       mol_type = protein
                       organism = synthetic construct
SEQUENCE: 18
SDPTRVETAT ETISLVTALH LVLGLSAVLG LLLLRWQFPA HYRRLRHALW PSLPDLHRVL  60
GQYLRDTAAL SPPKATVSDT CEEVEPSLLE ILPKSSERTP LPL                    103

SEQ ID NO: 19          moltype = AA  length = 104
FEATURE                Location/Qualifiers
REGION                 1..104
                       note = Description of Artificial Sequence: Synthetic
                        polypeptide
source                 1..104
                       mol_type = protein
                       organism = synthetic construct
SEQUENCE: 19
SDPTRVETAT ETLISLVTAL HLVLGLSAVL GLLLLRWQFP AHYRRLRHAL WPSLPDLHRV  60
LGQYLRDTAA LSPPKATVSD TCEEVEPSLL EILPKSSERT PLPL                   104

SEQ ID NO: 20          moltype = AA  length = 102
FEATURE                Location/Qualifiers
REGION                 1..102
                       note = Description of Artificial Sequence: Synthetic
                        polypeptide
source                 1..102
```

```
                        mol_type = protein
                        organism = synthetic construct
SEQUENCE: 20
SDPTRVETAT ETSLVTALHL VLGLSAVLGL LLLRWQFPAH YRRLRHALWP SLPDLHRVLG  60
QYLRDTAALS PPKATVSDTC EEVEPSLLEI LPKSSERTPL PL                    102

SEQ ID NO: 21           moltype = AA  length = 101
FEATURE                 Location/Qualifiers
REGION                  1..101
                        note = Description of Artificial Sequence: Synthetic
                         polypeptide
source                  1..101
                        mol_type = protein
                        organism = synthetic construct
SEQUENCE: 21
SDPTRVETAT ETLVTALHLV LGLSAVLGLL LLRWQFPAHY RRLRHALWPS LPDLHRVLGQ  60
YLRDTAALSP PKATVSDTCE EVEPSLLEIL PKSSERTPLP L                     101

SEQ ID NO: 22           moltype = AA  length = 102
FEATURE                 Location/Qualifiers
REGION                  1..102
                        note = Description of Artificial Sequence: Synthetic
                         polypeptide
source                  1..102
                        mol_type = protein
                        organism = synthetic construct
SEQUENCE: 22
SDPTRVETAT ETILVTALHL VLGLSAVLGL LLLRWQFPAH YRRLRHALWP SLPDLHRVLG  60
QYLRDTAALS PPKATVSDTC EEVEPSLLEI LPKSSERTPL PL                    102

SEQ ID NO: 23           moltype = AA  length = 100
FEATURE                 Location/Qualifiers
REGION                  1..100
                        note = Description of Artificial Sequence: Synthetic
                         polypeptide
source                  1..100
                        mol_type = protein
                        organism = synthetic construct
SEQUENCE: 23
SDPTRVETAT ETVTALHLVL GLSAVLGLLL LRWQFPAHYR RLRHALWPSL PDLHRVLGQY  60
LRDTAALSPP KATVSDTCEE VEPSLLEILP KSSERTPLPL                       100

SEQ ID NO: 24           moltype = AA  length = 99
FEATURE                 Location/Qualifiers
REGION                  1..99
                        note = Description of Artificial Sequence: Synthetic
                         polypeptide
source                  1..99
                        mol_type = protein
                        organism = synthetic construct
SEQUENCE: 24
SDPTRVETAT ETTALHLVLG LSAVLGLLLL RWQFPAHYRR LRHALWPSLP DLHRVLGQYL  60
RDTAALSPPK ATVSDTCEEV EPSLLEILPK SSERTPLPL                        99

SEQ ID NO: 25           moltype = AA  length = 98
FEATURE                 Location/Qualifiers
REGION                  1..98
                        note = Description of Artificial Sequence: Synthetic
                         polypeptide
source                  1..98
                        mol_type = protein
                        organism = synthetic construct
SEQUENCE: 25
SDPTRVETAT ETALHLVLGL SAVLGLLLLR WQFPAHYRRL RHALWPSLPD LHRVLGQYLR  60
DTAALSPPKA TVSDTCEEVE PSLLEILPKS SERTPLPL                         98

SEQ ID NO: 26           moltype = AA  length = 97
FEATURE                 Location/Qualifiers
REGION                  1..97
                        note = Description of Artificial Sequence: Synthetic
                         polypeptide
source                  1..97
                        mol_type = protein
                        organism = synthetic construct
SEQUENCE: 26
SDPTRVETAT ETLHLVLGLS AVLGLLLLRW QFPAHYRRLR HALWPSLPDL HRVLGQYLRD  60
TAALSPPKAT VSDTCEEVEP SLLEILPKSS ERTPLPL                          97

SEQ ID NO: 27           moltype = AA  length = 96
```

```
FEATURE               Location/Qualifiers
REGION                1..96
                      note = Description of Artificial Sequence: Synthetic
                       polypeptide
source                1..96
                      mol_type = protein
                      organism = synthetic construct
SEQUENCE: 27
SDPTRVETAT ETHLVLGLSA VLGLLLLRWQ FPAHYRRLRH ALWPSLPDLH RVLGQYLRDT  60
AALSPPKATV SDTCEEVEPS LLEILPKSSE RTPLPL                            96

SEQ ID NO: 28         moltype = AA  length = 95
FEATURE               Location/Qualifiers
REGION                1..95
                      note = Description of Artificial Sequence: Synthetic
                       polypeptide
source                1..95
                      mol_type = protein
                      organism = synthetic construct
SEQUENCE: 28
SDPTRVETAT ETLVLGLSAV LGLLLLRWQF PAHYRRLRHA LWPSLPDLHR VLGQYLRDTA  60
ALSPPKATVS DTCEEVEPSL LEILPKSSER TPLPL                             95

SEQ ID NO: 29         moltype = AA  length = 94
FEATURE               Location/Qualifiers
REGION                1..94
                      note = Description of Artificial Sequence: Synthetic
                       polypeptide
source                1..94
                      mol_type = protein
                      organism = synthetic construct
SEQUENCE: 29
SDPTRVETAT ETVLGLSAVL GLLLLRWQFP AHYRRLRHAL WPSLPDLHRV LGQYLRDTAA  60
LSPPKATVSD TCEEVEPSLL EILPKSSERT PLPL                              94

SEQ ID NO: 30         moltype = AA  length = 93
FEATURE               Location/Qualifiers
REGION                1..93
                      note = Description of Artificial Sequence: Synthetic
                       polypeptide
source                1..93
                      mol_type = protein
                      organism = synthetic construct
SEQUENCE: 30
SDPTRVETAT ETLGLSAVLG LLLLRWQFPA HYRRLRHALW PSLPDLHRVL GQYLRDTAAL  60
SPPKATVSDT CEEVEPSLLE ILPKSSERTP LPL                               93

SEQ ID NO: 31         moltype = AA  length = 92
FEATURE               Location/Qualifiers
REGION                1..92
                      note = Description of Artificial Sequence: Synthetic
                       polypeptide
source                1..92
                      mol_type = protein
                      organism = synthetic construct
SEQUENCE: 31
SDPTRVETAT ETGLSAVLGL LLLRWQFPAH YRRLRHALWP SLPDLHRVLG QYLRDTAALS  60
PPKATVSDTC EEVEPSLLEI LPKSSERTPL PL                                92

SEQ ID NO: 32         moltype = AA  length = 91
FEATURE               Location/Qualifiers
REGION                1..91
                      note = Description of Artificial Sequence: Synthetic
                       polypeptide
source                1..91
                      mol_type = protein
                      organism = synthetic construct
SEQUENCE: 32
SDPTRVETAT ETLSAVLGLL LLRWQFPAHY RRLRHALWPS LPDLHRVLGQ YLRDTAALSP  60
PKATVSDTCE EVEPSLLEIL PKSSERTPLP L                                 91

SEQ ID NO: 33         moltype = AA  length = 90
FEATURE               Location/Qualifiers
REGION                1..90
                      note = Description of Artificial Sequence: Synthetic
                       polypeptide
source                1..90
                      mol_type = protein
                      organism = synthetic construct
```

```
SEQUENCE: 33
SDPTRVETAT ETSAVLGLLL LRWQFPAHYR RLRHALWPSL PDLHRVLGQY LRDTAALSPP  60
KATVSDTCEE VEPSLLEILP KSSERTPLPL                                    90

SEQ ID NO: 34          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 34
SDPTRVETAT ETAVLGLLLL RWQFPAHYRR LRHALWPSLP DLHRVLGQYL RDTAALSPPK  60
ATVSDTCEEV EPSLLEILPK SSERTPLPL                                     89

SEQ ID NO: 35          moltype = AA  length = 88
FEATURE                Location/Qualifiers
REGION                 1..88
                       note = Description of Artificial Sequence: Synthetic
                        polypeptide
source                 1..88
                       mol_type = protein
                       organism = synthetic construct
SEQUENCE: 35
SDPTRVETAT ETVLGLLLLR WQFPAHYRRL RHALWPSLPD LHRVLGQYLR DTAALSPPKA  60
TVSDTCEEVE PSLLEILPKS SERTPLPL                                      88

SEQ ID NO: 36          moltype = AA  length = 87
FEATURE                Location/Qualifiers
REGION                 1..87
                       note = Description of Artificial Sequence: Synthetic
                        polypeptide
source                 1..87
                       mol_type = protein
                       organism = synthetic construct
SEQUENCE: 36
SDPTRVETAT ETLGLLLLRW QFPAHYRRLR HALWPSLPDL HRVLGQYLRD TAALSPPKAT  60
VSDTCEEVEP SLLEILPKSS ERTPLPL                                       87

SEQ ID NO: 37          moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 37
SDPTRVETAT ETAWLISLVT ALHLVLGLSA VLGLLLLRWQ FPAHYRRLRH ALWPSLPDLH  60
RVLGQYLRDT AALSPPKATV SDTCEEVEPS LLEILPKSSE RTPLPL                  106

SEQ ID NO: 38          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 38
SDPTRVETAT ETAWVLISLV TALHLVLGLS AVLGLLLLRW QFPAHYRRLR HALWPSLPDL  60
HRVLGQYLRD TAALSPPKAT VSDTCEEVEP SLLEILPKSS ERTPLPL                 107

SEQ ID NO: 39          moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 39
SDPTRVETAT ETAWLVLISL VTALHLVLGL SAVLGLLLLR WQFPAHYRRL RHALWPSLPD  60
LHRVLGQYLR DTAALSPPKA TVSDTCEEVE PSLLEILPKS SERTPLPL                108

SEQ ID NO: 40          moltype = AA  length = 109
FEATURE                Location/Qualifiers
REGION                 1..109
```

```
                         note = Description of Artificial Sequence: Synthetic
                          polypeptide
source                   1..109
                         mol_type = protein
                         organism = synthetic construct
SEQUENCE: 40
SDPTRVETAT ETAWILVLIS LVTALHLVLG LSAVLGLLLL RWQFPAHYRR LRHALWPSLP  60
DLHRVLGQYL RDTAALSPPK ATVSDTCEEV EPSLLEILPK SSERTPLPL             109

SEQ ID NO: 41            moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 41
SDPTRVETAT ETAWLILVLI SLVTALHLVL GLSAVLGLLL LRWQFPAHYR RLRHALWPSL  60
PDLHRVLGQY LRDTAALSPP KATVSDTCEE VEPSLLEILP KSSERTPLPL            110

SEQ ID NO: 42            moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 42
SDPTRVETAT ETAWLLILVL ISLVTALHLV LGLSAVLGLL LLRWQFPAHY RRLRHALWPS  60
LPDLHRVLGQ YLRDTAALSP PKATVSDTCE EVEPSLLEIL PKSSERTPLP L          111

SEQ ID NO: 43            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 43
SDPTRVETAT ETAWVLLILV LISLVTALHL VLGLSAVLGL LLLRWQFPAH YRRLRHALWP  60
SLPDLHRVLG QYLRDTAALS PPKATVSDTC EEVEPSLLEI LPKSSERTPL PL         112

SEQ ID NO: 44            moltype = AA  length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 44
SDPTRVETAT ETAWLVLLIL VLISLVTALH LVLGLSAVLG LLLLRWQFPA HYRRLRHALW  60
PSLPDLHRVL GQYLRDTAAL SPPKATVSDT CEEVEPSLLE ILPKSSERTP LPL        113

SEQ ID NO: 45            moltype = AA  length = 144
FEATURE                  Location/Qualifiers
REGION                   1..144
                         note = Description of Unknown: IL7R(316-459) sequence
source                   1..144
                         mol_type = protein
                         organism = unidentified
SEQUENCE: 45
ARDEVEGFLQ DTFPQQLEES EKQRLGGDVQ SPNCPSEDVV ITPESFGRDS SLTCLAGNVS  60
ACDAPILSSS RSLDCRESGK NGPHVYQDLL LSLGTTNSTL PPPFSLQSGI LTLNPVAQGQ  120
PILTSLGSNQ EEAYVTMSSF YQNQ                                        144

SEQ ID NO: 46            moltype = AA  length = 219
FEATURE                  Location/Qualifiers
REGION                   1..219
                         note = Description of Unknown: IL2Rb(333-551) sequence
source                   1..219
                         mol_type = protein
                         organism = unidentified
SEQUENCE: 46
VTQLLLQQDK VPEPASLSSN HSLTSCFTNQ GYFFFHLPDA LEIEACQVYF TYDPYSEEDP  60
DEGVAGAPTG SSPQPLQPLS GEDDAYCTFP SRDDLLLFSP SLLGGPSPPS TAPGGSGAGE  120
```

```
ERMPPSLQER VPRDWDPQPL GPPTPGVPDL VDFQPPPELV LREAGEEVPD AGPREGVSFP  180
WSRPPGQGEF RALNARLPLN TDAYLSLQEL QGQDPTHLV                         219

SEQ ID NO: 47          moltype = AA  length = 50
FEATURE                Location/Qualifiers
REGION                 1..50
                       note = Description of Unknown: IFNAR1(508-557) sequence
source                 1..50
                       mol_type = protein
                       organism = unidentified
SEQUENCE: 47
ISTIATVEET NQTDEDHKKY SSQTSQDSGN YSNEDESESK TSEELQQDFV             50

SEQ ID NO: 48          moltype = AA  length = 206
FEATURE                Location/Qualifiers
REGION                 1..206
                       note = Description of Unknown: IFNAR2(310-515) sequence
source                 1..206
                       mol_type = protein
                       organism = unidentified
SEQUENCE: 48
KKKVWDYNYD DESDSDTEAA PRTSGGGYTM HGLTVRPLGQ ASATSTESQL IDPESEEEPD  60
LPEVDVELPT MPKDSPQQLE LLSGPCERRK SPLQDPFPEE DYSSTEGSGG RITFNVDLNS  120
VFLRVLDDED SDDLEAPLML SSHLEEMVDP EDPDNVQSNH LLASGEGTQP TFPSPSSEGL  180
WSEDAPSDQS DTSESDVDLG DGYIMR                                       206

SEQ ID NO: 49          moltype = AA  length = 256
FEATURE                Location/Qualifiers
REGION                 1..256
                       note = Description of Artificial Sequence: Synthetic
                        polypeptide
source                 1..256
                       mol_type = protein
                       organism = synthetic construct
SEQUENCE: 49
ISTIATVEET NQTDEDHKKY SSQTSQDSGN YSNEDESESK TSEELQQDFV KKKVWDYNYD  60
DESDSDTEAA PRTSGGGYTM HGLTVRPLGQ ASATSTESQL IDPESEEEPD LPEVDVELPT  120
MPKDSPQQLE LLSGPCERRK SPLQDPFPEE DYSSTEGSGG RITFNVDLNS VFLRVLDDED  180
SDDLEAPLML SSHLEEMVDP EDPDNVQSNH LLASGEGTQP TFPSPSSEGL WSEDAPSDQS  240
DTSESDVDLG DGYIMR                                                  256

SEQ ID NO: 50          moltype = AA  length = 221
FEATURE                Location/Qualifiers
REGION                 1..221
                       note = Description of Unknown: IFNLR1(300-520) sequence
source                 1..221
                       mol_type = protein
                       organism = unidentified
SEQUENCE: 50
RGVRPTPRVR APATQQTRWK KDLAEDEEEE DEEDTEDGVS FQPYIEPPSF LGQEHQAPGH  60
SEAGGVDSGR PRAPLVPSEG SSAWDSSDRS WASTVDSSWD RAGSSGYLAE KGPGQGPGGD  120
GHQESLPPPE FSKDSGFLEE LPEDNLSSWA TWGTLPPEPN LVPGGPPVSL QTLTFCWESS  180
PEEEEEARES EIEDSDAGSW GAESTQRTED RGRTLGHYMA R                      221

SEQ ID NO: 51          moltype = AA  length = 35
FEATURE                Location/Qualifiers
REGION                 1..35
                       note = Description of Unknown: Common Gamma Chain(335-369)
                        sequence
source                 1..35
                       mol_type = protein
                       organism = unidentified
SEQUENCE: 51
IPPKGGALGE GPGASPCNQH SPYWAPPCYT LKPET                             35

SEQ ID NO: 52          moltype = AA  length = 166
FEATURE                Location/Qualifiers
REGION                 1..166
                       note = Description of Unknown: IL9R(356-521) sequence
source                 1..166
                       mol_type = protein
                       organism = unidentified
SEQUENCE: 52
TALLTCGPAR PWKSVALEEE QEGPGTRLPG NLSSEDVLPA GCTEWRVQTL AYLPQEDWAP  60
TSLTRPAPPD SEGSRSSSSS SSSNNNNYCA LGCYGGWHLS ALPGNTQSSG PIPALACGLS  120
CDHQGLETQQ GVAWVLAGHC QRPGLHEDLQ GMLLPSVLSK ARSWTF                 166

SEQ ID NO: 53          moltype = AA  length = 217
FEATURE                Location/Qualifiers
```

-continued

```
REGION                  1..217
                        note = Description of Unknown: IL21R(322-538) sequence
source                  1..217
                        mol_type = protein
                        organism = unidentified
SEQUENCE: 53
PRSPAKRLQL TELQEPAELV ESDGVPKPSF WPTAQNSGGS AYSEERDRPY GLVSIDTVTV  60
LDAEGPCTWP CSCEDDGYPA LDLDAGLEPS PGLEDPLLDA GTTVLSCGCV SAGSPGLGGP  120
LGSLLDRLKP PLADGEDWAG GLPWGGRSPG GVSESEAGSP LAGLDMDTFD SGFVGSDCSS  180
PVECDFTSPG DEGPPRSYLR QWVVIPPPLS SPGPQAS                          217

SEQ ID NO: 54           moltype = AA  length = 286
FEATURE                 Location/Qualifiers
source                  1..286
                        mol_type = protein
                        organism = Homo sapiens
SEQUENCE: 54
PDEKTEESDT DRLLSSDHEK SHSNLGVKDG DSGRTSCCEP DILETDFNAN DIHEGTSEVA  60
QPQRLKGEAD LLCLDQKNQN NSPYHDACPA TQQPSVIQAE KNKPQPLPTE GAESTHQAAH  120
IQLSNPSSLS NIDFYAQVSD ITPAGSVVLS PGQKNKAGMS QCDMHPEMVS LCQENFLMDN  180
AYFCEADAKK CIPVAPHIKV ESHIQPSLNQ EDIYITTESL TTAAGRPGTG EHVPGSEMPV  240
PDYTSIHIVQ SPQGLILNAT ALPLPDKEFL SSCGYVSTDQ LNKIMP                286

SEQ ID NO: 55           moltype = AA  length = 170
FEATURE                 Location/Qualifiers
source                  1..170
                        mol_type = protein
                        organism = Homo sapiens
SEQUENCE: 55
WGTMQAVEPG TDDEGPLLEP VGSEHAQDTY LVLDKWLLPR NPPSEDLPGP GGSVDIVAMD  60
EGSEASSCSS ALASKPSPEG ASAASFEYTI LDPSSQLLRP WTLCPELPPT PPHLKYLYLV  120
VSDSGISTDY SSGDSQGAQG GLSDGPYSNP YENSLIPAAE PLPPSYVACS            170

SEQ ID NO: 56           moltype = AA  length = 203
FEATURE                 Location/Qualifiers
source                  1..203
                        mol_type = protein
                        organism = Mus musculus
SEQUENCE: 56
AVQLLLLQKD SAPLPSPSGH SQASCFTNQG YFFFHLPNAL EIESCQVYFT YDPCVEEEVE  60
EDGSRLPEGS PHPPLLPLAG EQDDYCAFPP RDDLLLFSPS LSTPNTAYGG SRAPEERSPL  120
SLHEGLPSLA SRDLMGLQRP LERMPEGDGE GLSANSSGEQ ASVPEGNLHG QDQDRGQGPI  180
LTLNTDAYLS LQELQAQDSV HLI                                         203

SEQ ID NO: 57           moltype = AA  length = 144
FEATURE                 Location/Qualifiers
source                  1..144
                        mol_type = protein
                        organism = Mus musculus
SEQUENCE: 57
ARDEVESFLP NDLPAQPEEL ETQGHRAAVH SANRSPETSV SPPETVRRES PLRCLARNLS  60
TCNAPPLLSS RSPDYRDGDR NRPPVYQDLL PNSGNTNVPV PVPQPLPFQS GILIPVSQRQ  120
PISTSSVLNQ EEAYVTMSSF YQNK                                        144

SEQ ID NO: 58           moltype = AA  length = 231
FEATURE                 Location/Qualifiers
REGION                  1..231
                        note = Description of Unknown: EGFR(955-1186) sequence
source                  1..231
                        mol_type = protein
                        organism = unidentified
SEQUENCE: 58
VIQGDERMHL PSPTDSNFYR ALMDEEDMDD VVDADEYLIP QQGFFSSPST SRTPLLSSLS  60
ATSNNSTVAC IDRNGLQSCP IKEDSFLQRY SSDPTGALTE DSIDDTFLPV PEYINQSVPK  120
RPAGSVQNPV YHNQPLNPAP SRDPHYQDPH STAVGNPEYL NTVQPTCVNS TFDSPAHWAQ  180
KGSHQISLDN PDYQQDFFPK EAKPNGIFKG STAENAEYLR VAPQSSEFIG A          231

SEQ ID NO: 59           moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
SEQUENCE: 59
VIQGDERMHL PSPTDSNFFR ALMDEEDMDD VVDADEYLIP QQGFFSSPST SRTPLLSSLS  60
ATSNNSTVAC IDRNGLQSCP IKEDSFLQRI DDTFLPVPEY INQSVPKRPA GSVQNPVYHN  120
QPLNPAPSRD PHYQDPHSTA VGNPEYLNTV QPTCVNSTFD SPAHWAQKGS HQISLDNPDY  180
```

```
QQDFFPKEAK PNGIFKGSTA ENAEYLRVAP QSSEFIGA                  218

SEQ ID NO: 60          moltype = AA  length = 54
FEATURE                Location/Qualifiers
REGION                 1..54
                       note = Description of Artificial Sequence: Synthetic
                        polypeptide
source                 1..54
                       mol_type = protein
                       organism = synthetic construct
SEQUENCE: 60
VIQGDERMHL PSPTDSNFFR ALMDEEDMDD VVDADEYLIP QQGFFSSPST SRTP        54

SEQ ID NO: 61          moltype = AA  length = 54
FEATURE                Location/Qualifiers
REGION                 1..54
                       note = Description of Unknown: EGFR(1019-1085) sequence
source                 1..54
                       mol_type = protein
                       organism = unidentified
SEQUENCE: 61
NNSTVACIDR NGLQSCPIKE DSFLQRIDDT FLPVPEYINQ SVPKRPAGSV QNPV        54

SEQ ID NO: 62          moltype = AA  length = 54
FEATURE                Location/Qualifiers
REGION                 1..54
                       note = Description of Artificial Sequence: Synthetic
                        polypeptide
source                 1..54
                       mol_type = protein
                       organism = synthetic construct
SEQUENCE: 62
KEDSFLQRID DTFLPVPEFI NQSVPKRPAG SVQNPVYHNQ PLNPAPSRDP HFQD        54

SEQ ID NO: 63          moltype = AA  length = 54
FEATURE                Location/Qualifiers
REGION                 1..54
                       note = Description of Artificial Sequence: Synthetic
                        polypeptide
source                 1..54
                       mol_type = protein
                       organism = synthetic construct
SEQUENCE: 63
VPEFINQSVP KRPAGSVQNP VFHNQPLNPA PSRDPHYQDP HSTAVGNPEY LNTV        54

SEQ ID NO: 64          moltype = AA  length = 54
FEATURE                Location/Qualifiers
REGION                 1..54
                       note = Description of Unknown: EGFR(1122-1165) sequence
source                 1..54
                       mol_type = protein
                       organism = unidentified
SEQUENCE: 64
PEYLNTVQPT CVNSTFDSPA HWAQKGSHQI SLDNPDYQQD FFPKEAKPNG IFKG        54

SEQ ID NO: 65          moltype = AA  length = 54
FEATURE                Location/Qualifiers
REGION                 1..54
                       note = Description of Artificial Sequence: Synthetic
                        polypeptide
source                 1..54
                       mol_type = protein
                       organism = synthetic construct
SEQUENCE: 65
WAQKGSHQIS LDNPDFQQDF FPKEAKPNGI FKGSTAENAE YLRVAPQSSE FIGA        54

SEQ ID NO: 66          moltype = AA  length = 51
FEATURE                Location/Qualifiers
REGION                 1..51
                       note = Description of Unknown: IL12Rb2(775-825) sequence
source                 1..51
                       mol_type = protein
                       organism = unidentified
SEQUENCE: 66
SDPKPENPAC PWTVLPAGDL PTHDGYLPSN IDDLPSHEAP LADSLEELEP Q           51

SEQ ID NO: 67          moltype = AA  length = 41
FEATURE                Location/Qualifiers
REGION                 1..41
```

```
                       note = Description of Unknown: IL7R(376-416) sequence
source                 1..41
                       mol_type = protein
                       organism = unidentified
SEQUENCE: 67
ACDAPILSSS RSLDCRESGK NGPHVYQDLL LSLGTTNSTL P                      41

SEQ ID NO: 68          moltype = AA  length = 36
FEATURE                Location/Qualifiers
REGION                 1..36
                       note = Description of Unknown: IL7R(424-459) sequence
source                 1..36
                       mol_type = protein
                       organism = unidentified
SEQUENCE: 68
GILTLNPVAQ GQPILTSLGS NQEEAYVTMS SFYQNQ                            36

SEQ ID NO: 69          moltype = AA  length = 68
FEATURE                Location/Qualifiers
REGION                 1..68
                       note = Description of Artificial Sequence: Synthetic
                        polypeptide
source                 1..68
                       mol_type = protein
                       organism = synthetic construct
SEQUENCE: 69
ACDAPILSSS RSLDCRESGK NGPHVYQDLL LSLGTTNSTL PQGQPILTSL GSNQEEAYVT  60
MSSFYQNQ                                                           68

SEQ ID NO: 70          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 70
GILTLNPVAQ GQPILTSLGS NQEEAYVTMS SFFQNQ                            36

SEQ ID NO: 71          moltype = AA  length = 68
FEATURE                Location/Qualifiers
REGION                 1..68
                       note = Description of Artificial Sequence: Synthetic
                        polypeptide
source                 1..68
                       mol_type = protein
                       organism = synthetic construct
SEQUENCE: 71
ACDAPILSSS RSLDCRESGK NGPHVYQDLL LSLGTTNSTL PQGQPILTSL GSNQEEAYVT  60
MSSFFQNQ                                                           68

SEQ ID NO: 72          moltype = AA  length = 75
FEATURE                Location/Qualifiers
REGION                 1..75
                       note = Description of Unknown: IL2small(393-433) sequence
source                 1..75
                       mol_type = protein
                       organism = unidentified
SEQUENCE: 72
DEGVAGAPTG SSPQPLQPLS GEDDAYCTFP SRDDLLLFSP SGQGEFRALN ARLPLNTDAY  60
LSLQELQGQD PTHLV                                                   75

SEQ ID NO: 73          moltype = AA  length = 34
FEATURE                Location/Qualifiers
REGION                 1..34
                       note = Description of Unknown: IL2small(518-551) sequence
source                 1..34
                       mol_type = protein
                       organism = unidentified
SEQUENCE: 73
GQGEFRALNA RLPLNTDAYL SLQELQGQDP THLV                              34

SEQ ID NO: 74          moltype = AA  length = 82
FEATURE                Location/Qualifiers
REGION                 1..82
                       note = Description of Artificial Sequence: Synthetic
                        polypeptide
source                 1..82
```

```
                         mol_type = protein
                         organism = synthetic construct
SEQUENCE: 74
QQDKVPEPAS LSSNHSLTSC FTNQGYFFFH LPDALEIEAC QDEGVAGAPT GSSPQPLQPL  60
SGEDDAYCTF PSRDDLLLFS PS                                            82

SEQ ID NO: 75            moltype = AA  length = 75
FEATURE                  Location/Qualifiers
REGION                   1..75
                         note = Description of Artificial Sequence: Synthetic
                          polypeptide
source                   1..75
                         mol_type = protein
                         organism = synthetic construct
SEQUENCE: 75
QQDKVPEPAS LSSNHSLTSC FTNQGYFFFH LPDALEIEAC QGQGEFRALN ARLPLNTDAY  60
LSLQELQGQD PTHLV                                                    75

SEQ ID NO: 76            moltype = AA  length = 75
FEATURE                  Location/Qualifiers
REGION                   1..75
                         note = Description of Artificial Sequence: Synthetic
                          polypeptide
source                   1..75
                         mol_type = protein
                         organism = synthetic construct
SEQUENCE: 76
DEGVAGAPTG SSPQPLQPLS GEDDAYCTFP SRDDLLLFSP SGQGEFRALN ARLPLNTDAY  60
LSLQELQGQD PTHLV                                                    75

SEQ ID NO: 77            moltype = AA  length = 116
FEATURE                  Location/Qualifiers
REGION                   1..116
                         note = Description of Artificial Sequence: Synthetic
                          polypeptide
source                   1..116
                         mol_type = protein
                         organism = synthetic construct
SEQUENCE: 77
QQDKVPEPAS LSSNHSLTSC FTNQGYFFFH LPDALEIEAC QDEGVAGAPT GSSPQPLQPL  60
SGEDDAYCTF PSRDDLLLFS PSGQGEFRAL NARLPLNTDA YLSLQELQGQ DPTHLV      116

SEQ ID NO: 78            moltype = AA  length = 43
FEATURE                  Location/Qualifiers
REGION                   1..43
                         note = Description of Unknown: IFNAR2small(310-352) sequence
source                   1..43
                         mol_type = protein
                         organism = unidentified
SEQUENCE: 78
KKKVWDYNYD DESDSDTEAA PRTSGGGYTM HGLTVRPLGQ ASA                     43

SEQ ID NO: 79            moltype = AA  length = 29
FEATURE                  Location/Qualifiers
REGION                   1..29
                         note = Description of Unknown: IFNAR2small(486-515) sequence
source                   1..29
                         mol_type = protein
                         organism = unidentified
SEQUENCE: 79
EGLWSEDAPS DQSDTSESDV DLGDGYIMR                                     29

SEQ ID NO: 80            moltype = AA  length = 72
FEATURE                  Location/Qualifiers
REGION                   1..72
                         note = Description of Artificial Sequence: Synthetic
                          polypeptide
source                   1..72
                         mol_type = protein
                         organism = synthetic construct
SEQUENCE: 80
KKKVWDYNYD DESDSDTEAA PRTSGGGYTM HGLTVRPLGQ ASAEGLWSED APSDQSDTSE  60
SDVDLGDGYI MR                                                       72

SEQ ID NO: 81            moltype = AA  length = 156
FEATURE                  Location/Qualifiers
REGION                   1..156
                         note = Description of Unknown: BLNK(53-208) sequence
source                   1..156
```

```
                        mol_type = protein
                        organism = unidentified
SEQUENCE: 81
ASESPADEEE QWSDDFDSDY ENPDEHSDSE MYVMPAEENA DDSYEPPPVE QETRPVHPAL  60
PFARGEYIDN RSSQRHSPPF SKTLPSKPSW PSEKARLTST LPALTALQKP QVPPKPKGLL  120
EDEADYVVPV EDNDENYIHP TESSSPPPEK APMVNR                           156

SEQ ID NO: 82           moltype = AA  length = 156
FEATURE                 Location/Qualifiers
REGION                  1..156
                        note = Description of Artificial Sequence: Synthetic
                         polypeptide
source                  1..156
                        mol_type = protein
                        organism = synthetic construct
SEQUENCE: 82
ASESPADEEE QWSDDFDSDF ENPDEHSDSE MYVMPAEENA DDSYEPPPVE QETRPVHPAL  60
PFARGEYIDN RSSQRHSPPF SKTLPSKPSW PSEKARLTST LPALTALQKP QVPPKPKGLL  120
EDEADYVVPV EDNDENYIHP TESSSPPPEK APMVNR                           156

SEQ ID NO: 83           moltype = AA  length = 156
FEATURE                 Location/Qualifiers
REGION                  1..156
                        note = Description of Artificial Sequence: Synthetic
                         polypeptide
source                  1..156
                        mol_type = protein
                        organism = synthetic construct
SEQUENCE: 83
ASESPADEEE QWSDDFDSDF ENPDEHSDSE MYVMPAEENA DDSFEPPPVE QETRPVHPAL  60
PFARGEYIDN RSSQRHSPPF SKTLPSKPSW PSEKARLTST LPALTALQKP QVPPKPKGLL  120
EDEADYVVPV EDNDENYIHP TESSSPPPEK APMVNR                           156

SEQ ID NO: 84           moltype = AA  length = 170
FEATURE                 Location/Qualifiers
source                  1..170
                        mol_type = protein
                        organism = Homo sapiens
SEQUENCE: 84
WGTMQAVEPG TDDEGPLLEP VGSEHAQDTY LVLDKWLLPR NPPSEDLPGP GGSVDIVAMD  60
EGSEASSCSS ALASKPSPEG ASAASFEYTI LDPSSQLLRP WTLCPELPPT PPHLKYLYLV  120
VSDSGISTDY SSGDSQGAQG GLSDGPYSNP YENSLIPAAE PLPPSYVACS            170

SEQ ID NO: 85           moltype = AA  length = 149
FEATURE                 Location/Qualifiers
REGION                  1..149
                        note = Description of Unknown: IL12Rb2(714-862) sequence
source                  1..149
                        mol_type = protein
                        organism = unidentified
SEQUENCE: 85
VTPVFRHPPC SNWPQREKGI QGHQASEKDM MHSASSPPPP RALQAESRQL VDLYKVLESR  60
GSDPKPENPA CPWTVLPAGD LPTHDGYLPS NIDDLPSHEA PLADSLEELE PQHISLSVFP  120
SSSLHPLTFS CGDKLTLDQL KMRCDSLML                                   149

SEQ ID NO: 86           moltype = AA  length = 40
FEATURE                 Location/Qualifiers
REGION                  1..40
                        note = Description of Unknown: IL12Rb1(622-662) sequence
source                  1..40
                        mol_type = protein
                        organism = unidentified
SEQUENCE: 86
WDKGERTEPL EKTELPEGAP ELALDTELSL EDGDRCKAKM                       40

SEQ ID NO: 87           moltype = AA  length = 275
FEATURE                 Location/Qualifiers
REGION                  1..275
                        note = Description of Unknown: IL10R1(304-578) sequence
source                  1..275
                        mol_type = protein
                        organism = unidentified
SEQUENCE: 87
VSPELKNLDL HGSTDSGFGS TKPSLQTEEP QFLLPDPHPQ ADRTLGNREP PVLGDSCSSG  60
SSNSTDSGIC LQEPSLSPST GPTWEQQVGS NSRGQDDSGI DLVQNSEGRA GDTQGGSALG  120
HHSPPEPEVP GEEDPAAVAF QGYLRQTRCA EEKATKTGCL EEESPLTDGL GPKFGRCLVD  180
EAGLHPPALA KGYLKQDPLE MTLASSGAPT GQWNQPTEEW SLLALSSCSD LGISDWSFAH  240
DLAPLGCVAA PGGLLGSFNS DLVTLPLISS LQSSE                            275
```

```
SEQ ID NO: 88          moltype = AA  length = 487
FEATURE                Location/Qualifiers
REGION                 1..487
                       note = Description of Artificial Sequence: Synthetic
                        polypeptide
source                 1..487
                       mol_type = protein
                       organism = synthetic construct
SEQUENCE: 88
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQSDP TRVETATETA WISLVTALHL VLGLSAVLGL LLLRWQFPAH YRRLRHALWP  240
SLPDLHRVLG QYLRDTAALS PPKATVSDTC EEVEPSLLEI LPKSSERTPL PLARDEVEGF  300
LQDTFPQQLE ESEKQRLGGD VQSPNCPSED VVITPESFGR DSSLTCLAGN VSACDAPILS  360
SSRSLDCRES GKNGPHVYQD LLLSLGTTNS TLPPPFSLQS GILTLNPVAQ GQPILTSLGS  420
NQEEAYVTMS SFYQNQSDPK PENPACPWTV LPAGDLPTHD GYLPSNIDDL PSHEAPLADS  480
LEELEPQ                                                           487

SEQ ID NO: 89          moltype = AA  length = 479
FEATURE                Location/Qualifiers
REGION                 1..479
                       note = Description of Artificial Sequence: Synthetic
                        polypeptide
source                 1..479
                       mol_type = protein
                       organism = synthetic construct
SEQUENCE: 89
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQLTL MTLTPEGSEL HIILGLFGLL LLLTCLCGTA WLCCSPNRKN PLWPSVPDPA  240
HSSLGSWVPT IMEEDAFQLP GLGTPPITKL TVLEEDEKKP VPWEARDEVE GFLQDTFPQQ  300
LEESEKQRLG GDVQSPNCPS EDVVITPESF GRDSSLTCLA GNVSACDAPI LSSSRSLDCR  360
ESGKNGPHVY QDLLLSLGTT NSTLPPPFSL QSGILTLNPV AQGQPILTSL GSNQEEAYVT  420
MSSFYQNQSD PKPENPACPW TVLPAGDLPT HDGYLPSNID DLPSHEAPLA DSLEELEPQ   479

SEQ ID NO: 90          moltype = AA  length = 423
FEATURE                Location/Qualifiers
REGION                 1..423
                       note = Description of Artificial Sequence: Synthetic
                        polypeptide
source                 1..423
                       mol_type = protein
                       organism = synthetic construct
SEQUENCE: 90
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQTTP KFAQGEIEAI VVPVCLAFLL TTLLGVLFCF NKRDLIKKHI WPNVPDPSKS  240
HIAQWSPHTP PRHNFNSKDQ MYSDGNFTDV SVVEIEANDA RDEVEGFLQD TFPQQLEESE  300
KQRLGGDVQS PNCPSEDVVI TPESFGRDSS LTCLAGNVSA CDAPILSSSR SLDCRESGKN  360
GPHVYQDLLL SLGTTNSTLP PPFSLQSGIL TLNPVAQGQP ILTSLGSNQE EAYVTMSSFY  420
QNQ                                                               423

SEQ ID NO: 91          moltype = AA  length = 674
FEATURE                Location/Qualifiers
REGION                 1..674
                       note = Description of Artificial Sequence: Synthetic
                        polypeptide
source                 1..674
                       mol_type = protein
                       organism = synthetic construct
SEQUENCE: 91
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPGW FLDSPDRPWN PPTFSPALLV VTEGDNATFT CSFSNTSESF VLNWYRMSPS  240
NQTDKLAAFP EDRSQPGQDC RFRVTQLPNG RDFHMSVVRA RRNDSGTYLC GAISLAPKAQ  300
IKESLRAELR VTERRAEVPT AHPSPSPRPA GQFQTLVVGV VGGLLGSLVL LVWVLAVICS  360
RAARGTIGAR RTGQSDPTRV ETATETAWIS LVTALHLVLG LSAVLGLLLL RWQFPAHYRR  420
LRHALWPSLP DLHRVLGQYL RDTAALSPPK ATVSDTCEEV EPSLLEILPK SSERTPLPLA  480
RDEVEGFLQD TFPQQLEESE KQRLGGDVQS PNCPSEDVVI TPESFGRDSS LTCLAGNVSA  540
CDAPILSSSR SLDCRESGKN GPHVYQDLLL SLGTTNSTLP PPFSLQSGIL TLNPVAQGQP  600
ILTSLGSNQE EAYVTMSSFY QNQSDPKPEN PACPWTVLPA GDLPTHDGYL PSNIDDLPSH  660
EAPLADSLEE LEPQ                                                   674

SEQ ID NO: 92          moltype = AA  length = 861
FEATURE                Location/Qualifiers
```

```
REGION                  1..861
                        note = Description of Artificial Sequence: Synthetic
                         polypeptide
source                  1..861
                        mol_type = protein
                        organism = synthetic construct
SEQUENCE: 92
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPGW FLDSPDRPWN PPTFSPALLV VTEGDNATFT CSFSNTSESF VLNWYRMSPS  240
NQTDKLAAFP EDRSQPGQDC RFRVTQLPNG RDFHMSVVRA RRNDSGTYLC GAISLAPKAQ  300
IKESLRAELR VTERRAEVPT AHPSPSPRPA GQFQTLVVGV VGGLLGSLVL LVWVLAVICS  360
RAARGTIGAR RTGQPGWFLD SPDRPWNPPT FSPALLVVTE GDNATFTCSF SNTSESFVLN  420
WYRMSPSNQT DKLAAFPEDR SQPGQDCRFR VTQLPNGRDF HMSVVRARRN DSGTYLCGAI  480
SLAPKAQIKE SLRAELRVTE RRAEVPTAHP SPSPRPAGQF QTLVVGVVGG LLGSLVLLVW  540
VLAVICSRAA RGTIGARRTG QSDPTRVETA TETAWISLVT ALHLVLGLSA VLGLLLLRWQ  600
FPAHYRRLRH ALWPSLPDLH RVLGQYLRDT AALSPPKATV SDTCEEVEPS LLEILPKSSE  660
RTPLPLARDE VEGFLQDTFP QQLEESEKQR LGGDVQSPNC PSEDVVITPE SFGRDSSLTC  720
LAGNVSACDA PILSSSRSLD CRESGKNGPH VYQDLLLSLG TTNSTLPPPF SLQSGILTLN  780
PVAQGQPILT SLGSNQEEAY VTMSSFYQNQ SDPKPENPAC PWTVLPAGDL PTHDGYLPSN  840
IDDLPSHEAP LADSLEELEP Q                                          861

SEQ ID NO: 93           moltype = AA  length = 487
FEATURE                 Location/Qualifiers
REGION                  1..487
                        note = Description of Artificial Sequence: Synthetic
                         polypeptide
source                  1..487
                        mol_type = protein
                        organism = synthetic construct
SEQUENCE: 93
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WISLVTALHL VLGLSAVLGL LLLRWQFPAH YRRLRHALWP  240
SLPDLHRVLG QYLRDTAALS PPKATVSDTC EEVEPSLLEI LPKSSERTPL PLARDEVEGF  300
LQDTFPQQLE ESEKQRLGGD VQSPNCPSED VVITPESFGR DSSLTCLAGN VSACDAPILS  360
SSRSLDCRES GKNGPHVYQD LLLSLGTTNS TLPPPFSLQS GILTLNPVAQ GQPILTSLGS  420
NQEEAYVTMS SFYQNQSDPK PENPACPWTV LPAGDLPTHD GYLPSNIDDL PSHEAPLADS  480
LEELEPQ                                                          487

SEQ ID NO: 94           moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 94
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETW ISLVTALHLV LGLSAVLGLL LLRWQFPAHY RRLRHALWPS  240
LPDLHRVLGQ YLRDTAALSP PKATVSDTCE EVEPSLLEIL PKSSERTPLP LARDEVEGFL  300
QDTFPQQLEE SEKQRLGGDV QSPNCPSEDV VITPESFGRD SSLTCLAGNV SACDAPILSS  360
SRSLDCRESG KNGPHVYQDL LLSLGTTNST LPPPFSLQSG ILTLNPVAQG QPILTSLGSN  420
QEEAYVTMSS FYQNQSDPKP ENPACPWTVL PAGDLPTHDG YLPSNIDDLP SHEAPLADSL  480
EELEPQ                                                           486

SEQ ID NO: 95           moltype = AA  length = 485
FEATURE                 Location/Qualifiers
REGION                  1..485
                        note = Description of Artificial Sequence: Synthetic
                         polypeptide
source                  1..485
                        mol_type = protein
                        organism = synthetic construct
SEQUENCE: 95
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETI SLVTALHLVL GLSAVLGLLL LRWQFPAHYR RLRHALWPSL  240
PDLHRVLGQY LRDTAALSPP KATVSDTCEE VEPSLLEILP KSSERTPLPL ARDEVEGFLQ  300
DTFPQQLEES EKQRLGGDVQ SPNCPSEDVV ITPESFGRDS SLTCLAGNVS ACDAPILSSS  360
RSLDCRESGK NGPHVYQDLL LSLGTTNSTL PPPFSLQSGI LTLNPVAQGQ PILTSLGSNQ  420
EEAYVTMSSF YQNQSDPKPE NPACPWTVLP AGDLPTHDGY LPSNIDDLPS HEAPLADSLE  480
ELEPQ                                                            485
```

```
SEQ ID NO: 96          moltype = AA  length = 486
FEATURE               Location/Qualifiers
REGION                1..486
                      note = Description of Artificial Sequence: Synthetic
                       polypeptide
source                1..486
                      mol_type = protein
                      organism = synthetic construct
SEQUENCE: 96
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL ISLVTALHLV LGLSAVLGLL LLRWQFPAHY RRLRHALWPS  240
LPDLHRVLGQ YLRDTAALSP PKATVSDTCE EVEPSLLEIL PKSSERTPLP LARDEVEGFL  300
QDTFPQQLEE SEKQRLGGDV QSPNCPSEDV VITPESFGRD SSLTCLAGNV SACDAPILSS  360
SRSLDCRESG KNGPHVYQDL LLSLGTTNST LPPPFSLQSG ILTLNPVAQG QPILTSLGSN  420
QEEAYVTMSS FYQNQSDPKP ENPACPWTVL PAGDLPTHDG YLPSNIDDLP SHEAPLADSL  480
EELEPQ                                                             486

SEQ ID NO: 97          moltype = AA  length = 484
FEATURE               Location/Qualifiers
REGION                1..484
                      note = Description of Artificial Sequence: Synthetic
                       polypeptide
source                1..484
                      mol_type = protein
                      organism = synthetic construct
SEQUENCE: 97
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETS LVTALHLVLG LSAVLGLLLL RWQFPAHYRR LRHALWPSLP  240
DLHRVLGQYL RDTAALSPPK ATVSDTCEEV EPSLLEILPK SSERTPLPLA RDEVEGFLQD  300
TFPQQLEESE KQRLGGDVQS PNCPSEDVVI TPESFGRDSS LTCLAGNVSA CDAPILSSSR  360
SLDCRESGKN GPHVYQDLLL SLGTTNSTLP PPFSLQSGIL TLNPVAQGQP ILTSLGSNQE  420
EAYVTMSSFY QNQSDPKPEN PACPWTVLPA GDLPTHDGYL PSNIDDLPSH EAPLADSLEE  480
LEPQ                                                               484

SEQ ID NO: 98          moltype = AA  length = 483
FEATURE               Location/Qualifiers
REGION                1..483
                      note = Description of Artificial Sequence: Synthetic
                       polypeptide
source                1..483
                      mol_type = protein
                      organism = synthetic construct
SEQUENCE: 98
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL VTALHLVLGL SAVLGLLLLR WQFPAHYRRL RHALWPSLPD  240
LHRVLGQYLR DTAALSPPKA TVSDTCEEVE PSLLEILPKS SERTPLPLAR DEVEGFLQDT  300
FPQQLEESEK QRLGGDVQSP NCPSEDVVIT PESFGRDSSL TCLAGNVSAC DAPILSSSRS  360
LDCRESGKNG PHVYQDLLLS LGTTNSTLPP PFSLQSGILT LNPVAQGQPI LTSLGSNQEE  420
AYVTMSSFYQ NQSDPKPENP ACPWTVLPAG DLPTHDGYLP SNIDDLPSHE APLADSLEEL  480
EPQ                                                                483

SEQ ID NO: 99          moltype = AA  length = 484
FEATURE               Location/Qualifiers
REGION                1..484
                      note = Description of Artificial Sequence: Synthetic
                       polypeptide
source                1..484
                      mol_type = protein
                      organism = synthetic construct
SEQUENCE: 99
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETI LVTALHLVLG LSAVLGLLLL RWQFPAHYRR LRHALWPSLP  240
DLHRVLGQYL RDTAALSPPK ATVSDTCEEV EPSLLEILPK SSERTPLPLA RDEVEGFLQD  300
TFPQQLEESE KQRLGGDVQS PNCPSEDVVI TPESFGRDSS LTCLAGNVSA CDAPILSSSR  360
SLDCRESGKN GPHVYQDLLL SLGTTNSTLP PPFSLQSGIL TLNPVAQGQP ILTSLGSNQE  420
EAYVTMSSFY QNQSDPKPEN PACPWTVLPA GDLPTHDGYL PSNIDDLPSH EAPLADSLEE  480
LEPQ                                                               484

SEQ ID NO: 100         moltype = AA  length = 482
FEATURE               Location/Qualifiers
```

```
REGION                 1..482
                       note = Description of Artificial Sequence: Synthetic
                        polypeptide
source                 1..482
                       mol_type = protein
                       organism = synthetic construct
SEQUENCE: 100
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETV TALHLVLGLS AVLGLLLLRW QFPAHYRRLR HALWPSLPDL  240
HRVLGQYLRD TAALSPPKAT VSDTCEEVEP SLLEILPKSS ERTPLPLARD EVEGFLQDTF  300
PQQLEESEKQ RLGGDVQSPN CPSEDVVITP ESFGRDSSLT CLAGNVSACD APILSSSRSL  360
DCRESGKNGP HVYQDLLLSL GTTNSTLPPP FSLQSGILTL NPVAQGQPIL TSLGSNQEEA  420
YVTMSSFYQN QSDPKPENPA CPWTVLPAGD LPTHDGYLPS NIDDLPSHEA PLADSLEELE  480
PQ                                                                482

SEQ ID NO: 101         moltype = AA  length = 481
FEATURE                Location/Qualifiers
REGION                 1..481
                       note = Description of Artificial Sequence: Synthetic
                        polypeptide
source                 1..481
                       mol_type = protein
                       organism = synthetic construct
SEQUENCE: 101
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETT ALHLVLGLSA VLGLLLLRWQ FPAHYRRLRH ALWPSLPDLH  240
RVLGQYLRDT AALSPPKATV SDTCEEVEPS LLEILPKSSE RTPLPLARDE VEGFLQDTFP  300
QQLEESEKQR LGGDVQSPNC PSEDVVITPE SFGRDSSLTC LAGNVSACDA PILSSSRSLD  360
CRESGKNGPH VYQDLLLSLG TTNSTLPPPF SLQSGILTLN PVAQGQPILT SLGSNQEEAY  420
VTMSSFYQNQ SDPKPENPAC PWTVLPAGDL PTHDGYLPSN IDDLPSHEAP LADSLEELEP  480
Q                                                                 481

SEQ ID NO: 102         moltype = AA  length = 480
FEATURE                Location/Qualifiers
REGION                 1..480
                       note = Description of Artificial Sequence: Synthetic
                        polypeptide
source                 1..480
                       mol_type = protein
                       organism = synthetic construct
SEQUENCE: 102
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA LHLVLGLSAV LGLLLLRWQF PAHYRRLRHA LWPSLPDLHR  240
VLGQYLRDTA ALSPPKATVS DTCEEVEPSL LEILPKSSER TPLPLARDEV EGFLQDTFPQ  300
QLEESEKQRL GGDVQSPNCP SEDVVITPES FGRDSSLTCL AGNVSACDAP ILSSSRSLDC  360
RESGKNGPHV YQDLLLSLGT TNSTLPPPFS LQSGILTLNP VAQGQPILTS LGSNQEEAYV  420
TMSSFYQNQS DPKPENPACP WTVLPAGDLP THDGYLPSNI DDLPSHEAPL ADSLEELEPQ  480

SEQ ID NO: 103         moltype = AA  length = 479
FEATURE                Location/Qualifiers
REGION                 1..479
                       note = Description of Artificial Sequence: Synthetic
                        polypeptide
source                 1..479
                       mol_type = protein
                       organism = synthetic construct
SEQUENCE: 103
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL HLVLGLSAVL GLLLLRWQFP AHYRRLRHAL WPSLPDLHRV  240
LGQYLRDTAA LSPPKATVSD TCEEVEPSLL EILPKSSERT PLPLARDEVE GFLQDTFPQQ  300
LEESEKQRLG GDVQSPNCPS EDVVITPESF GRDSSLTCLA GNVSACDAPI LSSSRSLDCR  360
ESGKNGPHVY QDLLLSLGTT NSTLPPPFSL QSGILTLNPV AQGQPILTSL GSNQEEAYVT  420
MSSFYQNQSD PKPENPACPW TVLPAGDLPT HDGYLPSNID DLPSHEAPLA DSLEELEPQ   479

SEQ ID NO: 104         moltype = AA  length = 478
FEATURE                Location/Qualifiers
REGION                 1..478
                       note = Description of Artificial Sequence: Synthetic
                        polypeptide
source                 1..478
                       mol_type = protein
```

```
                         organism = synthetic construct
SEQUENCE: 104
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETH LVLGLSAVLG LLLLRWQFPA HYRRLRHALW PSLPDLHRVL  240
GQYLRDTAAL SPPKATVSDT CEEVEPSLLE ILPKSSERTP LPLARDEVEG FLQDTFPQQL  300
EESEKQRLGG DVQSPNCPSE DVVITPESFG RDSSLTCLAG NVSACDAPIL SSSRSLDCRE  360
SGKNGPHVYQ DLLLSLGTTN STLPPPFSLQ SGILTLNPVA QGQPILTSLG SNQEEAYVTM  420
SSFYQNQSDP KPENPACPWT VLPAGDLPTH DGYLPSNIDD LPSHEAPLAD SLEELEPQ    478

SEQ ID NO: 105           moltype = AA  length = 477
FEATURE                  Location/Qualifiers
REGION                   1..477
                         note = Description of Artificial Sequence: Synthetic
                          polypeptide
source                   1..477
                         mol_type = protein
                         organism = synthetic construct
SEQUENCE: 105
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL VLGLSAVLGL LLLRWQFPAH YRRLRHALWP SLPDLHRVLG  240
QYLRDTAALS PPKATVSDTC EEVEPSLLEI LPKSSERTPL PLARDEVEGF LQDTFPQQLE  300
ESEKQRLGGD VQSPNCPSED VVITPESFGR DSSLTCLAGN VSACDAPILS SSRSLDCRES  360
GKNGPHVYQD LLLSLGTTNS TLPPPFSLQS GILTLNPVAQ GQPILTSLGS NQEEAYVTMS  420
SFYQNQSDPK PENPACPWTV LPAGDLPTHD GYLPSNIDDL PSHEAPLADS LEELEPQ     477

SEQ ID NO: 106           moltype = AA  length = 476
FEATURE                  Location/Qualifiers
REGION                   1..476
                         note = Description of Artificial Sequence: Synthetic
                          polypeptide
source                   1..476
                         mol_type = protein
                         organism = synthetic construct
SEQUENCE: 106
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETV LGLSAVLGLL LLRWQFPAHY RRLRHALWPS LPDLHRVLGQ  240
YLRDTAALSP PKATVSDTCE EVEPSLLEIL PKSSERTPLP LARDEVEGFL QDTFPQQLEE  300
SEKQRLGGDV QSPNCPSEDV VITPESFGRD SSLTCLAGNV SACDAPILSS SRSLDCRESG  360
KNGPHVYQDL LLSLGTTNST LPPPFSLQSG ILTLNPVAQG QPILTSLGSN QEEAYVTMSS  420
FYQNQSDPKP ENPACPWTVL PAGDLPTHDG YLPSNIDDLP SHEAPLADSL EELEPQ      476

SEQ ID NO: 107           moltype = AA  length = 475
FEATURE                  Location/Qualifiers
REGION                   1..475
                         note = Description of Artificial Sequence: Synthetic
                          polypeptide
source                   1..475
                         mol_type = protein
                         organism = synthetic construct
SEQUENCE: 107
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL GLSAVLGLLL LRWQFPAHYR RLRHALWPSL PDLHRVLGQY  240
LRDTAALSPP KATVSDTCEE VEPSLLEILP KSSERTPLPL ARDEVEGFLQ DTFPQQLEES  300
EKQRLGGDVQ SPNCPSEDVV ITPESFGRDS SLTCLAGNVS ACDAPILSSS RSLDCRESGK  360
NGPHVYQDLL LSLGTTNSTL PPPFSLQSGI LTLNPVAQGQ PILTSLGSNQ EEAYVTMSSF  420
YQNQSDPKPE NPACPWTVLP AGDLPTHDGY LPSNIDDLPS HEAPLADSLE ELEPQ       475

SEQ ID NO: 108           moltype = AA  length = 474
FEATURE                  Location/Qualifiers
REGION                   1..474
                         note = Description of Artificial Sequence: Synthetic
                          polypeptide
source                   1..474
                         mol_type = protein
                         organism = synthetic construct
SEQUENCE: 108
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETG LSAVLGLLLL RWQFPAHYRR LRHALWPSLP DLHRVLGQYL  240
RDTAALSPPK ATVSDTCEEV EPSLLEILPK SSERTPLPLA RDEVEGFLQD TFPQQLEESE  300
```

```
KQRLGGDVQS PNCPSEDVVI TPESFGRDSS LTCLAGNVSA CDAPILSSSR SLDCRESGKN  360
GPHVYQDLLL SLGTTNSTLP PPFSLQSGIL TLNPVAQGQP ILTSLGSNQE EAYVTMSSFY  420
QNQSDPKPEN PACPWTVLPA GDLPTHDGYL PSNIDDLPSH EAPLADSLEE LEPQ        474

SEQ ID NO: 109         moltype = AA  length = 473
FEATURE                Location/Qualifiers
REGION                 1..473
                       note = Description of Artificial Sequence: Synthetic
                        polypeptide
source                 1..473
                       mol_type = protein
                       organism = synthetic construct
SEQUENCE: 109
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL SAVLGLLLLR WQFPAHYRRL RHALWPSLPD LHRVLGQYLR  240
DTAALSPPKA TVSDTCEEVE PSLLEILPKS SERTPLPLAR DEVEGFLQDT FPQQLEESEK  300
QRLGGDVQSP NCPSEDVVIT PESFGRDSSL TCLAGNVSAC DAPILSSSRS LDCRESGKNG  360
PHVYQDLLLS LGTTNSTLPP PFSLQSGILT LNPVAQGQPI LTSLGSNQEE AYVTMSSFYQ  420
NQSDPKPENP ACPWTVLPAG DLPTHDGYLP SNIDDLPSHE APLADSLEEL EPQ         473

SEQ ID NO: 110         moltype = AA  length = 472
FEATURE                Location/Qualifiers
REGION                 1..472
                       note = Description of Artificial Sequence: Synthetic
                        polypeptide
source                 1..472
                       mol_type = protein
                       organism = synthetic construct
SEQUENCE: 110
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETS AVLGLLLLRW QFPAHYRRLR HALWPSLPDL HRVLGQYLRD  240
TAALSPPKAT VSDTCEEVEP SLLEILPKSS ERTPLPLARD EVEGFLQDTF PQQLEESEKQ  300
RLGGDVQSPN CPSEDVVITP ESFGRDSSLT CLAGNVSACD APILSSSRSL DCRESGKNGP  360
HVYQDLLLSL GTTNSTLPPP FSLQSGILTL NPVAQGQPIL TSLGSNQEEA YVTMSSFYQN  420
QSDPKPENPA CPWTVLPAGD LPTHDGYLPS NIDDLPSHEA PLADSLEELE PQ          472

SEQ ID NO: 111         moltype = AA  length = 471
FEATURE                Location/Qualifiers
REGION                 1..471
                       note = Description of Artificial Sequence: Synthetic
                        polypeptide
source                 1..471
                       mol_type = protein
                       organism = synthetic construct
SEQUENCE: 111
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA VLGLLLLRWQ FPAHYRRLRH ALWPSLPDLH RVLGQYLRDT  240
AALSPPKATV SDTCEEVEPS LLEILPKSSE RTPLPLARDE VEGFLQDTFP QQLEESEKQR  300
LGGDVQSPNC PSEDVVITPE SFGRDSSLTC LAGNVSACDA PILSSSRSLD CRESGKNGPH  360
VYQDLLLSLG TTNSTLPPPF SLQSGILTLN PVAQGQPILT SLGSNQEEAY VTMSSFYQNQ  420
SDPKPENPAC PWTVLPAGDL PTHDGYLPSN IDDLPSHEAP LADSLEELEP Q           471

SEQ ID NO: 112         moltype = AA  length = 470
FEATURE                Location/Qualifiers
REGION                 1..470
                       note = Description of Artificial Sequence: Synthetic
                        polypeptide
source                 1..470
                       mol_type = protein
                       organism = synthetic construct
SEQUENCE: 112
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETV LGLLLLRWQF PAHYRRLRHA LWPSLPDLHR VLGQYLRDTA  240
ALSPPKATVS DTCEEVEPSL LEILPKSSER TPLPLARDEV EGFLQDTFPQ QLEESEKQRL  300
GGDVQSPNCP SEDVVITPES FGRDSSLTCL AGNVSACDAP ILSSSRSLDC RESGKNGPHV  360
YQDLLLSLGT TNSTLPPPFS LQSGILTLNP VAQGQPILTS LGSNQEEAYV TMSSFYQNQS  420
DPKPENPACP WTVLPAGDLP THDGYLPSNI DDLPSHEAPL ADSLEELEPQ             470

SEQ ID NO: 113         moltype = AA  length = 469
FEATURE                Location/Qualifiers
REGION                 1..469
```

```
                         note = Description of Artificial Sequence: Synthetic
                          polypeptide
source                   1..469
                         mol_type = protein
                         organism = synthetic construct
SEQUENCE: 113
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETL GLLLLRWQFP AHYRRLRHAL WPSLPDLHRV LGQYLRDTAA  240
LSPPKATVSD TCEEVEPSLL EILPKSSERT PLPLARDEVE GFLQDTFPQQ LEESEKQRLG  300
GDVQSPNCPS EDVVITPESF GRDSSLTCLA GNVSACDAPI LSSSRSLDCR ESGKNGPHVY  360
QDLLLSLGTT NSTLPPPFSL QSGILTLNPV AQGQPILTSL GSNQEEAYVT MSSFYQNQSD  420
PKPENPACPW TVLPAGDLPT HDGYLPSNID DLPSHEAPLA DSLEELEPQ             469

SEQ ID NO: 114           moltype = AA  length = 488
FEATURE                  Location/Qualifiers
REGION                   1..488
                         note = Description of Artificial Sequence: Synthetic
                          polypeptide
source                   1..488
                         mol_type = protein
                         organism = synthetic construct
SEQUENCE: 114
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WLISLVTALH LVLGLSAVLG LLLLRWQFPA HYRRLRHALW  240
PSLPDLHRVL GQYLRDTAAL SPPKATVSDT CEEVEPSLLE ILPKSSERTP LPLARDEVEG  300
FLQDTFPQQL EESEKQRLGG DVQSPNCPSE DVVITPESFG RDSSLTCLAG NVSACDAPIL  360
SSSRSLDCRE SGKNGPHVYQ DLLLSLGTTN STLPPPFSLQ SGILTLNPVA QGQPILTSLG  420
SNQEEAYVTM SSFYQNQSDP KPENPACPWT VLPAGDLPTH DGYLPSNIDD LPSHEAPLAD  480
SLEELEPQ                                                           488

SEQ ID NO: 115           moltype = AA  length = 489
FEATURE                  Location/Qualifiers
REGION                   1..489
                         note = Description of Artificial Sequence: Synthetic
                          polypeptide
source                   1..489
                         mol_type = protein
                         organism = synthetic construct
SEQUENCE: 115
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WVLISLVTAL HLVLGLSAVL GLLLLRWQFP AHYRRLRHAL  240
WPSLPDLHRV LGQYLRDTAA LSPPKATVSD TCEEVEPSLL EILPKSSERT PLPLARDEVE  300
GFLQDTFPQQ LEESEKQRLG GDVQSPNCPS EDVVITPESF GRDSSLTCLA GNVSACDAPI  360
LSSSRSLDCR ESGKNGPHVY QDLLLSLGTT NSTLPPPFSL QSGILTLNPV AQGQPILTSL  420
GSNQEEAYVT MSSFYQNQSD PKPENPACPW TVLPAGDLPT HDGYLPSNID DLPSHEAPLA  480
DSLEELEPQ                                                          489

SEQ ID NO: 116           moltype = AA  length = 490
FEATURE                  Location/Qualifiers
REGION                   1..490
                         note = Description of Artificial Sequence: Synthetic
                          polypeptide
source                   1..490
                         mol_type = protein
                         organism = synthetic construct
SEQUENCE: 116
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WLVLISLVTA LHLVLGLSAV LGLLLLRWQF PAHYRRLRHA  240
LWPSLPDLHR VLGQYLRDTA ALSPPKATVS DTCEEVEPSL LEILPKSSER TPLPLARDEV  300
EGFLQDTFPQ QLEESEKQRL GGDVQSPNCP SEDVVITPES FGRDSSLTCL AGNVSACDAP  360
ILSSSRSLDC RESGKNGPHV YQDLLLSLGT TNSTLPPPFS LQSGILTLNP VAQGQPILTS  420
LGSNQEEAYV TMSSFYQNQS DPKPENPACP WTVLPAGDLP THDGYLPSNI DDLPSHEAPL  480
ADSLEELEPQ                                                         490

SEQ ID NO: 117           moltype = AA  length = 491
FEATURE                  Location/Qualifiers
REGION                   1..491
                         note = Description of Artificial Sequence: Synthetic
                          polypeptide
source                   1..491
                         mol_type = protein
```

```
                         organism = synthetic construct
SEQUENCE: 117
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WILVLISLVT ALHLVLGLSA VLGLLLLRWQ FPAHYRRLRH  240
ALWPSLPDLH RVLGQYLRDT AALSPPKATV SDTCEEVEPS LLEILPKSSE RTPLPLARDE  300
VEGFLQDTFP QQLEESEKQR LGGDVQSPNC PSEDVVITPE SFGRDSSLTC LAGNVSACDA  360
PILSSSRSLD CRESGKNGPH VYQDLLLSLG TTNSTLPPPF SLQSGILTLN PVAQGQPILT  420
SLGSNQEEAY VTMSSFYQNQ SDPKPENPAC PWTVLPAGDL PTHDGYLPSN IDDLPSHEAP  480
LADSLEELEP Q                                                      491

SEQ ID NO: 118           moltype = AA  length = 492
FEATURE                  Location/Qualifiers
REGION                   1..492
                         note = Description of Artificial Sequence: Synthetic
                          polypeptide
source                   1..492
                         mol_type = protein
                         organism = synthetic construct
SEQUENCE: 118
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WLILVLISLV TALHLVLGLS AVLGLLLLRW QFPAHYRRLR  240
HALWPSLPDL HRVLGQYLRD TAALSPPKAT VSDTCEEVEP SLLEILPKSS ERTPLPLARD  300
EVEGFLQDTF PQQLEESEKQ RLGGDVQSPN CPSEDVVITP ESFGRDSSLT CLAGNVSACD  360
APILSSSRSL DCRESGKNGP HVYQDLLLSL GTTNSTLPPP FSLQSGILTL NPVAQGQPIL  420
TSLGSNQEEA YVTMSSFYQN QSDPKPENPA CPWTVLPAGD LPTHDGYLPS NIDDLPSHEA  480
PLADSLEELE PQ                                                     492

SEQ ID NO: 119           moltype = AA  length = 493
FEATURE                  Location/Qualifiers
REGION                   1..493
                         note = Description of Artificial Sequence: Synthetic
                          polypeptide
source                   1..493
                         mol_type = protein
                         organism = synthetic construct
SEQUENCE: 119
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WLLILVLISL VTALHLVLGL SAVLGLLLLR WQFPAHYRRL  240
RHALWPSLPD LHRVLGQYLR DTAALSPPKA TVSDTCEEVE PSLLEILPKS SERTPLPLAR  300
DEVEGFLQDT FPQQLEESEK QRLGGDVQSP NCPSEDVVIT PESFGRDSSL TCLAGNVSAC  360
DAPILSSSRS LDCRESGKNG PHVYQDLLLS LGTTNSTLPP PFSLQSGILT LNPVAQGQPI  420
LTSLGSNQEE AYVTMSSFYQ NQSDPKPENP ACPWTVLPAG DLPTHDGYLP SNIDDLPSHE  480
APLADSLEEL EPQ                                                    493

SEQ ID NO: 120           moltype = AA  length = 494
FEATURE                  Location/Qualifiers
REGION                   1..494
                         note = Description of Artificial Sequence: Synthetic
                          polypeptide
source                   1..494
                         mol_type = protein
                         organism = synthetic construct
SEQUENCE: 120
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WVLLILVLIS LVTALHLVLG LSAVLGLLLL RWQFPAHYRR  240
LRHALWPSLP DLHRVLGQYL RDTAALSPPK ATVSDTCEEV EPSLLEILPK SSERTPLPLA  300
RDEVEGFLQD TFPQQLEESE KQRLGGDVQS PNCPSEDVVI TPESFGRDSS LTCLAGNVSA  360
CDAPILSSSR SLDCRESGKN GPHVYQDLLL SLGTTNSTLP PPFSLQSGIL TLNPVAQGQP  420
ILTSLGSNQE EAYVTMSSFY QNQSDPKPEN PACPWTVLPA GDLPTHDGYL PSNIDDLPSH  480
EAPLADSLEE LEPQ                                                   494

SEQ ID NO: 121           moltype = AA  length = 495
FEATURE                  Location/Qualifiers
REGION                   1..495
                         note = Description of Artificial Sequence: Synthetic
                          polypeptide
source                   1..495
                         mol_type = protein
                         organism = synthetic construct
SEQUENCE: 121
PGWFLDSPDR PWNPPTFSPA LLVVTEGDNA TFTCSFSNTS ESFHVIWHRE SPSGQTDTLA  60
```

-continued

```
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQSDP TRVETATETA WLVLLILVLI SLVTALHLVL GLSAVLGLLL LRWQFPAHYR  240
RLRHALWPSL PDLHRVLGQY LRDTAALSPP KATVSDTCEE VEPSLLEILP KSSERTPLPL  300
ARDEVEGFLQ DTFPQQLEES EKQRLGGDVQ SPNCPSEDVV ITPESFGRDS SLTCLAGNVS  360
ACDAPILSSS RSLDCRESGK NGPHVYQDLL LSLGTTNSTL PPPFSLQSGI LTLNPVAQGQ  420
PILTSLGSNQ EEAYVTMSSF YQNQSDPKPE NPACPWTVLP AGDLPTHDGY LPSNIDDLPS  480
HEAPLADSLE ELEPQ                                                   495

SEQ ID NO: 122          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 122
IPNPLLGLDS T                                                       11

SEQ ID NO: 123          moltype = AA  length = 246
FEATURE                 Location/Qualifiers
REGION                  1..246
                        note = Description of Artificial Sequence: Synthetic
                         polypeptide
source                  1..246
                        mol_type = protein
                        organism = synthetic construct
SEQUENCE: 123
EIQLVQSGAE VKKPGESLRI SCKGSGFNIE DYYIHWVRQM PGKGLEWMGR IDPENDETKY  60
GPIFQGHVTI SADTSINTVY LQWSSLKASD TAMYYCAFRG GVYWGQGTTV TVSSGGGGSG  120
GGGSGGGGSG GGGSDVVMTQ SPDSLAVSLG ERATINCKSS QSLLDSDGKT YLNWLQQKPG  180
QPPKRLISLV SKLDSGVPDR FSGSGSGTDF TLTISSLQAE DVAVYYCWQG THFPGTFGGG  240
TKVEIK                                                            246

SEQ ID NO: 124          moltype = AA  length = 69
FEATURE                 Location/Qualifiers
REGION                  1..69
                        note = Description of Artificial Sequence: Synthetic
                         polypeptide
source                  1..69
                        mol_type = protein
                        organism = synthetic construct
SEQUENCE: 124
TTTPAPRPPT PAPTIASQPL SLRPEACRPA AGGAVHTRGL DFACDIYIWA PLAGTCGVLL  60
LSLVITLYC                                                          69

SEQ ID NO: 125          moltype = AA  length = 42
FEATURE                 Location/Qualifiers
REGION                  1..42
                        note = Description of Artificial Sequence: Synthetic
                         polypeptide
source                  1..42
                        mol_type = protein
                        organism = synthetic construct
SEQUENCE: 125
KRGRKKLLYI FKQPFMRPVQ TTQEEDGCSC RFPEEEEGGC EL                     42

SEQ ID NO: 126          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 126
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 127          moltype = AA  length = 233
FEATURE                 Location/Qualifiers
REGION                  1..233
                        note = Description of Artificial Sequence: Synthetic
                         polypeptide
source                  1..233
                        mol_type = protein
                        organism = synthetic construct
SEQUENCE: 127
MSELIKENMH MKLYMEGTVD NHHFKCTSEG EGKPYEGTQT MRIKVVEGGP LPFAFDILAT  60
```

```
SFLYGSKTFI NHTQGIPDFF KQSFPEGFTW ERVTTYEDGG VLTATQDTSL QDGCLIYNVK  120
IRGVNFTSNG PVMQKKTLGW EAFTETLYPA DGGLEGRNDM ALKLVGGSHL IANIKTTYRS  180
KKPAKNLKMP GVYYVDYRLE RIKEANNETY VEQHEVAVAR YCDLPSKLGH KLN         233

SEQ ID NO: 128         moltype = AA  length = 22
FEATURE                Location/Qualifiers
REGION                 1..22
                       note = Description of Artificial Sequence: Synthetic peptide
source                 1..22
                       mol_type = protein
                       organism = synthetic construct
SEQUENCE: 128
GSGATNFSLL KQAGDVEENP GP                                           22

SEQ ID NO: 129         moltype = AA  length = 208
FEATURE                Location/Qualifiers
REGION                 1..208
                       note = Description of Artificial Sequence: Synthetic
                        polypeptide
source                 1..208
                       mol_type = protein
                       organism = synthetic construct
SEQUENCE: 129
MALPVTALLL PLALLLHAAR PPGWFLDSPD RPWNPPTFSP ALLVVTEGDN ATFTCSFSNT  60
SESFVLNWYR MSPSNQTDKL AAFPEDRSQP GQDCRFRVTQ LPNGRDFHMS VVRARRNDSG  120
TYLCGAISLA PKAQIKESLR AELRVTERRA EVPTAHPSPS PRPAGQFQTL VVGVVGGLLG  180
SLVLLVWVLA VICSRAARGT IGARRTGQ                                     208

SEQ ID NO: 130         moltype = AA  length = 208
FEATURE                Location/Qualifiers
REGION                 1..208
                       note = Description of Artificial Sequence: Synthetic
                        polypeptide
source                 1..208
                       mol_type = protein
                       organism = synthetic construct
SEQUENCE: 130
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VVGVVGGLLG  180
SLVLLVWVLA VICSRAARGT IGARRTGQ                                     208

SEQ ID NO: 131         moltype = AA  length = 635
FEATURE                Location/Qualifiers
source                 1..635
                       mol_type = protein
                       organism = Homo sapiens
SEQUENCE: 131
MPSWALFMVT SCLLLAPQNL AQVSSQDVSL LASDSEPLKC FSRTFEDLTC FWDEEEAAPS  60
GTYQLLYAYP REKPRACPLS SQSMPHFGTR YVCQFPDQEE VRLFFPLHLW VKNVFLNQTR  120
TQRVLFVDSV GLPAPPSIIK AMGGSQPGEL QISWEEPAPE ISDFLRYELR YGPRDPKNST  180
GPTVIQLIAT ETCCPALQRP HSASALDQSP CAQPTMPWQD GPKQTSPSRE ASALTAEGGS  240
CLISGLQPGN SYWLQLRSEP DGISLGGSWG SWSLPVTVDL PGDAVALGLQ CFTLDLKNVT  300
CQWQQQDHAS SQGFFYHSRA RCCPRDRYPI WENCEEEEKT NPGLQTPQFS RCHFKSRNDS  360
IIHILVEVTT APGTVHSYLG SPFWIHQAVR LPTPNLHWRE ISSGHLELEW QHPSSWAAQE  420
TCYQLRYTGE GHQDWKVLEP PLGARGGTLE LRPRSRYRLQ LRARLNGPTY QGPWSSWSDP  480
TRVETATETA WISLVTALHL VLGLSAVLGL LLLRWQFPAH YRRLRHALWP SLPDLHRVLG  540
QYLRDTAALS PPKATVSDTC EEVEPSLLEI LPKSSERTPL PLCSSQAQMD YRRLQPSCLG  600
TMPLSVCPPM AESGSCCTTH IANHSYLPLS YWQQP                              635

SEQ ID NO: 132         moltype = AA  length = 150
FEATURE                Location/Qualifiers
REGION                 1..150
                       note = Description of Unknown: PD1 ectodomain sequence
source                 1..150
                       mol_type = protein
                       organism = unidentified
SEQUENCE: 132
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV                                   150

SEQ ID NO: 133         moltype = AA  length = 150
FEATURE                Location/Qualifiers
REGION                 1..150
                       note = Description of Unknown: High-affinity (HA) PD1
                        ectodomain sequence
source                 1..150
                       mol_type = protein
```

```
                         organism = unidentified
SEQUENCE: 133
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV                                   150

SEQ ID NO: 134           moltype = AA  length = 105
FEATURE                  Location/Qualifiers
REGION                   1..105
                         note = Description of Artificial Sequence: Synthetic
                          polypeptide
source                   1..105
                         mol_type = protein
                         organism = synthetic construct
SEQUENCE: 134
SDPTRVETAT ETAWISLVTA LLLVLGLNAV LGLLLLRKQF PAHYRRLRHA LWPSLPDLHR  60
VLGQYLRDTA ALSPPKATVS DTCEEVEPSL LEILPKSSER TPLPL                  105

SEQ ID NO: 135           moltype = AA  length = 105
FEATURE                  Location/Qualifiers
REGION                   1..105
                         note = Description of Artificial Sequence: Synthetic
                          polypeptide
source                   1..105
                         mol_type = protein
                         organism = synthetic construct
SEQUENCE: 135
SDPTRVETAT ETAWISLVTA LHLVLGLNAV LGLLLLRKQF PAHYRRLRHA LWPSLPDLHR  60
VLGQYLRDTA ALSPPKATVS DTCEEVEPSL LEILPKSSER TPLPL                  105

SEQ ID NO: 136           moltype = AA  length = 399
FEATURE                  Location/Qualifiers
REGION                   1..399
                         note = Description of Artificial Sequence: Synthetic
                          polypeptide
source                   1..399
                         mol_type = protein
                         organism = synthetic construct
SEQUENCE: 136
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LLLVLGLNAV  180
LGLLLLRKQF PAHYRRLRHA LWPSLPDLHR VLGQYLRDTA ALSPPKATVS DTCEEVEPSL  240
LEILPKSSER TPLPLARDEV EGFLQDTFPQ QLEESEKQRL GGDVQSPNCP SEDVVITPES  300
FGRDSSLTCL AGNVSACDAP ILSSSRSLDC RESGKNGPHV YQDLLLSLGT TNSTLPPPFS  360
LQSGILTLNP VAQGQPILTS LGSNQEEAYV TMSSFYQNQ                         399

SEQ ID NO: 137           moltype = AA  length = 330
FEATURE                  Location/Qualifiers
REGION                   1..330
                         note = Description of Artificial Sequence: Synthetic
                          polypeptide
source                   1..330
                         mol_type = protein
                         organism = synthetic construct
SEQUENCE: 137
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLNAV  180
LGLLLLRKQF PAHYRRLRHA LWPSLPDLHR VLGQYLRDTA ALSPPKATVS DTCEEVEPSL  240
LEILPKSSER TPLPLDEGVA GAPTGSSPQP LQPLSGEDDA YCTFPSRDDL LLFSPSGQGE  300
FRALNARLPL NTDAYLSLQE LQGQDPTHLV                                   330

SEQ ID NO: 138           moltype = AA  length = 187
FEATURE                  Location/Qualifiers
REGION                   1..187
                         note = Description of Artificial Sequence: Synthetic
                          polypeptide
source                   1..187
                         mol_type = protein
                         organism = synthetic construct
SEQUENCE: 138
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV VGVVGGLLGS LVLLVWVLAV ICSRAARGTI  180
GARRTGQ                                                            187

SEQ ID NO: 139           moltype = AA  length = 399
FEATURE                  Location/Qualifiers
```

```
REGION                  1..399
                        note = Description of Artificial Sequence: Synthetic
                         polypeptide
source                  1..399
                        mol_type = protein
                        organism = synthetic construct
SEQUENCE: 139
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLARDEV EGFLQDTFPQ QLEESEKQRL GGDVQSPNCP SEDVVITPES  300
FGRDSSLTCL AGNVSACDAP ILSSSRSLDC RESGKNGPHV YQDLLLSLGT TNSTLPPPFS  360
LQSGILTLNP VAQGQPILTS LGSNQEEAYV TMSSFYQNQ                         399

SEQ ID NO: 140          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 140
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLDEGVA GAPTGSSPQP LQPLSGEDDA YCTFPSRDDL LLFSPSGQGE  300
FRALNARLPL NTDAYLSLQE LQGQDPTHLV                                   330

SEQ ID NO: 141          moltype = AA  length = 420
FEATURE                 Location/Qualifiers
REGION                  1..420
                        note = Description of Artificial Sequence: Synthetic
                         polypeptide
source                  1..420
                        mol_type = protein
                        organism = synthetic construct
SEQUENCE: 141
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALLLVLGLNA VLGLLLLRKQ FPAHYRRLRH ALWPSLPDLH RVLGQYLRDT  240
AALSPPKATV SDTCEEVEPS LLEILPKSSE RTPLPLARDE VEGFLQDTFP QQLEESEKQR  300
LGGDVQSPNC PSEDVVITPE SFGRDSSLTC LAGNVSACDA PILSSSRSLD CRESGKNGPH  360
VYQDLLLSLG TTNSTLPPPF SLQSGILTLN PVAQGQPILT SLGSNQEEAY VTMSSFYQNQ  420

SEQ ID NO: 142          moltype = AA  length = 351
FEATURE                 Location/Qualifiers
REGION                  1..351
                        note = Description of Artificial Sequence: Synthetic
                         polypeptide
source                  1..351
                        mol_type = protein
                        organism = synthetic construct
SEQUENCE: 142
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALHLVLGLNA VLGLLLLRKQ FPAHYRRLRH ALWPSLPDLH RVLGQYLRDT  240
AALSPPKATV SDTCEEVEPS LLEILPKSSE RTPLPLDEGV AGAPTGSSPQ PLQPLSGEDD  300
AYCTFPSRDD LLLFSPSGQG EFRALNARLP LNTDAYLSLQ ELQGQDPTHL V           351

SEQ ID NO: 143          moltype = AA  length = 208
FEATURE                 Location/Qualifiers
REGION                  1..208
                        note = Description of Artificial Sequence: Synthetic
                         polypeptide
source                  1..208
                        mol_type = protein
                        organism = synthetic construct
SEQUENCE: 143
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VVGVVGGLLG  180
SLVLLVWVLA VICSRAARGT IGARRTGQ                                     208

SEQ ID NO: 144          moltype = AA  length = 420
```

```
FEATURE               Location/Qualifiers
REGION                1..420
                      note = Description of Artificial Sequence: Synthetic
                       polypeptide
source                1..420
                      mol_type = protein
                      organism = synthetic construct
SEQUENCE: 144
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALHLVLGLSA VLGLLLLRWQ FPAHYRRLRH ALWPSLPDLH RVLGQYLRDT  240
AALSPPKATV SDTCEEVEPS LLEILPKSSE RTPLPLARDE VEGFLQDTFP QQLEESEKQR  300
LGGDVQSPNC PSEDVVITPE SFGRDSSLTC LAGNVSACDA PILSSSRSLD CRESGKNGPH  360
VYQDLLLSLG TTNSTLPPPF SLQSGILTLN PVAQGQPILT SLGSNQEEAY VTMSSFYQNQ  420

SEQ ID NO: 145        moltype = AA  length = 351
FEATURE               Location/Qualifiers
REGION                1..351
                      note = Description of Artificial Sequence: Synthetic
                       polypeptide
source                1..351
                      mol_type = protein
                      organism = synthetic construct
SEQUENCE: 145
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALHLVLGLSA VLGLLLLRWQ FPAHYRRLRH ALWPSLPDLH RVLGQYLRDT  240
AALSPPKATV SDTCEEVEPS LLEILPKSSE RTPLPLDEGV AGAPTGSSPQ PLQPLSGEDD  300
AYCTFPSRDD LLLFSPSGQG EFRALNARLP LNTDAYLSLQ ELQGQDPTHL V           351

SEQ ID NO: 146        moltype = AA  length = 55
FEATURE               Location/Qualifiers
source                1..55
                      mol_type = protein
                      organism = Homo sapiens
SEQUENCE: 146
SDPTRVETAT ETAWISLVTA LHLVLGLSAV LGLLLLRWQF PAHYRRLRHA LWPSL       55

SEQ ID NO: 147        moltype = AA  length = 54
FEATURE               Location/Qualifiers
REGION                1..54
                      note = Description of Artificial Sequence: Synthetic
                       polypeptide
source                1..54
                      mol_type = protein
                      organism = synthetic construct
SEQUENCE: 147
SDPTRVETAT ETWISLVTAL HLVLGLSAVL GLLLLRWQFP AHYRRLRHAL WPSL        54

SEQ ID NO: 148        moltype = AA  length = 53
FEATURE               Location/Qualifiers
REGION                1..53
                      note = Description of Artificial Sequence: Synthetic
                       polypeptide
source                1..53
                      mol_type = protein
                      organism = synthetic construct
SEQUENCE: 148
SDPTRVETAT ETISLVTALH LVLGLSAVLG LLLLRWQFPA HYRRLRHALW PSL         53

SEQ ID NO: 149        moltype = AA  length = 54
FEATURE               Location/Qualifiers
REGION                1..54
                      note = Description of Artificial Sequence: Synthetic
                       polypeptide
source                1..54
                      mol_type = protein
                      organism = synthetic construct
SEQUENCE: 149
SDPTRVETAT ETLISLVTAL HLVLGLSAVL GLLLLRWQFP AHYRRLRHAL WPSL        54

SEQ ID NO: 150        moltype = AA  length = 52
FEATURE               Location/Qualifiers
REGION                1..52
                      note = Description of Artificial Sequence: Synthetic
                       polypeptide
source                1..52
```

```
                        mol_type = protein
                        organism = synthetic construct
SEQUENCE: 150
SDPTRVETAT ETSLVTALHL VLGLSAVLGL LLLRWQFPAH YRRLRHALWP SL          52

SEQ ID NO: 151          moltype = AA  length = 51
FEATURE                 Location/Qualifiers
REGION                  1..51
                        note = Description of Artificial Sequence: Synthetic
                         polypeptide
source                  1..51
                        mol_type = protein
                        organism = synthetic construct
SEQUENCE: 151
SDPTRVETAT ETLVTALHLV LGLSAVLGLL LLRWQFPAHY RRLRHALWPS L           51

SEQ ID NO: 152          moltype = AA  length = 52
FEATURE                 Location/Qualifiers
REGION                  1..52
                        note = Description of Artificial Sequence: Synthetic
                         polypeptide
source                  1..52
                        mol_type = protein
                        organism = synthetic construct
SEQUENCE: 152
SDPTRVETAT ETILVTALHL VLGLSAVLGL LLLRWQFPAH YRRLRHALWP SL          52

SEQ ID NO: 153          moltype = AA  length = 50
FEATURE                 Location/Qualifiers
REGION                  1..50
                        note = Description of Artificial Sequence: Synthetic
                         polypeptide
source                  1..50
                        mol_type = protein
                        organism = synthetic construct
SEQUENCE: 153
SDPTRVETAT ETVTALHLVL GLSAVLGLLL LRWQFPAHYR RLRHALWPSL             50

SEQ ID NO: 154          moltype = AA  length = 49
FEATURE                 Location/Qualifiers
REGION                  1..49
                        note = Description of Artificial Sequence: Synthetic
                         polypeptide
source                  1..49
                        mol_type = protein
                        organism = synthetic construct
SEQUENCE: 154
SDPTRVETAT ETTALHLVLG LSAVLGLLLL RWQFPAHYRR LRHALWPSL              49

SEQ ID NO: 155          moltype = AA  length = 48
FEATURE                 Location/Qualifiers
REGION                  1..48
                        note = Description of Artificial Sequence: Synthetic
                         polypeptide
source                  1..48
                        mol_type = protein
                        organism = synthetic construct
SEQUENCE: 155
SDPTRVETAT ETALHLVLGL SAVLGLLLLR WQFPAHYRRL RHALWPSL               48

SEQ ID NO: 156          moltype = AA  length = 47
FEATURE                 Location/Qualifiers
REGION                  1..47
                        note = Description of Artificial Sequence: Synthetic
                         polypeptide
source                  1..47
                        mol_type = protein
                        organism = synthetic construct
SEQUENCE: 156
SDPTRVETAT ETLHLVLGLS AVLGLLLLRW QFPAHYRRLR HALWPSL                47

SEQ ID NO: 157          moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
```

```
SEQUENCE: 157
SDPTRVETAT ETHLVLGLSA VLGLLLLRWQ FPAHYRRLRH ALWPSL                46

SEQ ID NO: 158         moltype = AA  length = 55
FEATURE                Location/Qualifiers
source                 1..55
                       mol_type = protein
                       organism = Homo sapiens
SEQUENCE: 158
SDPTRVETAT ETAWISLVTA LHLVLGLSAV LGLLLLRWQF PAHYRRLRHA LWPSL       55

SEQ ID NO: 159         moltype = AA  length = 56
FEATURE                Location/Qualifiers
REGION                 1..56
                       note = Description of Artificial Sequence: Synthetic
                        polypeptide
source                 1..56
                       mol_type = protein
                       organism = synthetic construct
SEQUENCE: 159
SDPTRVETAT ETAWLISLVT ALHLVLGLSA VLGLLLLRWQ FPAHYRRLRH ALWPSL      56

SEQ ID NO: 160         moltype = AA  length = 57
FEATURE                Location/Qualifiers
REGION                 1..57
                       note = Description of Artificial Sequence: Synthetic
                        polypeptide
source                 1..57
                       mol_type = protein
                       organism = synthetic construct
SEQUENCE: 160
SDPTRVETAT ETAWVLISLV TALHLVLGLS AVLGLLLLRW QFPAHYRRLR HALWPSL     57

SEQ ID NO: 161         moltype = AA  length = 58
FEATURE                Location/Qualifiers
REGION                 1..58
                       note = Description of Artificial Sequence: Synthetic
                        polypeptide
source                 1..58
                       mol_type = protein
                       organism = synthetic construct
SEQUENCE: 161
SDPTRVETAT ETAWLVLISL VTALHLVLGL SAVLGLLLLR WQFPAHYRRL RHALWPSL    58

SEQ ID NO: 162         moltype = AA  length = 59
FEATURE                Location/Qualifiers
REGION                 1..59
                       note = Description of Artificial Sequence: Synthetic
                        polypeptide
source                 1..59
                       mol_type = protein
                       organism = synthetic construct
SEQUENCE: 162
SDPTRVETAT ETAWILVLIS LVTALHLVLG LSAVLGLLLL RWQFPAHYRR LRHALWPSL   59

SEQ ID NO: 163         moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 163
SDPTRVETAT ETAWLILVLI SLVTALHLVL GLSAVLGLLL LRWQFPAHYR RLRHALWPSL  60

SEQ ID NO: 164         moltype = AA  length = 61
FEATURE                Location/Qualifiers
REGION                 1..61
                       note = Description of Artificial Sequence: Synthetic
                        polypeptide
source                 1..61
                       mol_type = protein
                       organism = synthetic construct
SEQUENCE: 164
SDPTRVETAT ETAWLLILVL ISLVTALHLV LGLSAVLGLL LLRWQFPAHY RRLRHALWPS  60
L                                                                  61

SEQ ID NO: 165         moltype = AA  length = 62
```

```
FEATURE                Location/Qualifiers
REGION                 1..62
                       note = Description of Artificial Sequence: Synthetic
                        polypeptide
source                 1..62
                       mol_type = protein
                       organism = synthetic construct
SEQUENCE: 165
SDPTRVETAT ETAWVLLILV LISLVTALHL VLGLSAVLGL LLLRWQFPAH YRRLRHALWP  60
SL                                                                62

SEQ ID NO: 166         moltype = AA  length = 63
FEATURE                Location/Qualifiers
REGION                 1..63
                       note = Description of Artificial Sequence: Synthetic
                        polypeptide
source                 1..63
                       mol_type = protein
                       organism = synthetic construct
SEQUENCE: 166
SDPTRVETAT ETAWLVLLIL VLISLVTALH LVLGLSAVLG LLLLRWQFPA HYRRLRHALW  60
PSL                                                               63

SEQ ID NO: 167         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 167
KPIPNPLLGL DST                                                    13

SEQ ID NO: 168         moltype = AA  length = 301
FEATURE                Location/Qualifiers
REGION                 1..301
                       note = Description of Artificial Sequence: Synthetic
                        polypeptide
source                 1..301
                       mol_type = protein
                       organism = synthetic construct
SEQUENCE: 168
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV GPGWFLDSPD RPWNPPTFSP ALLVVTEGDN  180
ATFTCSFSNT SESFVLNWYR MSPSNQTDKL AAFPEDRSQP GQDCRFRVTQ LPNGRDFHMS  240
VVRARRNDSG TYLCGAISLA PKAQIKESLR AELRVTERRA EVPTAHPSPS PRPAGQFQTL  300
V                                                                 301

SEQ ID NO: 169         moltype = AA  length = 452
FEATURE                Location/Qualifiers
REGION                 1..452
                       note = Description of Artificial Sequence: Synthetic
                        polypeptide
source                 1..452
                       mol_type = protein
                       organism = synthetic construct
SEQUENCE: 169
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV GPGWFLDSPD RPWNPPTFSP ALLVVTEGDN  180
ATFTCSFSNT SESFVLNWYR MSPSNQTDKL AAFPEDRSQP GQDCRFRVTQ LPNGRDFHMS  240
VVRARRNDSG TYLCGAISLA PKAQIKESLR AELRVTERRA EVPTAHPSPS PRPAGQFQTL  300
VGPGWFLDSP DRPWNPPTFS PALLVVTEGD NATFTCSFSN TSESFVLNWY RMSPSNQTDK  360
LAAFPEDRSQ PGQDCRFRVT QLPNGRDFHM SVVRARRNDS GTYLCGAISL APKAQIKESL  420
RAELRVTERR AEVPTAHPSP SPRPAGQFQT LV                               452

SEQ ID NO: 170         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 170
VTQLLLQQDK VPEPASLSSN HSLTSCFTNQ GYFFFHLPDA LEIEACQVSF TSDPSSEEDP  60
DEGVAGAPTG SSPQPLQPLS GEDDAYCTFP SRDDLLLFSP SLLGGPSPPS TAPGGSGAGE  120
ERMPPSLQER VPRDWDPQPL GPPTPGVPDL VDFQPPPELV LREAGEEVPD AGPREGVSFP  180
```

```
WSRPPGQGEF RALNARLPLN TDAYLSLQEL QGQDPTHLV                    219

SEQ ID NO: 171         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 171
VTQLLLQQDK VPEPASLSSN HSLTSCFTNQ GSFFFHLPDA LEIEACQVSF TSDPSSEEDP  60
DEGVAGAPTG SSPQPLQPLS GEDDAYCTFP SRDDLLLFSP SLLGGPSPPS TAPGGSGAGE  120
ERMPPSLQER VPRDWDPQPL GPPTPGVPDL VDFQPPPELV LREAGEEVPD AGPREGVSFP  180
WSRPPGQGEF RALNARLPLN TDAYLSLQEL QGQDPTHLV                    219

SEQ ID NO: 172         moltype = AA  length = 457
FEATURE                Location/Qualifiers
REGION                 1..457
                       note = Description of Artificial Sequence: Synthetic
                        polypeptide
source                 1..457
                       mol_type = protein
                       organism = synthetic construct
SEQUENCE: 172
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLLEARD EVEGFLQDTF PQQLEESEKQ RLGGDVQSPN CPSEDVVITP  300
ESFGRDSSLT CLAGNVSACD APILSSSRSL DCRESGKNGP HVYQDLLLSL GTTNSTLPPP  360
FSLQSGILTL NPVAQGQPIL TSLGSNQEEA YVTMSSFYQN QGSGSRSDPK PENPACPWTV  420
LPAGDLPTHD GYLPSNIDDL PSHEAPLADS LEELEPQ                      457

SEQ ID NO: 173         moltype = AA  length = 449
FEATURE                Location/Qualifiers
REGION                 1..449
                       note = Description of Artificial Sequence: Synthetic
                        polypeptide
source                 1..449
                       mol_type = protein
                       organism = synthetic construct
SEQUENCE: 173
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV LTLMTLTPEG SELHIILGLF GLLLLLTCLC  180
GTAWLCCSPN RKNPLWPSVP DPAHSSLGSW VPTIMEEDAF QLPGLGTPPI TKLTVLEEDE  240
KKPVPWELEA RDEVEGFLQD TFPQQLEESE KQRLGGDVQS PNCPSEDVVI TPESFGRDSS  300
LTCLAGNVSA CDAPILSSSR SLDCRESGKN GPHVYQDLLL SLGTTNSTLP PPFSLQSGIL  360
TLNPVAQGQP ILTSLGSNQE EAYVTMSSFY QNQGSGSRSD PKPENPACPW TVLPAGDLPT  420
HDGYLPSNID DLPSHEAPLA DSLEELEPQ                               449

SEQ ID NO: 174         moltype = AA  length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 174
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV TTPKFAQGEI EAIVVPVCLA FLLTTLLGVL  180
FCFNKRDLIK KHIWPNVPDP SKSHIAQWSP HTPPRHNFNS KDQMYSDGNF TDVSVVEIEA  240
NDLEARDEVE GFLQDTFPQQ LEESEKQRLG GDVQSPNCPS EDVVITPESF GRDSSLTCLA  300
GNVSACDAPI LSSSRSLDCR ESGKNGPHVY QDLLLSLGTT NSTLPPPFSL QSGILTLNPV  360
AQGQPILTSL GSNQEEAYVT MSSFYQNQGS GSRSDPKPEN PACPWTVLPA GDLPTHDGYL  420
PSNIDDLPSH EAPLADSLEE LEPQ                                    444

SEQ ID NO: 175         moltype = AA  length = 608
FEATURE                Location/Qualifiers
REGION                 1..608
                       note = Description of Artificial Sequence: Synthetic
                        polypeptide
source                 1..608
                       mol_type = protein
                       organism = synthetic construct
SEQUENCE: 175
```

-continued

```
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV GPGWFLDSPD RPWNPPTFSP ALLVVTEGDN  180
ATFTCSFSNT SESFVLNWYR MSPSNQTDKL AAFPEDRSQP GQDCRFRVTQ LPNGRDFHMS  240
VVRARRNDSG TYLCGAISLA PKAQIKESLR AELRVTERRA EVPTAHPSPS PRPAGQFQTL  300
VSDPTRVETA TETAWISLVT ALHLVLGLSA VLGLLLLRWQ FPAHYRRLRH ALWPSLPDLH  360
RVLGQYLRDT AALSPPKATV SDTCEEVEPS LLEILPKSSE RTPLPLLEAR DEVEGFLQDT  420
FPQQLEESEK QRLGGDVQSP NCPSEDVVIT PESFGRDSSL TCLAGNVSAC DAPILSSSRS  480
LDCRESGKNG PHVYQDLLLS LGTTNSTLPP PFSLQSGILT LNPVAQGQPI LTSLGSNQEE  540
AYVTMSSFYQ NQGSGSRSDP KPENPACPWT VLPAGDLPTH DGYLPSNIDD LPSHEAPLAD  600
SLEELEPQ                                                          608

SEQ ID NO: 176         moltype = AA  length = 759
FEATURE                Location/Qualifiers
REGION                 1..759
                       note = Description of Artificial Sequence: Synthetic
                        polypeptide
source                 1..759
                       mol_type = protein
                       organism = synthetic construct
SEQUENCE: 176
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV GPGWFLDSPD RPWNPPTFSP ALLVVTEGDN  180
ATFTCSFSNT SESFVLNWYR MSPSNQTDKL AAFPEDRSQP GQDCRFRVTQ LPNGRDFHMS  240
VVRARRNDSG TYLCGAISLA PKAQIKESLR AELRVTERRA EVPTAHPSPS PRPAGQFQTL  300
VGPGWFLDSP DRPWNPPTFS PALLVVTEGD NATFTCSFSN TSESFVLNWY RMSPSNQTDK  360
LAAFPEDRSQ PGQDCRFRVT QLPNGRDFHM SVVRARRNDS GTYLCGAISL APKAQIKESL  420
RAELRVTERR AEVPTAHPSP SPRPAGQFQT LVSDPTRVET ATETAWISLV TALHLVLGLS  480
AVLGLLLLRW QFPAHYRRLR HALWPSLPDL HRVLGQYLRD TAALSPPKAT VSDTCEEVEP  540
SLLEILPKSS ERTPLPLLEA RDEVEGFLQD TFPQQLEESE KQRLGGDVQS PNCPSEDVVI  600
TPESFGRDSS LTCLAGNVSA CDAPILSSSR SLDCRESGKN GPHVYQDLLL SLGTTNSTLP  660
PPFSLQSGIL TLNPVAQGQP ILTSLGSNQE EAYVTMSSFY QNQGSGSRSD PKPENPACPW  720
TVLPAGDLPT HDGYLPSNID DLPSHEAPLA DSLEELEPQ                        759

SEQ ID NO: 177         moltype = AA  length = 457
FEATURE                Location/Qualifiers
REGION                 1..457
                       note = Description of Artificial Sequence: Synthetic
                        polypeptide
source                 1..457
                       mol_type = protein
                       organism = synthetic construct
SEQUENCE: 177
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLLEARD EVEGFLQDTF PQQLEESEKQ RLGGDVQSPN CPSEDVVITP  300
ESFGRDSSLT CLAGNVSACD APILSSSRSL DCRESGKNGP HVYQDLLLSL GTTNSTLPPP  360
FSLQSGILTL NPVAQGQPIL TSLGSNQEEA YVTMSSFYQN QGSGSRSDPK PENPACPWTV  420
LPAGDLPTHD GYLPSNIDDL PSHEAPLADS LEELEPQ                          457

SEQ ID NO: 178         moltype = AA  length = 456
FEATURE                Location/Qualifiers
REGION                 1..456
                       note = Description of Artificial Sequence: Synthetic
                        polypeptide
source                 1..456
                       mol_type = protein
                       organism = synthetic construct
SEQUENCE: 178
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETWISLVTAL HLVLGLSAVL  180
GLLLLRWQFP AHYRRLRHAL WPSLPDLHRV LGQYLRDTAA LSPPKATVSD TCEEVEPSLL  240
EILPKSSERT PLPLLEARDE VEGFLQDTFP QQLEESEKQR LGGDVQSPNC PSEDVVITPE  300
SFGRDSSLTC LAGNVSACDA PILSSSRSLD CRESGKNGPH VYQDLLLSLG TTNSTLPPPF  360
SLQSGILTLN PVAQGQPILT SLGSNQEEAY VTMSSFYQNQ GSGSRSDPKP ENPACPWTVL  420
PAGDLPTHDG YLPSNIDDLP SHEAPLADSL EELEPQ                           456

SEQ ID NO: 179         moltype = AA  length = 455
FEATURE                Location/Qualifiers
REGION                 1..455
                       note = Description of Artificial Sequence: Synthetic
                        polypeptide
source                 1..455
                       mol_type = protein
                       organism = synthetic construct
```

```
SEQUENCE: 179
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETISLVTALH LVLGLSAVLG  180
LLLLRWQFPA HYRRLRHALW PSLPDLHRVL GQYLRDTAAL SPPKATVSDT CEEVEPSLLE  240
ILPKSSERTP LPLLEARDEV EGFLQDTFPQ QLEESEKQRL GGDVQSPNCP SEDVVITPES  300
FGRDSSLTCL AGNVSACDAP ILSSSRSLDC RESGKNGPHV YQDLLLSLGT TNSTLPPPFS  360
LQSGILTLNP VAQGQPILTS LGSNQEEAYV TMSSFYQNQG SGSRSDPKPE NPACPWTVLP  420
AGDLPTHDGY LPSNIDDLPS HEAPLADSLE ELEPQ                            455

SEQ ID NO: 180         moltype = AA  length = 456
FEATURE                Location/Qualifiers
REGION                 1..456
                       note = Description of Artificial Sequence: Synthetic
                        polypeptide
source                 1..456
                       mol_type = protein
                       organism = synthetic construct
SEQUENCE: 180
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLISLVTAL HLVLGLSAVL  180
GLLLLRWQFP AHYRRLRHAL WPSLPDLHRV LGQYLRDTAA LSPPKATVSD TCEEVEPSLL  240
EILPKSSERT PLPLLEARDE VEGFLQDTFP QQLEESEKQR LGGDVQSPNC PSEDVVITPE  300
SFGRDSSLTC LAGNVSACDA PILSSSRSLD CRESGKNGPH VYQDLLLSLG TTNSTLPPPF  360
SLQSGILTLN PVAQGQPILT SLGSNQEEAY VTMSSFYQNQ GSGSRSDPKP ENPACPWTVL  420
PAGDLPTHDG YLPSNIDDLP SHEAPLADSL EELEPQ                           456

SEQ ID NO: 181         moltype = AA  length = 454
FEATURE                Location/Qualifiers
REGION                 1..454
                       note = Description of Artificial Sequence: Synthetic
                        polypeptide
source                 1..454
                       mol_type = protein
                       organism = synthetic construct
SEQUENCE: 181
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETSLVTALHL VLGLSAVLGL  180
LLLRWQFPAH YRRLRHALWP SLPDLHRVLG QYLRDTAALS PPKATVSDTC EEVEPSLLEI  240
LPKSSERTPL PLLEARDEVE GFLQDTFPQQ LEESEKQRLG GDVQSPNCPS EDVVITPESF  300
GRDSSLTCLA GNVSACDAPI LSSSRSLDCR ESGKNGPHVY QDLLLSLGTT NSTLPPPFSL  360
QSGILTLNPV AQGQPILTSL GSNQEEAYVT MSSFYQNQGS GSRSDPKPEN PACPWTVLPA  420
GDLPTHDGYL PSNIDDLPSH EAPLADSLEE LEPQ                             454

SEQ ID NO: 182         moltype = AA  length = 453
FEATURE                Location/Qualifiers
REGION                 1..453
                       note = Description of Artificial Sequence: Synthetic
                        polypeptide
source                 1..453
                       mol_type = protein
                       organism = synthetic construct
SEQUENCE: 182
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLVTALHLV LGLSAVLGLL  180
LLRWQFPAHY RRLRHALWPS LPDLHRVLGQ YLRDTAALSP PKATVSDTCE EVEPSLLEIL  240
PKSSERTPLP LLEARDEVEG FLQDTFPQQL EESEKQRLGG DVQSPNCPSE DVVITPESFG  300
RDSSLTCLAG NVSACDAPIL SSSRSLDCRE SGKNGPHVYQ DLLLSLGTTN STLPPPFSLQ  360
SGILTLNPVA QGQPILTSLG SNQEEAYVTM SSFYQNQGSG SRSDPKPENP ACPWTVLPAG  420
DLPTHDGYLP SNIDDLPSHE APLADSLEEL EPQ                              453

SEQ ID NO: 183         moltype = AA  length = 454
FEATURE                Location/Qualifiers
REGION                 1..454
                       note = Description of Artificial Sequence: Synthetic
                        polypeptide
source                 1..454
                       mol_type = protein
                       organism = synthetic construct
SEQUENCE: 183
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETILVTALHL VLGLSAVLGL  180
LLLRWQFPAH YRRLRHALWP SLPDLHRVLG QYLRDTAALS PPKATVSDTC EEVEPSLLEI  240
LPKSSERTPL PLLEARDEVE GFLQDTFPQQ LEESEKQRLG GDVQSPNCPS EDVVITPESF  300
GRDSSLTCLA GNVSACDAPI LSSSRSLDCR ESGKNGPHVY QDLLLSLGTT NSTLPPPFSL  360
```

```
QSGILTLNPV AQGQPILTSL GSNQEEAYVT MSSFYQNQGS GSRSDPKPEN PACPWTVLPA  420
GDLPTHDGYL PSNIDDLPSH EAPLADSLEE LEPQ                              454

SEQ ID NO: 184         moltype = AA  length = 452
FEATURE                Location/Qualifiers
REGION                 1..452
                       note = Description of Artificial Sequence: Synthetic
                        polypeptide
source                 1..452
                       mol_type = protein
                       organism = synthetic construct
SEQUENCE: 184
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETVTALHLVL GLSAVLGLLL  180
LRWQFPAHYR RLRHALWPSL PDLHRVLGQY LRDTAALSPP KATVSDTCEE VEPSLLEILP  240
KSSERTPLPL LEARDEVEGF LQDTFPQQLE ESEKQRLGGD VQSPNCPSED VVITPESFGR  300
DSSLTCLAGN VSACDAPILS SSRSLDCRES GKNGPHVYQD LLLSLGTTNS TLPPPFSLQS  360
GILTLNPVAQ GQPILTSLGS NQEEAYVTMS SFYQNQGSGS RSDPKPENPA CPWTVLPAGD  420
LPTHDGYLPS NIDDLPSHEA PLADSLEELE PQ                                452

SEQ ID NO: 185         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 185
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETTALHLVLG LSAVLGLLLL  180
RWQFPAHYRR LRHALWPSLP DLHRVLGQYL RDTAALSPPK ATVSDTCEEV EPSLLEILPK  240
SSERTPLPLL EARDEVEGFL QDTFPQQLEE SEKQRLGGDV QSPNCPSEDV VITPESFGRD  300
SSLTCLAGNV SACDAPILSS SRSLDCRESG KNGPHVYQDL LLSLGTTNST LPPPFSLQSG  360
ILTLNPVAQG QPILTSLGSN QEEAYVTMSS FYQNQGSGSR SDPKPENPAC PWTVLPAGDL  420
PTHDGYLPSN IDDLPSHEAP LADSLEELEP Q                                 451

SEQ ID NO: 186         moltype = AA  length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 186
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETALHLVLGL SAVLGLLLLR  180
WQFPAHYRRL RHALWPSLPD LHRVLGQYLR DTAALSPPKA TVSDTCEEVE PSLLEILPKS  240
SERTPLPLLE ARDEVEGFLQ DTFPQQLEES EKQRLGGDVQ SPNCPSEDVV ITPESFGRDS  300
SLTCLAGNVS ACDAPILSSS RSLDCRESGK NGPHVYQDLL LSLGTTNSTL PPPFSLQSGI  360
LTLNPVAQGQ PILTSLGSNQ EEAYVTMSSF YQNQGSGSRS DPKPENPACP WTVLPAGDLP  420
THDGYLPSNI DDLPSHEAPL ADSLEELEPQ                                   450

SEQ ID NO: 187         moltype = AA  length = 449
FEATURE                Location/Qualifiers
REGION                 1..449
                       note = Description of Artificial Sequence: Synthetic
                        polypeptide
source                 1..449
                       mol_type = protein
                       organism = synthetic construct
SEQUENCE: 187
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLHLVLGLS AVLGLLLLRW  180
QFPAHYRRLR HALWPSLPDL HRVLGQYLRD TAALSPPKAT VSDTCEEVEP SLLEILPKSS  240
ERTPLPLLEA RDEVEGFLQD TFPQQLEESE KQRLGGDVQS PNCPSEDVVI TPESFGRDSS  300
LTCLAGNVSA CDAPILSSSR SLDCRESGKN GPHVYQDLLL SLGTTNSTLP PPFSLQSGIL  360
TLNPVAQGQP ILTSLGSNQE EAYVTMSSFY QNQGSGSRSD PKPENPACPW TVLPAGDLPT  420
HDGYLPSNID DLPSHEAPLA DSLEELEPQ                                    449

SEQ ID NO: 188         moltype = AA  length = 448
FEATURE                Location/Qualifiers
REGION                 1..448
                       note = Description of Artificial Sequence: Synthetic
```

```
                        polypeptide
source                  1..448
                        mol_type = protein
                        organism = synthetic construct
SEQUENCE: 188
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETHLVLGLSA VLGLLLLRWQ  180
FPAHYRRLRH ALWPSLPDLH RVLGQYLRDT AALSPPKATV SDTCEEVEPS LLEILPKSSE  240
RTPLPLLEAR DEVEGFLQDT FPQQLEESEK QRLGGDVQSP NCPSEDVVIT PESFGRDSSL  300
TCLAGNVSAC DAPILSSSRS LDCRESGKNG PHVYQDLLLS LGTTNSTLPP PFSLQSGILT  360
LNPVAQGQPI LTSLGSNQEE AYVTMSSFYQ NQGSGSRSDP KPENPACPWT VLPAGDLPTH  420
DGYLPSNIDD LPSHEAPLAD SLEELEPQ                                    448

SEQ ID NO: 189          moltype = AA  length = 447
FEATURE                 Location/Qualifiers
REGION                  1..447
                        note = Description of Artificial Sequence: Synthetic
                        polypeptide
source                  1..447
                        mol_type = protein
                        organism = synthetic construct
SEQUENCE: 189
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLVLGLSAV LGLLLLRWQF  180
PAHYRRLRHA LWPSLPDLHR VLGQYLRDTA ALSPPKATVS DTCEEVEPSL LEILPKSSER  240
TPLPLLEARD EVEGFLQDTF PQQLEESEKQ RLGGDVQSPN CPSEDVVITP ESFGRDSSLT  300
CLAGNVSACD APILSSSRSL DCRESGKNGP HVYQDLLLSL GTTNSTLPPP FSLQSGILTL  360
NPVAQGQPIL TSLGSNQEEA YVTMSSFYQN QGSGSRSDPK PENPACPWTV LPAGDLPTHD  420
GYLPSNIDDL PSHEAPLADS LEELEPQ                                     447

SEQ ID NO: 190          moltype = AA  length = 446
FEATURE                 Location/Qualifiers
REGION                  1..446
                        note = Description of Artificial Sequence: Synthetic
                        polypeptide
source                  1..446
                        mol_type = protein
                        organism = synthetic construct
SEQUENCE: 190
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETVLGLSAVL GLLLLRWQFP  180
AHYRRLRHAL WPSLPDLHRV LGQYLRDTAA LSPPKATVSD TCEEVEPSLL EILPKSSERT  240
PLPLLEARDE VEGFLQDTFP QQLEESEKQR LGGDVQSPNC PSEDVVITPE SFGRDSSLTC  300
LAGNVSACDA PILSSSRSLD CRESGKNGPH VYQDLLLSLG TTNSTLPPPF SLQSGILTLN  360
PVAQGQPILT SLGSNQEEAY VTMSSFYQNQ GSGSRSDPKP ENPACPWTVL PAGDLPTHDG  420
YLPSNIDDLP SHEAPLADSL EELEPQ                                      446

SEQ ID NO: 191          moltype = AA  length = 445
FEATURE                 Location/Qualifiers
REGION                  1..445
                        note = Description of Artificial Sequence: Synthetic
                        polypeptide
source                  1..445
                        mol_type = protein
                        organism = synthetic construct
SEQUENCE: 191
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLGLSAVLG LLLLRWQFPA  180
HYRRLRHALW PSLPDLHRVL GQYLRDTAAL SPPKATVSDT CEEVEPSLLE ILPKSSERTP  240
LPLLEARDEV EGFLQDTFPQ QLEESEKQRL GGDVQSPNCP SEDVVITPES FGRDSSLTCL  300
AGNVSACDAP ILSSSRSLDC RESGKNGPHV YQDLLLSLGT TNSTLPPPFS LQSGILTLNP  360
VAQGQPILTS LGSNQEEAYV TMSSFYQNQG SGSRSDPKPE NPACPWTVLP AGDLPTHDGY  420
LPSNIDDLPS HEAPLADSLE ELEPQ                                       445

SEQ ID NO: 192          moltype = AA  length = 444
FEATURE                 Location/Qualifiers
REGION                  1..444
                        note = Description of Artificial Sequence: Synthetic
                        polypeptide
source                  1..444
                        mol_type = protein
                        organism = synthetic construct
SEQUENCE: 192
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
```

```
ELRVTERRAE VPTAHPSPSP RPAGQFQTLV SDPTRVETAT ETGLSAVLGL LLLRWQFPAH  180
YRRLRHALWP SLPDLHRVLG QYLRDTAALS PPKATVSDTC EEVEPSLLEI LPKSSERTPL  240
PLLEARDEVE GFLQDTFPQQ LEESEKQRLG GDVQSPNCPS EDVVITPESF GRDSSLTCLA  300
GNVSACDAPI LSSSRSLDCR ESGKNGPHVY QDLLLSLGTT NSTLPPPFSL QSGILTLNPV  360
AQGQPILTSL GSNQEEAYVT MSSFYQNQGS GSRSDPKPEN PACPWTVLPA GDLPTHDGYL  420
PSNIDDLPSH EAPLADSLEE LEPQ                                        444

SEQ ID NO: 193         moltype = AA  length = 443
FEATURE                Location/Qualifiers
REGION                 1..443
                       note = Description of Artificial Sequence: Synthetic
                        polypeptide
source                 1..443
                       mol_type = protein
                       organism = synthetic construct
SEQUENCE: 193
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLSAVLGLL LLRWQFPAHY  180
RRLRHALWPS LPDLHRVLGQ YLRDTAALSP PKATVSDTCE EVEPSLLEIL PKSSERTPLP  240
LLEARDEVEG FLQDTFPQQL EESEKQRLGG DVQSPNCPSE DVVITPESFG RDSSLTCLAG  300
NVSACDAPIL SSSRSLDCRE SGKNGPHVYQ DLLLSLGTTN STLPPPFSLQ SGILTLNPVA  360
QGQPILTSLG SNQEEAYVTM SSFYQNQGSG SRSDPKPENP ACPWTVLPAG DLPTHDGYLP  420
SNIDDLPSHE APLADSLEEL EPQ                                         443

SEQ ID NO: 194         moltype = AA  length = 442
FEATURE                Location/Qualifiers
REGION                 1..442
                       note = Description of Artificial Sequence: Synthetic
                        polypeptide
source                 1..442
                       mol_type = protein
                       organism = synthetic construct
SEQUENCE: 194
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETSAVLGLLL LRWQFPAHYR  180
RLRHALWPSL PDLHRVLGQY LRDTAALSPP KATVSDTCEE VEPSLLEILP KSSERTPLPL  240
LEARDEVEGF LQDTFPQQLE ESEKQRLGGD VQSPNCPSED VVITPESFGR DSSLTCLAGN  300
VSACDAPILS SSRSLDCRES GKNGPHVYQD LLLSLGTTNS TLPPPFSLQS GILTLNPVAQ  360
GQPILTSLGS NQEEAYVTMS SFYQNQGSGS RSDPKPENPA CPWTVLPAGD LPTHDGYLPS  420
NIDDLPSHEA PLADSLEELE PQ                                          442

SEQ ID NO: 195         moltype = AA  length = 441
FEATURE                Location/Qualifiers
REGION                 1..441
                       note = Description of Artificial Sequence: Synthetic
                        polypeptide
source                 1..441
                       mol_type = protein
                       organism = synthetic construct
SEQUENCE: 195
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAVLGLLLL RWQFPAHYRR  180
LRHALWPSLP DLHRVLGQYL RDTAALSPPK ATVSDTCEEV EPSLLEILPK SSERTPLPLL  240
EARDEVEGFL QDTFPQQLEE SEKQRLGGDV QSPNCPSEDV VITPESFGRD SSLTCLAGNV  300
SACDAPILSS SRSLDCRESG KNGPHVYQDL LLSLGTTNST LPPPFSLQSG ILTLNPVAQG  360
QPILTSLGSN QEEAYVTMSS FYQNQGSGSR SDPKPENPAC PWTVLPAGDL PTHDGYLPSN  420
IDDLPSHEAP LADSLEELEP Q                                           441

SEQ ID NO: 196         moltype = AA  length = 440
FEATURE                Location/Qualifiers
REGION                 1..440
                       note = Description of Artificial Sequence: Synthetic
                        polypeptide
source                 1..440
                       mol_type = protein
                       organism = synthetic construct
SEQUENCE: 196
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETVLGLLLLR WQFPAHYRRL  180
RHALWPSLPD LHRVLGQYLR DTAALSPPKA TVSDTCEEVE PSLLEILPKS SERTPLPLLE  240
ARDEVEGFLQ DTFPQQLEES EKQRLGGDVQ SPNCPSEDVV ITPESFGRDS SLTCLAGNVS  300
ACDAPILSSS RSLDCRESGK NGPHVYQDLL LSLGTTNSTL PPPFSLQSGI LTLNPVAQGQ  360
PILTSLGSNQ EEAYVTMSSF YQNQGSGSRS DPKPENPACP WTVLPAGDLP THDGYLPSNI  420
DDLPSHEAPL ADSLEELEPQ                                             440
```

```
SEQ ID NO: 197          moltype = AA  length = 439
FEATURE                 Location/Qualifiers
REGION                  1..439
                        note = Description of Artificial Sequence: Synthetic
                         polypeptide
source                  1..439
                        mol_type = protein
                        organism = synthetic construct
SEQUENCE: 197
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLGLLLLRW QFPAHYRRLR  180
HALWPSLPDL HRVLGQYLRD TAALSPPKAT VSDTCEEVEP SLLEILPKSS ERTPLPLLEA  240
RDEVEGFLQD TFPQQLEESE KQRLGGDVQS PNCPSEDVVI TPESFGRDSS LTCLAGNVSA  300
CDAPILSSSR SLDCRESGKN GPHVYQDLLL SLGTTNSTLP PPFSLQSGIL TLNPVAQGQP  360
ILTSLGSNQE EAYVTMSSFY QNQGSGSRSD PKPENPACPW TVLPAGDLPT HDGYLPSNID  420
DLPSHEAPLA DSLEELEPQ                                              439

SEQ ID NO: 198          moltype = AA  length = 458
FEATURE                 Location/Qualifiers
REGION                  1..458
                        note = Description of Artificial Sequence: Synthetic
                         polypeptide
source                  1..458
                        mol_type = protein
                        organism = synthetic construct
SEQUENCE: 198
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWLISLVT ALHLVLGLSA  180
VLGLLLLRWQ FPAHYRRLRH ALWPSLPDLH RVLGQYLRDT AALSPPKATV SDTCEEVEPS  240
LLEILPKSSE RTPLPLLEAR DEVEGFLQDT FPQQLEESEK QRLGGDVQSP NCPSEDVVIT  300
PESFGRDSSL TCLAGNVSAC DAPILSSSRS LDCRESGKNG PHVYQDLLLS LGTTNSTLPP  360
PFSLQSGILT LNPVAQGQPI LTSLGSNQEE AYVTMSSFYQ NQGSGSRSDP KPENPACPWT  420
VLPAGDLPTH DGYLPSNIDD LPSHEAPLAD SLEELEPQ                         458

SEQ ID NO: 199          moltype = AA  length = 459
FEATURE                 Location/Qualifiers
REGION                  1..459
                        note = Description of Artificial Sequence: Synthetic
                         polypeptide
source                  1..459
                        mol_type = protein
                        organism = synthetic construct
SEQUENCE: 199
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWVLISLV TALHLVLGLS  180
AVLGLLLLRW QFPAHYRRLR HALWPSLPDL HRVLGQYLRD TAALSPPKAT VSDTCEEVEP  240
SLLEILPKSS ERTPLPLLEA RDEVEGFLQD TFPQQLEESE KQRLGGDVQS PNCPSEDVVI  300
TPESFGRDSS LTCLAGNVSA CDAPILSSSR SLDCRESGKN GPHVYQDLLL SLGTTNSTLP  360
PPFSLQSGIL TLNPVAQGQP ILTSLGSNQE EAYVTMSSFY QNQGSGSRSD PKPENPACPW  420
TVLPAGDLPT HDGYLPSNID DLPSHEAPLA DSLEELEPQ                        459

SEQ ID NO: 200          moltype = AA  length = 460
FEATURE                 Location/Qualifiers
REGION                  1..460
                        note = Description of Artificial Sequence: Synthetic
                         polypeptide
source                  1..460
                        mol_type = protein
                        organism = synthetic construct
SEQUENCE: 200
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWLVLISL VTALHLVLGL  180
SAVLGLLLLR WQFPAHYRRL RHALWPSLPD LHRVLGQYLR DTAALSPPKA TVSDTCEEVE  240
PSLLEILPKS SERTPLPLLE ARDEVEGFLQ DTFPQQLEES EKQRLGGDVQ SPNCPSEDVV  300
ITPESFGRDS SLTCLAGNVS ACDAPILSSS RSLDCRESGK NGPHVYQDLL LSLGTTNSTL  360
PPPFSLQSGI LTLNPVAQGQ PILTSLGSNQ EEAYVTMSSF YQNQGSGSRS DPKPENPACP  420
WTVLPAGDLP THDGYLPSNI DDLPSHEAPL ADSLEELEPQ                       460

SEQ ID NO: 201          moltype = AA  length = 461
FEATURE                 Location/Qualifiers
REGION                  1..461
                        note = Description of Artificial Sequence: Synthetic
                         polypeptide
source                  1..461
                        mol_type = protein
```

```
                        organism = synthetic construct
SEQUENCE: 201
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWILVLIS LVTALHLVLG  180
LSAVLGLLLL RWQFPAHYRR LRHALWPSLP DLHRVLGQYL RDTAALSPPK ATVSDTCEEV  240
EPSLLEILPK SSERTPLPLL EARDEVEGFL QDTFPQQLEE SEKQRLGGDV QSPNCPSEDV  300
VITPESFGRD SSLTCLAGNV SACDAPILSS SRSLDCRESG KNGPHVYQDL LLSLGTTNST  360
LPPPFSLQSG ILTLNPVAQG QPILTSLGSN QEEAYVTMSS FYQNQGSGSR SDPKPENPAC  420
PWTVLPAGDL PTHDGYLPSN IDDLPSHEAP LADSLEELEP Q                     461

SEQ ID NO: 202          moltype = AA  length = 462
FEATURE                 Location/Qualifiers
REGION                  1..462
                        note = Description of Artificial Sequence: Synthetic
                         polypeptide
source                  1..462
                        mol_type = protein
                        organism = synthetic construct
SEQUENCE: 202
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWLILVLI SLVTALHLVL  180
GLSAVLGLLL LRWQFPAHYR RLRHALWPSL PDLHRVLGQY LRDTAALSPP KATVSDTCEE  240
VEPSLLEILP KSSERTPLPL LEARDEVEGF LQDTFPQQLE ESEKQRLGGD VQSPNCPSED  300
VVITPESFGR DSSLTCLAGN VSACDAPILS SSRSLDCRES GKNGPHVYQD LLLSLGTTNS  360
TLPPPFSLQS GILTLNPVAQ GQPILTSLGS NQEEAYVTMS SFYQNQGSGS RSDPKPENPA  420
CPWTVLPAGD LPTHDGYLPS NIDDLPSHEA PLADSLEELE PQ                    462

SEQ ID NO: 203          moltype = AA  length = 463
FEATURE                 Location/Qualifiers
REGION                  1..463
                        note = Description of Artificial Sequence: Synthetic
                         polypeptide
source                  1..463
                        mol_type = protein
                        organism = synthetic construct
SEQUENCE: 203
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWLLILVL ISLVTALHLV  180
LGLSAVLGLL LLRWQFPAHY RRLRHALWPS LPDLHRVLGQ YLRDTAALSP PKATVSDTCE  240
EVEPSLLEIL PKSSERTPLP LLEARDEVEG FLQDTFPQQL EESEKQRLGG DVQSPNCPSE  300
DVVITPESFG RDSSLTCLAG NVSACDAPIL SSSRSLDCRE SGKNGPHVYQ DLLLSLGTTN  360
STLPPPFSLQ SGILTLNPVA QGQPILTSLG SNQEEAYVTM SSFYQNQGSG SRSDPKPENP  420
ACPWTVLPAG DLPTHDGYLP SNIDDLPSHE APLADSLEEL EPQ                   463

SEQ ID NO: 204          moltype = AA  length = 464
FEATURE                 Location/Qualifiers
REGION                  1..464
                        note = Description of Artificial Sequence: Synthetic
                         polypeptide
source                  1..464
                        mol_type = protein
                        organism = synthetic construct
SEQUENCE: 204
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWVLLILV LISLVTALHL  180
VLGLSAVLGL LLLRWQFPAH YRRLRHALWP SLPDLHRVLG QYLRDTAALS PPKATVSDTC  240
EEVEPSLLEI LPKSSERTPL PLLEARDEVE GFLQDTFPQQ LEESEKQRLG GDVQSPNCPS  300
EDVVITPESF GRDSSLTCLA GNVSACDAPI LSSSRSLDCR ESGKNGPHVY QDLLLSLGTT  360
NSTLPPPFSL QSGILTLNPV AQGQPILTSL GSNQEEAYVT MSSFYQNQGS GSRSDPKPEN  420
PACPWTVLPA GDLPTHDGYL PSNIDDLPSH EAPLADSLEE LEPQ                  464

SEQ ID NO: 205          moltype = AA  length = 465
FEATURE                 Location/Qualifiers
REGION                  1..465
                        note = Description of Artificial Sequence: Synthetic
                         polypeptide
source                  1..465
                        mol_type = protein
                        organism = synthetic construct
SEQUENCE: 205
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWLVLLIL VLISLVTALH  180
LVLGLSAVLG LLLLRWQFPA HYRRLRHALW PSLPDLHRVL GQYLRDTAAL SPPKATVSDT  240
CEEVEPSLLE ILPKSSERTP LPLLEARDEV EGFLQDTFPQ QLEESEKQRL GGDVQSPNCP  300
```

```
SEDVVITPES FGRDSSLTCL AGNVSACDAP ILSSSRSLDC RESGKNGPHV YQDLLLSLGT  360
TNSTLPPPFS LQSGILTLNP VAQGQPILTS LGSNQEEAYV TMSSFYQNQG SGSRSDPKPE  420
NPACPWTVLP AGDLPTHDGY LPSNIDDLPS HEAPLADSLE ELEPQ                 465

SEQ ID NO: 206         moltype = AA  length = 401
FEATURE                Location/Qualifiers
REGION                 1..401
                       note = Description of Artificial Sequence: Synthetic
                        polypeptide
source                 1..401
                       mol_type = protein
                       organism = synthetic construct
SEQUENCE: 206
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LLLVLGLNAV  180
LGLLLLRKQF PAHYRRLRHA LWPSLPDLHR VLGQYLRDTA ALSPPKATVS DTCEEVEPSL  240
LEILPKSSER TPLPLLEARD EVEGFLQDTF PQQLEESEKQ RLGGDVQSPN CPSEDVVITP  300
ESFGRDSSLT CLAGNVSACD APILSSSRSL DCRESGKNGP HVYQDLLLSL GTTNSTLPPP  360
FSLQSGILTL NPVAQGQPIL TSLGSNQEEA YVTMSSFYQN Q                     401

SEQ ID NO: 207         moltype = AA  length = 332
FEATURE                Location/Qualifiers
REGION                 1..332
                       note = Description of Artificial Sequence: Synthetic
                        polypeptide
source                 1..332
                       mol_type = protein
                       organism = synthetic construct
SEQUENCE: 207
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLNAV  180
LGLLLLRKQF PAHYRRLRHA LWPSLPDLHR VLGQYLRDTA ALSPPKATVS DTCEEVEPSL  240
LEILPKSSER TPLPLLEDEG VAGAPTGSSP QPLQPLSGED DAYCTFPSRD DLLLFSPSGQ  300
GEFRALNARL PLNTDAYLSL QELQGQDPTH LV                               332

SEQ ID NO: 208         moltype = AA  length = 401
FEATURE                Location/Qualifiers
REGION                 1..401
                       note = Description of Artificial Sequence: Synthetic
                        polypeptide
source                 1..401
                       mol_type = protein
                       organism = synthetic construct
SEQUENCE: 208
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLLEARD EVEGFLQDTF PQQLEESEKQ RLGGDVQSPN CPSEDVVITP  300
ESFGRDSSLT CLAGNVSACD APILSSSRSL DCRESGKNGP HVYQDLLLSL GTTNSTLPPP  360
FSLQSGILTL NPVAQGQPIL TSLGSNQEEA YVTMSSFYQN Q                     401

SEQ ID NO: 209         moltype = AA  length = 332
FEATURE                Location/Qualifiers
REGION                 1..332
                       note = Description of Artificial Sequence: Synthetic
                        polypeptide
source                 1..332
                       mol_type = protein
                       organism = synthetic construct
SEQUENCE: 209
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLLEDEG VAGAPTGSSP QPLQPLSGED DAYCTFPSRD DLLLFSPSGQ  300
GEFRALNARL PLNTDAYLSL QELQGQDPTH LV                               332

SEQ ID NO: 210         moltype = AA  length = 422
FEATURE                Location/Qualifiers
REGION                 1..422
                       note = Description of Artificial Sequence: Synthetic
                        polypeptide
source                 1..422
                       mol_type = protein
                       organism = synthetic construct
SEQUENCE: 210
```

```
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALLLVLGLNA VLGLLLLRKQ FPAHYRRLRH ALWPSLPDLH RVLGQYLRDT  240
AALSPPKATV SDTCEEVEPS LLEILPKSSE RTPLPLLEAR DEVEGFLQDT FPQQLEESEK  300
QRLGGDVQSP NCPSEDVVIT PESFGRDSSL TCLAGNVSAC DAPILSSSRS LDCRESGKNG  360
PHVYQDLLLS LGTTNSTLPP PFSLQSGILT LNPVAQGQPI LTSLGSNQEE AYVTMSSFYQ  420
NQ                                                                422

SEQ ID NO: 211         moltype = AA  length = 353
FEATURE                Location/Qualifiers
REGION                 1..353
                       note = Description of Artificial Sequence: Synthetic
                        polypeptide
source                 1..353
                       mol_type = protein
                       organism = synthetic construct
SEQUENCE: 211
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALHLVLGLNA VLGLLLLRKQ FPAHYRRLRH ALWPSLPDLH RVLGQYLRDT  240
AALSPPKATV SDTCEEVEPS LLEILPKSSE RTPLPLLEDE GVAGAPTGSS PQPLQPLSGE  300
DDAYCTFPSR DDLLLFSPSG QGEFRALNAR LPLNTDAYLS LQELQGQDPT HLV         353

SEQ ID NO: 212         moltype = AA  length = 422
FEATURE                Location/Qualifiers
REGION                 1..422
                       note = Description of Artificial Sequence: Synthetic
                        polypeptide
source                 1..422
                       mol_type = protein
                       organism = synthetic construct
SEQUENCE: 212
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALHLVLGLSA VLGLLLLRWQ FPAHYRRLRH ALWPSLPDLH RVLGQYLRDT  240
AALSPPKATV SDTCEEVEPS LLEILPKSSE RTPLPLLEAR DEVEGFLQDT FPQQLEESEK  300
QRLGGDVQSP NCPSEDVVIT PESFGRDSSL TCLAGNVSAC DAPILSSSRS LDCRESGKNG  360
PHVYQDLLLS LGTTNSTLPP PFSLQSGILT LNPVAQGQPI LTSLGSNQEE AYVTMSSFYQ  420
NQ                                                                422

SEQ ID NO: 213         moltype = AA  length = 353
FEATURE                Location/Qualifiers
REGION                 1..353
                       note = Description of Artificial Sequence: Synthetic
                        polypeptide
source                 1..353
                       mol_type = protein
                       organism = synthetic construct
SEQUENCE: 213
MALPVTALLL PLALLLHAAR PPGWFLDSPD RPWNPPTFSP ALLVVTEGDN ATFTCSFSNT  60
SESFHVIWHR ESPSGQTDTL AAFPEDRSQP GQDCRFRVTQ LPNGRDFHMS VVRARRNDSG  120
TYVCGVISLA PKIQIKESLR AELRVTERRA EVPTAHPSPS PRPAGQFQTL VSDPTRVETA  180
TETAWISLVT ALHLVLGLSA VLGLLLLRWQ FPAHYRRLRH ALWPSLPDLH RVLGQYLRDT  240
AALSPPKATV SDTCEEVEPS LLEILPKSSE RTPLPLLEDE GVAGAPTGSS PQPLQPLSGE  300
DDAYCTFPSR DDLLLFSPSG QGEFRALNAR LPLNTDAYLS LQELQGQDPT HLV         353

SEQ ID NO: 214         moltype = AA  length = 373
FEATURE                Location/Qualifiers
REGION                 1..373
                       note = Description of Artificial Sequence: Synthetic
                        polypeptide
source                 1..373
                       mol_type = protein
                       organism = synthetic construct
SEQUENCE: 214
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLNAV  180
LGLLLLRKQF PAHYRRLRHA LWPSLPDLHR VLGQYLRDTA ALSPPKATVS DTCEEVEPSL  240
LEILPKSSER TPLPLLEQQD KVPEPASLSS NHSLTSCFTN QGYFFFHLPD ALEIEACQDE  300
GVAGAPTGSS PQPLQPLSGE DDAYCTFPSR DDLLLFSPSG QGEFRALNAR LPLNTDAYLS  360
LQELQGQDPT HLV                                                    373

SEQ ID NO: 215         moltype = AA  length = 373
FEATURE                Location/Qualifiers
REGION                 1..373
```

```
                          note = Description of Artificial Sequence: Synthetic
                           polypeptide
source                    1..373
                          mol_type = protein
                          organism = synthetic construct
SEQUENCE: 215
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LLLVLGLNAV  180
LGLLLLRKQF PAHYRRLRHA LWPSLPDLHR VLGQYLRDTA ALSPPKATVS DTCEEVEPSL  240
LEILPKSSER TPLPLLEQQD KVPEPASLSS NHSLTSCFTN QGYFFFHLPD ALEIEACQDE  300
GVAGAPTGSS PQPLQPLSGE DDAYCTFPSR DDLLLFSPSG QGEFRALNAR LPLNTDAYLS  360
LQELQGQDPT HLV                                                     373

SEQ ID NO: 216            moltype = AA  length = 373
FEATURE                   Location/Qualifiers
REGION                    1..373
                          note = Description of Artificial Sequence: Synthetic
                           polypeptide
source                    1..373
                          mol_type = protein
                          organism = synthetic construct
SEQUENCE: 216
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLSAV  180
LGLLLLRWQF PAHYRRLRHA LWPSLPDLHR VLGQYLRDTA ALSPPKATVS DTCEEVEPSL  240
LEILPKSSER TPLPLLEQQD KVPEPASLSS NHSLTSCFTN QGYFFFHLPD ALEIEACQDE  300
GVAGAPTGSS PQPLQPLSGE DDAYCTFPSR DDLLLFSPSG QGEFRALNAR LPLNTDAYLS  360
LQELQGQDPT HLV                                                     373

SEQ ID NO: 217            moltype = AA  length = 325
FEATURE                   Location/Qualifiers
REGION                    1..325
                          note = Description of Artificial Sequence: Synthetic
                           polypeptide
source                    1..325
                          mol_type = protein
                          organism = synthetic construct
SEQUENCE: 217
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETALHLVLGL SAVLGLLLLR  180
WQFPAHYRRL RHALWPSLPD LHRVLGQYLR DTAALSPPKA TVSDTCEEVE PSLLEILPKS  240
SERTPLPLLE DEGVAGAPTG SSPQPLQPLS GEDDAYCTFP SRDDLLLFSP SGQGEFRALN  300
ARLPLNTDAY LSLQELQGQD PTHLV                                        325

SEQ ID NO: 218            moltype = AA  length = 324
FEATURE                   Location/Qualifiers
REGION                    1..324
                          note = Description of Artificial Sequence: Synthetic
                           polypeptide
source                    1..324
                          mol_type = protein
                          organism = synthetic construct
SEQUENCE: 218
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLHLVLGLS AVLGLLLLRW  180
QFPAHYRRLR HALWPSLPDL HRVLGQYLRD TAALSPPKAT VSDTCEEVEP SLLEILPKSS  240
ERTPLPLLED EGVAGAPTGS SPQPLQPLSG EDDAYCTFPS RDDLLLFSPS GQGEFRALNA  300
RLPLNTDAYL SLQELQGQDP THLV                                         324

SEQ ID NO: 219            moltype = AA  length = 323
FEATURE                   Location/Qualifiers
REGION                    1..323
                          note = Description of Artificial Sequence: Synthetic
                           polypeptide
source                    1..323
                          mol_type = protein
                          organism = synthetic construct
SEQUENCE: 219
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETHLVLGLSA VLGLLLLRWQ  180
FPAHYRRLRH ALWPSLPDLH RVLGQYLRDT AALSPPKATV SDTCEEVEPS LLEILPKSSE  240
RTPLPLLEDE GVAGAPTGSS PQPLQPLSGE DDAYCTFPSR DDLLLFSPSG QGEFRALNAR  300
LPLNTDAYLS LQELQGQDPT HLV                                          323
```

```
SEQ ID NO: 220         moltype = AA  length = 366
FEATURE                Location/Qualifiers
REGION                 1..366
                       note = Description of Artificial Sequence: Synthetic
                        polypeptide
source                 1..366
                       mol_type = protein
                       organism = synthetic construct
SEQUENCE: 220
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETALHLVLGL SAVLGLLLLR  180
WQFPAHYRRL RHALWPSLPD LHRVLGQYLR DTAALSPPKA TVSDTCEEVE PSLLEILPKS  240
SERTPLPLLE QQDKVPEPAS LSSNHSLTSC FTNQGYFFFH LPDALEIEAC QDEGVAGAPT  300
GSSPQPLQPL SGEDDAYCTF PSRDDLLLFS PSGQGEFRAL NARLPLNTDA YLSLQELQGQ  360
DPTHLV                                                            366

SEQ ID NO: 221         moltype = AA  length = 365
FEATURE                Location/Qualifiers
REGION                 1..365
                       note = Description of Artificial Sequence: Synthetic
                        polypeptide
source                 1..365
                       mol_type = protein
                       organism = synthetic construct
SEQUENCE: 221
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETLHLVLGLS AVLGLLLLRW  180
QFPAHYRRLR HALWPSLPDL HRVLGQYLRD TAALSPPKAT VSDTCEEVEP SLLEILPKSS  240
ERTPLPLLEQ QDKVPEPASL SSNHSLTSCF TNQGYFFFHL PDALEIEACQ DEGVAGAPTG  300
SSPQPLQPLS GEDDAYCTFP SRDDLLLFSP SGQGEFRALN ARLPLNTDAY LSLQELQGQD  360
PTHLV                                                             365

SEQ ID NO: 222         moltype = AA  length = 364
FEATURE                Location/Qualifiers
REGION                 1..364
                       note = Description of Artificial Sequence: Synthetic
                        polypeptide
source                 1..364
                       mol_type = protein
                       organism = synthetic construct
SEQUENCE: 222
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETHLVLGLSA VLGLLLLRWQ  180
FPAHYRRLRH ALWPSLPDLH RVLGQYLRDT AALSPPKATV SDTCEEVEPS LLEILPKSSE  240
RTPLPLLEQQ DKVPEPASLS SNHSLTSCFT NQGYFFFHLP DALEIEACQD EGVAGAPTGS  300
SPQPLQPLSG EDDAYCTFPS RDDLLLFSPS GQGEFRALNA RLPLNTDAYL SLQELQGQDP  360
THLV                                                              364

SEQ ID NO: 223         moltype = AA  length = 332
FEATURE                Location/Qualifiers
REGION                 1..332
                       note = Description of Artificial Sequence: Synthetic
                        polypeptide
source                 1..332
                       mol_type = protein
                       organism = synthetic construct
SEQUENCE: 223
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LLLVLGLNAV  180
LGLLLLRKQF PAHYRRLRHA LWPSLPDLHR VLGQYLRDTA ALSPPKATVS DTCEEVEPSL  240
LEILPKSSER TPLPLLEDEG VAGAPTGSSP QPLQPLSGED DAYCTFPSRD DLLLFSPSGQ  300
GEFRALNARL PLNTDAYLSL QELQGQDPTH LV                               332

SEQ ID NO: 224         moltype = AA  length = 401
FEATURE                Location/Qualifiers
REGION                 1..401
                       note = Description of Artificial Sequence: Synthetic
                        polypeptide
source                 1..401
                       mol_type = protein
                       organism = synthetic construct
SEQUENCE: 224
PGWFLDSPDR PWNPPTFSPA LLVVTEGDNA TFTCSFSNTS ESFHVIWHRE SPSGQTDTLA  60
AFPEDRSQPG QDCRFRVTQL PNGRDFHMSV VRARRNDSGT YVCGVISLAP KIQIKESLRA  120
ELRVTERRAE VPTAHPSPSP RPAGQFQTLV SDPTRVETAT ETAWISLVTA LHLVLGLNAV  180
```

-continued

| | | | | | | |
|---|---|---|---|---|---|---|
| LGLLLLRKQF | PAHYRRLRHA | LWPSLPDLHR | VLGQYLRDTA | ALSPPKATVS | DTCEEVEPSL | 240 |
| LEILPKSSER | TPLPLLEARD | EVEGFLQDTF | PQQLEESEKQ | RLGGDVQSPN | CPSEDVVITP | 300 |
| ESFGRDSSLT | CLAGNVSACD | APILSSSRSL | DCRESGKNGP | HVYQDLLLSL | GTTNSTLPPP | 360 |
| FSLQSGILTL | NPVAQGQPIL | TSLGSNQEEA | YVTMSSFYQN | Q | | 401 |

CHIMERIC CYTOKINE RECEPTORS BEARING A PD-1 ECTODOMAIN

CROSS REFERENCE TO RELATED APPLICATIONS

This application is a divisional of U.S. application Ser. No. 16/804,545, filed Feb. 28, 2020, which claims the benefit of priority to U.S. Provisional Application No. 62/812,799, filed on Mar. 1, 2019; U.S. Provisional Application No. 62/894,659, filed on Aug. 30, 2019; and U.S. Provisional Application No. 62/980,737, filed on Feb. 24, 2020, the contents of all of which are hereby incorporated by reference in their entireties.

SEQUENCE LISTING

The instant application contains a Sequence Listing which has been submitted electronically in XML format and is hereby incorporated by reference in its entirety. Said XML copy, created on Jul. 31, 2023, is named AT-024_05_SL.xml and is 341,206 bytes in size.

BACKGROUND

Adoptive transfer of immune cells (e.g. T-cells) genetically modified to recognize malignancy-associated antigens is showing promise as a new approach to treating cancer. For example, T-cells can be genetically modified to express chimeric antigen receptors (CARs), which are fusion proteins comprised of an antigen recognition moiety and T-cell activation domains.

T-cell proliferation, cytotoxic potency and persistence is driven by signal transduction pathways. Conventional CAR designs provide two signals—CD3zeta activation (Signal 1) and co-stimulation (Signal 2, e.g. via 4-1BB, OX40, and/or CD28 expression). In some contexts, a third signal (Signal 3), cytokine-induced cytokine receptor signaling (e.g. cytokine support for immune potentiation), may be desirable. Approaches to provide Signal 3 have however been met with significant limitations.

One approach to provide cytokine support includes combining CAR-T-cell therapy with systemic infusions of recombinant cytokines/cytokine mimetics, and engineering CAR-T-cells to secrete/express cytokines extracellularly. As cytokines have pleiotropic effects and can also impact the function of other cell types, the systemic administration or production of immune-potentiating cytokines by CAR-T-cells have at least two major drawbacks: (i) these approaches can cause systemic toxicity in humans, and (ii) in the context of allogeneic CAR-T-cell therapy, these approaches may cause bystander host immune-activation that could accelerate the rejection of allogeneic CAR-T-cells, thereby compromising therapeutic efficacy. Another approach to provide cytokine support was based on introducing a constitutively activated dimerized cytokine receptor, an IL-7Ra—this limits the nature (IL-7 signaling only) and magnitude of signaling output. Yet another approach to provide cytokine support involved incorporating Signal 3 directly into the CAR molecule (Nat Med. 2018 March; 24(3):352-359.). A limitation of this approach is that the strength of Signal 3 dependent on the strength of CAR activation. In the absence of target (and CAR activation), Signal 3 would not be transduced.

Needed are solutions to circumvent these drawbacks by targeting cytokine signals specifically to CAR-T-cells in a context-dependent manner, thus allowing for an improved safety profile and therapeutic efficacy. Provided herein and compositions and methods that address this need.

SUMMARY

Provided herein are inducible PD-1 chimeric cytokine receptors, active, for example, when engaged with PD-1 ligands or activated with an anti-PD-1 antibody. When present on chimeric antigen receptor (CAR)-bearing immune cells, and engaged with PD-1 ligands and/or activated with an anti-PD-1 antibody, such receptors allow for increased cytokine receptor signaling (Signal 3), leading to increased immune cell activation, proliferation, persistence, and/or potency of the CAR-bearing immune cells. Accordingly, the PD-1 chimeric cytokine receptors of the disclosure allow for cytokine signals to be transmitted into the immune cell with endogenous PD-1 ligands (PD-L1, PD-L2), whereby blocking their immune-suppressive signals, and converting them into immune-potentiating signals that can work in concert with, or synergize, CAR-driven activity. Moreover, as clinically approved anti-PD-1 antibodies can cluster and activate the PD-1 chimeric cytokine receptors of the disclosures, patients treated with anti-PD-1 may benefit not only from the blockage of the endogenous PD-1 signaling, but from also the activation of cytokine signaling in cells bearing the PD-1 chimeric cytokine receptors.

In some embodiments, provided herein are constitutively active PD-1 chimeric cytokine receptors. When present on chimeric antigen receptor (CAR)-bearing immune cells, these constitutively active receptors allow for increased basal cytokine receptor signaling (Signal 3). In some embodiments, the activity of the constitutively active PD-1 chimeric cytokine receptors can be increased when engaged with PD-1 ligands or activated with an anti-PD-1 antibody.

Accordingly, in one aspect, provided herein is a PD-1 chimeric cytokine receptor comprising: (a) a PD-1 ectodomain; (b) a transmembrane domain; (c) a Janus Kinase (JAK)-binding domain; and (d) a recruiting domain. The PD-1 ectodomain may comprise a portion of the extracellular region of a PD-1 protein, or may comprise a PD-1 ligand antigen binding domain.

In a related aspect provided herein is a polynucleotide encoding any one of the chimeric cytokine receptors of the disclosure, and an expression vector comprising such polynucleotide. In some embodiments, the polynucleotide further encodes for a chimeric antigen receptor (CAR), wherein the CAR binds to a target of interest. The target of interest can be any molecule of interest, including, for example, without limitation any one or more of those presented in Table 11.

In another aspect, provided herein is an engineered immune cells comprising at least one chimeric antigen receptor (CAR) and at least one chimeric cytokine receptor of the disclosure. In some embodiments the immune cell is a T-cell. In some embodiments the immune cell is an allogeneic immune cell. In other embodiments, the immune cell is an autologous immune cell. The immune cell may be selected from the group consisting of: T-cell, dendritic cell, killer dendritic cell, mast cell, NK-cell, macrophage, monocyte, B-cell and an immune cell derived from a stem cell. In a related aspect, provided herein is a pharmaceutical composition comprising any of the engineered immune cells of the disclosure, and a kit comprising such a pharmaceutical composition.

In another aspect, provided herein is a method of treating a cancer in a subject, comprising administering to the subject a therapeutically effective amount of any of the engineered immune cells described herein.

BRIEF DESCRIPTION OF THE DRAWINGS

FIG. 1B also shows a schematic of the PD-1 chimeric cytokine receptor—CAR vector

FIG. 5A shows the prototypic WT PD-1 chimeric cytokine receptor bearing the TpoR(478-582) TM/JAK2-activating domain; FIG. 5B shows the 2×PD-1 chimeric cytokine receptor bearing two WT PD-1 ectodomains in tandem; FIG. 5C shows the 3×PD-1 chimeric cytokine receptor bearing three WT PD-1 ectodomains in tandem; FIG. 5D shows the high affinity (HA) PD-1 chimeric cytokine receptor with ectodomain mutations.

FIGS. 10A-10B show the amino acid sequences for the wild type TpoR and the various TM deletion (FIG. 10*a*) or insertion (FIG. 10*b*) variants.

DETAILED DESCRIPTION

Figure 1A:
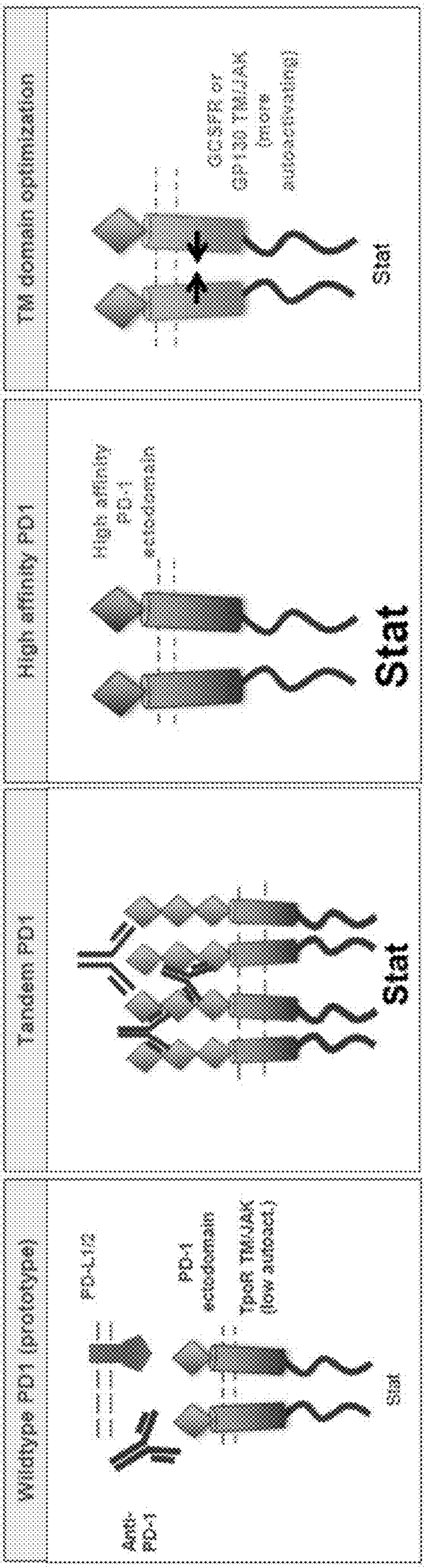
FIG. 1A shows a schematic of the certain embodiments of the PD-1 chimeric cytokine receptors of the disclosure.

Provided herein are inducible PD-1 chimeric cytokine receptors, active when engaged with PD-1 ligands or activated with an anti-PD-1 antibody. Also provided herein are constitutively active PD-1 chimeric cytokine receptors. Provided herein are chimeric antigen receptor (CAR)-bearing immune cells (CAR-I cells, e.g. CAR-T-cells), expressing the PD-1 chimeric cytokine receptors of the disclosure. Also provided herein are methods of making and using the PD-1 chimeric cytokine receptors.

I. PD-1 Chimeric Cytokine Receptors

The inducible PD-1 chimeric cytokine receptors of the disclosure activate signaling upon, for example, binding a PD-1 ligand (e.g. PD-L1, PD-L2), or a PD-1 antibody. These receptors activate signaling when monomers of the receptor cluster and/or dimerize. In some embodiments, a monomer of the PD-1 chimeric cytokine receptor of the disclosure comprises: (a) a PD-1 ectodomain; (b) a transmembrane domain; (c) a Janus Kinase (JAK)-binding domain; and; (d) a STAT-recruiting domain (e.g. from the cytoplasmic domain of a receptor; e.g. from a cytokine receptor). In some embodiments, a monomer of the PD-1 chimeric cytokine receptor of the disclosure comprises: (a) a PD-1 ectodomain; (b) a transmembrane domain; (c) a Janus Kinase (JAK)-binding domain; and; (d) a recruiting domain (e.g. from the cytoplasmic domain of a receptor; e.g. from a cytokine receptor). The recruiting domain can be a STAT-recruiting domain, an AP1-recruiting domain, a Myc/Max-recruiting domain; or a NFkB-recruiting domain. The PD-1 chimeric cytokine receptors can bind to PD-1 ligands, and/or are clustered and activated with an anti-PD-1 antibody. The PD-1 chimeric cytokine receptors activate signaling upon for example binding a PD-L1 ligand, PD-L2 ligand, and/or a PD-1 antibody.

The constitutively active PD-1 chimeric cytokine receptors of the disclosure are active regardless of PD-1 ligand availability, but may increase activity in the presence of a PD-ligand. In some embodiments, a monomer of the constitutively active PD-1 chimeric cytokine receptor of the disclosure comprises: (a) a PD-1 ectodomain; (b) a transmembrane domain; (c) a Janus Kinase (JAK)-binding domain; and; (d) a STAT-recruiting domain (e.g. from the cytoplasmic domain of a receptor; e.g. from a cytokine receptor). In some embodiments, a monomer of the constitutively active PD-1 chimeric cytokine receptor of the disclosure comprises: (a) a PD-1 ectodomain; (b) a transmembrane domain; (c) a Janus Kinase (JAK)-binding domain; and; (d) a recruiting domain (e.g. from the cytoplasmic domain of a receptor; e.g. from a cytokine receptor). The recruiting domain can be a STAT-recruiting domain, an AP1-recruiting domain, a Myc/Max-recruiting domain; or a NFkB-recruiting domain. In some embodiments, constitutively active PD-1 chimeric cytokine receptors can bind to PD-1 ligands or an anti-PD-1 antibody, and/or are clustered and the activity of the receptors can be further increased by engagement with PD-1 ligands or an anti-PD-1 antibody.

A. PD-1 Ectodomains

The PD-1 chimeric cytokine receptors of the disclosure comprise a PD-1 ectodomain. The PD-1 ectodomain is the domain of the chimeric cytokine receptor that extends into the extracellular space. PD-1 ectodomains of the disclosure are capable of binding PD-1 ligands (e.g. PD-L1, PD-L2) and anti-PD-1 antibodies, leading to binding-induced signal transduction. As contemplated herein, the term "PD-1 ectodomain" comprises at least a portion of the extracellular domain of a PD-1 protein or comprises a PD-1 ligand antigen binding domain (e.g. a PD-L1 antigen binding domain, or a PD-L2 antigen binding domain).

In some embodiments, the PD-1 ectodomain comprises a portion of a wild type PD-1. In some embodiments, the PD-1 ectodomain comprises mutations to the wild-type PD-1. In some embodiments, the PD-1 ectodomain comprises repeats of wild-type and/or mutated PD-1 amino acid sequences.

In some embodiments, the PD-1 ectodomain comprises a PD-1 ligand antigen binding domain, for example, the antigen binding domain of an anti-PD-L1 antibody or an anti-PD-L2 antibody. In some embodiments, the antigen binding domain is an scFv. In some embodiments, the antigen binding domain is a single chain antibody. In some embodiments, the antigen binding domain comprises a Fab portion of a PD-1 ligand antibody.

Table 1 shows exemplary PD1 amino acid ectodomain sequences of the disclosure. It is noted that the expression and extracellular location of the exemplary PD1 amino acid sequences can be achieved with the use of a signal sequence. In an exemplary embodiment, a CD8 signal sequence (CD8SS) MALPVTALLLPLALLLHAARP (SEQ TD NO: 1) is utilized.

TABLE 1

Exemplary Ectodomain Sequences

| Ectodomain | Amino acid sequence | SEQ ID NO: |
|---|---|---|
| Wild type (WT) PD1 ectodomain (PD-1(21-207)) | PGWFLDSPDRPWNPPTFSPALLVVTEGDNATFTC<br>SFSNTSESFVLNWYRMSPSNQTDKLAAFPEDRSQ<br>PGQDCRFRVTQLPNGRDFHMSVVRARRNDSGTY<br>LCGAISLAPKAQIKESLRAELRVTERRAEVPTAHP<br>SPSPRPAGQFQTLV<br>VGVVGGLLGSLVLLVWVLAVICSRAARGTIGAR<br>RTGQ | 2 |
| 2x WTPD1 ectodomain (PD-1(21-207)-PD-1(21-207)) | PGWFLDSPDRPWNPPTFSPALLVVTEGDNATFTC<br>SFSNTSESFVLNWYRMSPSNQTDKLAAFPEDRSQ<br>PGQDCRFRVTQLPNGRDFHMSVVRARRNDSGTY<br>LCGAISLAPKAQIKESLRAELRVTERRAEVPTAHP<br>SPSPRPAGQFQTLVVGVVGGLLGSLVLLVWVLA<br>VICSRAARGTIGARRTGQPGWFLDSPDRPWNPPT<br>FSPALLVVTEGDNATFTCSFSNTSESFVLNWYRM<br>SPSNQTDKLAAFPEDRSQPGQDCRFRVTQLPNGR<br>DFHMSVVRARRNDSGTYLCGAISLAPKAQIKESL<br>RAELRVTERRAEVPTAHPSPSPRPAGQFQTLVVG<br>VVGGLLGSLVLLVWVLAVICSRAARGTIGARRT<br>GQ | 3 |
| 3x WTPD1 ectodomain (PD-1(21-207)-PD-1(21-207)-PD-1(21-207)) | PGWFLDSPDRPWNPPTFSPALLVVTEGDNATFTC<br>SFSNTSESFVLNWYRMSPSNQTDKLAAFPEDRSQ<br>PGQDCRFRVTQLPNGRDFHMSVVRARRNDSGTY<br>LCGAISLAPKAQIKESLRAELRVTERRAEVPTAHP<br>SPSPRPAGQFQTLVVGVVGGLLGSLVLLVWVLA<br>VICSRAARGTIGARRTGQPGWFLDSPDRPWNPPT<br>FSPALLVVTEGDNATFTCSFSNTSESFVLNWYRM<br>SPSNQTDKLAAFPEDRSQPGQDCRFRVTQLPNGR<br>DFHMSVVRARRNDSGTYLCGAISLAPKAQIKESL<br>RAELRVTERRAEVPTAHPSPSPRPAGQFQTLVVG<br>VVGGLLGSLVLLVWVLAVICSRAARGTIGARRT<br>GQPGWFLDSPDRPWNPPTFSPALLVVTEGDNATF<br>TCSFSNTSESFVLNWYRMSPSNQTDKLAAFPEDR<br>SQPGQDCRFRVTQLPNGRDFHMSVVRARRNDSG<br>TYLCGAISLAPKAQIKESLRAELRVTERRAEVPTA<br>HPSPSPRPAGQFQTLVVGVVGGLLGSLVLLVWV<br>LAVICSRAARGTIGARRTGQ | 4 |
| High-affinity (HA) PD1 ectodomain | PGWFLDSPDRPWNPPTFSPALLVVTEGDNATFTC<br>SFSNTSESFHVIWHRESPSGQTDTLAAFPEDRSQP<br>GQDCRFRVTQLPNGRDFHMSVVRARRNDSGTY<br>VCGVISLAPKIQIKESLRAELRVTERRAEVPTAHP<br>SPSPRPAGQFQTLVVGVVGGLLGSLVLLVWVLA<br>VICSRAARGTIGARRTGQ | 5 |

TABLE 1-continued

| Exemplary Ectodomain Sequences | | |
|---|---|---|
| Ectodomain | Amino acid sequence | SEQ ID NO: |
| FKBP(F36V) | MGVQVETISPGDGRTFPKRGQTCVVHYTGMLED GKKVDSSRDRNKPFKFMLGKQEVIRGWEEGVA QMSVGQRAKLTISPDYAYGATGHPGIIPPHATLV FDVELLKLE | 6 |
| Wildtype (WT) PD1 ectodomain (PD-1(21-170)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLV | 132 |
| High-affinity (HA) PD1 ectodomain (21-170) | PGWFLDSPDRPWNPPTFSPALLVVTEGDNATFTC SFSNTSESFHVIWHRESPSGQTDTLAAFPEDRSQP GQDCRFRVTQLPNGRDFHMSVVRARRNDSGTY VCGVISLAPKIQIKESLRAELRVTERRAEVPTAHP SPSPRPAGQFQTLV | 133 |
| 2x WTPD1 ectodomain (PD-1(21-170)-G-PD-1(21-170)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLVGPGWFLDSPDRPWNPPTFSP ALLVVTEGDNATFTCSFSNTSESFVLNWYRMSPS NQTDKLAAFPEDRSQPGQDCRFRVTQLPNGRDF HMSVVRARRNDSGTYLCGAISLAPKAQIKESLRA ELRVTERRAEVPTAHPSPSPRPAGQFQTLV | 168 |
| 3x WTPD1 ectodomain (PD-1(21-170)-G-PD-1(21-170)-G-PD-1(21-170)) | PGWFLDSPDRPWNPPTFSPALLVVTEGDNATFTC SFSNTSESFVLNWYRMSPSNQTDKLAAFPEDRSQ PGQDCRFRVTQLPNGRDFHMSVVRARRNDSGTY LCGAISLAPKAQIKESLRAELRVTERRAEVPTAHP SPSPRPAGQFQTLVGPGWFLDSPDRPWNPPTFSP ALLVVTEGDNATFTCSFSNTSESFVLNWYRMSPS NQTDKLAAFPEDRSQPGQDCRFRVTQLPNGRDF HMSVVRARRNDSGTYLCGAISLAPKAQIKESLRA ELRVTERRAEVPTAHPSPSPRPAGQFQTLVGPGW FLDSPDRPWNPPTFSPALLVVTEGDNATFTCSFSN TSESFVLNWYRMSPSNQTDKLAAFPEDRSQPGQ DCRFRVTQLPNGRDFHMSVVRARRNDSGTYLCG AISLAPKAQIKESLRAELRVTERRAEVPTAHPSPS PRPAGQFQTLV | 169 |

In some embodiments, the PD-1 ectodomain comprises a wild type PD-1 ectodomain.

In some embodiments, the PD-1 ectodomain comprises a wild type PD-1 and comprises the amino acid sequence of SEQ TD NO: 2. In some embodiments, the PD-1 ectodomain comprises a wild type PD-1 and comprises the amino acid sequence of SEQ ID NO: 132.

In some embodiments, the PD-1 ectodomain comprises mutations to the wild type PD-1 ectodomain sequence. In some embodiments, the PD-1 ectodomain sequence is a high affinity PD-1 ectodomain. In some embodiments, the PD-1 ectodomain sequence is a high affinity PD-1 ectodomain and comprises the amino acid sequence of SEQ ID NO: 5. In some embodiments, the PD-1 ectodomain sequence is a high affinity PD-1 ectodomain and comprises the amino acid sequence of SEQ ID NO: 133.

In some embodiments, the PD-1 ectodomain comprises a tandem arrangement of greater than one wild type PD-1 ectodomain sequence, for example at least two, at least three, at least four, or at least five wild type PD-1 ectodomain sequences. In some embodiments, the PD-1 ectodomain comprises a tandem arrangement of two wild type PD-1 ectodomain sequences and comprises the amino acid sequence of SEQ ID NO: 3. In some embodiments, the PD-1 ectodomain comprises a tandem arrangement of two wild type PD-1 ectodomain sequences and comprises the amino acid sequence of SEQ ID NO: 168. In some embodiments, the PD-1 ectodomain comprises a tandem arrangement of three wild type PD-1 ectodomain sequences and comprises the amino acid sequence of SEQ ID NO: 4. In some embodiments, the PD-1 ectodomain comprises a tandem arrangement of three wild type PD-1 ectodomain sequences and comprises the amino acid sequence of SEQ ID NO: 169.

In some embodiments, the PD-1 ectodomain comprises a tandem arrangement of greater than one high affinity PD-1 ectodomain sequence, for example at least two, at least three, at least four, or at least five high affinity PD-1 ectodomain sequences.

In some embodiments, the PD-1 ectodomain comprises a high affinity PD-1 and comprises the amino acid sequence of SEQ ID NO: 5. In some embodiments, the high affinity PD-1 ectodomain comprises the amino acid sequence of SEQ ID NO: 133. In some embodiments, the PD-1 ectodomain comprises a tandem arrangement of two high affinity PD-1 ectodomain sequences. In some embodiments, the PD-1 ectodomain comprises a tandem arrangement of three high affinity PD-1 ectodomain sequences.

In some embodiments, the PD-1 ectodomain comprises a tandem arrangement of a combination of wild type and high affinity PD-1 ectodomain sequences, for example a combination of at least two, at least three, at least four, or at least five wild type and high affinity PD-1 ectodomain sequences.

In some embodiments, the greater than one wide type PD-1 ectodomain, or greater than one high affinity PD-1 ectodomain, or a combination thereof, can be connected either directly, or via a linker. In some embodiments, the linker can comprise one or more amino acid residues. In some embodiments, the linker is a Gly.

In some embodiments, the PD-1 ectodomain is a dominant negative. Table 2 shows exemplary PD-1 dominant negative (DN) sequences of the disclosure. The DN sequences of Table 2 may be expressed with the aid of a signal sequence, e.g. a CD8SS signal sequence of SEQ ID NO: 1

In some embodiments, the transmembrane domains of the disclosure are engineered and do not resemble any naturally occurring transmembrane domain, e.g. they are non-naturally occurring.

In other embodiments, the transmembrane domains of the disclosure are derived from naturally occurring receptors.

In some embodiments, the transmembrane and/or JAK domains of the disclosure are derived from, for example, one or more of the following receptors: erythropoietin receptor (EpoR), Interleukin 6 signal transducer (GP130 or IL6ST), prolactin receptor (PrlR), growth hormone receptor (GHR), granulocyte colony-stimulating factor receptor (GCSFR), and thrombopoietin receptor/myeloproliferative leukemia protein receptor (TPOR/MPLR).

When derived from naturally occurring receptors, the entire receptor, or the entire transmembrane sequence of the receptor may not be necessary to effectuate constitutive activation and constitutive JAK binding/activation on the intracellular portion. Accordingly fragments of naturally occurring receptors may be utilized. Furthermore, certain mutations may be introduced into the transmembrane domains derived from naturally occurring receptors, to further tune the downstream JAK-dependent signaling.

In some embodiments, the transmembrane and/or JAK domains of the disclosure is derived from the naturally occurring EpoR receptor.

In some embodiments, the transmembrane and/or JAK domains of the disclosure is derived from the naturally occurring GP130 receptor.

TABLE 2

PD1 dominant negative (DN) sequences:

| PD1 DN | Amino acid sequence | SEQ ID NO: |
|---|---|---|
| Dominant negative wild type PD1 (21-207) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ | 7 |
| Dominant negative high affinity PD1 | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ | 8 |

B. Transmembrane Domains

The PD-1 chimeric cytokine receptors of the disclosure comprise transmembrane domains. Such transmembrane domains are coupled to the extracellular PD-1 ectodomain on the N-terminus, and to additional intracellular/cytoplasmic domains on the C-terminus. In some embodiments, the coupling is achieved optionally through a linker. In some embodiments, the linker can comprise one or more amino acid residues.

As used herein, the transmembrane domains are capable of insertion into the membrane of a cell in which it is expressed. In some embodiments, the transmembrane domains of the disclosure span a cellular membrane, and comprise an extracellular portion, and/or an intracellular portion.

In some embodiments, the transmembrane and/or JAK domains of the disclosure is derived from the naturally occurring PrlR receptor.

In some embodiments, the transmembrane and/or JAK domains of the disclosure is derived from the naturally occurring GHR receptor.

In some embodiments, the transmembrane and/or JAK domains of the disclosure is derived from the naturally occurring GCSF receptor.

In some embodiments, the transmembrane and/or JAK domains of the disclosure is derived from the naturally occurring TPOR receptor.

Table 3 provides exemplary full length sequences of naturally occurring receptors provided in the disclosure, from which the transmembrane and/or JAK domains are derived.

TABLE 3

| Exemplary Naturally Occurring Receptors | |
|---|---|
| Naturally Occurring Receptor Name | SEQ ID NO: |
| >AAI12154.1 Erythropoietin receptor [*Homo sapiens*]<br>MDHLGASLWPQVGSLCLLLAGAAWAPPPNLPDPKFESKAALLAARGPEELLCFTERLEDLVCFWEEAASA<br>GVGPGNYSFSYQLEDEPWKLCRLHQAPTARGAVRFWCSLPTADTSSFVPLELRVTAASGAPRYHRVIHIN<br>EVVLLDAPVGLVARLADESGHVVLRWLPPPETPMTSHIRYEVDVSAGNGAGSVQRVEILEGRTECVLSNL<br>RGRTRYTFAVRARMAEPSFGGFWSAWSEPVSLLTPSDLDPLILTLSLILVVILVLLTVLALLSHRRALKQ<br>KIWPGIPSPESEFEGLFTTHKGNFQLWLYQNDGCLWWSPCTPFTEDPPASLEVLSERCWGTMQAVEPGTD<br>DEGPLLEPVGSEHAQDTYLVLDKWLLPRNPPSEDLPGPGGSVDIVAMDEGSEASSCSSALASKPSPEGAS<br>AASFEYTILDPSSQLLRPWTLCPELPPTPPHLKYLYLVVSDSGISTDYSSGDSQGAQGGLSDGPYSNPYE<br>NSLIPAAEPLPPSYVACS | 9 |
| >AAI17403.1 Interleukin 6 signal transducer (GP130, oncostatin M receptor) [*Homo sapiens*]<br>MLTLQTWLVQALFIFLTTESTGELLDPCGYISPESPVVQLHSNFTAVCVLKEKCMDYFHVNANYIVWKTN<br>HFTIPKEQYTIINRTASSVTFTDIASLNIQLTCNILTFGQLEQNVYGITIISGLPPEKPKNLSCIVNEGK<br>KMRCEWDRGRETHLETNFTLKSEWATHKFADCKAKRDTPTSCTVDYSTVYFVNIEVWVEAENALGKVTSD<br>HINFDPVYKVKPNPPHNLSVINSEELSSILKLTWTNPSIKSVIILKYNIQYRTKDASTWSQIPPEDTAST<br>RSSFTVQDLKPFTEYVFRIRCMKEDGKGYWSDWSEEASGITYEDRPSKAPSFWYKIDPSHTQGYRTVQLV<br>WKTLPPFEANGKILDYEVTLTRWKSHLQNYTVNATKLTVNLTNDRYVATLTVRNLVGKSDAAVLTIPACD<br>FQATHPVMDLKAFPKDNMLWVEWTTPRESVKKYILEWCVLSDKAPCITDWQQEDGTVHRTYLRGNLAESK<br>CYLITVTPVYADGPGSPESIKAYLKQAPPSKGPTVRTKKVGKNEAVLEWDQLPVDVQNGFIRNYTIFYRT<br>IIGNETAVNVDSSHTEYTLSSLTSDTLYMVRMAAYTDEGGKDGPEFTFTTPKFAQGEIEAIVVPVCLAFL<br>LTTLLGVLFCFNKRDLIKKHIWPNVPDPSKSHIAQWSPHTPPRHNFNSKDQMYSDGNFTDVSVVEIEAND<br>KKPFPEDLKSLDLFKKEKINTEGHSSGIGGSSCMSSSRPSISSSDENESSQNTSSTVQYSTVVHSGYRHQ<br>VPSVQVFSRSESTQPLLDSEERPEDLQLVDHVDGGDGILPRQQYFKQNCSQHESSPDISHFERSKQVSSV<br>NEEDFVRLKQQISDHISQSCGSGQMKMFQEVSAADAFGPGTEGQVERFETVGMEAATDEGMPKSYLPQTV<br>RQGGYMPQ | 10 |
| >XP_011512371.1 prolactin receptor isoform X2 [*Homo sapiens*]<br>MKENVASATVFTLLLFLNTCLLNGQLPPGKPEIFKCRSPNKETFTCWWRPGTDGGLPTNYSLTYHREGET<br>LMHECPDYITGGPNSCHFGKQYTSMWRTYIMMVNATNQMGSSFSDELYVDVTYIVQPDPPLELAVEVKQP<br>EDRKPYLWIKWSPPTLIDLKTGWFTLLYEIRLKPEKAAEWEIHFAGQQTEFKILSLHPGQKYLVQVRCKP<br>DHGYWSAWSPATFIQIPSDFTMNDTTVWISVAVLSAVICLIIVWAVALKGYSMVTCIFPPVPGPKIKGFD<br>AHLLEKGKSEELLSALGCQDFPPTSDYEDLLVEYLEVDDSEDQHLMSVHSKEHPSQGMKPTYLDPDTDSG<br>RGSCDSPSLLSEKCEEPQANPSTFYDPEVIEKPENPETTHTWDPQCISMEGKIPYFHAGGSKCSTWPLPQ<br>PSQHNPRSSYHNITDVCELAVGPAGAPATLLNEAGKDALKSSQTIKSREEGKATQQREVESFHSETDQDT<br>PWLLPQEKTPFGSAKPLDYVEIHKVNKDGALSLLPKQRENSGKPKKPGTPENNKEYAKVSGVMDNNILVL<br>VPDPHAKNVACFEESAKEAPPSLEQNQAEKALANFTATSSKCRLQLGGLDYLDPACFTHSFH | 11 |
| >NP_000154.1 growth hormone receptor isoform 1 precursor [*Homo sapiens*]<br>MDLWQLLLTLALAGSSDAFSGSEATAAILSRAPWSLQSVNPGLKTNSSKEPKFTKCRSPERETFSCHWTD<br>EVHHGTKNLGPIQLFYTRRNTQEWTQEWKECPDYVSAGENSCYFNSSFTSIWIPYCIKLTSNGGTVDEKC<br>FSVDEIVQPDPPIALNWTLLNVSLTGIHADIQVRWEAPRNADIQKGWMVLEYELQYKEVNETKWKMMDPI<br>LTTSVPVYSLKVDKEYEVRVRSKQRNSGNYGEFSEVLYVTLPQMSQFTCEEDFYFPWLLIIIFGIFGLTV<br>MLFVFLFSKQQRIKMLILPPVPVPKIKGIDPDLLKEGKLEEVNTILAIHDSYKPEFHSDDSWVEFIELDI<br>DEPDEKTEESDTDRLLSSDHEKSHSNLGVKDGDSGRTSCCEPDILETDFNANDIHEGTSEVAQPQRLKGE<br>ADLLCLDQKNQNNSPYHDACPATQQPSVIQAEKNKPQPLPTEGAESTHQAAHIQLSNPSSLSNIDFYAQV<br>SDITPAGSVVLSPGQKNKAGMSQCDMHPEMVSLCQENFLMDNAYFCEADAKKCIPVAPHIKVESHIQPSL<br>NQEDIYITTESLTTAAGRPGTGEHVPGSEMPVPDYTSIHIVQSPQGLILNATALPLPDKEFLSSCGYVST<br>DQLNKIMP | 12 |
| >XP_016855859.1 granulocyte colony-stimulating factor receptor isoform X1 [*Homo sapiens*]<br>MARLGNCSLTWAALIILLLPGSLEECGHISVSAPIVHLGDPITASCIIKQNCSHLDPEPQILWRLGAELQ<br>PGGRQQRLSDGTQESIITLPHLNHTQAFLSCCLNWGNSLQILDQVELRAGYPPAIPHNLSCLMNLTTSSL<br>ICQWEPGPETHLPTSFTLKSFKSRGNCQTQGDSILDCVPKDGQSHCCIPRKHLLLYQNMGIWVQAENALG<br>TSMSPQLCLDPMDVVKLEPPMLRTMDPSPEAAPPQAGCLQLCWEPWQPGLHINQKCELRHKPQRGEASWA<br>LVGPLPLEALQYELCGLLPATAYTLQIRCIRWPLPGHWSDWSPSLELRTTERAPTVRLDTWWRQRQLDPR<br>TVQLFWKPVPLEEDSGRIQGYVVSWRPSGQAGAILPLCNTTELSCTFHLPSEAQEVALVAYNSAGTSRPT<br>PVVFSESRGPALTRLHAMARDPHSLWVGWEPPNPWPQGYVIEWGLGPPSASNSNKTWRMEQNGRATGFLL<br>KENIRPFQLYEIIVTPLYQDTMGPSQHVYAYSQEMAPSHAPELHLKHIGKTWAQLEWVPEPPELGKSPLT<br>HYTIFWTNAQNQSFSAILNASSRGFVLHGLEPASLYHIHLMAASQAGATNSTVLTLMTLTPEGSELHIIL<br>GLFGLLLLLTCLCGTAWLCCSPNRKNPLWPSVPDPAHSSLGSWVPTIMEELPGPRQGQWLGQTSEMSRAL<br>TPHPCVQDAFQLPGLGTPPITKLTVLEEDEKKPVPWESHNSSETCGLPTLVQTYVLQGDPRAVSTQPQSQ<br>SGTSDQVLYGQLLGSPTSPGPGHYLRCDSTQPLLAGLTPSPKSYENLWFQASPLGTLVTPAPSQEDDCVF<br>GPLLNFPLLQGIRVHGMEALGSF | 13 |

TABLE 3-continued

| Exemplary Naturally Occurring Receptors | |
|---|---|
| Naturally Occurring Receptor Name | SEQ ID NO: |
| >NP_005364.1 thrombopoietin receptor precursor [*Homo sapiens*]<br>MPSWALFMVTSCLLLAPQNLAQVSSQDVSLLASDSEPLKCFSRTFEDLTCFWDEEEAAPSGTYQLLYAYP<br>REKPRACPLSSQSMPHFGTRYVCQFPDQEEVRLFFPLHLWVKNVFLNQTRTQRVLFVDSVGLPAPPSIIK<br>AMGGSQPGELQISWEEPAPEISDFLRYELRYGPRDPKNSTGPTVIQLIATETCCPALQRPHSASALDQSP<br>CAQPTMPWQDGPKQTSPSREASALTAEGGSCLISGLQPGNSYWLQLRSEPDGISLGGSWGSWSLPVTVDL<br>PGDAVALGLQCFTLDLKNVTCQWQQQDHASSQGFFYHSRARCCPRDRYPIWENCEEEEKTNPGLQTPQFS<br>RCHFKSRNDSIIHILVEVTTAPGTVHSYLGSPFWIHQAVRLPTPNLHWREISSGHLELEWQHPSSWAAQE<br>TCYQLRYTGEGHQDWKVLEPPLGARGGTLELRPRSRYRLQLRARLNGPTYQGPWSSWSDPTRVETATETA<br>WISLVTALHLVLGLSAVLGLLLLRWQFPAHYRRLRHALWPSLPDLHRVLGQYLRDTAALSPPKATVSDTC<br>EEVEPSLLEILPKSSERTPLPLCSSQAQMDYRRLQPSCLGTMPLSVCPPMAESGSCCTTHIANHSYLPLS<br>YWQQP | 131 |

In some embodiments, the transmembrane domain of the disclosure is derived from a truncated, or otherwise modified version of the naturally occurring TPOR/MPLR receptor shown in Table 3.

FIGS. 10A-B show the amino acid sequences for the wild type TpoR and the various transmembrane deletion (FIG. 10A) or insertion (FIG. 10B) variants.

Table 4 shows exemplary transmembrane amino acid sequences, coupled to intracellular JAK2 binding domain sequences.

In some embodiments, the transmembrane domain of the PD-1 chimeric cytokine receptor comprises the amino acid sequence of SEQ ID NO: 14. In some embodiments, the transmembrane domain of the PD-1 chimeric cytokine receptor comprises the amino acid sequence of SEQ ID NO: 15. In some embodiments, the transmembrane domain of the PD-1 chimeric cytokine receptor comprises the amino acid sequence of SEQ ID NO: 16. In some embodiments, the transmembrane domain of the PD-1 chimeric cytokine receptor comprises the amino acid sequence of SEQ ID NO: 17. In some embodiments, the transmembrane domain of the PD-1 chimeric cytokine receptor comprises the amino acid sequence of SEQ ID NO: 18. In some embodiments, the transmembrane domain of the PD-1 chimeric cytokine receptor comprises the amino acid sequence of SEQ ID NO: 19. In some embodiments, the transmembrane domain of the PD-1 chimeric cytokine receptor comprises the amino acid sequence of SEQ ID NO: 20. In some embodiments, the transmembrane domain of the PD-1 chimeric cytokine receptor comprises the amino acid sequence of SEQ ID NO: 21. In some embodiments, the transmembrane domain of the PD-1 chimeric cytokine receptor comprises the amino acid sequence of SEQ ID NO: 22. In some embodiments, the transmembrane domain of the PD-1 chimeric cytokine receptor comprises the amino acid sequence of SEQ ID NO: 23. In some embodiments, the transmembrane domain of the PD-1 chimeric cytokine receptor comprises the amino acid sequence of SEQ ID NO: 24. In some embodiments, the transmembrane domain of the PD-1 chimeric cytokine receptor comprises the amino acid sequence of SEQ ID NO: 25. In some embodiments, the transmembrane domain of the PD-1 chimeric cytokine receptor comprises the amino acid sequence of SEQ ID NO: 26. In some embodiments, the transmembrane domain of the PD-1 chimeric cytokine receptor comprises the amino acid sequence of SEQ ID NO: 27. In some embodiments, the transmembrane domain of the PD-1 chimeric cytokine receptor comprises the amino acid sequence of SEQ ID NO: 28. In some embodiments, the transmembrane domain of the PD-1 chimeric cytokine receptor comprises the amino acid sequence of SEQ ID NO: 29. In some embodiments, the transmembrane domain of the PD-1 chimeric cytokine receptor comprises the amino acid sequence of SEQ ID NO: 30. In some embodiments, the transmembrane domain of the PD-1 chimeric cytokine receptor comprises the amino acid sequence of SEQ ID NO: 31. In some embodiments, the transmembrane domain of the PD-1 chimeric cytokine receptor comprises the amino acid sequence of SEQ ID NO: 32. In some embodiments, the transmembrane domain of the PD-1 chimeric cytokine receptor comprises the amino acid sequence of SEQ ID NO: 33. In some embodiments, the transmembrane domain of the PD-1 chimeric cytokine receptor comprises the amino acid sequence of SEQ ID NO: 34. In some embodiments, the transmembrane domain of the PD-1 chimeric cytokine receptor comprises the amino acid sequence of SEQ ID NO: 35. In some embodiments, the transmembrane domain of the PD-1 chimeric cytokine receptor comprises the amino acid sequence of SEQ ID NO: 36. In some embodiments, the transmembrane domain of the PD-1 chimeric cytokine receptor comprises the amino acid sequence of SEQ ID NO: 37. In some embodiments, the transmembrane domain of the PD-1 chimeric cytokine receptor comprises the amino acid sequence of SEQ ID NO: 38. In some embodiments, the transmembrane domain of the PD-1 chimeric cytokine receptor comprises the amino acid sequence of SEQ ID NO: 39. In some embodiments, the transmembrane domain of the PD-1 chimeric cytokine receptor comprises the amino acid sequence of SEQ ID NO: 40. In some embodiments, the transmembrane domain of the PD-1 chimeric cytokine receptor comprises the amino acid sequence of SEQ ID NO: 41. In some embodiments, the transmembrane domain of the PD-1 chimeric cytokine receptor comprises the amino acid sequence of SEQ ID NO: 42. In some embodiments, the transmembrane domain of the PD-1 chimeric cytokine receptor comprises the amino acid sequence of SEQ ID NO: 43. In some embodiments, the transmembrane domain of the PD-1 chimeric cytokine receptor comprises the amino acid sequence of SEQ ID NO: 44. In some embodiments, the transmembrane domain of the PD-1 chimeric cytokine receptor comprises the amino acid sequence of SEQ ID NO: 134. In some embodiments, the transmembrane domain of the PD-1 chimeric cytokine receptor comprises the amino acid sequence of SEQ ID NO: 135. In some embodiments, the PD-1 chimeric cytokine receptor of the disclosure comprises an amino acid sequence of the transmembrane+JAK2 binding domain that is at least 80%, 85%, 90%, 95%, 98%, 99%, or 100% identical to the amino acid sequence of any one of the sequences shown in Table 4.

TABLE 4

| Exemplary Transmembrane + JAK2 Binding Domain Sequences | | |
|---|---|---|
| Transmembrane and JAK2 binding domain | Amino acid sequence | SEQ ID NO: |
| GCSFR(614-710) | LTLMTLTPEGSELHIILGLFGLLLLLTCLCGTAWL CCSPNRKNPLWPSVPDPAHSSLGSWVPTIMEEDA FQLPGLGTPPITKLTVLEEDEKKPVPWE | 14 |
| GP130(609-700) | TTPKFAQGEIEAIVVPVCLAFLLTTLLGVLFCFNK RDLIKKHIWPNVPDPSKSHIAQWSPHTPPRHNFN SKDQMYSDGNFTDVSVVEIEAND | 15 |
| TPOR/MPLR(478-582) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PL | 16 |
| TPOR/MPLR(N-1) | SDPTRVETATETWISLVTALHLVLGLSAVLGLLL LRWQFPAHYRRLRHALWPSLPDLHRVLGQYLRD TAALSPPKATVSDTCEEVEPSLLEILPKSSERTPLP L | 17 |
| TPOR/MPLR(N-2) | SDPTRVETATETISLVTALHLVLGLSAVLGLLLLR WQFPAHYRRLRHALWPSLPDLHRVLGQYLRDT AALSPPKATVSDTCEEVEPSLLEILPKSSERTPLPL | 18 |
| TPOR/MPLR(N-2 + 1) | SDPTRVETATETLISLVTALHLVLGLSAVLGLLLL RWQFPAHYRRLRHALWPSLPDLHRVLGQYLRDT AALSPPKATVSDTCEEVEPSLLEILPKSSERTPLPL | 19 |
| TPOR/MPLR(N-3) | SDPTRVETATETSLVTALHLVLGLSAVLGLLLLR WQFPAHYRRLRHALWPSLPDLHRVLGQYLRDT AALSPPKATVSDTCEEVEPSLLEILPKSSERTPLPL | 20 |
| TPOR/MPLR(N-4) | SDPTRVETATETLVTALHLVLGLSAVLGLLLLRW QFPAHYRRLRHALWPSLPDLHRVLGQYLRDTAA LSPPKATVSDTCEEVEPSLLEILPKSSERTPLPL | 21 |
| TPOR/MPLR(N-4 + 1) | SDPTRVETATETILVTALHLVLGLSAVLGLLLLR WQFPAHYRRLRHALWPSLPDLHRVLGQYLRDT AALSPPKATVSDTCEEVEPSLLEILPKSSERTPLPL | 22 |
| TPOR/MPLR(N-5) | SDPTRVETATETVTALHLVLGLSAVLGLLLLRW QFPAHYRRLRHALWPSLPDLHRVLGQYLRDTAA LSPPKATVSDTCEEVEPSLLEILPKSSERTPLPL | 23 |
| TPOR/MPLR(N-6) | SDPTRVETATETTALHLVLGLSAVLGLLLLRWQF PAHYRRLRHALWPSLPDLHRVLGQYLRDTAALS PPKATVSDTCEEVEPSLLEILPKSSERTPLPL | 24 |
| TPOR/MPLR(N-7) | SDPTRVETATETALHLVLGLSAVLGLLLLRWQFP AHYRRLRHALWPSLPDLHRVLGQYLRDTAALSP PKATVSDTCEEVEPSLLEILPKSSERTPLPL | 25 |
| TPOR/MPLR(N-8) | SDPTRVETATETLHLVLGLSAVLGLLLLRWQFPA HYRRLRHALWPSLPDLHRVLGQYLRDTAALSPP KATVSDTCEEVEPSLLEILPKSSERTPLPL | 26 |
| TPOR/MPLR(N-9) | SDPTRVETATETHLVLGLSAVLGLLLLRWQFPAH YRRLRHALWPSLPDLHRVLGQYLRDTAALSPPK ATVSDTCEEVEPSLLEILPKSSERTPLPL | 27 |
| TPOR/MPLR(N-10) | SDPTRVETATETLVLGLSAVLGLLLLRWQFPAHY RRLRHALWPSLPDLHRVLGQYLRDTAALSPPKA TVSDTCEEVEPSLLEILPKSSERTPLPL | 28 |
| TPOR/MPLR(N-11) | SDPTRVETATETVLGLSAVLGLLLLRWQFPAHYR RLRHALWPSLPDLHRVLGQYLRDTAALSPPKAT VSDTCEEVEPSLLEILPKSSERTPLPL | 29 |
| TPOR/MPLR(N-12) | SDPTRVETATETLGLSAVLGLLLLRWQFPAHYRR LRHALWPSLPDLHRVLGQYLRDTAALSPPKATV SDTCEEVEPSLLEILPKSSERTPLPL | 30 |
| TPOR/MPLR(N-13) | SDPTRVETATETGLSAVLGLLLLRWQFPAHYRRL RHALWPSLPDLHRVLGQYLRDTAALSPPKATVS DTCEEVEPSLLEILPKSSERTPLPL | 31 |

TABLE 4-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N-14) | SDPTRVETATETLSAVLGLLLLRWQFPAHYRRLR HALWPSLPDLHRVLGQYLRDTAALSPPKATVSD TCEEVEPSLLEILPKSSERTPLPL | 32 |
| TPOR/MPLR(N-15) | SDPTRVETATETSAVLGLLLLRWQFPAHYRRLRH ALWPSLPDLHRVLGQYLRDTAALSPPKATVSDT CEEVEPSLLEILPKSSERTPLPL | 33 |
| TPOR/MPLR(N-16) | SDPTRVETATETAVLGLLLLRWQFPAHYRRLRH ALWPSLPDLHRVLGQYLRDTAALSPPKATVSDT CEEVEPSLLEILPKSSERTPLPL | 34 |
| TPOR/MPLR(N-17) | SDPTRVETATETVLGLLLLRWQFPAHYRRLRHA LWPSLPDLHRVLGQYLRDTAALSPPKATVSDTCE EVEPSLLEILPKSSERTPLPL | 35 |
| TPOR/MPLR(N-18) | SDPTRVETATETLGLLLLRWQFPAHYRRLRHAL WPSLPDLHRVLGQYLRDTAALSPPKATVSDTCEE VEPSLLEILPKSSERTPLPL | 36 |
| TPOR/MPLR(N+1) | SDPTRVETATETAWLISLVTALHLVLGLSAVLGL LLLRWQFPAHYRRLRHALWPSLPDLHRVLGQYL RDTAALSPPKATVSDTCEEVEPSLLEILPKSSERTP LPL | 37 |
| TPOR/MPLR(N+2) | SDPTRVETATETAWVLISLVTALHLVLGLSAVLG LLLLRWQFPAHYRRLRHALWPSLPDLHRVLGQY LRDTAALSPPKATVSDTCEEVEPSLLEILPKSSER TPLPL | 38 |
| TPOR/MPLR(N + 3) | SDPTRVETATETAWLVLISLVTALHLVLGLSAVL GLLLLRWQFPAHYRRLRHALWPSLPDLHRVLGQ YLRDTAALSPPKATVSDTCEEVEPSLLEILPKSSE RTPLPL | 39 |
| TPOR/MPLR(N + 4) | SDPTRVETATETAWILVLISLVTALHLVLGLSAVL GLLLLRWQFPAHYRRLRHALWPSLPDLHRVLGQ YLRDTAALSPPKATVSDTCEEVEPSLLEILPKSSE RTPLPL | 40 |
| TPOR/MPLR(N + 5) | SDPTRVETATETAWLILVLISLVTALHLVLGLSAV LGLLLLRWQFPAHYRRLRHALWPSLPDLHRVLG QYLRDTAALSPPKATVSDTCEEVEPSLLEILPKSS ERTPLPL | 41 |
| TPOR/MPLR(N + 6) | SDPTRVETATETAWLLILVLISLVTALHLVLGLSA VLGLLLLRWQFPAHYRRLRHALWPSLPDLHRVL GQYLRDTAALSPPKATVSDTCEEVEPSLLEILPKS SERTPLPL | 42 |
| TPOR/MPLR(N + 7) | SDPTRVETATETAWVLLILVLISLVTALHLVLGLS AVLGLLLLRWQFPAHYRRLRHALWPSLPDLHRV LGQYLRDTAALSPPKATVSDTCEEVEPSLLEILPK SSERTPLPL | 43 |
| TPOR/MPLR(N + 8) | SDPTRVETATETAWLVLLILVLISLVTALHLVLGL SAVLGLLLLRWQFPAHYRRLRHALWPSLPDLHR VLGQYLRDTAALSPPKATVSDTCEEVEPSLLEILP KSSERTPLPL | 44 |
| TPOR/MPLR(478-582; H499L, S505N, W515K) | SDPTRVETATETAWISLVTAL**L**LVLGL**N**AVLGLL LLR**K**QFPAHYRRLRHALWPSLPDLHRVLGQYLR DTAALSPPKATVSDTCEEVEPSLLEILPKSSERTPL PL | 134 |
| TPOR/MPLR(478-582; S505N, W515K) | SDPTRVETATETAWISLVTALHLVLGL**N**AVLGLL LLR**K**QFPAHYRRLRHALWPSLPDLHRVLGQYLR DTAALSPPKATVSDTCEEVEPSLLEILPKSSERTPL PL | 135 |

C. Janus Kinase (JAK)-Binding Domains

The PD-1 chimeric cytokine receptors of the disclosure comprise intracellular JAK-binding domains. The JAK-binding domain is coupled to the C-terminus of the transmembrane domain, either directly, or via a linker. In some embodiments, the linker can comprise one or more amino acid residues. The JAK-binding domain is coupled to the transmembrane domain on the intracellular side of the chimeric cytokine receptor.

In some embodiments, the JAK-binding domain is a JAK-1-binding domain, a JAK-2 binding domain, a JAK-3 binding domain, or a TYK2 binding domain.

In some embodiments, the JAK-binding domains of the PD-1 chimeric cytokine receptors of the disclosure are naturally occurring, and derived from a naturally occurring receptor.

In some embodiments, the JAK-binding domains of the PD-1 chimeric cytokine receptors of the disclosure are synthetic.

Table 4 provides exemplary amino acid sequences for Transmembrane and JAK2 Binding domains of the disclosure.

D. Recruiting Domains

The PD-1 chimeric cytokine receptors of the disclosure comprise cytoplasmic domains comprising recruiting domains. The recruiting domain can be a STAT-recruiting domain, an AP1-recruiting domain, a Myc/Max-recruiting domain; or an NFkB-recruiting domain. In some embodiments, the recruiting domain is a Signal Transducer and Activator of Transcription (STAT)—recruiting (Stat-activating) domains from receptor tails (cytotails) or from cytokine receptor tails. These intracellular recruiting domains of the PD-1 chimeric cytokine receptors of the disclosure allow for the propagation of Signal 3 in an immune cell comprising a CAR and a chimeric cytokine receptor (e.g. a CAR-T-cell with a chimeric cytokine receptor of the disclosure). Cytokine signaling propagated through the Stat-recruiting domain allows for the cytokine-based immune potentiation of the cell. In some embodiments, the immune-potentiation is homeostatic, e.g. signaling gives rise to increase in immune cells bearing the CAR. In some embodiments, the immune-potentiation is inflammatory, e.g. signaling gives rise to increase in the potency of the immune cells bearing the CAR. In some embodiments, the immune-potentiation prevents exhaustion, e.g. signaling maintains the long-term functionality of immune cells bearing the CAR.

In some embodiments, the recruiting domains of the disclosure are synthetic, and do not resemble any naturally occurring receptor fragment.

In some embodiments, the Stat-recruiting domains of the disclosure are synthetic, and do not resemble any naturally occurring receptor fragment.

In some embodiments the recruiting domain is connected to the C-terminus of the JAK binding domain, either directly, or via a linker. In some embodiments, the linker can comprise one or more amino acid residues.

In other embodiments, the Stat-recruiting domains of the disclosure are derived from cytoplasmic tails of naturally occurring receptors, e.g. derived from naturally occurring cytokine receptors. These cytoplasmic tails of naturally occurring receptors may be the regions downstream of the JAK-activating domains of the transmembrane domain of the receptor. The Stat-recruiting domains of the chimeric cytokine receptors comprise at least one STAT-recruiting domain from at least one receptor. In some embodiments, the Stat-recruiting domain comprises at least one STAT1-recruiting domain. In some embodiments, the Stat-recruiting domain comprises at least one STAT2-recruiting domain. In some embodiments, the Stat-recruiting domain comprises at least one STAT3-recruiting domain. In some embodiments, the Stat-recruiting domain comprises at least one STAT4-recruiting domain. In some embodiments, the Stat-recruiting domain comprises at least one STAT5-recruiting domain. In some embodiments, the Stat-recruiting domain comprises at least one STAT6-recruiting domain. In some embodiments, the Stat-recruiting domain comprises at least one STAT7-recruiting domain.

In some embodiments, the naturally occurring receptor from which the Stat-recruiting domain is derived, is a not a cytokine receptor.

In some embodiments, the naturally occurring receptor from which the Stat-recruiting domain is derived, is a cytokine receptor. Exemplary cytokine receptors through which T-cell-immune potentiating cytokines signal include, but are not limited to IL-2 receptor, IL-7 receptor, IL-15 receptor and IL-21 receptor. In alternative embodiments, the receptor from which the Stat-recruiting domain is derived, is not a cytokine receptor. By choosing the Stat-recruiting domain of the chimeric cytokine receptor, the receptor can be redirected to signaling of choice.

Table 5 provides exemplary receptors from which Stat-recruiting domains of the chimeric cytokine receptors of the disclosure are derived. Table 6a provides exemplary amino acid sequences of recruiting domains of the disclosure.

In some embodiments, the PD-1 chimeric cytokine receptor of the disclosure comprises the amino acid sequence of the STAT-recruiting domain of SEQ ID NO: 45. In some embodiments, the PD-1 chimeric cytokine receptor of the disclosure comprises the amino acid sequence of the STAT-recruiting domain of SEQ ID NO: 46. In some embodiments, the PD-1 chimeric cytokine receptor of the disclosure comprises the amino acid sequence of the STAT-recruiting domain of SEQ ID NO: 47. In some embodiments, the PD-1 chimeric cytokine receptor of the disclosure comprises the amino acid sequence of the STAT-recruiting domain of SEQ ID NO: 48. In some embodiments, the PD-1 chimeric cytokine receptor of the disclosure comprises the amino acid sequence of the STAT-recruiting domain of SEQ ID NO: 49. In some embodiments, the PD-1 chimeric cytokine receptor of the disclosure comprises the amino acid sequence of the STAT-recruiting domain of SEQ ID NO: 50. In some embodiments, the PD-1 chimeric cytokine receptor of the disclosure comprises the amino acid sequence of the STAT-recruiting domain of SEQ ID NO: 51. In some embodiments, the PD-1 chimeric cytokine receptor of the disclosure comprises the amino acid sequence of the STAT-recruiting domain of SEQ ID NO: 52. In some embodiments, the PD-1 chimeric cytokine receptor of the disclosure comprises the amino acid sequence of the STAT-recruiting domain of SEQ ID NO: 53. In some embodiments, the PD-1 chimeric cytokine receptor of the disclosure comprises the amino acid sequence of the STAT-recruiting domain of SEQ ID NO: 54. In some embodiments, the PD-1 chimeric cytokine receptor of the disclosure comprises the amino acid sequence of the STAT-recruiting domain of SEQ ID NO: 55. In some embodiments, the PD-1 chimeric cytokine receptor of the disclosure comprises the amino acid sequence of the STAT-recruiting domain of SEQ ID NO: 56. In some embodiments, the PD-1 chimeric cytokine receptor of the disclosure comprises the amino acid sequence of the STAT-recruiting domain of SEQ ID NO: 57. In some embodiments, the PD-1 chimeric cytokine receptor of the disclosure comprises the amino acid sequence of the STAT-recruiting domain of SEQ ID NO: 58. In some embodiments, the PD-1 chimeric cytokine receptor of the disclosure comprises the amino acid sequence of the STAT-recruiting domain of SEQ ID NO: 59. In some embodiments, the PD-1 chimeric cytokine receptor of the disclosure comprises the amino acid sequence of the STAT-recruiting domain of SEQ ID NO: 60. In some embodiments, the PD-1 chimeric cytokine receptor of the disclosure comprises the amino acid sequence of the STAT-recruiting domain of SEQ ID NO: 61. In some embodiments, the PD-1 chimeric cytokine receptor of the disclosure comprises the amino acid sequence of the STAT-recruiting domain of SEQ ID NO: 62. In some embodiments, the PD-1 chimeric cytokine receptor of the disclosure comprises the amino acid sequence of the STAT-recruiting domain of SEQ ID NO: 63. In some embodiments, the PD-1 chimeric cytokine receptor of the disclosure comprises the amino acid sequence of the STAT-recruiting domain of SEQ ID NO: 64. In some embodiments, the PD-1 chimeric cytokine receptor of the disclosure comprises the amino acid sequence of the STAT-recruiting domain of SEQ ID NO: 65. In some embodiments, the PD-1 chimeric cytokine receptor of the disclosure comprises the amino acid sequence of the STAT-recruiting domain of SEQ ID NO: 66. In some embodiments, the PD-1 chimeric cytokine receptor of the disclosure comprises the amino acid sequence of the STAT-recruiting domain of SEQ ID NO: 67. In some embodiments, the PD-1 chimeric cytokine receptor of the disclosure comprises the amino acid sequence of the STAT-recruiting domain of SEQ ID NO: 68. In some embodiments, the PD-1 chimeric cytokine receptor of the disclosure comprises the amino acid sequence of the STAT-recruiting domain of SEQ ID NO: 69. In some embodiments, the PD-1 chimeric cytokine receptor of the disclosure comprises the amino acid sequence of the STAT-recruiting domain of SEQ ID NO: 70. In some embodiments, the PD-1 chimeric cytokine receptor of the disclosure comprises the amino acid sequence of the STAT-recruiting domain of SEQ ID NO: 71. In some embodiments, the PD-1 chimeric cytokine receptor of the disclosure comprises the amino acid sequence of the STAT-recruiting domain of SEQ ID NO: 72. In some embodiments, the PD-1 chimeric cytokine receptor of the disclosure comprises the amino acid sequence of the STAT-recruiting domain of SEQ ID NO: 73. In some embodiments, the PD-1 chimeric cytokine receptor of the disclosure comprises the amino acid sequence of the STAT-recruiting domain of SEQ ID NO: 74. In some embodiments, the PD-1 chimeric cytokine receptor of the disclosure comprises the amino acid sequence of the STAT-recruiting domain of SEQ ID NO: 75. In some embodiments, the PD-1 chimeric cytokine receptor of the disclosure comprises the amino acid sequence of the STAT-recruiting domain of SEQ ID NO: 76. In some embodiments, the PD-1 chimeric cytokine receptor of the disclosure comprises the amino acid sequence of the STAT-recruiting domain of SEQ ID NO: 77. In some embodiments, the PD-1 chimeric cytokine receptor of the disclosure comprises the amino acid sequence of the STAT-recruiting domain of SEQ ID NO: 78. In some embodiments, the PD-1 chimeric cytokine receptor of the disclosure comprises the amino acid sequence of the STAT-recruiting domain of SEQ ID NO: 79. In some embodiments, the PD-1 chimeric cytokine receptor of the disclosure comprises the amino acid sequence of the STAT-recruiting domain of SEQ ID NO: 80. In some embodiments, the PD-1 chimeric cytokine receptor of the disclosure comprises the amino acid sequence of the STAT-recruiting domain of SEQ ID NO: 81. In some embodiments, the PD-1 chimeric cytokine receptor of the disclosure comprises the amino acid sequence of the STAT-recruiting domain of SEQ ID NO: 82. In some embodiments, the PD-1 chimeric cytokine receptor of the disclosure comprises the amino acid sequence of the STAT-recruiting domain of SEQ ID NO: 83. In some embodiments, the PD-1 chimeric cytokine receptor of the disclosure comprises the amino acid sequence of the STAT-recruiting domain of SEQ ID NO: 84. In some embodiments, the PD-1 chimeric cytokine receptor of the disclosure comprises the amino acid sequence of the STAT-recruiting domain of SEQ ID NO: 85. In some embodiments, the PD-1 chimeric cytokine receptor of the disclosure comprises the amino acid sequence of the STAT-recruiting domain of SEQ ID NO: 86. In some embodiments, the PD-1 chimeric cytokine receptor of the disclosure comprises the amino acid sequence of the STAT-recruiting domain of SEQ ID NO: 87. In some embodiments, the PD-1 chimeric cytokine receptor of the disclosure comprises the amino acid sequence of the STAT-recruiting domain of SEQ ID NO: 170. In some embodiments, the PD-1 chimeric cytokine receptor of the disclosure comprises the amino acid sequence of the STAT-recruiting domain of SEQ ID NO: 171. In some embodiments, the PD-1 chimeric cytokine receptor of the disclosure comprises an amino acid sequence of the STAT-recruiting domain that is at least 80%, 85%, 90%, 95%, 98%, 99%, or 100% identical to the amino acid sequence of any one of the sequences shown in Table 6a.

TABLE 5

| Source for recruiting domains |
|---|
| BLNK |
| IL2RG |
| EGFR |
| EpoR |
| GHR |
| IFNAR1 |
| IFNAR2 |
| IFNAR1/2 |
| IFNLR1 |
| IL10R1 |
| IL12Rb1 |
| IL12Rb2 |
| IL21R |
| IL2Rb |
| IL2small |
| IL7R |
| IL7Ra |
| IL9R |
| IL15R |
| IL21R |

TABLE 6a

Recruiting domain Sequences (Cytotail Sequences)

| Recruiting domain | Amino acid sequence | SEQ ID NO: |
|---|---|---|
| IL7R(316-459) | ARDEVEGFLQDTFPQQLEESEKQRLGGDVQSPN<br>CPSEDVVITPESFGRDSSLTCLAGNVSACDAPILS<br>SSRSLDCRESGKNGPHVYQDLLLSLGTTNSTLPPP | 45 |

TABLE 6a-continued

| Recruiting domain Sequences (Cytotail Sequences) | | |
|---|---|---|
| Recruiting domain | Amino acid sequence | SEQ ID NO: |
| | FSLQSGILTLNPVAQGQPILTSLGSNQEEAYVTMS SFYQNQ | |
| IL2Rb(333-551) | VTQLLLQQDKVPEPASLSSNHSLTSCFTNQGYFF FHLPDALEIEACQVYFTYDPYSEEDPDEGVAGAP TGSSPQPLQPLSGEDDAYCTFPSRDDLLLFSPSLL GGPSPPSTAPGGSGAGEERMPPSLQERVPRDWDP QPLGPPTPGVPDLVDFQPPPELVLREAGEEVPDA GPREGVSFPWSRPPGQGEFRALNARLPLNTDAYL SLQELQGQDPTHLV | 46 |
| IFNAR1(508-557) | ISTIATVEETNQTDEDHKKYSSQTSQDSGNYSNE DESESKTSEELQQDFV | 47 |
| IFNAR2(310-515) | KKKVWDYNYDDESDSDTEAAPRTSGGGYTMHG LTVRPLGQASATSTESQLIDPESEEEPDLPEVDVE LPTMPKDSPQQLELLSGPCERRKSPLQDPFPEEDY SSTEGSGGRITFNVDLNSVFLRVLDDEDSDDLEA PLMLSSHLEEMVDPEDPDNVQSNHLLASGEGTQ PTFPSPSSEGLWSEDAPSDQSDTSESDVDLGDGYI MR | 48 |
| IFNAR1/2(IFNAR1 residues 508-557-IFNAR2 residues 310-515) | ISTIATVEETNQTDEDHKKYSSQTSQDSGNYSNE DESESKTSEELQQDFVKKKVWDYNYDDESDSDT EAAPRTSGGGYTMHGLTVRPLGQASATSTESQLI DPESEEEPDLPEVDVELPTMPKDSPQQLELLSGPC ERRKSPLQDPFPEEDYSSTEGSGGRITFNVDLNSV FLRVLDDEDSDDLEAPLMLSSHLEEMVDPEDPD NVQSNHLLASGEGTQPTFPSPSSEGLWSEDAPSD QSDTSESDVDLGDGYIMR | 49 |
| IFNLR1(300-520) | RGVRPTPRVRAPATQQTRWKKDLAEDEEEEDEE DTEDGVSFQPYIEPPSFLGQEHQAPGHSEAGGVD SGRPRAPLVPSEGSSAWDSSDRSWASTVDSSWD RAGSSGYLAEKGPGQGPGGDGHQESLPPPEFSKD SGFLEELPEDNLSSWATWGTLPPEPNLVPGGPPV SLQTLTFCWESSPEEEEEARESEIEDSDAGSWGAE STQRTEDRGRTLGHYMAR | 50 |
| Common Gamma Chain(335-369) | IPPKGGALGEGPGASPCNQHSPYWAPPCYTLKPE T | 51 |
| IL9R(356-521) | TALLTCGPARPWKSVALEEEQEGPGTRLPGNLSS EDVLPAGCTEWRVQTLAYLPQEDWAPTSLTRPA PPDSEGSRSSSSSSSSNNNNYCALGCYGGWHLSA LPGNTQSSGPIPALACGLSCDHQGLETQQGVAW VLAGHCQRPGLHEDLQGMLLPSVLSKARSWTF | 52 |
| IL21R(322-538) | PRSPAKRLQLTELQEPAELVESDGVPKPSFWPTA QNSGGSAYSEERDRPYGLVSIDTVTVLDAEGPCT WPCSCEDDGYPALDLDAGLEPSPGLEDPLLDAG TTVLSCGCVSAGSPGLGGPLGSLLDRLKPPLADG EDWAGGLPWGGRSPGGVSESEAGSPLAGLDMD TFDSGFVGSDCSSPVECDFTSPGDEGPPRSYLRQ WVVIPPPLSSPGPQAS | 53 |
| GHR(353-638) | PDEKTEESDTDRLLSSDHEKSHSNLGVKDGDSGR TSCCEPDILETDFNANDIHEGTSEVAQPQRLKGE ADLLCLDQKNQNNSPYHDACPATQQPSVIQAEK NKPQPLPTEGAESTHQAAHIQLSNPSSLSNIDFYA QVSDITPAGSVVLSPGQKNKAGMSQCDMHPEM VSLCQENFLMDNAYFCEADAKKCIPVAPHIKVES HIQPSLNQEDIYITTESLTTAAGRPGTGEHVPGSE MPVPDYTSIHIVQSPQGLILNATALPLPDKEFLSS CGYVSTDQLNKIMP | 54 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 55 |
| murine IL2Rb(337-539) | AVQLLLLQKDSAPLPSPSGHSQASCFTNQGYFFF HLPNALEIESCQVYFTYDPCVEEEVEEDGSRLPE GSPHPPLLPLAGEQDDYCAFPPRDDLLLFSPSLST | 56 |

TABLE 6a-continued

| Recruiting domain Sequences (Cytotail Sequences) | | |
|---|---|---|
| Recruiting domain | Amino acid sequence | SEQ ID NO: |
| | PNTAYGGSRAPEERSPLSLHEGLPSLASRDLMGL QRPLERMPEGDGEGLSANSSGEQASVPEGNLHG QDQDRGQGPILTLNTDAYLSLQELQAQDSVHLI | |
| murine IL7Ra(316-459) | ARDEVESFLPNDLPAQPEELETQGHRAAVHSAN RSPETSVSPPETVRRESPLRCLARNLSTCNAPPLL SSRSPDYRDGDRNRPPVYQDLLPNSGNTNVPVPV PQPLPFQSGILIPVSQRQPISTSSVLNQEEAYVTMS SFYQNK | 57 |
| EGFR(955-1186) | VIQGDERMHLPSPTDSNFYRALMDEEDMDDVVD ADEYLIPQQGFFSSPSTSRTPLLSSLSATSNNSTVA CIDRNGLQSCPIKEDSFLQRYSSDPTGALTEDSID DTFLPVPEYINQSVPKRPAGSVQNPVYHNQPLNP APSRDPHYQDPHSTAVGNPEYLNTVQPTCVNSTF DSPAHWAQKGSHQISLDNPDYQQDFFPKEAKPN GIFKGSTAENAEYLRVAPQSSEFIGA | 58 |
| EGFR(955-1186; Y974F, d1045-1057) | VIQGDERMHLPSPTDSNFFRALMDEEDMDDVVD ADEYLIPQQGFFSSPSTSRTPLLSSLSATSNNSTVA CIDRNGLQSCPIKEDSFLQRIDDTFLPVPEYINQSV PKRPAGSVQNPVYHNQPLNPAPSRDPHYQDPHS TAVGNPEYLNTVQPTCVNSTFDSPAHWAQKGSH QISLDNPDYQQDFFPKEAKPNGIFKGSTAENAEY LRVAPQSSEFIGA | 59 |
| EGFR(955-1009; Y974F) | VIQGDERMHLPSPTDSNFFRALMDEEDMDDVVD ADEYLIPQQGFFSSPSTSRTP | 60 |
| EGFR(1019-1085) | NNSTVACIDRNGLQSCPIKEDSFLQRIDDTFLPVP EYINQSVPKRPAGSVQNPV | 61 |
| EGFR(1037-1103; Y1068/1101F, d1045-1057) | KEDSFLQRIDDTFLPVPEFINQSVPKRPAGSVQNP VYHNQPLNPAPSRDPHFQD | 62 |
| EGFR(1066-1118; Y1068/1086F) | VPEFINQSVPKRPAGSVQNPVFHNQPLNPAPSRD PHYQDPHSTAVGNPEYLNTV | 63 |
| EGFR(1122-1165) | PEYLNTVQPTCVNSTFDSPAHWAQKGSHQISLDN PDYQQDFFPKEAKPNGIFKG | 64 |
| EGFR(1133-1186; Y1148F) | WAQKGSHQISLDNPDFQQDFFPKEAKPNGIFKGS TAENAEYLRVAPQSSEFIGA | 65 |
| IL12Rb2(775-825) | SDPKPENPACPWTVLPAGDLPTHDGYLPSNIDDL PSHEAPLADSLEELEPQ | 66 |
| IL7R(376-416) | ACDAPILSSSRSLDCRESGKNGPHVYQDLLLSLG TTNSTLP | 67 |
| IL7R(424-459) | GILTLNPVAQGQPILTSLGSNQEEAYVTMSSFYQ NQ | 68 |
| IL7R(376-416, 424-459) | ACDAPILSSSRSLDCRESGKNGPHVYQDLLLSLG TTNSTLPQGQPILTSLGSNQEEAYVTMSSFYQNQ | 69 |
| IL7R(424-459; Y456F) | GILTLNPVAQGQPILTSLGSNQEEAYVTMSSFFQN Q | 70 |
| IL7R(376-416, 424-459, Y456F) | ACDAPILSSSRSLDCRESGKNGPHVYQDLLLSLG TTNSTLPQGQPILTSLGSNQEEAYVTMSSFFQNQ | 71 |
| IL2Rbsmall(393-433) | DEGVAGAPTGSSPQPLQPLSGEDDAYCTFPSRDD LLLFSPSGQGEFRALNARLPLNTDAYLSLQELQG QDPTHLV | 72 |
| IL2Rbsmall(518-551) | GQGEFRALNARLPLNTDAYLSLQELQGQDPTHL V | 73 |
| IL2Rbsmall(339-379, 393-433) | QQDKVPEPASLSSNHSLTSCFTNQGYFFFHLPDA LEIEACQDEGVAGAPTGSSPQPLQPLSGEDDAYC TFPSRDDLLLFSPS | 74 |

TABLE 6a-continued

| Recruiting domain Sequences (Cytotail Sequences) | | |
|---|---|---|
| Recruiting domain | Amino acid sequence | SEQ ID NO: |
| IL2Rbsmall(339-379, 518-551) | QQDKVPEPASLSSNHSLTSCFTNQGYFFFHLPDA LEIEACQ GQGEFRALNARLPLNTDAYLSLQELQGQDPTHL V | 75 |
| IL2Rbsmall(393-433, 518-551) | DEGVAGAPTGSSPQPLQPLSGEDDAYCTFPSRDD LLLFSPSGQGEFRALNARLPLNTDAYLSLQELQG QDPTHLV | 76 |
| IL2Rbsmall(339-379, 393-433, 518-551) | QQDKVPEPASLSSNHSLTSCFTNQGYFFFHLPDA LEIEACQDEGVAGAPTGSSPQPLQPLSGEDDAYC TFPSRDDLLLFSPSGQGEFRALNARLPLNTDAYLS LQELQGQDPTHLV | 77 |
| IFNAR2small(310-352) | KKKVWDYNYDDESDSDTEAAPRTSGGGYTMHG LTVRPLGQASA | 78 |
| IFNAR2small(486-515) | EGLWSEDAPSDQSDTSESDVDLGDGYIMR | 79 |
| IFNAR2small(310-352, 486-515) | KKKVWDYNYDDESDSDTEAAPRTSGGGYTMHG LTVRPLGQASA EGLWSEDAPSDQSDTSESDVDLGDGYIMR | 80 |
| BLNK(53-208) | ASESPADEEEQWSDDFDSDYENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 81 |
| BLNK(53-208; Y72F) | ASESPADEEEQWSDDFDSDFENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 82 |
| BLNK(53-208; Y72F, Y96F) | ASESPADEEEQWSDDFDSDFENPDEHSDSEMYV MPAEENADDSFEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 83 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 84 |
| IL12Rb2(714-862) | VTPVFRHPPCSNWPQREKGIQGHQASEKDMMHS ASSPPPPRALQAESRQLVDLYKVLESRGSDPKPE NPACPWTVLPAGDLPTHDGYLPSNIDDLPSHEAP LADSLEELEPQHISLSVFPSSSLHPLTFSCGDKLTL DQLKMRCDSLML | 85 |
| IL12Rb1(622-662) | WDKGERTEPLEKTELPEGAPELALDTELSLEDGD RCKAKM | 86 |
| IL10R1(304-578) | VSPELKNLDLHGSTDSGFGSTKPSLQTEEPQFLLP DPHPQADRTLGNREPPVLGDSCSSGSSNSTDSGIC LQEPSLSPSTGPTWEQQVGSNSRGQDDSGIDLVQ NSEGRAGDTQGGSALGHHSPPEPEVPGEEDPAA VAFQGYLRQTRCAEEKATKTGCLEEESPLTDGL GPKFGRCLVDEAGLHPPALAKGYLKQDPLEMTL ASSGAPTGQWNQPTEEWSLLALSSCSDLGISDWS FAHDLAPLGCVAAPGGLLGSFNSDLVTLPLISSLQ SSE | 87 |
| IL2Rb(333-551, Y381S, Y384S, Y387S) | VTQLLLQQDKVPEPASLSSNHSLTSCFTNQGYFF FHLPDALEIEACQV**S**FT**S**DP**S**SEEDPDEGVAGAPT GSSPQPLQPLSGEDDAYCTFPSRDDLLLFSPSLLG GPSPPSTAPGGSGAGEERMPPSLQERVPRDWDPQ PLGPPTPGVPDLVDFQPPPELVLREAGEEVPDAG PREGVSFPWSRPPGQGEFRALNARLPLNTDAYLS LQELQGQDPTHLV | 170 |

TABLE 6a-continued

| Recruiting domain Sequences (Cytotail Sequences) | | |
|---|---|---|
| Recruiting domain | Amino acid sequence | SEQ ID NO: |
| IL2Rb(333-551, Y364S, Y381S, Y384S, Y387S) | VTQLLLQQDKVPEPASLSSNHSLTSCFTNQGSFFF HLPDALEIEACQVSFTSDPSSEEDPDEGVAGAPTG SSPQPLQPLSGEDDAYCTFPSRDDLLLFSPSLLGG PSPPSTAPGGSGAGEERMPPSLQERVPRDWDPQP LGPPTPGVPDLVDFQPPPELVLREAGEEVPDAGP REGVSFPWSRPPGQGEFRALNARLPLNTDAYLSL QELQGQDPTHLV | 171 |

In some embodiments, the Stat-recruiting domain of a chimeric cytokine receptor of the disclosure comprises a STAT-recruiting domain from one receptor.

In order to generate multiple outputs, one or more STAT-recruiting domains may be joined in tandem to mimic signaling from one or more cytokines.

In some embodiments, the STAT-recruiting domain comprises portions of more than one receptor, e.g. comprising more than one STAT-recruiting domain. In such embodiments, a tandem cytokine signaling domain is provided, allowing for enhanced signaling. Accordingly, in some embodiments, the STAT-recruiting domain of a monomer of the chimeric cytokine receptor of the disclosure comprises the STAT-recruiting domains from more than one receptor, e.g. comprises the STAT-recruiting domains from two, three, four, five, or even six receptors. For example, in some embodiments, STAT-recruiting domains can be linked in tandem to stimulate multiple pathways (e.g., the IL7R(316-459)-IL12Rb2(775-825) fragment fusion for pro-persistence STAT5 and pro-inflammatory STAT4; IL7R(316-459)-IL2Rbsmall(393-433,518-551) for pro-persistence; IL7R (316-459)-EGFR(1122-1165) for pro-persistence and anti-exhaustion; IL2Rbsmall(393-433,518-551)-EGFR(1122-1165) for pro-persistence and anti-exhaustion).

In some embodiments, the more than one STAT-recruiting domains can be connected either directly, or via a linker. In some embodiments, the linker can comprise one or more amino acid residues.

When generating multiple outputs, the proximity of individual STAT-recruiting domains to the cell membrane can influence the strength of their respective signaling outputs. Table 6b shows examples of PD-1 chimeric cytokine receptors with the dual outputs, where each output can be placed either proximal or distal to the cell membrane.

TABLE 6b

| Examples of PD-1 chimeric cytokine receptors with dual outputs | | |
|---|---|---|
| Dual output STAT-recruiting domain | Membrane proximal | Membrane distal |
| IL2Rbsmall(393-433, 518-551)/IL21R(322-538) | IL2Rbsmall(393-433, 518-551) | IL21R(322-538) |
| IL21R(322-538)/IL2Rbsmall(393-433, 518-551) | IL21R(322-538) | IL2Rbsmall(393-433, 518-551) |
| IL2Rbsmall(339-379, 393-433, 518-551)/IL21R(322-538) | IL2Rbsmall(339-379, 393-433, 518-551) | IL21R(322-538) |
| IL21R(322-538)/IL2Rbsmall(339-379, 393-433, 518-551) | IL21R(322-538) | IL2Rbsmall(339-379, 393-433, 518-551) |
| IL7R (316-459)/IL21R(322-538) | IL7R (316-459) | IL21R(322-538) |
| IL21R(322-538)/IL7R (316-459) | IL21R(322-538) | IL7R (316-459) |

Without being bound to theory or mechanism, in some embodiments, a JAK-protein (JAK1, JAK2, JAK3, or TYK2) is bound to a PD-1 chimeric cytokine receptor of the disclosure (comprising a PD-1 ectodomain, a transmembrane domain, a JAK-binding domain, and a recruiting domain). In some embodiments, in the presence of (e.g. binding to) PD-L1, PD-L2, or an anti-PD-1 antibody, the PD-1 chimeric cytokine receptor clusters and allows for the two bound JAK-proteins to become activated, which in turn phosphorylate tyrosine residues on the recruiting domain of the chimeric receptor. The phosphorylated recruiting domains are then capable of binding the recruited proteins (e.g. a phosphorylated STAT-recruiting domain binds a STAT-protein), which in turn effectuate transcription events in the nucleus.

E. Exemplary PD-1 Chimeric Cytokine Receptors

Table 7 shows exemplary context-dependent cytokine receptor sequences of the disclosure. The receptors may be expressed with a signal sequence, e.g. a CD8SS of SEQ ID NO: 1.

In some embodiments, the PD-1 chimeric cytokine receptor of the disclosure comprises the amino acid sequence of SEQ ID NO: 88. In some embodiments, the PD-1 chimeric cytokine receptor of the disclosure comprises the amino acid sequence of SEQ ID NO: 89. In some embodiments, the PD-1 chimeric cytokine receptor of the disclosure comprises the amino acid sequence of SEQ ID NO: 90. In some embodiments, the PD-1 chimeric cytokine receptor of the disclosure comprises the amino acid sequence of SEQ ID NO: 91. In some embodiments, the PD-1 chimeric cytokine receptor of the disclosure comprises the amino acid sequence of SEQ ID NO: 92. In some embodiments, the PD-1 chimeric cytokine receptor of the disclosure comprises the amino acid sequence of SEQ ID NO: 93. In some embodiments, the PD-1 chimeric cytokine receptor of the disclosure comprises the amino acid sequence of SEQ ID NO: 94. In some embodiments, the PD-1 chimeric cytokine receptor of the disclosure comprises the amino acid sequence of SEQ ID NO: 95. In some embodiments, the PD-1 chimeric cytokine receptor of the disclosure comprises the amino acid sequence of SEQ ID NO: 96. In some embodiments, the PD-1 chimeric cytokine receptor of the disclosure comprises the amino acid sequence of SEQ ID NO: 97. In some embodiments, the PD-1 chimeric cytokine receptor of the disclosure comprises the amino acid sequence of SEQ ID NO: 98. In some embodiments, the PD-1 chimeric cytokine receptor of the disclosure comprises the amino acid sequence of SEQ ID NO: 99. In some embodiments, the PD-1 chimeric cytokine receptor of the disclosure comprises the amino acid sequence of SEQ ID NO: 100. In some embodiments, the PD-1 chimeric cytokine receptor of the disclosure comprises the amino acid sequence of SEQ ID NO: 101. In some embodiments, the PD-1 chimeric cytokine receptor of the disclosure comprises the amino acid sequence of SEQ ID NO: 102. In some embodiments, the PD-1 chimeric cytokine receptor of the disclosure comprises the amino acid sequence of SEQ ID NO: 103. In some embodiments, the PD-1 chimeric cytokine receptor of the disclosure comprises the amino acid sequence of SEQ ID NO: 104. In some embodiments, the PD-1 chimeric cytokine receptor of the disclosure comprises the amino acid sequence of SEQ ID NO: 105. In some embodiments, the PD-1 chimeric cytokine receptor of the disclosure comprises the amino acid sequence of SEQ ID NO: 106. In some embodiments, the PD-1 chimeric cytokine receptor of the disclosure comprises the amino acid sequence of SEQ ID NO: 107. In some embodiments, the PD-1 chimeric cytokine receptor of the disclosure comprises the amino acid sequence of SEQ ID NO: 108. In some embodiments, the PD-1 chimeric cytokine receptor of the disclosure comprises the amino acid sequence of SEQ ID NO: 109. In some embodiments, the PD-1 chimeric cytokine receptor of the disclosure comprises the amino acid sequence of SEQ ID NO: 110. In some embodiments, the PD-1 chimeric cytokine receptor of the disclosure comprises the amino acid sequence of SEQ ID NO: 111. In some embodiments, the PD-1 chimeric cytokine receptor of the disclosure comprises the amino acid sequence of SEQ ID NO: 112. In some embodiments, the PD-1 chimeric cytokine receptor of the disclosure comprises the amino acid sequence of SEQ ID NO: 113. In some embodiments, the PD-1 chimeric cytokine receptor of the disclosure comprises the amino acid sequence of SEQ ID NO: 114. In some embodiments, the PD-1 chimeric cytokine receptor of the disclosure comprises the amino acid sequence of SEQ ID NO: 115. In some embodiments, the PD-1 chimeric cytokine receptor of the disclosure comprises the amino acid sequence of SEQ ID NO: 116. In some embodiments, the PD-1 chimeric cytokine receptor of the disclosure comprises the amino acid sequence of SEQ ID NO: 117. In some embodiments, the PD-1 chimeric cytokine receptor of the disclosure comprises the amino acid sequence of SEQ ID NO: 118. In some embodiments, the PD-1 chimeric cytokine receptor of the disclosure comprises the amino acid sequence of SEQ ID NO: 119. In some embodiments, the PD-1 chimeric cytokine receptor of the disclosure comprises the amino acid sequence of SEQ ID NO: 120. In some embodiments, the PD-1 chimeric cytokine receptor of the disclosure comprises the amino acid sequence of SEQ ID NO: 121. In some embodiments, the PD-1 chimeric cytokine receptor of the disclosure comprises the amino acid sequence of any one of SEQ ID NOs: 88-121, SEQ ID NOs: 136-145, and SEQ ID NOs: 172-213. In some embodiments, the PD-1 chimeric cytokine receptor of the disclosure comprises an amino acid sequence that is at least 80%, 85%, 90%, 95%, 98%, 99%, or 100% identical to the amino acid sequence of any one of SEQ ID NOs: 88-121, SEQ ID NOs: 172-213.

TABLE 7

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| WTPD1(21-207). TpoR(478-582). IL7Ra(316-459). IL12Rb2 (775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 88 |
| WTPD1(21-207). GCSFR(614-710). IL7Ra(316-459). IL12Rb2 (775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ LTLMTLTPEGSELHIILGLFGLLLLLTCLCGTAWLCCSPNRKN PLWPSVPDPAHSSLGSWVPTIMEEDAFQLPGLGTPPITKLTVL EEDEKKPVPWE ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 89 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| WTPD1(21-207).<br>GP130(609-700).<br>IL7Ra(316-459).<br>IL12Rb2<br>(775-825) | PGWFLDSPDRPWNPPTFSPALLVVTEGDNATFTCSFSNTSESF<br>VLNWYRMSPSNQTDKLAAFPEDRSQPGQDCRFRVTQLPNGR<br>DFHMSVVRARRNDSGTYLCGAISLAPKAQIKESLRAELRVTE<br>RRAEVPTAHPSPSPRPAGQFQTLVVGVVGGLLGSLVLLVWV<br>LAVICSRAARGTIGARRTGQ<br>TTPKFAQGEIEAIVVPVCLAFLLTTLLGVLFCENKRDLIKKHI<br>WPNVPDPSKSHIAQWSPHTPPRHNFNSKDQMYSDGNFTDVS<br>VVEIEAND<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ | 90 |
| 2xWTPD1(21-207).<br>TpoR(478-582).<br>IL7Ra(316-459).<br>IL12Rb2<br>(775-825) | PGWFLDSPDRPWNPPTFSPALLVVTEGDNATFTCSFSNTSESF<br>VLNWYRMSPSNQTDKLAAFPEDRSQPGQDCRFRVTQLPNGR<br>DFHMSVVRARRNDSGTYLCGAISLAPKAQIKESLRAELRVTE<br>RRAEVPTAHPSPSPRPAGQFQTLVVGVVGGLLGSLVLLVWV<br>LAVICSRAARGTIGARRTGQPGWFLDSPDRPWNPPTFSPALL<br>VVTEGDNATFTCSFSNTSESFVLNWYRMSPSNQTDKLAAFPE<br>DRSQPGQDCRFRVTQLPNGRDFHMSVVRARRNDSGTYLCG<br>AISLAPKAQIKESLRAELRVTERRAEVPTAHPSPSPRPAGQFQ<br>TLVVGVVGGLLGSLVLLVWVLAVICSRAARGTIGARRTGQ<br>SDPTRVETATETAWISLVTALHLVLGLSAVLGLLLLRWQFPA<br>HYRRLRHALWPSLPDLHRVLGQYLRDTAALSPPKATVSDTC<br>EEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 91 |
| 3xWTPD1(21-207).<br>TpoR(478-582).<br>IL7Ra(316-459).<br>IL12Rb2<br>(775-825) | PGWFLDSPDRPWNPPTFSPALLVVTEGDNATFTCSFSNTSESF<br>VLNWYRMSPSNQTDKLAAFPEDRSQPGQDCRFRVTQLPNGR<br>DFHMSVVRARRNDSGTYLCGAISLAPKAQIKESLRAELRVTE<br>RRAEVPTAHPSPSPRPAGQFQTLVVGVVGGLLGSLVLLVWV<br>LAVICSRAARGTIGARRTGQPGWFLDSPDRPWNPPTFSPALL<br>VVTEGDNATFTCSFSNTSESFVLNWYRMSPSNQTDKLAAFPE<br>DRSQPGQDCRFRVTQLPNGRDFHMSVVRARRNDSGTYLCG<br>AISLAPKAQIKESLRAELRVTERRAEVPTAHPSPSPRPAGQFQ<br>TLVVGVVGGLLGSLVLLVWVLAVICSRAARGTIGARRTGQP<br>GWFLDSPDRPWNPPTFSPALLVVTEGDNATFTCSFSNTSESF<br>VLNWYRMSPSNQTDKLAAFPEDRSQPGQDCRFRVTQLPNGR<br>DFHMSVVRARRNDSGTYLCGAISLAPKAQIKESLRAELRVTE<br>RRAEVPTAHPSPSPRPAGQFQTLVVGVVGGLLGSLVLLVWV<br>LAVICSRAARGTIGARRTGQ<br>SDPTRVETATETAWISLVTALHLVLGLSAVLGLLLLRWQFPA<br>HYRRLRHALWPSLPDLHRVLGQYLRDTAALSPPKATVSDTC<br>EEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 92 |
| HAPD1.TpoR<br>(478-582).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETAWISLVTALHLVLGLSAVLGLLLLRWQFPA<br>HYRRLRHALWPSLPDLHRVLGQYLRDTAALSPPKATVSDTC<br>EEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 93 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1.TpoR(N-1). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETWISLVTALHLVLGLSAVLGLLLLRWQFPAH<br>YRRLRHALWPSLPDLHRVLGQYLRDTAALSPPKATVSDTCE<br>EVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 94 |
| HAPD1.TpoR(N-2). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETISLVTALHLVLGLSAVLGLLLLRWQFPAHY<br>RRLRHALWPSLPDLHRVLGQYLRDTAALSPPKATVSDTCEE<br>VEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 95 |
| HAPD1.TpoR (N-2 + 1). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETLISLVTALHLVLGLSAVLGLLLLRWQFPAH<br>YRRLRHALWPSLPDLHRVLGQYLRDTAALSPPKATVSDTCE<br>EVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 96 |
| HAPD1.TpoR (N-3). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETSLVTALHLVLGLSAVLGLLLLRWQFPAHYR<br>RLRHALWPSLPDLHRVLGQYLRDTAALSPPKATVSDTCEEV<br>EPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 97 |
| HAPD1.TpoR (N-4). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETLVTALHLVLGLSAVLGLLLLRWQFPAHYR<br>RLRHALWPSLPDLHRVLGQYLRDTAALSPPKATVSDTCEEV<br>EPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ | 98 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | SDPKPENPACPWTVLPAGDLPTHDGYLPSNIDDLPSHEAPLA DSLEELEPQ | |
| HAPD1.TpoR (N-4 + 1). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETILVTALHLVLGLSAVLGLLLLRWQFPAHYR RLRHALWPSLPDLHRVLGQYLRDTAALSPPKATVSDTCEEV EPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 99 |
| HAPD1.TpoR (N-5). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETVTALHLVLGLSAVLGLLLLRWQFPAHYRR LRHALWPSLPDLHRVLGQYLRDTAALSPPKATVSDTCEEVEP SLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 100 |
| HAPD1.TpoR (N-6). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETTALHLVLGLSAVLGLLLLRWQFPAHYRRLR HALWPSLPDLHRVLGQYLRDTAALSPPKATVSDTCEEVEPSL LEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 101 |
| HAPD1.TpoR (N-7). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETALHLVLGLSAVLGLLLLRWQFPAHYRRLR HALWPSLPDLHRVLGQYLRDTAALSPPKATVSDTCEEVEPSL LEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 102 |
| HAPD1.TpoR (N-8). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLHLVLGLSAVLGLLLLRWQFPAHYRRLRH ALWPSLPDLHRVLGQYLRDTAALSPPKATVSDTCEEVEPSLL EILPKSSERTPLPL ARDEVEGFLQDTFPQQLEESEKQRLGGDVQSPNCPSEDVVIT | 103 |

TABLE 7-continued

| PD1 chimeric cytokine receptor | Amino acid sequence | SEQ ID NO: |
|---|---|---|
| | Exemplary PD1 chimeric cytokine receptor sequences (assembled PD1 chimeric cytokine receptors): | |
| | PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | |
| HAPD1.TpoR<br>(N-9).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETHLVLGLSAVLGLLLLLRWQFPAHYRRLRHA<br>LWPSLPDLHRVLGQYLRDTAALSPPKATVSDTCEEVEPSLLEI<br>LPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 104 |
| HAPD1.TpoR<br>(N-10).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETLVLGLSAVLGLLLLLRWQFPAHYRRLRHAL<br>WPSLPDLHRVLGQYLRDTAALSPPKATVSDTCEEVEPSLLEIL<br>PKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 105 |
| HAPD1.TpoR<br>(N-11).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETVLGLSAVLGLLLLLRWQFPAHYRRLRHALW<br>PSLPDLHRVLGQYLRDTAALSPPKATVSDTCEEVEPSLLEILP<br>KSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 106 |
| HAPD1.TpoR<br>(N-12).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETLGLSAVLGLLLLLRWQFPAHYRRLRHALWP<br>SLPDLHRVLGQYLRDTAALSPPKATVSDTCEEVEPSLLEILPK<br>SSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 107 |
| HAPD1.TpoR<br>(N-13).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETGLSAVLGLLLLLRWQFPAHYRRLRHALWPS | 108 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | LPDLHRVLGQYLRDTAALSPPKATVSDTCEEVEPSLLEILPKS<br>SERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | |
| HAPD1.TpoR<br>(N-14).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETLSAVLGLLLLRWQFPAHYRRLRHALWPSLP<br>DLHRVLGQYLRDTAALSPPKATVSDTCEEVEPSLLEILPKSSE<br>RTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 109 |
| HAPD1.TpoR<br>(N-15).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETSAVLGLLLLRWQFPAHYRRLRHALWPSLP<br>DLHRVLGQYLRDTAALSPPKATVSDTCEEVEPSLLEILPKSSE<br>RTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 110 |
| HAPD1.TpoR<br>(N-16).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETAVLGLLLLRWQFPAHYRRLRHALWPSLPD<br>LHRVLGQYLRDTAALSPPKATVSDTCEEVEPSLLEILPKSSER<br>TPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 111 |
| HAPD1.TpoR<br>(N-17).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETVLGLLLLRWQFPAHYRRLRHALWPSLPDL<br>HRVLGQYLRDTAALSPPKATVSDTCEEVEPSLLEILPKSSERT<br>PLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 112 |

TABLE 7-continued

| Exemplary PD1 chimeric cytokine receptor sequences (assembled PD1 chimeric cytokine receptors): | | |
|---|---|---|
| PD1 chimeric cytokine receptor | Amino acid sequence | SEQ ID NO: |
| HAPD1.TpoR (N-18). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETLGLLLLRWQFPAHYRRLRHALWPSLPDLH RVLGQYLRDTAALSPPKATVSDTCEEVEPSLLEILPKSSERTP LPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 113 |
| HAPD1.TpoR (N + 1). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLISLVTALHLVLGLSAVLGLLLLRWQFP AHYRRLRHALWPSLPDLHRVLGQYLRDTAALSPPKATVSDT CEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 114 |
| HAPD1.TpoR (N + 2). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWVLISLVTALHLVLGLSAVLGLLLLRWQF PAHYRRLRHALWPSLPDLHRVLGQYLRDTAALSPPKATVSD TCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 115 |
| HAPD1.Tpo R(N + 3). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWLVLISLVTALHLVLGLSAVLGLLLLRWQ FPAHYRRLRHALWPSLPDLHRVLGQYLRDTAALSPPKATVS DTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ SDPKPENPACPWTVLPAGDLPTHDGYLPSNIDDLPSHEAPLA DSLEELEPQ | 116 |
| HAPD1.TpoR (N + 4). IL7Ra(316-459). IL12Rb2 (775-825) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ SDPTRVETATETAWILVLISLVTALHLVLGLSAVLGLLLLRW QFPAHYRRLRHALWPSLPDLHRVLGQYLRDTAALSPPKATV SDTCEEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN | 117 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | QEEAYVTMSSFYQNQ<br>SDPKPENPACPWTVLPAGDLPTHDGYLPSNIDDLPSHEAPLA<br>DSLEELEPQ | |
| HAPD1.TpoR (N + 5). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETAWLILVLISLVTALHLVLGLSAVLGLLLLR<br>WQFPAHYRRLRHALWPSLPDLHRVLGQYLRDTAALSPPKAT<br>VSDTCEEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 118 |
| HAPD1.TpoR (N + 6). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETAWLLILVLISLVTALHLVLGLSAVLGLLLLR<br>WQFPAHYRRLRHALWPSLPDLHRVLGQYLRDTAALSPPKAT<br>VSDTCEEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 119 |
| HAPD1.TpoR (N + 7). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETAWVLLILVLISLVTALHLVLGLSAVLGLLLL<br>RWQFPAHYRRLRHALWPSLPDLHRVLGQYLRDTAALSPPKA<br>TVSDTCEEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 120 |
| HAPD1.TpoR (N + 8). IL7Ra(316-459). IL12Rb2 (775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ<br>SDPTRVETATETAWLVLLILVLISLVTALHLVLGLSAVLGLLL<br>LRWQFPAHYRRLRHALWPSLPDLHRVLGQYLRDTAALSPPK<br>ATVSDTCEEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ<br>SDPKPENPACPWTVLPAGDLPTHDGYLPSNIDDLPSHEAPLA<br>DSLEELEPQ | 121 |
| HAPD1(21-170). TPOR/MPLR(478-582; H499L, S505N, W515K). IL7Ra(316-459) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLV<br>SDPTRVETATETAWISLVTAL**L**LVLGL**N**AVLGLLLLR**K**QFPA<br>HYRRLRHALWPSLPDLHRVLGQYLRDTAALSPPKATVSDTC<br>EEVEPSLLEILPKSSERTPLPL<br>ARDEVEGFLQDTFPQQLEESEKQRLGGDVQSPNCPSEDVVIT | 136 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | |
| HAPD1(21-170). TpoR(478-582; S505N, W515K). IL2small(393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTALHLVLGL**N**AVLGLLLLR**K**QFPA HYRRLRHALWPSLPDLHRVLGQYLRDTAALSPPKATVSDTC EEVEPSLLEILPKSSERTPLPL DEGVAGAPTGSSPQPLQPLSGEDDAYCTFPSRDDLLLFSPSG QGEFRALNARLPLNTDAYLSLQELQGQDPTHLV | 137 |
| HAPDIDN (HAPD1 Dominant Negative) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ | 138 |
| HAPD1(21-170). TpoR(478-582). IL7Ra(316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT PESFGRDSSLTCLAGNVSACDAPILSSSRSLDCRESGKNGPHV YQDLLLSLGTTNSTLPPPFSLQSGILTLNPVAQGQPILTSLGSN QEEAYVTMSSFYQNQ | 139 |
| HAPD1(21-170). TpoR(478-582). IL2small (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTALHLVLGLSAVLGLLLLRWQFPA HYRRLRHALWPSLPDLHRVLGQYLRDTAALSPPKATVSDTC EEVEPSLLEILPKSSERTPLPL DEGVAGAPTGSSPQPLQPLSGEDDAYCTFPSRDDLLLFSPSG QGEFRALNARLPLNTDAYLSLQELQGQDPTHLV | 140 |
| WTPD1(21-170). TpoR(478-582). IL7Ra(316-459). IL12Rb2 (775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVSDPTRVETATETAWISLVT ALHLVLGLSAVLGLLLLRWQFPAHYRRLRHALWPSLPDLHR VLGQYLRDTAALSPPKATVSDTCEEVEPSLLEILPKSSERTPL PLLEARDEVEGFLQDTFPQQLEESEKQRLGGDVQSPNCPSED VVITPESFGRDSSLTCLAGNVSACDAPILSSSRSLDCRESGKN GPHVYQDLLLSLGTTNSTLPPPFSLQSGILTLNPVAQGQPILTS LGSNQEEAYVTMSSFYQNQGSGSRSDPKPENPACPWTVLPA GDLPTHDGYLPSNIDDLPSHEAPLADSLEELEPQ | 172 |
| WTPD1(21-170). GCSFR(614-710). IL7Ra(316-459). IL12Rb2 (775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVLTLMTLTPEGSELHIILGLF GLLLLLTCLCGTAWLCCSPNRKNPLWPSVPDPAHSSLGSWV PTIMEEDAFQLPGLGTPPITKLTVLEEDEKKPVPWELEARDEV EGFLQDTFPQQLEESEKQRLGGDVQSPNCPSEDVVITPESFGR DSSLTCLAGNVSACDAPILSSSRSLDCRESGKNGPHVYQDLL LSLGTTNSTLPPPFSLQSGILTLNPVAQGQPILTSLGSNQEEAY VTMSSFYQNQGSGSRSDPKPENPACPWTVLPAGDLPTHDGY LPSNIDDLPSHEAPLADSLEELEPQ | 173 |
| WTPD1(21-170). GP130(609-700). IL7Ra(316-459). IL12Rb2 (775-825) | PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVTTPKFAQGEIEAIVVPVCL AFLLTTLLGVLFCFNKRDLIKKHIWPNVPDPSKSHIAQWSPHT PPRHNFNSKDQMYSDGNFTDVSVVEIEANDLEARDEVEGFL | 174 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | QDTFPQQLEESEKQRLGGDVQSPNCPSEDVVITPESFGRDSSL<br>TCLAGNVSACDAPILSSSRSLDCRESGKNGPHVYQDLLLSLG<br>TTNSTLPPPFSLQSGILTLNPVAQGQPILTSLGSNQEEAYVTM<br>SSFYQNQGSGSRSDPKPENPACPWTVLPAGDLPTHDGYLPSN<br>IDDLPSHEAPLADSLEELEPQ | |
| 2xWTPD1(21-170).<br>TpoR(478-582).<br>IL7Ra(316-459).<br>IL12Rb2<br>(775-825) | PGWFLDSPDRPWNPPTFSPALLVVTEGDNATFTCSFSNTSESF<br>VLNWYRMSPSNQTDKLAAFPEDRSQPGQDCRFRVTQLPNGR<br>DFHMSVVRARRNDSGTYLCGAISLAPKAQIKESLRAELRVTE<br>RRAEVPTAHPSPSPRPAGQFQTLVGPGWFLDSPDRPWNPPTF<br>SPALLVVTEGDNATFTCSFSNTSESFVLNWYRMSPSNQTDKL<br>AAFPEDRSQPGQDCRFRVTQLPNGRDFHMSVVRARRNDSGT<br>YLCGAISLAPKAQIKESLRAELRVTERRAEVPTAHPSPSPRPA<br>GQFQTLVSDPTRVETATETAWISLVTALHLVLGLSAVLGLLL<br>LRWQFPAHYRRLRHALWPSLPDLHRVLGQYLRDTAALSPPK<br>ATVSDTCEEVEPSLLEILPKSSERTPLPLLEARDEVEGFLQDTF<br>PQQLEESEKQRLGGDVQSPNCPSEDVVITPESFGRDSSLTCLA<br>GNVSACDAPILSSSRSLDCRESGKNGPHVYQDLLLSLGTTNS<br>TLPPPFSLQSGILTLNPVAQGQPILTSLGSNQEEAYVTMSSFY<br>QNQGSGSRSDPKPENPACPWTVLPAGDLPTHDGYLPSNIDDL<br>PSHEAPLADSLEELEPQ | 175 |
| 3xWTPD1(21-170).<br>TpoR(478-582).<br>IL7Ra(316-459).<br>IL12Rb2<br>(775-825) | PGWFLDSPDRPWNPPTFSPALLVVTEGDNATFTCSFSNTSESF<br>VLNWYRMSPSNQTDKLAAFPEDRSQPGQDCRFRVTQLPNGR<br>DFHMSVVRARRNDSGTYLCGAISLAPKAQIKESLRAELRVTE<br>RRAEVPTAHPSPSPRPAGQFQTLVGPGWFLDSPDRPWNPPTF<br>SPALLVVTEGDNATFTCSFSNTSESFVLNWYRMSPSNQTDKL<br>AAFPEDRSQPGQDCRFRVTQLPNGRDFHMSVVRARRNDSGT<br>YLCGAISLAPKAQIKESLRAELRVTERRAEVPTAHPSPSPRPA<br>GQFQTLVGPGWFLDSPDRPWNPPTFSPALLVVTEGDNATFTC<br>SFSNTSESFVLNWYRMSPSNQTDKLAAFPEDRSQPGQDCRFR<br>VTQLPNGRDFHMSVVRARRNDSGTYLCGAISLAPKAQIKESL<br>RAELRVTERRAEVPTAHPSPSPRPAGQFQTLVSDPTRVETAT<br>ETAWISLVTALHLVLGLSAVLGLLLLRWQFPAHYRRLRHAL<br>WPSLPDLHRVLGQYLRDTAALSPPKATVSDTCEEVEPSLLEIL<br>PKSSERTPLPLLEARDEVEGFLQDTFPQQLEESEKQRLGGDV<br>QSPNCPSEDVVITPESFGRDSSLTCLAGNVSACDAPILSSSRSL<br>DCRESGKNGPHVYQDLLLSLGTTNSTLPPPFSLQSGILTLNPV<br>AQGQPILTSLGSNQEEAYVTMSSFYQNQGSGSRSDPKPENPA<br>CPWTVLPAGDLPTHDGYLPSNIDDLPSHEAPLADSLEELEPQ | 176 |
| HAPD1(21-170).<br>TpoR(478-582).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWISLVTA<br>LHLVLGLSAVLGLLLLRWQFPAHYRRLRHALWPSLPDLHRV<br>LGQYLRDTAALSPPKATVSDTCEEVEPSLLEILPKSSERTPLPL<br>LEARDEVEGFLQDTFPQQLEESEKQRLGGDVQSPNCPSEDVV<br>ITPESFGRDSSLTCLAGNVSACDAPILSSSRSLDCRESGKNGP<br>HVYQDLLLSLGTTNSTLPPPFSLQSGILTLNPVAQGQPILTSLG<br>SNQEEAYVTMSSFYQNQGSGSRSDPKPENPACPWTVLPAGD<br>LPTHDGYLPSNIDDLPSHEAPLADSLEELEPQ | 177 |
| HAPD1(21-170).<br>TpoR(N-1).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETWISLVTAL<br>HLVLGLSAVLGLLLLRWQFPAHYRRLRHALWPSLPDLHRVL<br>GQYLRDTAALSPPKATVSDTCEEVEPSLLEILPKSSERTPLPLL<br>EARDEVEGFLQDTFPQQLEESEKQRLGGDVQSPNCPSEDVVI<br>TPESFGRDSSLTCLAGNVSACDAPILSSSRSLDCRESGKNGPH<br>VYQDLLLSLGTTNSTLPPPFSLQSGILTLNPVAQGQPILTSLGS<br>NQEEAYVTMSSFYQNQGSGSRSDPKPENPACPWTVLPAGDL<br>PTHDGYLPSNIDDLPSHEAPLADSLEELEPQ | 178 |
| HAPD1(21-170).<br>TpoR(N-2).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETISLVTALH<br>LVLGLSAVLGLLLLRWQFPAHYRRLRHALWPSLPDLHRVLG<br>QYLRDTAALSPPKATVSDTCEEVEPSLLEILPKSSERTPLPLLE<br>ARDEVEGFLQDTFPQQLEESEKQRLGGDVQSPNCPSEDVVIT | 179 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQGSGSRSDPKPENPACPWTVLPAGDLP<br>THDGYLPSNIDDLPSHEAPLADSLEELEPQ | |
| HAPD1(21-170).<br>TpoR(N2 + 1).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLISLVTAL<br>HLVLGLSAVLGLLLLRWQFPAHYRRLRHALWPSLPDLHRVL<br>GQYLRDTAALSPPKATVSDTCEEVEPSLLEILPKSSERTPLPLL<br>EARDEVEGFLQDTFPQQLEESEKQRLGGDVQSPNCPSEDVVI<br>TPESFGRDSSLTCLAGNVSACDAPILSSSRSLDCRESGKNGPH<br>VYQDLLLSLGTTNSTLPPPFSLQSGILTLNPVAQGQPILTSLGS<br>NQEEAYVTMSSFYQNQGSGSRSDPKPENPACPWTVLPAGDL<br>PTHDGYLPSNIDDLPSHEAPLADSLEELEPQ | 180 |
| HAPD1(21-170).<br>TpoR(N-3).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETSLVTALHL<br>VLGLSAVLGLLLLRWQFPAHYRRLRHALWPSLPDLHRVLGQ<br>YLRDTAALSPPKATVSDTCEEVEPSLLEILPKSSERTPLPLLEA<br>RDEVEGFLQDTFPQQLEESEKQRLGGDVQSPNCPSEDVVITP<br>ESFGRDSSLTCLAGNVSACDAPILSSSRSLDCRESGKNGPHVY<br>QDLLLSLGTTNSTLPPPFSLQSGILTLNPVAQGQPILTSLGSNQ<br>EEAYVTMSSFYQNQGSGSRSDPKPENPACPWTVLPAGDLPT<br>HDGYLPSNIDDLPSHEAPLADSLEELEPQ | 181 |
| HAPD1(21-170).<br>TpoR(N-4).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLVTALHL<br>VLGLSAVLGLLLLRWQFPAHYRRLRHALWPSLPDLHRVLGQ<br>YLRDTAALSPPKATVSDTCEEVEPSLLEILPKSSERTPLPLLEA<br>RDEVEGFLQDTFPQQLEESEKQRLGGDVQSPNCPSEDVVITP<br>ESFGRDSSLTCLAGNVSACDAPILSSSRSLDCRESGKNGPHVY<br>QDLLLSLGTTNSTLPPPFSLQSGILTLNPVAQGQPILTSLGSNQ<br>EEAYVTMSSFYQNQGSGSRSDPKPENPACPWTVLPAGDLPT<br>HDGYLPSNIDDLPSHEAPLADSLEELEPQ | 182 |
| HAPD1(21-170).<br>TpoR(N-4 + 1).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETILVTALHL<br>VLGLSAVLGLLLLRWQFPAHYRRLRHALWPSLPDLHRVLGQ<br>YLRDTAALSPPKATVSDTCEEVEPSLLEILPKSSERTPLPLLEA<br>RDEVEGFLQDTFPQQLEESEKQRLGGDVQSPNCPSEDVVITP<br>ESFGRDSSLTCLAGNVSACDAPILSSSRSLDCRESGKNGPHVY<br>QDLLLSLGTTNSTLPPPFSLQSGILTLNPVAQGQPILTSLGSNQ<br>EEAYVTMSSFYQNQGSGSRSDPKPENPACPWTVLPAGDLPT<br>HDGYLPSNIDDLPSHEAPLADSLEELEPQ | 183 |
| HAPD1(21-170).<br>TpoR(N-5).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETVTALHLV<br>LGLSAVLGLLLLRWQFPAHYRRLRHALWPSLPDLHRVLGQY<br>LRDTAALSPPKATVSDTCEEVEPSLLEILPKSSERTPLPLLEAR<br>DEVEGFLQDTFPQQLEESEKQRLGGDVQSPNCPSEDVVITPES<br>FGRDSSLTCLAGNVSACDAPILSSSRSLDCRESGKNGPHVYQ<br>DLLLSLGTTNSTLPPPFSLQSGILTLNPVAQGQPILTSLGSNQE<br>EAYVTMSSFYQNQGSGSRSDPKPENPACPWTVLPAGDLPTH<br>DGYLPSNIDDLPSHEAPLADSLEELEPQ | 184 |
| HAPD1(21-170).<br>TpoR(N-6).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETTALHLVL<br>GLSAVLGLLLLRWQFPAHYRRLRHALWPSLPDLHRVLGQYL<br>RDTAALSPPKATVSDTCEEVEPSLLEILPKSSERTPLPLLEARD<br>EVEGFLQDTFPQQLEESEKQRLGGDVQSPNCPSEDVVITPESF | 185 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | GRDSSLTCLAGNVSACDAPILSSSRSLDCRESGKNGPHVYQD<br>LLLSLGTTNSTLPPPFSLQSGILTLNPVAQGQPILTSLGSNQEE<br>AYVTMSSFYQNQGSGSRSDPKPENPACPWTVLPAGDLPTHD<br>GYLPSNIDDLPSHEAPLADSLEELEPQ | |
| HAPD1(21-170).<br>TpoR(N-7).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETALHLVLG<br>LSAVLGLLLLRWQFPAHYRRLRHALWPSLPDLHRVLGQYLR<br>DTAALSPPKATVSDTCEEVEPSLLEILPKSSERTPLPLLEARDE<br>VEGFLQDTFPQQLEESEKQRLGGDVQSPNCPSEDVVITPESFG<br>RDSSLTCLAGNVSACDAPILSSSRSLDCRESGKNGPHVYQDL<br>LLSLGTTNSTLPPPFSLQSGILTLNPVAQGQPILTSLGSNQEEA<br>YVTMSSFYQNQGSGSRSDPKPENPACPWTVLPAGDLPTHDG<br>YLPSNIDDLPSHEAPLADSLEELEPQ | 186 |
| HAPD1(21-170).<br>TpoR(N-8).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLHLVLGLS<br>AVLGLLLLRWQFPAHYRRLRHALWPSLPDLHRVLGQYLRDT<br>AALSPPKATVSDTCEEVEPSLLEILPKSSERTPLPLLEARDEVE<br>GFLQDTFPQQLEESEKQRLGGDVQSPNCPSEDVVITPESFGRD<br>SSLTCLAGNVSACDAPILSSSRSLDCRESGKNGPHVYQDLLLS<br>LGTTNSTLPPPFSLQSGILTLNPVAQGQPILTSLGSNQEEAYVT<br>MSSFYQNQGSGSRSDPKPENPACPWTVLPAGDLPTHDGYLP<br>SNIDDLPSHEAPLADSLEELEPQ | 187 |
| HAPD1(21-170).<br>TpoR(N9).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETHLVLGLS<br>AVLGLLLLRWQFPAHYRRLRHALWPSLPDLHRVLGQYLRDT<br>AALSPPKATVSDTCEEVEPSLLEILPKSSERTPLPLLEARDEVE<br>GFLQDTFPQQLEESEKQRLGGDVQSPNCPSEDVVITPESFGRD<br>SSLTCLAGNVSACDAPILSSSRSLDCRESGKNGPHVYQDLLLS<br>LGTTNSTLPPPFSLQSGILTLNPVAQGQPILTSLGSNQEEAYVT<br>MSSFYQNQGSGSRSDPKPENPACPWTVLPAGDLPTHDGYLP<br>SNIDDLPSHEAPLADSLEELEPQ | 188 |
| HAPD1(21-170).<br>TpoR(N10).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLVLGLSA<br>VLGLLLLRWQFPAHYRRLRHALWPSLPDLHRVLGQYLRDTA<br>ALSPPKATVSDTCEEVEPSLLEILPKSSERTPLPLLEARDEVEG<br>FLQDTFPQQLEESEKQRLGGDVQSPNCPSEDVVITPESFGRDS<br>SLTCLAGNVSACDAPILSSSRSLDCRESGKNGPHVYQDLLLS<br>LGTTNSTLPPPFSLQSGILTLNPVAQGQPILTSLGSNQEEAYVT<br>MSSFYQNQGSGSRSDPKPENPACPWTVLPAGDLPTHDGYLP<br>SNIDDLPSHEAPLADSLEELEPQ | 189 |
| HAPD1(21-170).<br>TpoR(N-11).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETVLGLSAV<br>LGLLLLRWQFPAHYRRLRHALWPSLPDLHRVLGQYLRDTAA<br>LSPPKATVSDTCEEVEPSLLEILPKSSERTPLPLLEARDEVEGF<br>LQDTFPQQLEESEKQRLGGDVQSPNCPSEDVVITPESFGRDSS<br>LTCLAGNVSACDAPILSSSRSLDCRESGKNGPHVYQDLLLSL<br>GTTNSTLPPPFSLQSGILTLNPVAQGQPILTSLGSNQEEAYVT<br>MSSFYQNQGSGSRSDPKPENPACPWTVLPAGDLPTHDGYLP<br>SNIDDLPSHEAPLADSLEELEPQ | 190 |
| HAPD1(21-170).<br>TpoR(N-12).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLGLSAVL<br>GLLLLRWQFPAHYRRLRHALWPSLPDLHRVLGQYLRDTAAL<br>SPPKATVSDTCEEVEPSLLEILPKSSERTPLPLLEARDEVEGFL<br>QDTFPQQLEESEKQRLGGDVQSPNCPSEDVVITPESFGRDSSL | 191 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
| --- | --- | --- |
| | TCLAGNVSACDAPILSSSRSLDCRESGKNGPHVYQDLLLSLG<br>TTNSTLPPPFSLQSGILTLNPVAQGQPILTSLGSNQEEAYVTM<br>SSFYQNQGSGSRSDPKPENPACPWTVLPAGDLPTHDGYLPSN<br>IDDLPSHEAPLADSLEELEPQ | |
| HAPD1(21-170).<br>TpoR(N-13).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETGLSAVLG<br>LLLLRWQFPAHYRRLRHALWPSLPDLHRVLGQYLRDTAALS<br>PPKATVSDTCEEVEPSLLEILPKSSERTPLPLLEARDEVEGFLQ<br>DTFPQQLEESEKQRLGGDVQSPNCPSEDVVITPESFGRDSSLT<br>CLAGNVSACDAPILSSSRSLDCRESGKNGPHVYQDLLLSLGT<br>TNSTLPPPFSLQSGILTLNPVAQGQPILTSLGSNQEEAYVTMSS<br>FYQNQGSGSRSDPKPENPACPWTVLPAGDLPTHDGYLPSNID<br>DLPSHEAPLADSLEELEPQ | 192 |
| HAPD1(21-170).<br>TpoR(N14).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLSAVLGLL<br>LLRWQFPAHYRRLRHALWPSLPDLHRVLGQYLRDTAALSPP<br>KATVSDTCEEVEPSLLEILPKSSERTPLPLLEARDEVEGFLQD<br>TFPQQLEESEKQRLGGDVQSPNCPSEDVVITPESFGRDSSLTC<br>LAGNVSACDAPILSSSRSLDCRESGKNGPHVYQDLLLSLGTT<br>NSTLPPPFSLQSGILTLNPVAQGQPILTSLGSNQEEAYVTMSSF<br>YQNQGSGSRSDPKPENPACPWTVLPAGDLPTHDGYLPSNIDD<br>LPSHEAPLADSLEELEPQ | 193 |
| HAPD1(21-170).<br>TpoR(N-15).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETSAVLGLLL<br>LRWQFPAHYRRLRHALWPSLPDLHRVLGQYLRDTAALSPPK<br>ATVSDTCEEVEPSLLEILPKSSERTPLPLLEARDEVEGFLQDTF<br>PQQLEESEKQRLGGDVQSPNCPSEDVVITPESFGRDSSLTCLA<br>GNVSACDAPILSSSRSLDCRESGKNGPHVYQDLLLSLGTTNS<br>TLPPPFSLQSGILTLNPVAQGQPILTSLGSNQEEAYVTMSSFY<br>QNQGSGSRSDPKPENPACPWTVLPAGDLPTHDGYLPSNIDDL<br>PSHEAPLADSLEELEPQ | 194 |
| HAPD1(21-170).<br>TpoR(N16).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAVLGLLLL<br>RWQFPAHYRRLRHALWPSLPDLHRVLGQYLRDTAALSPPKA<br>TVSDTCEEVEPSLLEILPKSSERTPLPLLEARDEVEGFLQDTFP<br>QQLEESEKQRLGGDVQSPNCPSEDVVITPESFGRDSSLTCLAG<br>NVSACDAPILSSSRSLDCRESGKNGPHVYQDLLLSLGTTNSTL<br>PPPFSLQSGILTLNPVAQGQPILTSLGSNQEEAYVTMSSFYQN<br>QGSGSRSDPKPENPACPWTVLPAGDLPTHDGYLPSNIDDLPS<br>HEAPLADSLEELEPQ | 195 |
| HAPD1(21-170).<br>poR(N-17).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETVLGLLLLR<br>WQFPAHYRRLRHALWPSLPDLHRVLGQYLRDTAALSPPKAT<br>VSDTCEEVEPSLLEILPKSSERTPLPLLEARDEVEGFLQDTFPQ<br>QLEESEKQRLGGDVQSPNCPSEDVVITPESFGRDSSLTCLAGN<br>VSACDAPILSSSRSLDCRESGKNGPHVYQDLLLSLGTTNSTLP<br>PPFSLQSGILTLNPVAQGQPILTSLGSNQEEAYVTMSSFYQNQ<br>GSGSRSDPKPENPACPWTVLPAGDLPTHDGYLPSNIDDLPSH<br>EAPLADSLEELEPQ | 196 |
| HAPD1(21-170).<br>TpoR(N-18).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETLGLLLLR<br>WQFPAHYRRLRHALWPSLPDLHRVLGQYLRDTAALSPPKAT<br>VSDTCEEVEPSLLEILPKSSERTPLPLLEARDEVEGFLQDTFPQ<br>QLEESEKQRLGGDVQSPNCPSEDVVITPESFGRDSSLTCLAGN | 197 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | VSACDAPILSSSRSLDCRESGKNGPHVYQDLLLSLGTTNSTLP<br>PPFSLQSGILTLNPVAQGQPILTSLGSNQEEAYVTMSSFYQNQ<br>GSGSRSDPKPENPACPWTVLPAGDLPTHDGYLPSNIDDLPSH<br>EAPLADSLEELEPQ | |
| HAPD1(21-170).<br>TpoR(N + 1).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWLISLVT<br>ALHLVLGLSAVLGLLLLRWQFPAHYRRLRHALWPSLPDLHR<br>VLGQYLRDTAALSPPKATVSDTCEEVEPSLLEILPKSSERTPL<br>PLLEARDEVEGFLQDTFPQQLEESEKQRLGGDVQSPNCPSED<br>VVITPESFGRDSSLTCLAGNVSACDAPILSSSRSLDCRESGKN<br>GPHVYQDLLLSLGTTNSTLPPPFSLQSGILTLNPVAQGQPILTS<br>LGSNQEEAYVTMSSFYQNQGSGSRSDPKPENPACPWTVLPA<br>GDLPTHDGYLPSNIDDLPSHEAPLADSLEELEPQ | 198 |
| HAPD1(21-170).<br>TpoR(N + 2).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWVLISLV<br>TALHLVLGLSAVLGLLLLRWQFPAHYRRLRHALWPSLPDLH<br>RVLGQYLRDTAALSPPKATVSDTCEEVEPSLLEILPKSSERTP<br>LPLLEARDEVEGFLQDTFPQQLEESEKQRLGGDVQSPNCPSE<br>DVVITPESFGRDSSLTCLAGNVSACDAPILSSSRSLDCRESGK<br>NGPHVYQDLLLSLGTTNSTLPPPFSLQSGILTLNPVAQGQPIL<br>TSLGSNQEEAYVTMSSFYQNQGSGSRSDPKPENPACPWTVLP<br>AGDLPTHDGYLPSNIDDLPSHEAPLADSLEELEPQ | 199 |
| HAPD1(21-170).<br>TpoR(N + 3).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWLVLISL<br>VTALHLVLGLSAVLGLLLLRWQFPAHYRRLRHALWPSLPDL<br>HRVLGQYLRDTAALSPPKATVSDTCEEVEPSLLEILPKSSERT<br>PLPLLEARDEVEGFLQDTFPQQLEESEKQRLGGDVQSPNCPS<br>EDVVITPESFGRDSSLTCLAGNVSACDAPILSSSRSLDCRESG<br>KNGPHVYQDLLLSLGTTNSTLPPPFSLQSGILTLNPVAQGQPI<br>LTSLGSNQEEAYVTMSSFYQNQGSGSRSDPKPENPACPWTV<br>LPAGDLPTHDGYLPSNIDDLPSHEAPLADSLEELEPQ | 200 |
| HAPD1(21-170).<br>TpoR(N + 4).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWILVLIS<br>LVTALHLVLGLSAVLGLLLLRWQFPAHYRRLRHALWPSLPD<br>LHRVLGQYLRDTAALSPPKATVSDTCEEVEPSLLEILPKSSER<br>TPLPLLEARDEVEGFLQDTFPQQLEESEKQRLGGDVQSPNCP<br>SEDVVITPESFGRDSSLTCLAGNVSACDAPILSSSRSLDCRESG<br>KNGPHVYQDLLLSLGTTNSTLPPPFSLQSGILTLNPVAQGQPI<br>LTSLGSNQEEAYVTMSSFYQNQGSGSRSDPKPENPACPWTV<br>LPAGDLPTHDGYLPSNIDDLPSHEAPLADSLEELEPQ | 201 |
| HAPD1(21-170).<br>TpoR(N + 5).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWLILVLI<br>SLVTALHLVLGLSAVLGLLLLRWQFPAHYRRLRHALWPSLP<br>DLHRVLGQYLRDTAALSPPKATVSDTCEEVEPSLLEILPKSSE<br>RTPLPLLEARDEVEGFLQDTFPQQLEESEKQRLGGDVQSPNC<br>PSEDVVITPESFGRDSSLTCLAGNVSACDAPILSSSRSLDCRES<br>GKNGPHVYQDLLLSLGTTNSTLPPPFSLQSGILTLNPVAQGQP<br>ILTSLGSNQEEAYVTMSSFYQNQGSGSRSDPKPENPACPWTV<br>LPAGDLPTHDGYLPSNIDDLPSHEAPLADSLEELEPQ | 202 |
| HAPD1(21-170).<br>TpoR(N + 6).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWLLILVL<br>ISLVTALHLVLGLSAVLGLLLLRWQFPAHYRRLRHALWPSLP<br>DLHRVLGQYLRDTAALSPPKATVSDTCEEVEPSLLEILPKSSE<br>RTPLPLLEARDEVEGFLQDTFPQQLEESEKQRLGGDVQSPNC | 203 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| | PSEDVVITPESFGRDSSLTCLAGNVSACDAPILSSSRSLDCRES<br>GKNGPHVYQDLLLSLGTTNSTLPPPFSLQSGILTLNPVAQGQP<br>ILTSLGSNQEEAYVTMSSFYQNQGSGSRSDPKPENPACPWTV<br>LPAGDLPTHDGYLPSNIDDLPSHEAPLADSLEELEPQ | |
| HAPD1(21-170).<br>TpoR(N + 7).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWVLLIL<br>VLISLVTALHLVLGLSAVLGLLLLRWQFPAHYRRLRHALWP<br>SLPDLHRVLGQYLRDTAALSPPKATVSDTCEEVEPSLLEILPK<br>SSERTPLPLLEARDEVEGFLQDTFPQQLEESEKQRLGGDVQSP<br>NCPSEDVVITPESFGRDSSLTCLAGNVSACDAPILSSSRSLDCR<br>ESGKNGPHVYQDLLLSLGTTNSTLPPPFSLQSGILTLNPVAQG<br>QPILTSLGSNQEEAYVTMSSFYQNQGSGSRSDPKPENPACPW<br>TVLPAGDLPTHDGYLPSNIDDLPSHEAPLADSLEELEPQ | 204 |
| HAPD1(21-170).<br>TpoR(N + 8).<br>IL7Ra(316-459).<br>IL12Rb2<br>(775-825) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWLVLLIL<br>VLISLVTALHLVLGLSAVLGLLLLRWQFPAHYRRLRHALWP<br>SLPDLHRVLGQYLRDTAALSPPKATVSDTCEEVEPSLLEILPK<br>SSERTPLPLLEARDEVEGFLQDTFPQQLEESEKQRLGGDVQSP<br>NCPSEDVVITPESFGRDSSLTCLAGNVSACDAPILSSSRSLDCR<br>ESGKNGPHVYQDLLLSLGTTNSTLPPPFSLQSGILTLNPVAQG<br>QPILTSLGSNQEEAYVTMSSFYQNQGSGSRSDPKPENPACPW<br>TVLPAGDLPTHDGYLPSNIDDLPSHEAPLADSLEELEPQ | 205 |
| HAPD1(21-107).<br>TPOR/<br>MPLR(478-582;<br>H499L, S505N,<br>W515K).<br>IL7Ra(316-459) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWISLVTA<br>LLLVLGLNAVLGLLLLRKQFPAHYRRLRHALWPSLPDLHRV<br>LGQYLRDTAALSPPKATVSDTCEEVEPSLLEILPKSSERTPLPL<br>LEARDEVEGFLQDTFPQQLEESEKQRLGGDVQSPNCPSEDVV<br>ITPESFGRDSSLTCLAGNVSACDAPILSSSRSLDCRESGKNGP<br>HVYQDLLLSLGTTNSTLPPPFSLQSGILTLNPVAQGQPILTSLG<br>SNQEEAYVTMSSFYQNQ | 206 |
| HAPD1.TpoR<br>(478-582; S505N,<br>W515K).<br>IL2Rbsmall<br>(393-433, 518-<br>551) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWISLVTA<br>LHLVLGLNAVLGLLLLRKQFPAHYRRLRHALWPSLPDLHRV<br>LGQYLRDTAALSPPKATVSDTCEEVEPSLLEILPKSSERTPLPL<br>LEDEGVAGAPTGSSPQPLQPLSGEDDAYCTFPSRDDLLLFSPS<br>GQGEFRALNARLPLNTDAYLSLQELQGQDPTHLV | 207 |
| HAPD1(21-107).<br>TpoR(478-582).<br>IL7Ra(316-459) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWISLVTA<br>LHLVLGLSAVLGLLLLRWQFPAHYRRLRHALWPSLPDLHRV<br>LGQYLRDTAALSPPKATVSDTCEEVEPSLLEILPKSSERTPLPL<br>LEARDEVEGFLQDTFPQQLEESEKQRLGGDVQSPNCPSEDVV<br>ITPESFGRDSSLTCLAGNVSACDAPILSSSRSLDCRESGKNGP<br>HVYQDLLLSLGTTNSTLPPPFSLQSGILTLNPVAQGQPILTSLG<br>SNQEEAYVTMSSFYQNQ | 208 |
| HAPD1.TpoR<br>(478-582).<br>IL2Rbsmall(393-<br>433, 518-551) | PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVSDPTRVETATETAWISLVTA<br>LHLVLGLSAVLGLLLLRWQFPAHYRRLRHALWPSLPDLHRV<br>LGQYLRDTAALSPPKATVSDTCEEVEPSLLEILPKSSERTPLPL<br>LEDEGVAGAPTGSSPQPLQPLSGEDDAYCTFPSRDDLLLFSPS<br>GQGEFRALNARLPLNTDAYLSLQELQGQDPTHLV | 209 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-107) TpoR(478-582; S505N, W515K). IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLNAVLGLLLLRKQFPAHYRRLRHALWPSLPDLHRV LGQYLRDTAALSPPKATVSDTCEEVEPSLLEILPKSSERTPLPL LEQQDKVPEPASLSSNHSLTSCFTNQGYFFFHLPDALEIEACQ DEGVAGAPTGSSPQPLQPLSGEDDAYCTFPSRDDLLLFSPSG QGEFRALNARLPLNTDAYLSLQELQGQDPTHLV | 214 |
| HAPD1(21-107). TpoR(478-582; H499L, S505N, W515K). IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LLLVLGLNAVLGLLLLRKQFPAHYRRLRHALWPSLPDLHRV LGQYLRDTAALSPPKATVSDTCEEVEPSLLEILPKSSERTPLPL LEQQDKVPEPASLSSNHSLTSCFTNQGYFFFHLPDALEIEACQ DEGVAGAPTGSSPQPLQPLSGEDDAYCTFPSRDDLLLFSPSG QGEFRALNARLPLNTDAYLSLQELQGQDPTHLV | 215 |
| HAPD1(21-170). TpoR(478-582). IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLSAVLGLLLLRWQFPAHYRRLRHALWPSLPDLHRV LGQYLRDTAALSPPKATVSDTCEEVEPSLLEILPKSSERTPLPL LEQQDKVPEPASLSSNHSLTSCFTNQGYFFFHLPDALEIEACQ DEGVAGAPTGSSPQPLQPLSGEDDAYCTFPSRDDLLLFSPSG QGEFRALNARLPLNTDAYLSLQELQGQDPTHLV | 216 |
| HAPD1(21-107). TpoR(N-7). IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETALHLVLG LSAVLGLLLLRWQFPAHYRRLRHALWPSLPDLHRVLGQYLR DTAALSPPKATVSDTCEEVEPSLLEILPKSSERTPLPLLEDEGV AGAPTGSSPQPLQPLSGEDDAYCTFPSRDDLLLFSPSGQGEFR ALNARLPLNTDAYLSLQELQGQDPTHLV | 217 |
| HAPD1(21-107). TpoR(N-8). IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLHLVLGLS AVLGLLLLRWQFPAHYRRLRHALWPSLPDLHRVLGQYLRDT AALSPPKATVSDTCEEVEPSLLEILPKSSERTPLPLLEDEGVAG APTGSSPQPLQPLSGEDDAYCTFPSRDDLLLFSPSGQGEFRAL NARLPLNTDAYLSLQELQGQDPTHLV | 218 |
| HAPD1(21-107). TpoR(N-9). IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETHLVLGLS AVLGLLLLRWQFPAHYRRLRHALWPSLPDLHRVLGQYLRDT AALSPPKATVSDTCEEVEPSLLEILPKSSERTPLPLLEDEGVAG APTGSSPQPLQPLSGEDDAYCTFPSRDDLLLFSPSGQGEFRAL NARLPLNTDAYLSLQELQGQDPTHLV | 219 |
| HAPD1(21-107). TpoR(N-7). IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETALHLVLG LSAVLGLLLLRWQFPAHYRRLRHALWPSLPDLHRVLGQYLR DTAALSPPKATVSDTCEEVEPSLLEILPKSSERTPLPLLEQQDK VPEPASLSSNHSLTSCFTNQGYFFFHLPDALEIEACQDEGVAG APTGSSPQPLQPLSGEDDAYCTFPSRDDLLLFSPSGQGEFRAL NARLPLNTDAYLSLQELQGQDPTHLV | 220 |

TABLE 7-continued

Exemplary PD1 chimeric cytokine receptor sequences (assembled PD1 chimeric cytokine receptors):

| PD1 chimeric cytokine receptor | Amino acid sequence | SEQ ID NO: |
|---|---|---|
| HAPD1(21-107). TpoR(N-8). IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETLHLVLGLS AVLGLLLLRWQFPAHYRRLRHALWPSLPDLHRVLGQYLRDT AALSPPKATVSDTCEEVEPSLLEILPKSSERTPLPLLEQQDKVP EPASLSSNHSLTSCFTNQGYFFFHLPDALEIEACQDEGVAGAP TGSSPQPLQPLSGEDDAYCTFPSRDDLLLFSPSGQGEFRALNA RLPLNTDAYLSLQELQGQDPTHLV | 221 |
| HAPD1(21-107). TpoR(N-19). IL2Rbsmall (339-379, 393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETHLVLGLS AVLGLLLLRWQFPAHYRRLRHALWPSLPDLHRVLGQYLRDT AALSPPKATVSDTCEEVEPSLLEILPKSSERTPLPLLEQQDKVP EPASLSSNHSLTSCFTNQGYFFFHLPDALEIEACQDEGVAGAP TGSSPQPLQPLSGEDDAYCTFPSRDDLLLFSPSGQGEFRALNA RLPLNTDAYLSLQELQGQDPTHLV | 222 |
| HAPD1(21-170). TpoR(478-582; H499L, S505N, W515K). IL2Rbsmall (393-433, 518-551) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LLLVLGLNAVLGLLLLRKQFPAHYRRLRHALWPSLPDLHRV LGQYLRDTAALSPPKATVSDTCEEVEPSLLEILPKSSERTPLPL LEDEGVAGAPTGSSPQPLQPLSGEDDAYCTFPSRDDLLLFSPS GQGEFRALNARLPLNTDAYLSLQELQGQDPTHLV | 223 |
| HAPD1(21-170). TpoR(478-582; S505N, W515K). IL7Ra(316-459) | PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVSDPTRVETATETAWISLVTA LHLVLGLNAVLGLLLLRKQFPAHYRRLRHALWPSLPDLHRV LGQYLRDTAALSPPKATVSDTCEEVEPSLLEILPKSSERTPLPL LEARDEVEGFLQDTFPQQLEESEKQRLGGDVQSPNCPSEDVV ITPESFGRDSSLTCLAGNVSACDAPILSSSRSLDCRESGKNGP HVYQDLLLSLGTTNSTLPPPFSLQSGILTLNPVAQGQPILTSLG SNQEEAYVTMSSFYQNQ | 224 |

F. Expression of PD-1 Chimeric Cytokine Receptors

Provided herein are polynucleotides encoding any one of the chimeric cytokine receptors provided herein. Likewise, provided herein are expression vectors comprising such polynucleotides. In some embodiments, the vector is a viral vector. In some embodiments, the vector is not a viral vector.

In some embodiments, the vector comprises a polynucleotide encoding a PD-1chimeric cytokine receptor, and a polynucleotide expressing a chimeric antigen receptor (CAR).

In some embodiments, expression of the chimeric cytokine receptor and the CAR are expressed as a single polypeptide chain, separated by a linker. FIGS. 1B and 1D show schematics of a vector that can be used to co-express the chimeric cytokine receptor and CAR of the disclosure. One or more STAT-recruiting domains may be joined in tandem to mimic signaling from one or more cytokines.

II. CAR-Bearing Immune Cells

Provided herein are engineered immune cells comprising a polynucleotide encoding a chimeric antigen receptor and a PD-1 chimeric cytokine receptor of the disclosure; and provided herein are engineered immune cells expressing a chimeric antigen receptor (CAR-I cell) and a PD-1 chimeric cytokine receptor of the disclosure. Examples of immune cells include T-cells, e.g., alpha/beta T-cells and gamma/delta T-cells, B cells, natural killer (NK) cells, natural killer T (NKT) cells, invariant NKT cells, mast cells, myeloic-derived phagocytes, dendritic cells, killer dendritic cells, macrophages, and monocytes. Immune cells also refer to cells derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

Accordingly in some embodiments, provided herein are CAR-T-cells comprising a PD-1 chimeric cytokine receptor of the disclosure.

In some embodiments, a CAR can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain of a CAR specifically binds to a target of interest. The target of interest can be any molecule of interest, including, for example, without limitation any one or more of those presented in Table 11.

TABLE 11

| List of targets of interest |
|---|
| BCMA |
| EGFRvIII |
| Flt-3 |
| WT-1 |
| CD20 |
| CD23 |
| CD30 |
| CD38 |
| CD70 |
| CD33 |
| CD133 |
| MHC- WT1 |
| TSPAN10 |
| MHC-PRAME |
| Liv1 |
| ADAM10 |
| CHRNA2 |
| LeY |
| NKG2D |
| CS1 |
| CD44v6 |
| ROR1 |
| CD19 |
| Claudin-18.2 (Claudin-18A2 or Claudin18 isoform 2) |
| DLL3 (Delta-like protein 3, *Drosophila* Delta homolog 3, Delta3) |
| Muc17 (Mucin17, Muc3, Muc3) |
| FAP alpha (Fibroblast Activation Protein alpha) |
| Ly6G6D (Lymphocyte antigen 6 complex locus protein G6d |
| c6orf23 |
| G6D |
| MEGT1 |
| NG25) |
| RNF43 (E3 ubiquitin-protein ligase RNF43, RING finger protein 43) |
| ErbB2 (HER2/neu) |
| carcinoembryonic antigen (CEA) |
| epithelial cell adhesion molecule (EpCAM) |
| epidermal growth factor receptor (EGFR) |
| CD40 |
| disialoganglioside GD2 |
| GD3 |
| C-type lectin-like molecule-1 (CLL-1) |
| ductal-epithelial mucine |
| gp36 |
| TAG-72 |
| glycosphingolipids |
| glioma-associated antigen |
| β-human chorionic gonadotropin |
| alphafetoprotein (AFP) |
| lectin-reactive AFP |
| thyroglobulin |
| RAGE-1 |
| MN-CA IX |
| human telomerase reverse transcriptase |
| RU1 |
| RU2 (AS) |
| intestinal carboxyl esterase |
| mut hsp70-2 |
| M-CSF |
| prostase |
| prostase specific antigen (PSA) |
| PAP |
| NY-ESO-1 |
| LAGA-la |
| p53 |
| prostein |
| PSMA |
| survivin and telomerase |
| prostate-carcinoma tumor antigen-1 (PCTA-1) |
| MAGE |
| ELF2M |
| neutrophil elastase |
| ephrin B2 |
| CD22 |
| insulin growth factor (IGFl)-l |
| IGF-II |
| IGFI receptor |
| mesothelin |
| a major histocompatibility complex (MHC) molecule presenting a tumor-specific peptide epitope |
| 5T4 |
| O 1 |
| Nkp30 |
| tumor stromal antigens |
| the extra domain A (EDA) and extra domain B (EDB) of fibronectin and the AI domain of tenascin-C (TnC AI) and fibroblast associated protein (fap) |
| LRP6 |
| melamona-associated Chondroitin Sulfate Proteoglycan (MCSP) |
| MARTI |
| MUC1 |
| LMP2 |
| Idiotype |
| NY-ESO-1 |
| Ras mutant |
| gp100 |
| proteinase 3 |
| bcr-abl |
| tyrosinase |
| hTERT |
| EphA2 |
| ML-TAP |
| ERG |
| NA17 |
| PAX3 |
| ALK |
| Androgen receptor |
| a lineage-specific or tissue specific antigen such as CD3 |
| CD4 |
| CD8 |
| CD24 |
| CD25 |
| CD34 |
| CD79 |
| CD116 |
| CD117 |
| CD135 |
| CD123 |
| CD138 |
| CTLA-4 |
| B7-1 (CD80) |
| B7-2 (CD86) |
| endoglin |
| a major histocompatibility complex (MHC) molecule |
| MUC16 |
| PSCA |
| Trop2 |
| CD171 (L1CAM) |
| CA9 |
| STEAP1 |
| VEGFR2 |

In some embodiments, the extracellular ligand-binding domain of a CAR comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988) (e.g. glycine-serine containing linkers). In general, linkers can be short, flexible polypeptides and are generally comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The intracellular signaling domain of a CAR according to the invention is responsible for intracellular signaling following the binding of extracellular ligand-binding domain to the target resulting in the activation of the immune cell and immune response (Signals 1 and/or 2). The intracellular signaling domain has the ability to activate at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3ζ signaling domain. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of fragment of 41BB (GenBank: AAA53133.) and CD28 (NP_006130.1).

CARs are expressed on the surface membrane of the cell. Thus, the CAR comprises a transmembrane domain. Suitable transmembrane domains for a CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (a chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8a chain (e.g., NP_001139345.1). The transmembrane domain can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8a chain (e.g., NP_001139345.1). In another particular embodiment, said transmembrane and hinge domains comprise a part of human CD8a chain. In some embodiments, CARs disclosed herein can comprise an extracellular ligand-binding domain that specifically binds BCMA, CD8a human hinge and transmembrane domains, the CD3(signaling domain, and 4-1BB signaling domain.

In some embodiments, a CAR can be introduced into an immune cell as a transgene via a plasmid vector. In some embodiments, the plasmid vector can also contain, for example, a selection marker which provides for identification and/or selection of cells which received the vector.

Table 8 provides exemplary sequences of CAR components that can be used in the CARs disclosed herein.

TABLE 8

Exemplary Sequences

| Domain | Amino acid sequence | SEQ ID NO: |
|---|---|---|
| V5 epitope tag | IPNPLLGLDST | 122 |
| 2173 scFv | EIQLVQSGAEVKKPGESLRISCKGSGFNIEDYYIH WVRQMPGKGLEWMGRIDPENDETKYGPIFQGH VTISADTSINTVYLQWSSLKASDTAMYYCAFRG GVYWGQGTTVTVSSGGGGSGGGGSGGGGSGGG GSDVVMTQSPDSLAVSLGERATINCKSSQSLLDS DGKTYLNWLQQKPGQPPKRLISLVSKLDSGVPD RFSGSGSGTDFTLTISSLQAEDVAVYYCWQGTHF PGTFGGGTKVEIK | 123 |

TABLE 8-continued

Exemplary Sequences

| Domain | Amino acid sequence | SEQ ID NO: |
|---|---|---|
| CD8 hinge and transmembrane | TTTPAPRPPTPAPTIASQPLSLRPEACRPAAGGAV HTRGLDFACDIYIWAPLAGTCGVLLLSLVITLYC | 124 |
| 4-1BB intracellular signaling | KRGRKKLLYIFKQPFMRPVQTTQEEDGCSCRFPE EEEGGCEL | 125 |
| CD3z intracellular signaling | RVKFSRSADAPAYQQGQNQLYNELNLGRREEYD VLDKRRGRDPEMGGKPRRKNPQEGLYNELQKD KMAEAYSEIGMKGERRRGKGHDGLYQGLSTAT KDTYDALHMQALPPR | 126 |
| BFP (blue fluorescent protein) | MSELIKENMHMKLYMEGTVDNHHFKCTSEGEG KPYEGTQTMRIKVVEGGPLPFAFDILATSFLYGS KTFINHTQGIPDFFKQSFPEGFTWERVTTYEDGG VLTATQDTSLQDGCLIYNVKIRGVNFTSNGPVM QKKTLGWEAFTETLYPADGGLEGRNDMALKLV GGSHLIANIKTTYRSKKPAKNLKMPGVYYVDYR LERIKEANNETYVEQHEVAVARYCDLPSKLGHK LN | 127 |
| P2A | GSGATNFSLLKQAGDVEENPGP | 128 |

In some embodiments, the CAR-immune cell (e.g., CAR-T cell) of the disclosure comprises a polynucleotide encoding a suicide polypeptide, such as for example RQR8. See, e.g., WO2013153391A, which is hereby incorporated by reference in its entirety. In some embodiments, a suicide polypeptide is expressed on the surface of the cell. In some embodiments, a suicide polypeptide is included in the CAR construct. In some embodiments, a suicide polypeptide is not part of the CAR construct.

In some embodiments, the extracellular domain of any one of CARs disclosed herein may comprise one or more epitopes specific for (specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprise antigen binding domains that specifically bind to a target of interest and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, allowing for depletion provides a safety switch in case of deleterious effects, e.g., upon administration to a subject.

Methods of preparing immune cells for use in immunotherapy are also provided herein. In some embodiments, the methods comprise introducing a PD-1 chimeric cytokine receptor and a CAR into immune cells, and expanding the cells. In some embodiments, the invention relates to a method of engineering an immune cell comprising: providing a cell and expressing a PD-1 chimeric cytokine receptor, and expressing at the surface of the cell at least one CAR. In some embodiments, the method comprises: transfecting the cell with at least one polynucleotide encoding a PD-1 chimeric cytokine receptor, and at least one polynucleotide encoding a CAR, and expressing the polynucleotides in the cell. In some embodiments, the method comprises: transfecting the cell with at least one polynucleotide encoding a PD-1 chimeric cytokine receptor, at least one polynucleotide encoding a CAR, and expressing the polynucleotides in the cell.

In some embodiments, the polynucleotides encoding the PD-1 chimeric cytokine receptor and CAR are present in one or more expression vectors for stable expression in the cells. In some embodiments, the polynucleotides are present in viral vectors for stable expression in the cells. In some embodiments, the viral vectors may be for example, lentiviral vectors or adenoviral vectors.

In some embodiments, polynucleotides encoding polypeptides according to the present disclosure can be mRNA which is introduced directly into the cells, for example by electroporation. In some embodiments, CytoPulse electroporation technology, such as PulseAgile, can be used to transiently permeabilize living cells for delivery of material into the cells (e.g. U.S. Pat. No. 6,078,490; PCT/US2011/000827; and PCT/US2004/005237). Parameters can be modified in order to determine conditions for high transfection efficiency with minimal mortality.

Also provided herein are methods of transfecting an immune cell, e.g a T-cell. In some embodiments, the method comprises: contacting a T-cell with RNA and applying to the T-cell an agile pulse sequence. In some embodiments, a method of transfecting an immune cell (e.g. T-cell) comprising contacting the immune cell with RNA and applying to the cell an agile pulse sequence.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, CD52, GR, deoxycytidine kinase (DCK), PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or CRISPR-based endonuclease (e.g Cas-9 or Cas12a).

In another aspect, a step of genetically modifying cells can comprise: modifying immune cells (e.g. T-cells) by inactivating at least one gene expressing a target for an immunosuppressive agent, and; expanding the cells, optionally in presence of the immunosuppressive agent.

In some embodiments, the engineered immune cells (e.g. T-cells) provided herein exhibit improved cytotoxicity, increased expansion, and/or increased levels of memory phenotype markers upon contact with a PD-L1 or PD-L2 ligand or PD-1 antibody that binds to the ectodomain of the PD-1 chimeric cytokine receptor relative to engineered immune cells that do not express the PD-1 chimeric cytokine receptor.

In some embodiments, the engineered immune cells (e.g. T-cells) provided herein exhibit (i) increased in vivo persistence, (ii) increased STAT activation, (iii) increased cytotoxicity, (iv) increased levels of memory phenotype markers, (v) increased expansion (proliferation), or combinations of these functional features, upon contact with a PD-L1 or PD-L2 ligand or PD-1 antibody that binds to the ectodomain of the PD-1 chimeric cytokine receptor relative to engineered immune cells that do not express the PD-1 chimeric cytokine receptor. In some embodiments, the improvement in the one or more functional features described herein is dose-dependent, i.e., the functional activity of the immune cell comprising the PD-1 chimeric cytokine receptors increases upon contact with increasing doses of the PD-L1/PD-L2/PD-1 antibody. In some embodiments, STATs activated by the engineered immune cell comprising one or more PD-1 chimeric cytokine receptors disclosed are STAT1, STAT2, STAT3, STAT4, STAT5, STAT6, or combinations thereof. In one embodiment, memory phenotype markers increased or maintained by the immune cell comprising the inducible chimeric cytokine receptor include stem cell memory (Tscm) marker and central memory (Tcm) marker.

In some embodiments, the improvement in one or more functional features exhibited by an engineered immune cell comprising an inducible chimeric cytokine receptor provided herein is at least about 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 40 fold, 50 fold, 60 fold, 70 fold, 80 fold, 90 fold, 100 fold, 125 fold, 150 fold, 200 fold, 250 fold, 300 fold, 350 fold, 400 fold, 450 fold, or even about 10500 fold, including values and ranges therebetween, compared to an immune cell that does not express the PD-1 chimeric cytokine receptor.

In some embodiments, the improvement in one or more functional features exhibited by an engineered immune cell comprising a PD-1 chimeric cytokine receptor provided herein is at least about 10%, 20%, 25%, 30%, 35%, 40%, 45%, 50%, 55%, 60%, 70%, 75%, 80%, 90%, 100%, 125%, 150%, 200%, 250%, 300%, 350%, 400%, or even about 80%500%, including values and ranges therebetween, compared to an engineered immune cell that does not express the PD-1 chimeric cytokine receptor.

III. Therapeutic Methods

Provided herein are pharmaceutical compositions comprising cells bearing the chimeric cytokine receptors and CARs of the disclosure.

Engineered PD-1 chimeric cytokine receptor-bearing and CAR-bearing immune cells (e.g. T-cells) obtained by the methods described above, or cell lines derived from such engineered immune cells, can be used as a medicament. In some embodiments, such a medicament can be used for treating a disorder such as for example a viral disease, a bacterial disease, a cancer, an inflammatory disease, an immune disease, or an aging-associated disease. In some embodiments, the cancer is a solid cancer. In some embodiments the cancer is a liquid cancer. The cancer can be selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, engineered immune cells, or cell line derived from the engineered immune cells, can be used in the manufacture of a medicament for treatment of a disorder in a subject in need thereof. In some embodiments, the disorder can be, for example, a cancer, an autoimmune disorder, or an infection.

Also provided herein are methods for treating subjects in need of such treatment.

As used herein, the term "subject" refers to any vertebrate including, without limitation, humans and other primates (e.g., chimpanzees, cynomologous monkeys, and other apes and monkey species), farm animals (e.g., cattle, sheep, pigs, goats and horses), domestic mammals (e.g., dogs and cats), laboratory animals (e.g., rabbits, rodents such as mice, rats, and guinea pigs), and birds (e.g., domestic, wild and game birds such as chickens, turkeys and other gallinaceous birds, ducks, geese, and the like). In some embodiments, the subject is a mammal. In exemplary embodiments, the subject is a human.

In some embodiments the method comprises providing immune cells of the disclosure, bearing the PD-1 chimeric cytokine receptors and CARs described herein to a subject in need thereof.

In some embodiments, PD-1 chimeric cytokine receptor and CAR-bearing T-cells of the invention can undergo robust in vivo T-cell expansion and can persist for an extended amount of time.

Methods of treatment of the invention can be ameliorating, curative or prophylactic. The method of the invention may be either part of an autologous immunotherapy or part of an allogenic immunotherapy treatment.

In another aspect, the invention provides a method of inhibiting tumor growth or progression in a subject who has a tumor, comprising administering to the subject an effective amount of PD-1 chimeric cytokine receptor-expressing and CAR-expressing immune cells as described herein. In another aspect, the invention provides a method of inhibiting or preventing metastasis of cancer cells in a subject, comprising administering to the subject in need thereof an effective amount of engineered immune cells as described herein. In another aspect, the invention provides a method of inducing tumor regression in a subject who has a tumor, comprising administering to the subject an effective amount of engineered immune cells as described herein.

In some embodiments, the engineered T-cells herein can be administered parenterally in a subject.

Also provided is the use of any of the engineered T-cells provided herein in the manufacture of a medicament for the treatment of cancer or for inhibiting tumor growth or progression in a subject in need thereof.

In some embodiments, treatment can be administrated into subjects undergoing an immunosuppressive treatment. Indeed, the invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. Cells bearing the CARs of the disclosure or the pharmaceutical compositions thereof may be administered via one or more of the following routes of administration: intravenous, intraocular, intravitreal, intramuscular, subcutaneous, topical, oral, transdermal, intraperitoneal, intraorbital, by implantation, by inhalation, intrathecal, intraventricular, via the ear, or intranasal.

In some embodiments the administration of the cells or population of cells (bearing the chimeric cytokine receptors and CARs of the disclosure) can comprise administration of, for example, about $10^4$ to about $10^9$ cells per kg body weight including all integer values of cell numbers within those ranges. In some embodiments the administration of the cells or population of cells can comprise administration of about $10^4$ to $10^5$ cells per kg body weight, $10^5$ to $10^6$ cells per kg body weight, $10^6$ to $10^7$ cells per kg body weight, $10^7$ to $10^8$ cells per kg body weight, or $10^8$ to $10^9$ cells per kg body weight. The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

The methods can further comprise administering one or more agents to a subject prior to administering the engineered immune cells bearing a CAR and a PD-1 chimeric cytokine receptor provided herein. In certain embodiments, the agent is a lymphodepleting (preconditioning) regimen. For example, methods of lymphodepleting a subject in need of such therapy comprise administering to the subject specified beneficial doses of cyclophosphamide (between 200 mg/m$^2$/day and 2000 mg/m$^2$/day, about 100 mg/m$^2$/day and about 2000 mg/m$^2$/day; e.g., about 100 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1500 mg/m$^2$/day or about 2000 mg/m$^2$/day) and specified doses of fludarabine (between 20 mg/m$^2$/day and 900 mg/m$^2$/day, between about 10 mg/m$^2$/day and about 900 mg/m$^2$/day; e.g., about 10 mg/m$^2$/day, about 20 mg/m$^2$/day, about 30 mg/m$^2$/day, about 40 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 500 mg/m$^2$/day or about 900 mg/m$^2$/day). An exemplary dosing regimen involves treating a subject comprising administering daily to the patient about 300 mg/m$^2$/day of cyclophosphamide in combination or before or after administering about 30 mg/m$^2$/day of fludarabine for three days prior to administration of a therapeutically effective amount of engineered immune cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab. In some embodiments, the CD52 antibody is administered at a dose of about 1-20 mg/day IV, e.g., about 13 mg/day IV for 1, 2, 3 or more days. The antibody can be administered in combination with, before, or after administration of other elements of a lymphodepletion regime (e.g., cyclophosphamide and/or fludarabine).

In certain embodiments, compositions comprising CAR-expressing immune effector cells disclosed herein may be administered in conjunction with any number of chemotherapeutic agents.

IV. Kits and Articles of Manufacture

The present disclosure provides kits comprising any one or more of the PD-1 chimeric cytokine receptors and PD-1 chimeric cytokine receptors-bearing cells described herein, and pharmaceutical compositions thereof. The present disclosure also provides articles of manufacture comprising any one or more of the PD-1 chimeric cytokine receptors and PD-1 chimeric cytokine receptors-bearing CAR-I cells described herein, pharmaceutical compositions thereof, and kits described herein.

The following examples are included for illustrative purposes and are not intend to limit the scope of the disclosure.

All patent and non-patent documents referenced throughout this disclosure are incorporated by reference herein in their entirety for all purposes.

EXAMPLES

In referring to the chimeric cytokine receptors of the disclosure it is noted that certain figures refer to a "switch." As used herein, a "switch" is used interchangeably with a "chimeric cytokine receptor".

The following notations are used throughout the drawings and examples.

FKBP switch=a FKBP chimeric cytokine receptor

WT PD1 switch=a chimeric cytokine receptor with a wild type PD-1 ectodomain

2×PD1 switch=a chimeric cytokine receptor with 2 PD-1 ectodomains in tandem

3×PD1 switch=a chimeric cytokine receptor with 3 PD-1 ectodomains in tandem

HA PD1 switch=a chimeric cytokine receptor with a high affinity PD-1 ecotodomain HA PD1 DN=a chimeric cytokine receptor with a dominant negative high affinity PD-1 domain Example 1: Coupling of PD-1 Engagement with Cytokine Signaling To couple simultaneous PD-1 engagement with cytokine signaling, a PD-1 chimeric cytokine receptor was constructed, composed of the following modules: (i) the wild type (WT) PD-1 ectodomain (21-207), (ii) a transmembrane domain with an intracellular portion having a JAK2-activating domain and (iii) STAT-recruiting domains comprising Stat-recruiting (Stat-activating) domains from cytokine receptor tails (cytotails). With this design, it was determined whether clustering or dimerization of the PD-1 chimeric cytokine receptor, in response to PD-1 ligands or anti-PD-1 antibodies, respectively, could activate the JAK-Stat pathway and mimic cytokine signaling. In order to minimize the transgene payload in the lentiviral vector, JAK2-activating domains derived from natural cytokine receptors known to signal as homodimers, such as TpoR (TPOR/MPLR(478-582)), GCSFR (GCSFR(614-710)) and GP130 (GP130(609-700)), were selected for initial evaluation.

Two Stat-activating cytoplasmic domains derived from IL7R(316-459) and IL12Rb(775-825) were linked in tandem mimic signaling in response to IL7 and IL12, respectively. To demonstrate the utility of the PD-1 chimeric cytokine receptor in the context of CAR-T-cells, the PD-1 chimeric cytokine receptor was cloned into a lentiviral vector encoding a second generation EGFRvIII-specific CAR (2173scFv; described in Sci Transl Med. 2015 Feb. 18; 7(275): 275ra22.); furthermore, to permit stoichiometric co-expression of the PD-1 chimeric cytokine receptor and the CAR, both genes were linked via a P2A peptide linker. To facilitate the detection of transduced cells, a v5 epitope tag (KPIPNPLLGLDST (SEQ ID NO: 167)) was inserted between the scFv and CD8 hinge domain of the CAR.

A HEK293T-cell reporter assay was used to test the inducibility and magnitude of cytokine signaling. Briefly, 20,000 HEK293T-cells were plated into each well of a poly-L-lysine-coated 96-well flat-bottom plate and allowed to adhere overnight. A PD-1 chimeric cytokine receptor (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a positive control, a FKBP chimeric cytokine receptor was used, in which the WT PD-1 ectodomain was replaced with FKBP12(F36V), so that cytokine signaling could be inducible by the small molecule, AP1903. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 24 hours after transfection, cells were either left untreated, or treated with the indicated concentrations of anti-PD-1 (Nivolumab; Selleck Chemical), recombinant human PD-L1-Fc (Biolegend), anti-Human IgG Fc gamma secondary antibody (Thermo Fisher), or AP1903 (Apex Bio). As negative controls, hIgG4 and hIgG1 isotype controls were added in place of anti-PD-1 and PD-L1-Fc, respectively. All treatments were diluted in serum-free media. 24 hours after treatment, Stat reporter activity was evaluated using the Dual-Glo Luciferase Assay System (Promega). Fold induction of Stat5 reporter activity was normalized to that of HEK293T-cells transfected with all vectors except for the chimeric cytokine receptor and that were left untreated.

Figure 1B:
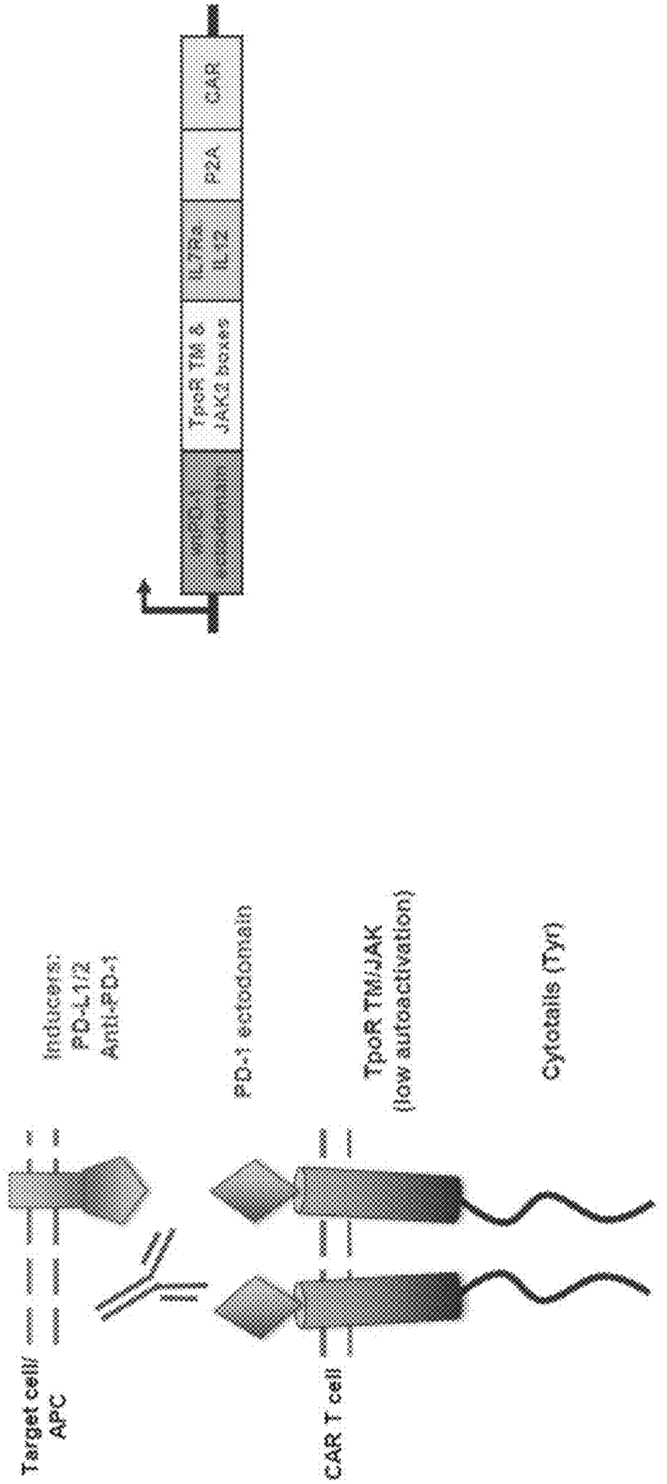
FIG. 1B shows a schematic of the PD-1 chimeric cytokine receptor of the disclosure with a wild type PD-1 ectodomain.
Figure 1C:
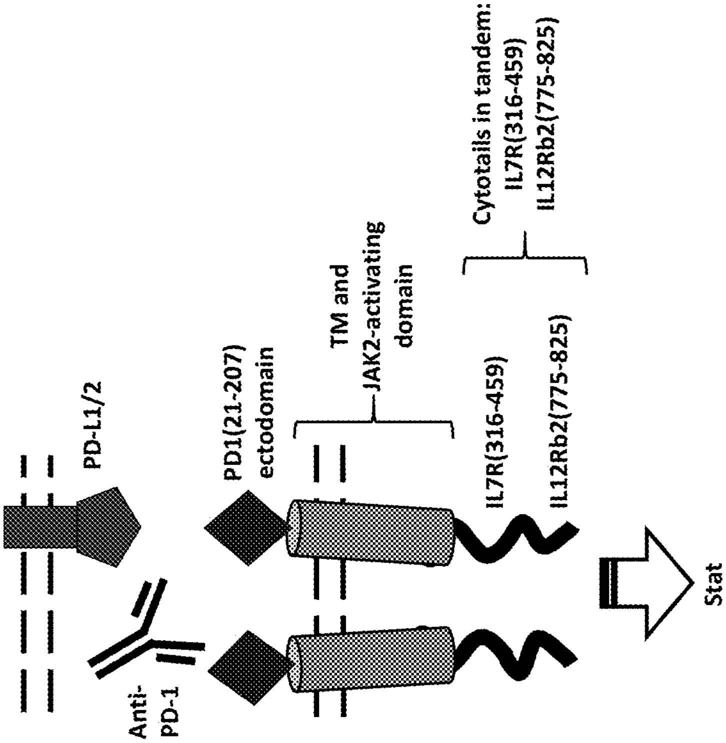
FIG. 1C shows a schematic of an exemplary PD-1 chimeric cytokine receptor of the disclosure.
Figure 1D:
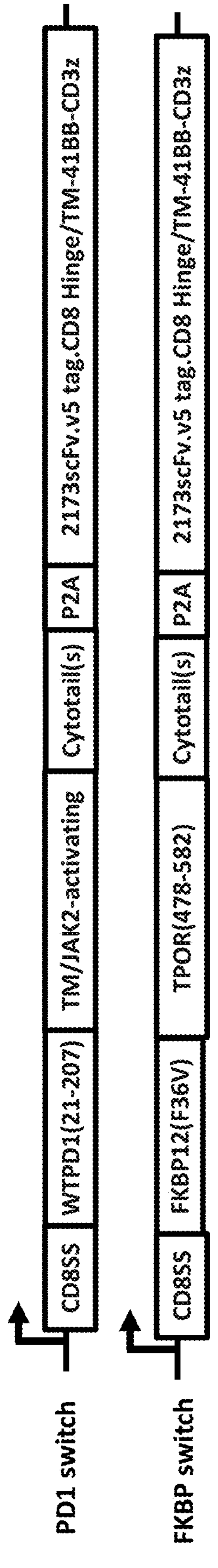
FIG. 1D shows a schematic of the PD-1 chimeric cytokine receptor—CAR vector, and the control FKBP chimeric cytokine receptor CAR vector.

FIGS. 1A-C show schematics of the various embodiments of the PD-1 chimeric cytokine receptor.

FIG. 1B shows a schematic of the PD-1 chimeric cytokine receptor CAR vector. FIG. 1D shows a schematic of the PD-1 chimeric cytokine receptor CAR vector, and the positive control FKBP chimeric cytokine receptor CAR vector.

Figure 2A:
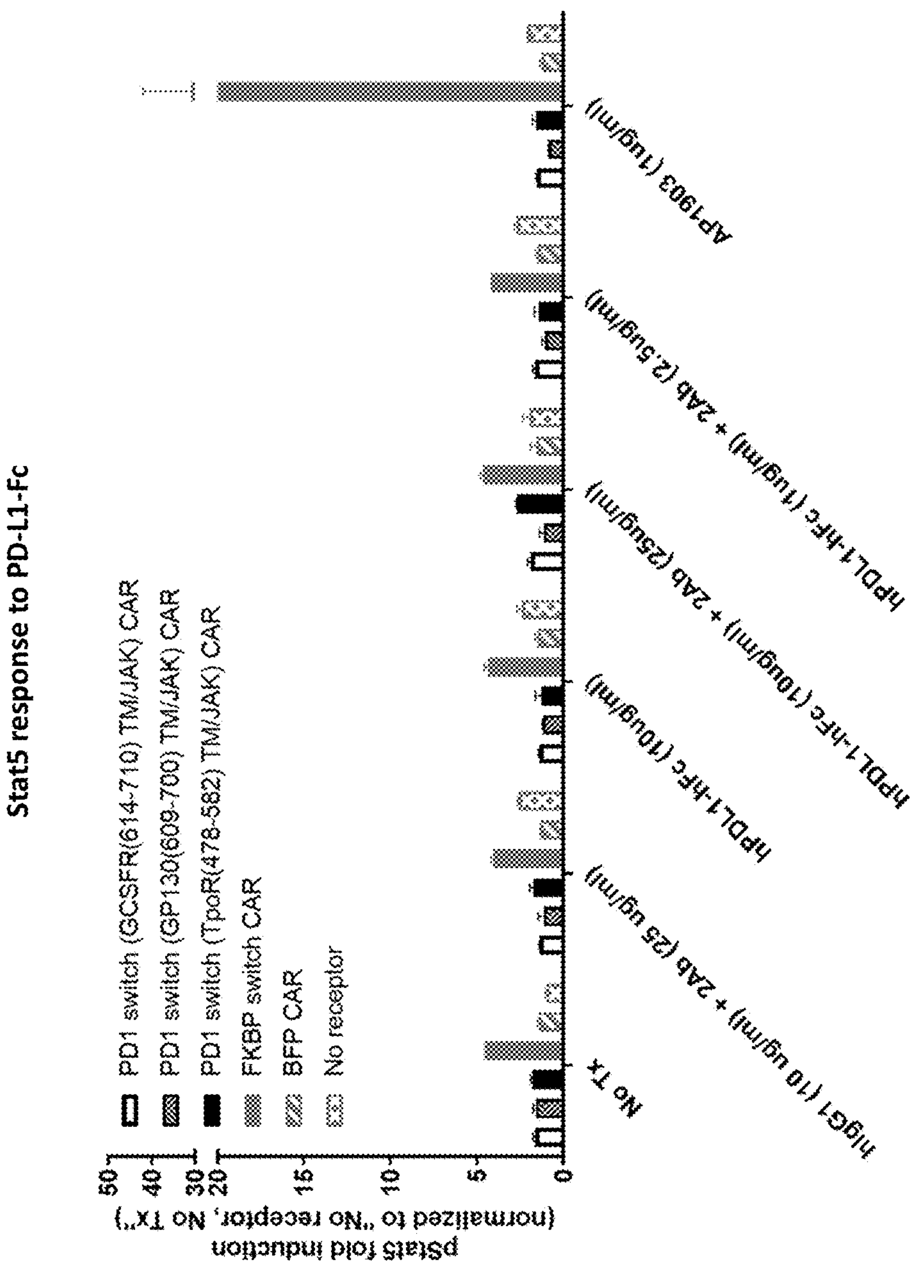
FIGS. 2A-2D show Stat reporter activity of the PD-1 chimeric cytokine receptor in response to PD-L1-Fc (FIGS. 2A-B) and anti-PD-1 (FIGS. 2C-D).
Figure 2B:
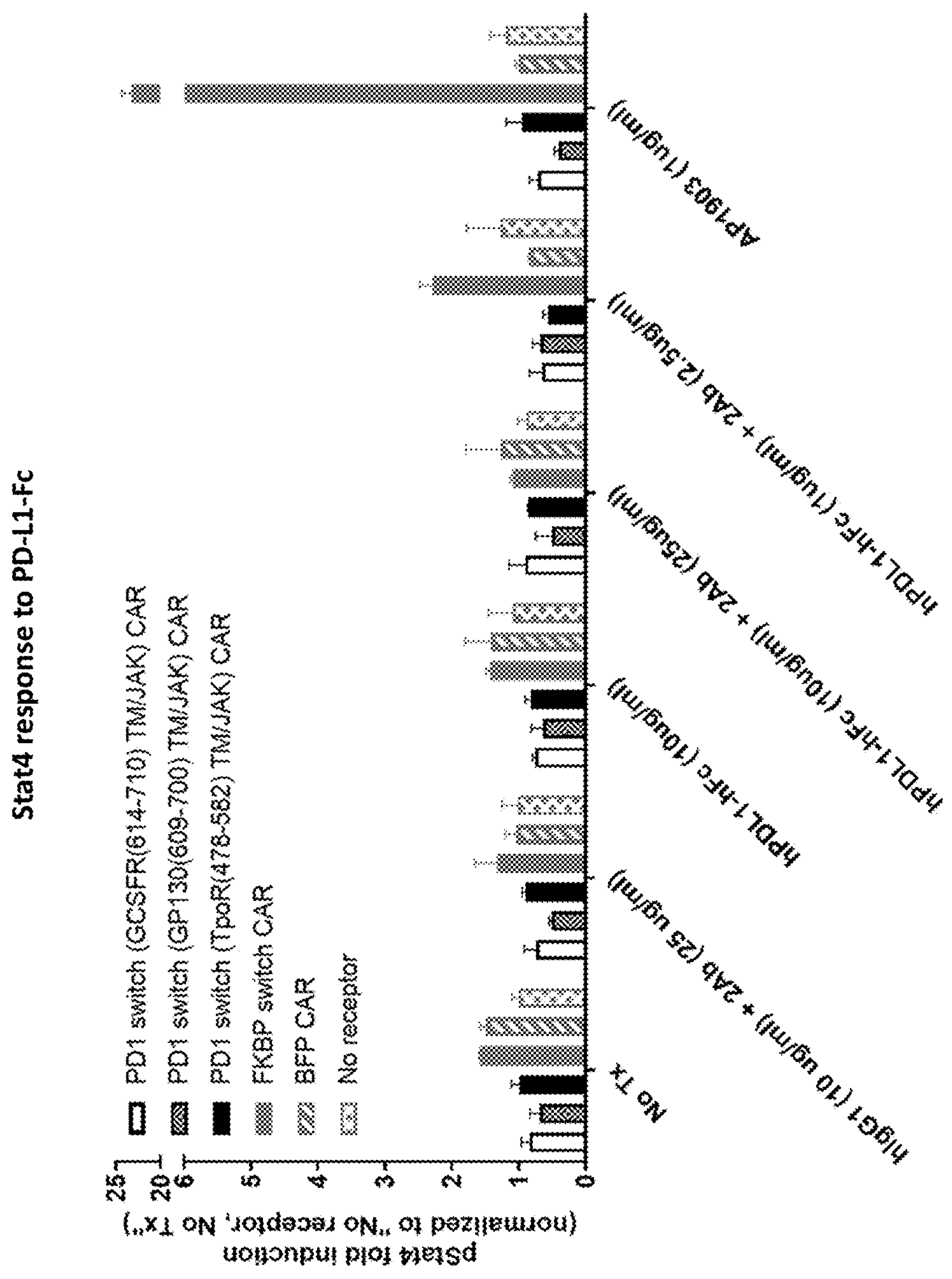
Figure 2C:
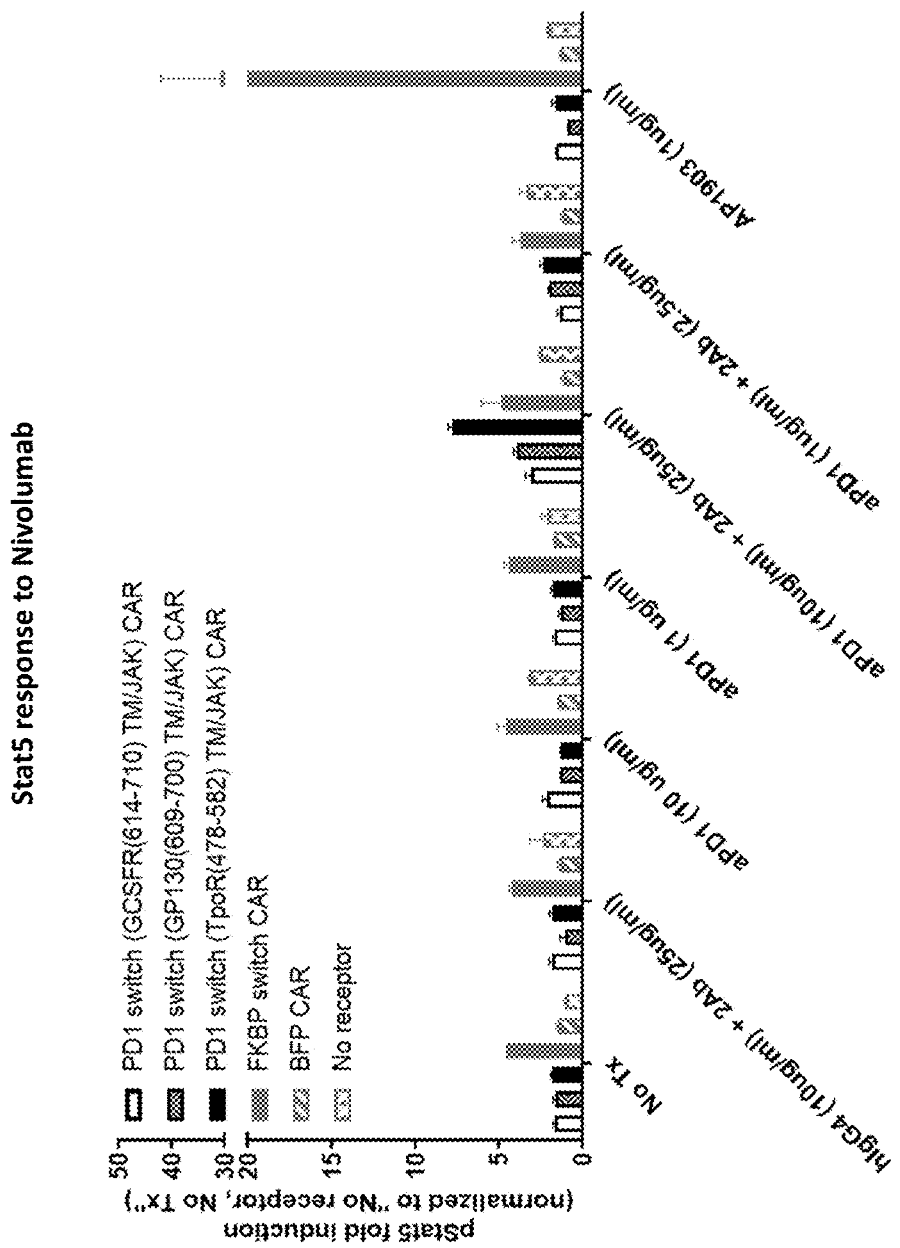
Figure 2D:
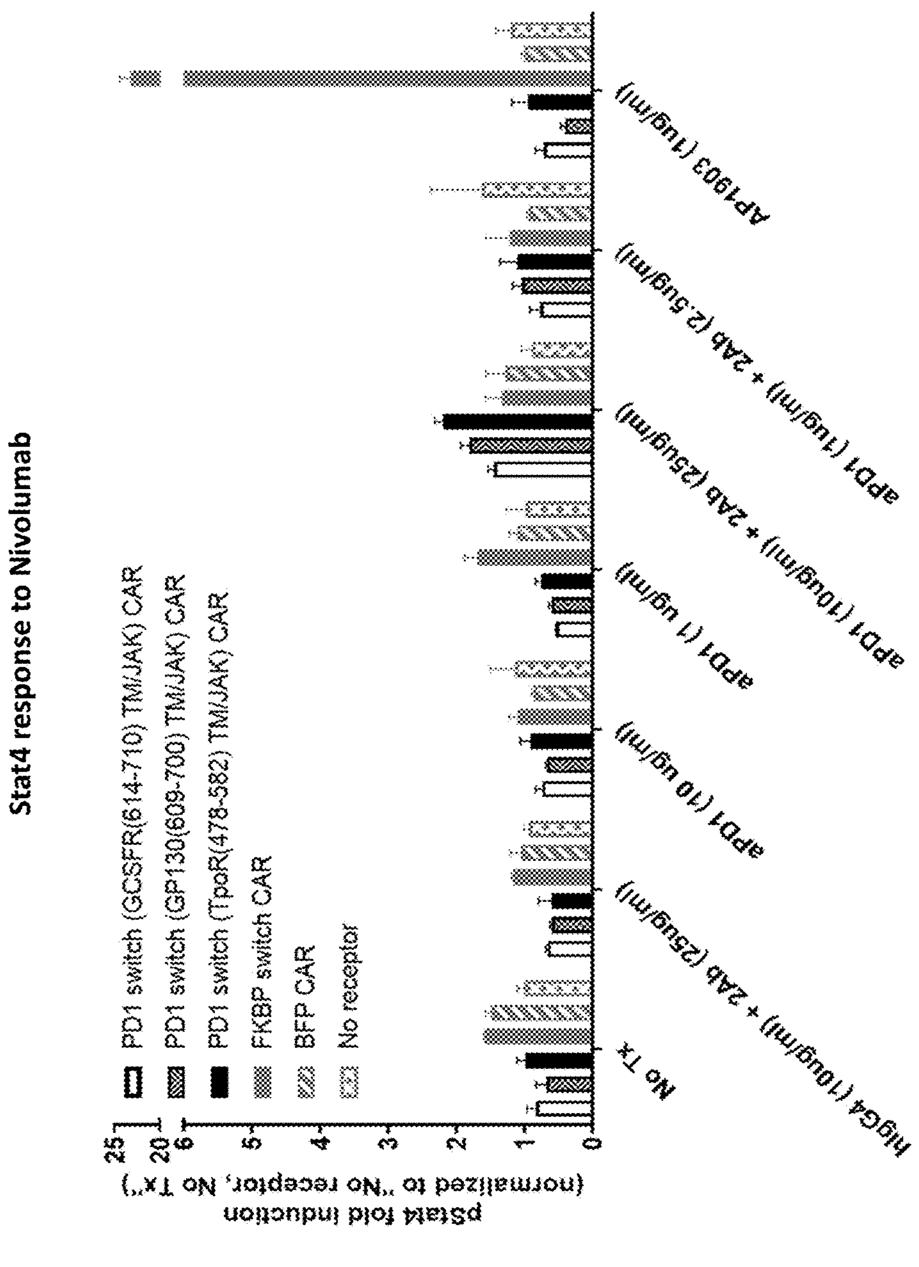

FIGS. 2A-D show Stat reporter activity in response to PD-L1-Fc (FIGS. 2A-B) and anti-PD-1 (FIGS. 2C-D). FIGS. 2A-B show that as compared to their untreated counterparts, PD-1 chimeric cytokine receptors induced weak Stat reporter activity in response to high concentrations of crosslinked PD-L1 (i.e. hPD-L1-Fc (10 ug/ml)+2Ab (25 ug/ml)). FIGS. 2C-D show that as compared to their untreated counterparts, PD-1 chimeric cytokine receptors induced weak Stat reporter activity in response to high concentrations of crosslinked anti-PD-1 (i.e. aPD-1 (10 ug/ml)+2Ab (25 ug/ml)), with the TpoR(478-582) TM/JAK variant showing the best response. Although the FKBP chimeric cytokine receptor positive control showed basal activity in the absence of AP1903, it induced high Stat reporter activity in response to AP1903.

Similar experiments were then carried out in the context of primary human CAR-T-cells. To make lentivirus encoding PD-1 chimeric cytokine receptor CARs, HEK293T-cells were plated at 0.45 million cells per mL in 2 mL of DMEM (Gibco) supplemented with 10% FBS (Hyclone) per well of a 6-well plate on Day −1. On Day 0, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. On Day 0, purified T-cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 1, the media from each well of HEK293T-cells in the 6-well plate was replaced with 2 mL per well of T-cell transduction media, i.e., X-Vivo-15 supplemented with 10% FBS. On Day 2, T-cells were resuspended at 0.5 million cells per mL in 1 mL of T-cell transduction media per well of a Grex-24 plate. The lentiviral supernatants from HEK293T-cells were harvested and passed through a 0.45 micron filter (EMD Millipore) to remove cell debris, and then added to the T-cells along with 100 IU/mL human IL-2. On Day 5, 4.5 mL of T-cell expansion media, i.e., X-Vivo-15 supplemented with 5% human AB serum (Gemini Bio) and 100 IU/mL human IL-2 was added to each well of a Grex-24 plate. Cells were expanded into larger G-Rex vessels (Wilson Wolf) as needed using T-cell expansion media. On Day 13 or 14, transduction efficiency and PD-1 chimeric cytokine receptor expression was determined by detecting the percentage of T-cells that bound a FITC-conjugated v5 tag monoclonal antibody (Thermo Fisher) and a PE/Cy7-conjugated anti-human PD-1 (Biolegend) using flow cytometry. On Day 14 or 15, the CAR-T-cell products were cryopreserved and thawed as needed for further assays.

Figure 3:
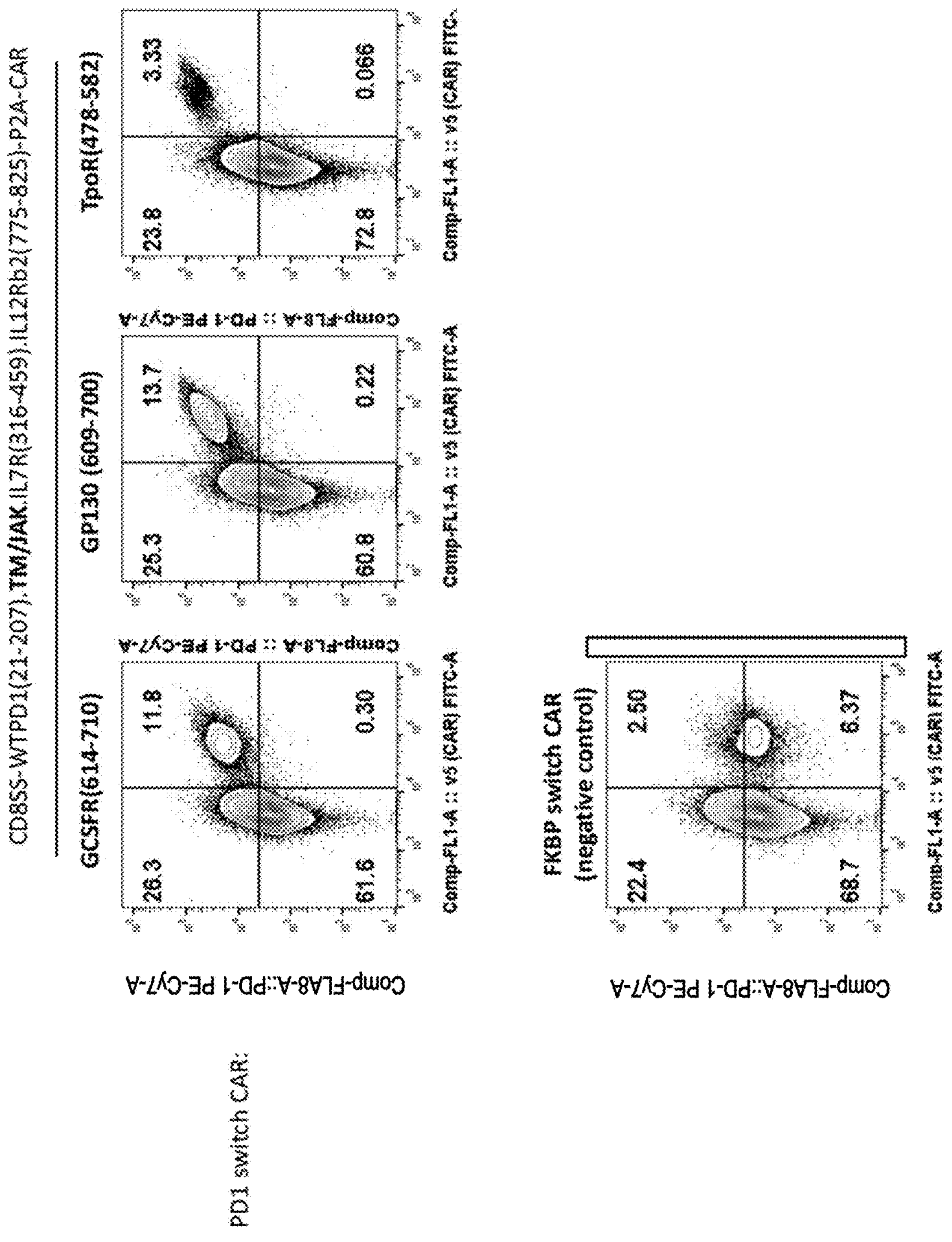
FIG. 3 shows CAR and PD-1 chimeric cytokine receptor co-expression on the Day 14 following transduction of the CAR and the PD-1 chimeric cytokine receptor.

FIG. 3 shows CAR and PD-1 chimeric cytokine receptor expression on the Day 14 CAR-T-cell product. As compared to FKBP chimeric cytokine receptor CAR-T-cells on which little to no PD-1 was detected, high levels of PD-1 was detected on PD-1 chimeric cytokine receptor CAR-T-cells, indicating that the CAR and PD-1 chimeric cytokine receptor were coexpressed.

To determine the inducibility and magnitude of cytokine signaling in PD-1 chimeric cytokine receptor CAR-T-cells, the thawed CAR-T-cell product was serum starved in 100 uL serum-free RPMI (Corning) for 4 hours in humidified incubator at 37 °C with 5% $CO_2$, then treated with anti-PD-1 (10 ug/mL Nivolumab; Selleck Chemical), recombinant human PD-L1-Fc (10 ug/mL; Biolegend), anti-Human IgG Fc gamma secondary antibody (25 ug/mL; Thermo Fisher) for 1 hour. 40 minutes into the treatment, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. After 1 hour of treatment, cells were fixed by the addition of 35 uL of 16% paraformaldehyde was added to each 100 uL sample and allowed to incubate for 15 minutes at 37 °C Cells were then washed three times with PBS, and permeabilized in 100% cold methanol for 1 or 2 nights at −20 °C. On the day of FACS analysis, cells were washed three times with PBS, Fc-blocked, and stained with AlexaFluor647-conjugated anti-mouse/human Stat5 (pY694) (BD Biosciences) diluted in PBS+1% BSA. After a 1 hour incubation at room temperature in the dark, cells were washed three times before FACS analysis.

Figure 4A:
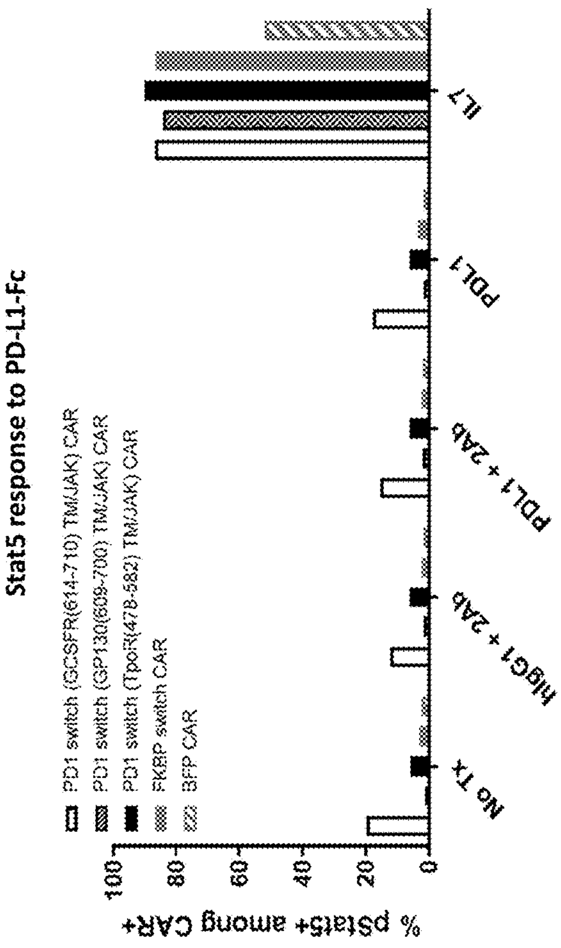
FIGS. 4A-4B show phospho-Stat5 staining in human CAR-T-cells following the treatment with PD-L1-Fc (FIG. 4A) or anti-PD-1 (FIG. 4B).
Figure 4B:
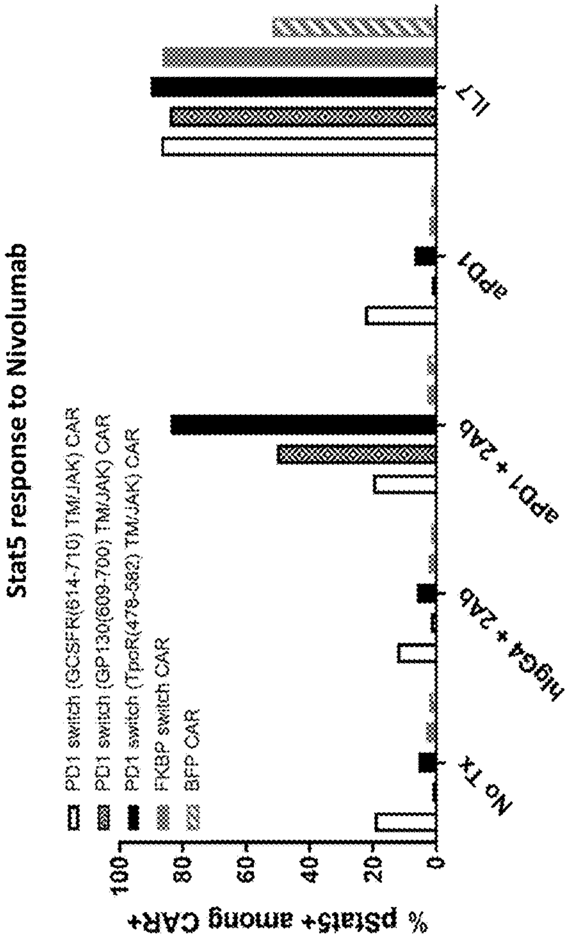

FIGS. 4A-B show phospho-Stat5 staining in human CAR-T-cells following the treatment with PD-L1-Fc (FIG. 4A) or anti-PD-1 (FIG. 4B). PD-1 chimeric cytokine receptor CAR-T-cells bearing the GCSFR(614-710) TM/JAK2-activating domain showed high basal activity in the absence of treatment, and no induction of pStat5 in the presence of treatment. PD-1 chimeric cytokine receptor CAR-T-cells bearing the GP130(609-700) TM/JAK2-activating domain showed the lowest basal activity in the absence of treatment, no pStat5 induction in response to PD-L1 or anti-PD-1, and moderate pStat5 induction in response to crosslinked anti-PD-1. PD-1 chimeric cytokine receptor CAR-T-cells bearing the TpoR(478-582) TM/JAK2-activating domain showed the moderate basal activity in the absence of treatment, no pStat5 induction in response to PD-L1 or anti-PD-1, and strong pStat5 induction in response to crosslinked anti-PD-1.

Example 2: Optimization of the PD-1 Chimeric Cytokine Receptor

Compared to the high affinity interaction between Nivolumab and PD-1 (<10 pM), PD-1 binds to PD-L1 and PD-L2 through a low-affinity (1-10 uM), monomeric interaction. The observation that crosslinked anti-PD-1 (Nivolumab) was able to activate the PD-1 chimeric cytokine receptor bearing the TpoR(478-582) TM/JAK2-activating domain indicating that PD-1 chimeric cytokine receptor activation could be made more efficient by enhancing its affinity or avidity of interaction with its inducer (PD-1 ligands or anti-PD-1). To increase the avidity of the PD-1 chimeric cytokine receptor, multiple WT PD-1 ectodomains were engineered in tandem. To increase the affinity of the PD-1 chimeric cytokine receptor, mutations to the PD-1 ectodomains were introduced, aimed at increasing binding affinity to its ligands (henceforth referred to as "high affinity (HA) PD-1").

To demonstrate the utility of these PD-1 chimeric cytokine receptors in the context of CAR-T-cells, each PD-1 chimeric cytokine receptor was cloned into a lentiviral vector encoding a second generation EGFRvIII-specific CAR (2173scFv; described in Sci Transl Med. 2015 Feb. 18; 7(275): 275ra22.); furthermore, to permit stoichiometric co-expression of the PD-1 chimeric cytokine receptor and the CAR, both genes were linked via a P2A peptide linker. To facilitate the detection of transduced cells, a v5 epitope tag (KPIPNPLLGLDST (SEQ ID NO: 167)) was inserted between the scFv and CD8 hinge domain.

Figures 5A, 5B, 5C, 5D:
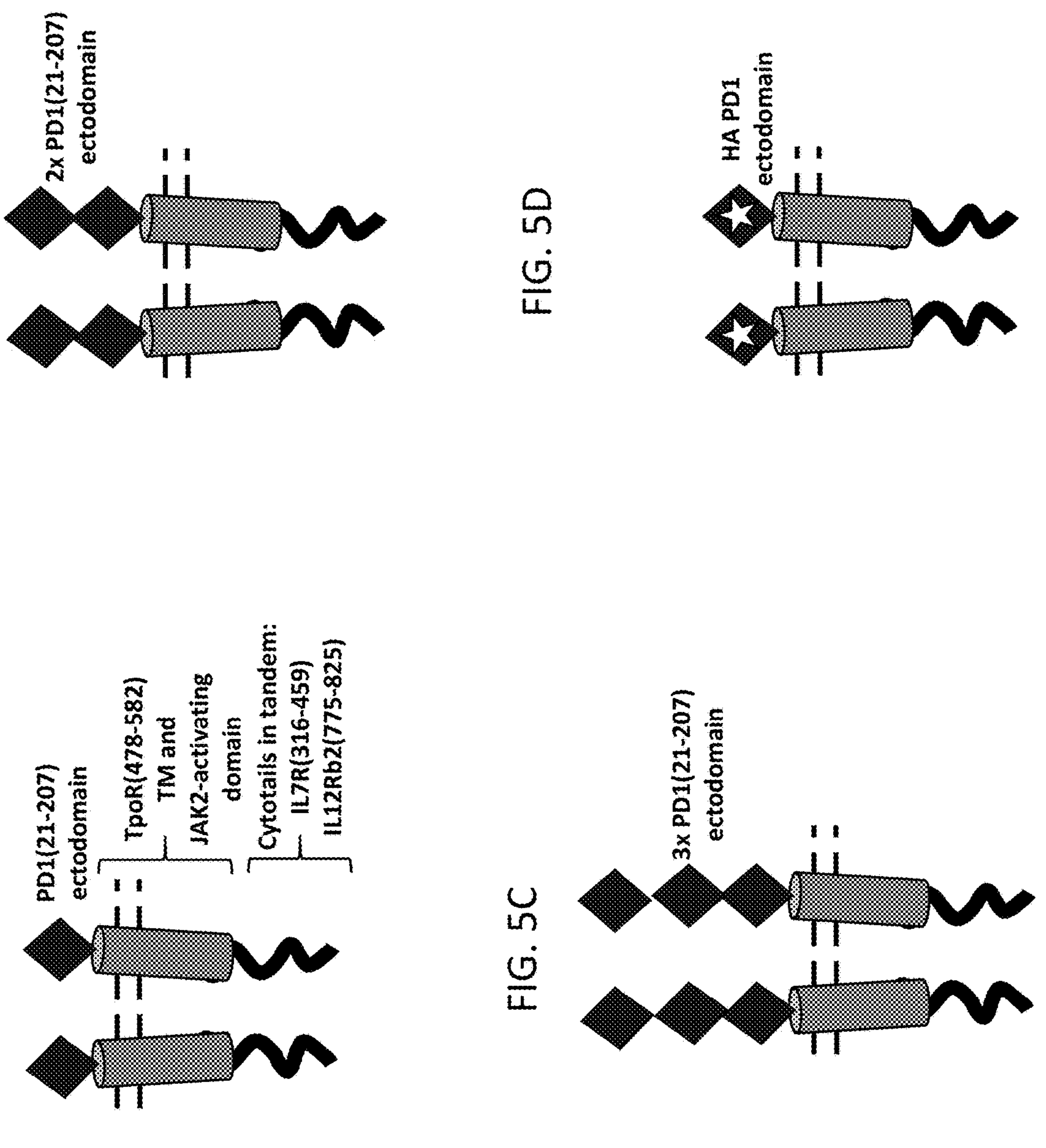
FIGS. 5A-5D show a schematic of PD-1 chimeric cytokine receptors with various ectodomains engineered for enhanced avidity or affinity.

FIGS. 5A-D show a schematic of PD-1 chimeric cytokine receptors with various ectodomains engineered for enhanced avidity or affinity. FIG. 5A shows the prototypic WT PD-1 chimeric cytokine receptor bearing the TpoR(478-582) TM/JAK2-activating domain; FIG. 5B shows the 2×PD-1 chimeric cytokine receptor bearing two WT PD-1 ectodomains in tandem; FIG. 5C shows the 3×PD-1 chimeric cytokine receptor bearing three WT PD-1 ectodomains in tandem; FIG. 5D shows the high affinity (HA) PD-1 chimeric cytokine receptor with ectodomain mutations.

A HEK293T-cell reporter assay was used to test the inducibility and magnitude of cytokine signaling. Briefly, 20,000 HEK293T-cells were plated into each well of a poly-L-lysine-coated 96-well flat-bottom plate and allowed to adhere overnight. A PD-1 chimeric cytokine receptor (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a positive control, a FKBP chimeric cytokine receptor was used, in which the WT PD-1 ectodomain was replaced with FKBP12(F36V), so that cytokine signaling could be inducible by the small molecule, AP1903. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 24 hours after transfection, cells were either left untreated, or treated with the indicated concentrations of anti-PD-1 (Nivolumab; Selleck Chemical), recombinant human PD-L1-Fc (Biolegend), anti-Human IgG Fc gamma secondary antibody (Thermo Fisher), or AP1903 (Apex Bio). As negative controls, hIgG4 and hIgG1 isotype controls were added in place of anti-PD-1 and PD-L1-Fc, respectively. All treatments were diluted in serum-free media. 24 hours after treatment, Stat reporter activity was evaluated using the Dual-Glo Luciferase Assay System (Promega). Fold induction of Stat5 reporter activity was normalized to that of HEK293T-cells transfected with all vectors except for the chimeric cytokine receptor and that were left untreated.

Figure 6A:
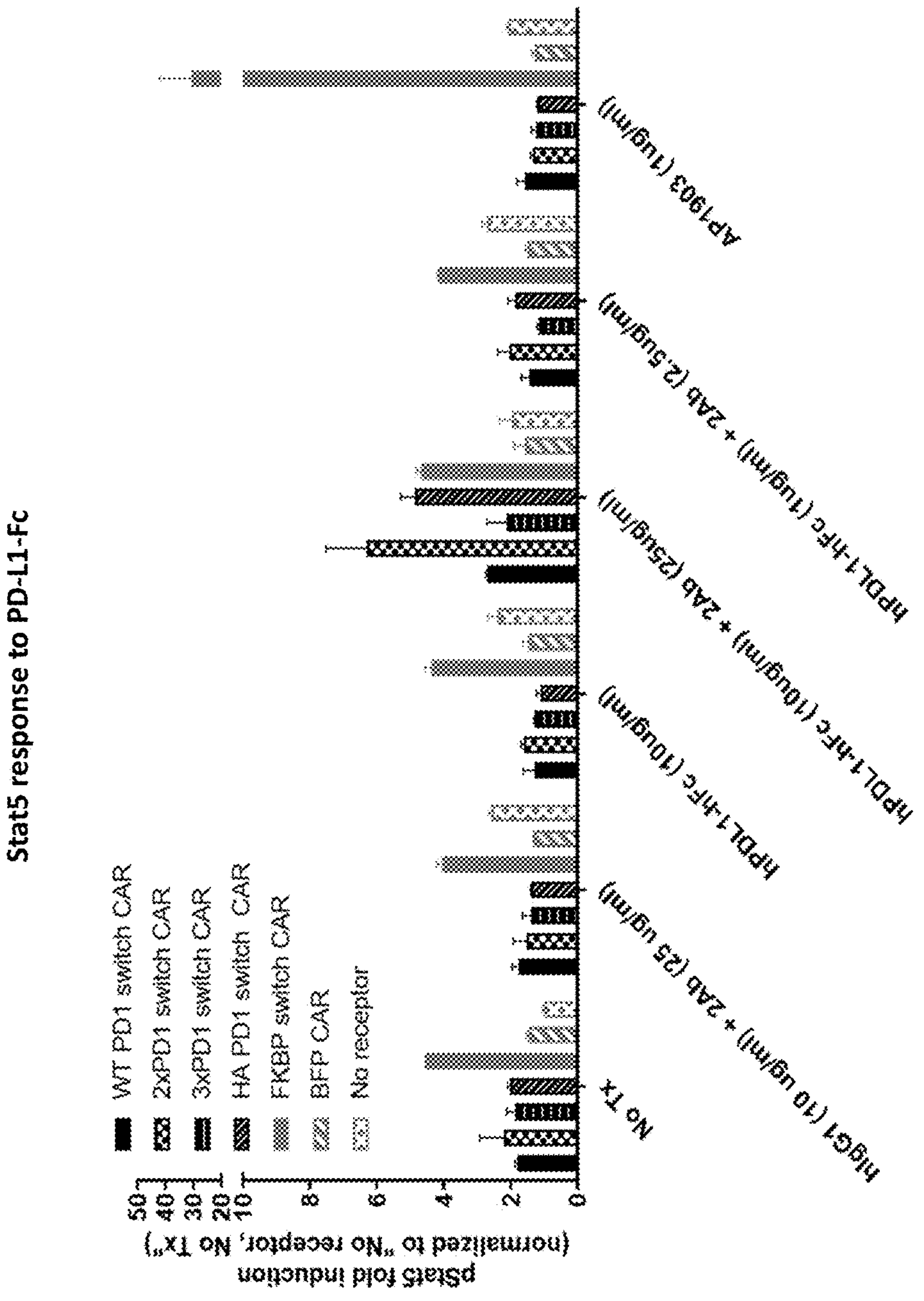
FIGS. 6A-6D show the response of PD-1 chimeric cytokine receptors bearing ectodomain modifications following treatment with PD-L1-Fc (FIGS. 6A-6B) and anti-PD-1 (FIGS. 6C-D).
Figure 6B:
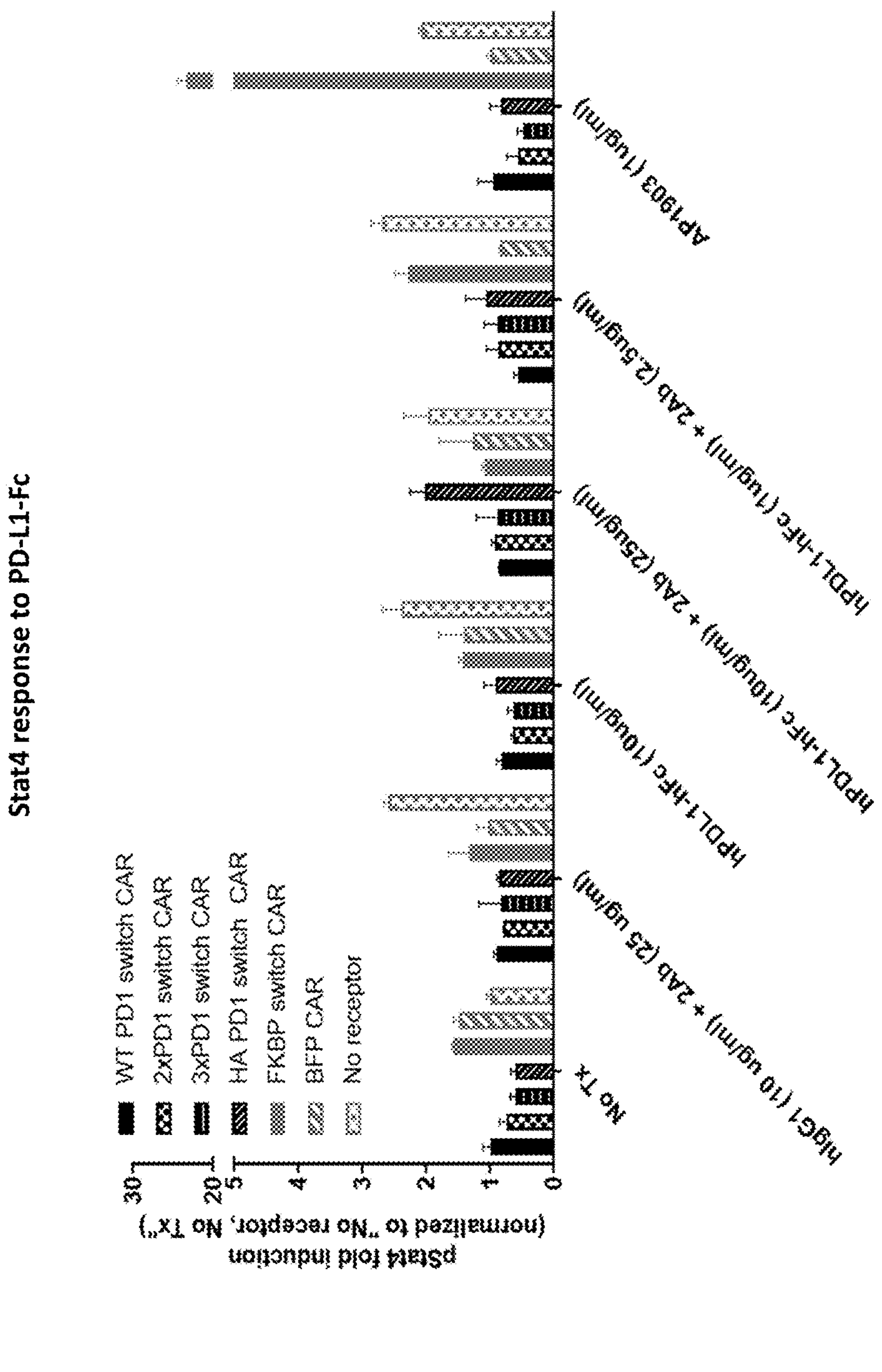
Figure 6C:
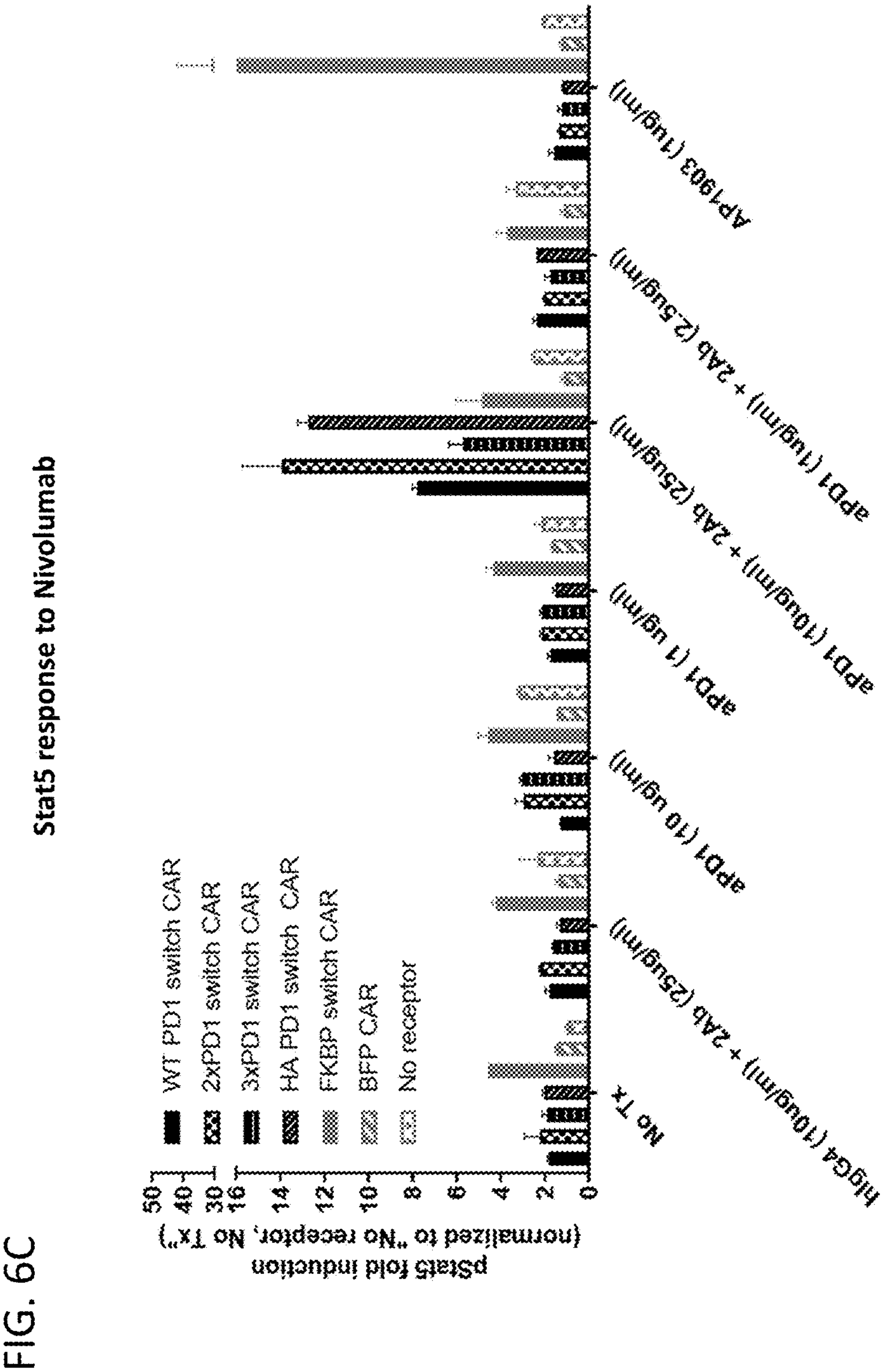
Figure 6D:
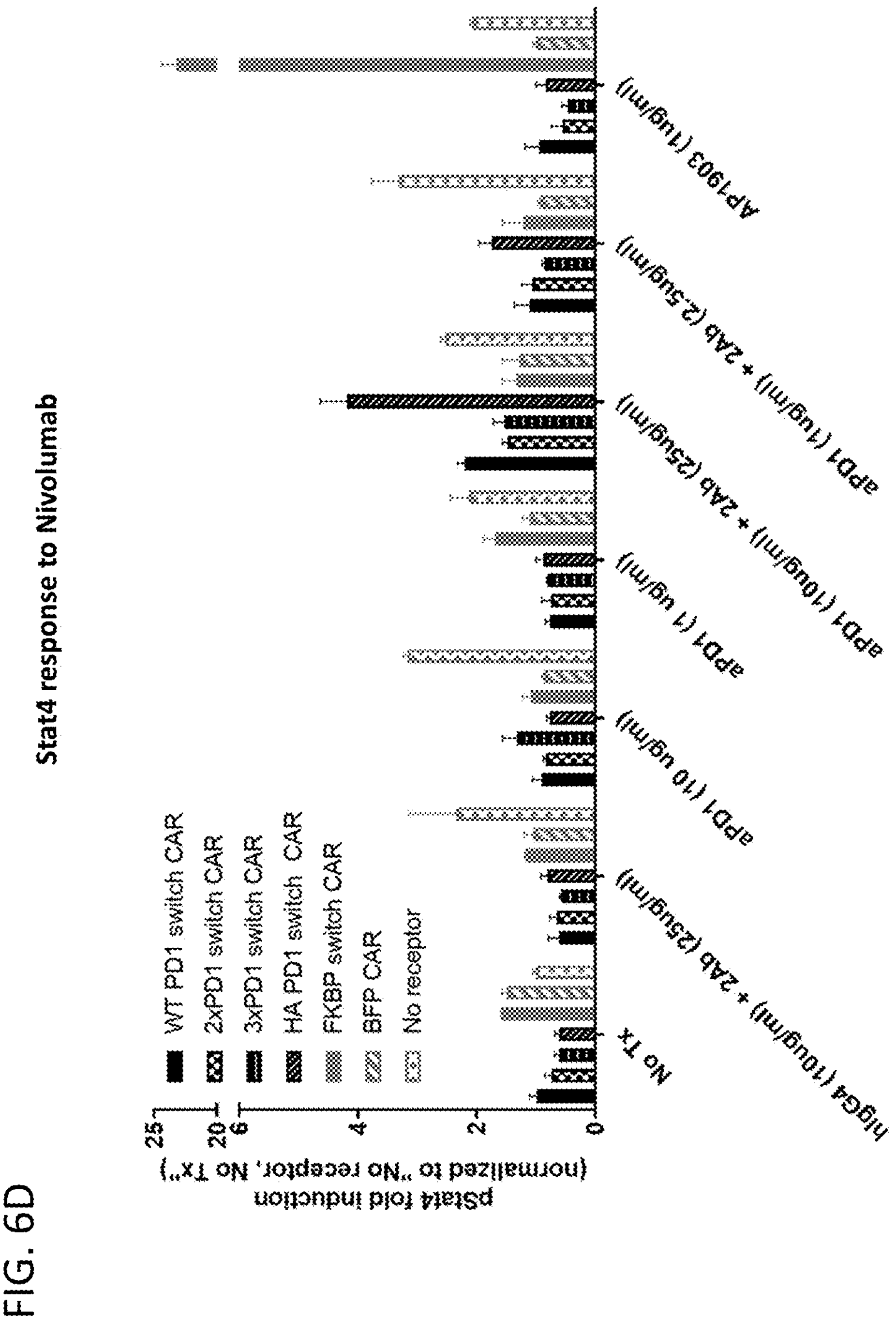

FIGS. 6A-D show the response of PD-1 chimeric cytokine receptors bearing ectodomain modifications following treatment with PD-L1-Fc (FIGS. 6A-B) and anti-PD-1 (FIGS. 6C-D). FIGS. 6A-B show that compared to its untreated counterpart and to the WT PD-1 chimeric cytokine receptor, the HA PD-1 chimeric cytokine receptor permitted enhanced Stat5 (FIG. 6A) and Stat4 (FIG. 6B) reporter activity in response to high concentrations of crosslinked PD-L1-Fc; whereas the 2×PD-1 chimeric cytokine receptor permitted enhanced Stat5, but not Stat4, reporter activity. FIGS. 6C-d show that compared to its untreated counterpart and to the WT PD-1 chimeric cytokine receptor, the HA PD-1 chimeric cytokine receptor permitted enhanced Stat5 (FIG. 6C) and Stat4 (FIG. 6D) reporter activity in response to high concentrations of crosslinked anti-PD-1; whereas the 2×PD-1 chimeric cytokine receptor permitted enhanced Stat5, but not Stat4, reporter activity. These indicated that enhancing the avidity of the ectodomain via tandem PD-1, or enhancing the affinity of the ectodomain via mutations, increase the responsiveness of the PD-1 chimeric cytokine receptor. Furthermore, the fact that the HA PD-1 chimeric cytokine receptor may be activated by anti-PD-1 indicates that the mutant HA ectodomain retains the ability to bind anti-PD-1 (i.e. Nivolumab).

Similar experiments were then carried out in the context of primary human CAR-T-cells. To make lentivirus encoding PD-1 chimeric cytokine receptor CARs, HEK293T-cells were plated at 0.45 million cells per mL in 2 mL of DMEM (Gibco) supplemented with 10% FBS (Hyclone) per well of a 6-well plate on Day −1. On Day 0, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. On Day 0, purified T-cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 1, the media from each well of HEK293T-cells in the 6-well plate was replaced with 2 mL per well of T-cell transduction media, i.e., X-Vivo-15 supplemented with 10% FBS. On Day 2, T-cells were resuspended at 0.5 million cells per mL in 1 mL of T-cell transduction media per well of a Grex-24 plate. The lentiviral supernatants from HEK293T-cells were harvested and passed through a 0.45 micron filter (EMD Millipore) to remove cell debris, and then added to the T-cells along with 100 IU/mL human IL-2. On Day 5, 4.5 mL of T-cell expansion media, i.e., X-Vivo-15 supplemented with 5% human AB serum (Gemini Bio) and 100 IU/mL human IL-2 was added to each well of a Grex-24 plate. Cells were expanded into larger G-Rex vessels (Wilson Wolf) as needed using T-cell expansion media. On Day 13 or 14, transduction efficiency and PD-1 chimeric cytokine receptor expression was determined by detecting the percentage of T-cells that bound a FITC-conjugated v5 tag monoclonal antibody (Thermo Fisher) using flow cytometry. On Day 14 or 15, the CAR-T-cell products were cryopreserved and thawed as needed for further assays.

To determine if the HA PD-1 ectodomain indeed enhances binding affinity to PD-L1, while retaining interactions with clinically-approved anti-PD-1 antibodies, the ability of HA PD-1 chimeric cytokine receptor CAR-T-cells to bind Nivolumab and Pembrolizumab was tested in a cell-binding assay. Briefly, WT PD-1 chimeric cytokine receptor CAR-T-cells or HA PD-1 chimeric cytokine receptor CAR-T-cells were Fc-blocked, and then incubated with the indicated concentrations of anti-PD-1 (i.e. Nivolumab or Pembrolizumab) diluted in PBS+1% BSA. After a 20 minute incubation at 4 °C, cells were washed in PBS, and incubated with a PE-conjugated anti-human IgG Fc secondary antibody (Biolegend) diluted in PBS+1% BSA. After a 20 minute incubation at 4 °C, cells were washed in PBS and analyzed by flow cytometry.

Figure 7A:
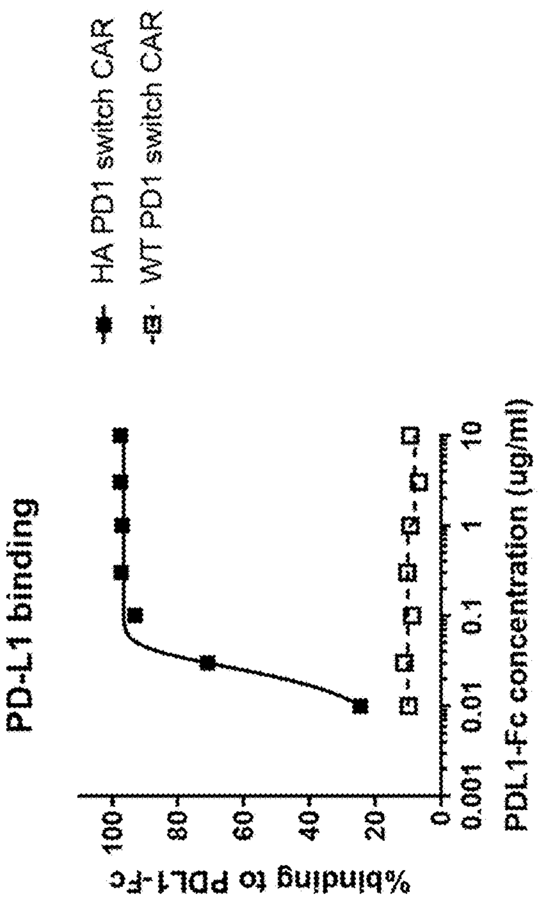
FIGS. 7A-7B show results from the cell binding assay between PD-1 chimeric cytokine receptor CAR-T-cells and PD-L1-Fc (FIG. 7A) or clinically-approved anti-PD-1 antibodies (FIG. 7B).
Figure 7B:
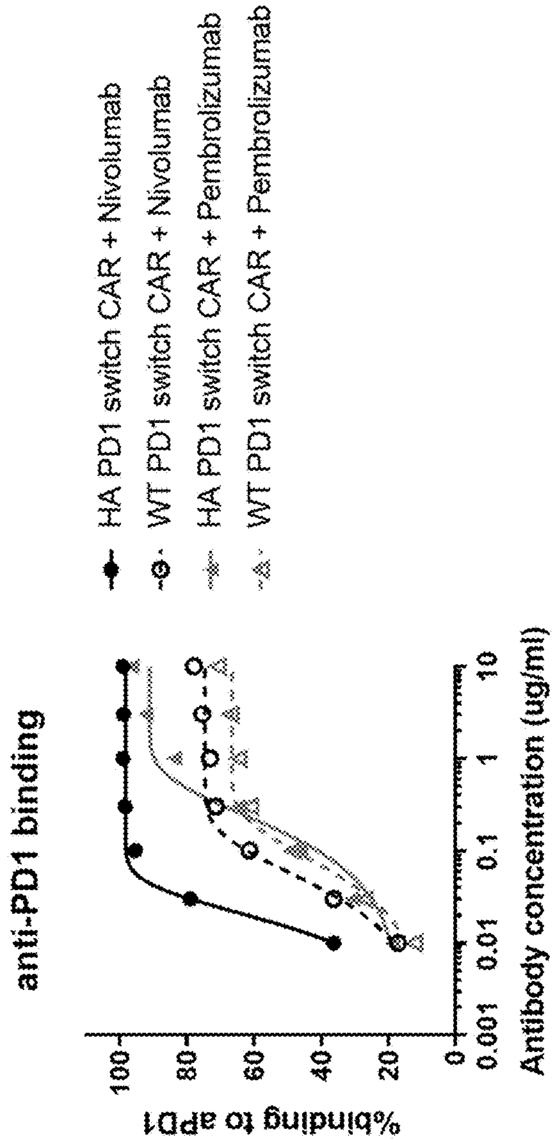

FIGS. 7A-B show results from the cell binding assay between PD-1 chimeric cytokine receptor CAR-T-cells and PD-L1-Fc (FIG. 7A) or clinically-approved anti-PD-1 antibodies (FIG. 7B). FIG. 7A shows that while the WT PD-1 chimeric cytokine receptor did not bind to PD-L1-Fc at the concentrations tested, the HA PD-1 chimeric cytokine receptor dramatically improved binding to PD-L1-Fc. FIG. 7B shows that modification to the HA PD-1 ectodomain improved maximal binding ($C_{max}$) to Pembrolizumab, and improved both maximal binding ($C_{max}$) and sensitivity ($EC_{50}$) to Nivolumab. The HA PD-1 ectodomain variant improves responsiveness to both PD-L1 and clinically-approved anti-PD-1 antibodies.

To analyze the inducibility and magnitude of cytokine signaling in CAR-T-cells bearing these PD-1 chimeric cytokine receptor ectodomain variants, the thawed CAR-T-cell product was serum starved in 100 uL serum-free RPMI (Corning) for 4 hours in humidified incubator at 37 °C with 5% $CO_2$, then treated with anti-PD-1 (10 ug/mL Nivolumab; Selleck Chemical), recombinant human PD-L1-Fc (10 ug/mL; Biolegend), anti-Human IgG Fc gamma secondary antibody (25 ug/mL; Thermo Fisher) for 1 hour. 40 minutes into the treatment, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. After 1 hour of treatment, cells were fixed by the addition of 35 uL of 16% paraformaldehyde was added to each 100 uL sample and allowed to incubate for 15 minutes at 37 °C. Cells were then washed three times with PBS, and permeabilized in 100% cold methanol for 1 or 2 nights at −20 °C. On the day of FACS analysis, cells were washed three times with PBS, Fc-blocked, and stained with AlexaFluor647-conjugated anti-mouse/human Stat5 (pY694) (BD Biosciences) diluted in PBS+1% BSA. After a 1 hour incubation at room temperature in the dark, cells were washed three times before FACS analysis.

Figure 8A:
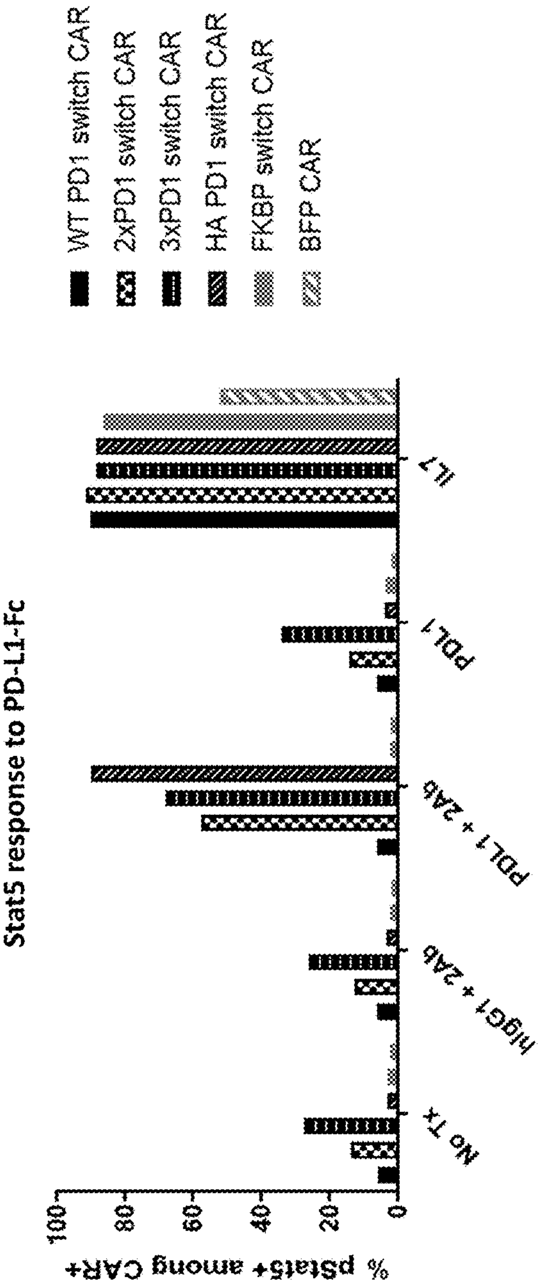
FIGS. 8A-8B show the response of CAR-T-cells bearing PD-1 chimeric cytokine receptor ectodomain variants following treatment with PD-L1-Fc (FIG. 8A) or anti-PD-1 (FIG. 8B).
Figure 8B:
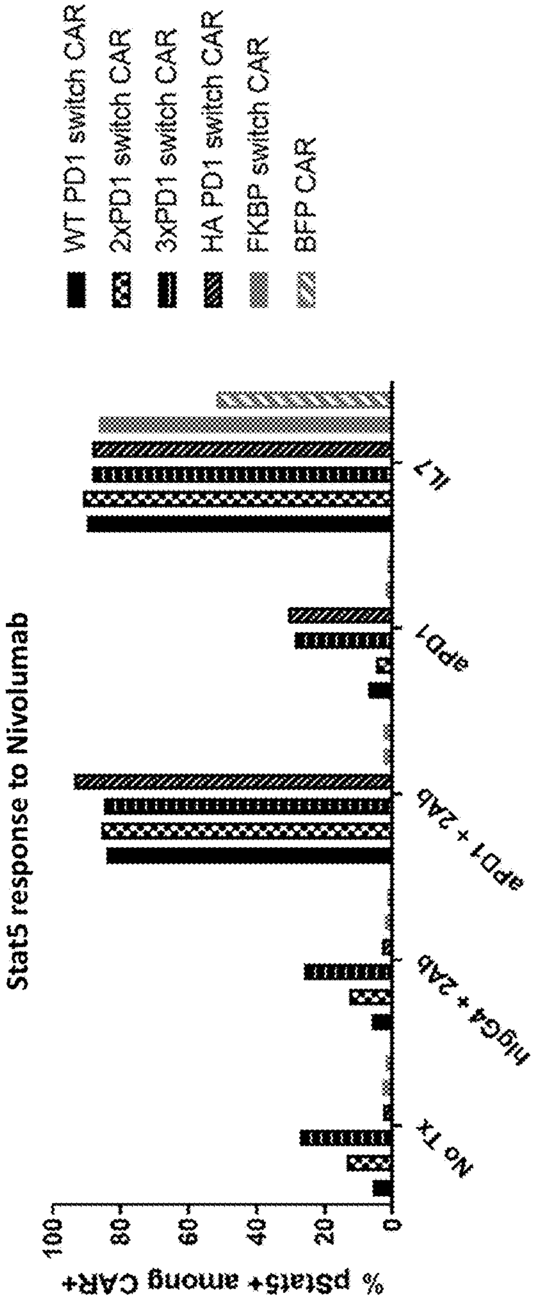

FIGS. 8A-B show the response of CAR-T-cells bearing PD-1 chimeric cytokine receptor ectodomain variants following treatment with PD-L1-Fc (FIG. 8A) or anti-PD-1 (FIG. 8B). 2×PD-1 and 3×PD-1 chimeric cytokine receptor CAR-T-cells showed high levels of basal signaling, even in the absence of PD-L1 or anti-PD-1. Compared to WT PD-1 chimeric cytokine receptor CAR-T-cells, CAR-T-cells bearing the 2×PD-1 chimeric cytokine receptor, 3×PD-1 chimeric cytokine receptor and HA PD-1 chimeric cytokine receptor showed enhanced response to crosslinked PD-L1-Fc, with the HA PD-1 chimeric cytokine receptor providing the greatest response (FIG. 8A). In response to anti-PD-1 alone, the HA PD-1 chimeric cytokine receptor was the only ectodomain variant that induced increased pStat5; neither the 2×PD-1 chimeric cytokine receptor nor the 3×PD-1 chimeric cytokine receptor induced pStat5 beyond their levels of basal activity (FIG. 8B). Based on this analysis, the HA PD-1 chimeric cytokine receptor was the ectodomain variant that provided the lowest basal activity and greatest inducibility.

To evaluate the cytotoxic activity of PD-1 chimeric cytokine receptor CAR-T-cells, the U87KO-EGFRvIII-nucGFP target cell line that endogenously expresses PD-L1 and PD-L2. U87KO-EGFRvIII (gift from Cellectis SA (Paris, France)). U87KO-EGFRvIII was derived from the parental cell line, U87MG (ATCC), by first knocking out endogenous wild type EGFR using Transcription Activator-Like Effector Nucleases (TALEN), and then stably overexpressing full-length human EGFRvIII via lentiviral transduction. To facilitate target cell imaging via the IncuCyte Live Cell Analysis Imaging System, U87KO-EGFRvIII-nucGFP target cells were derived from U87KO-EGFRvIII by a second lentiviral transduction with IncuCyte NucLight Green Lentivirus Reagent (Sartorius). PD-L1 and PD-L2 expression on U87KO-EGFRvIII-nucGFP was determined by staining with an APC-conjugated anti-human PD-L1 (Biolegend) and a PE-conjugated anti-human PD-L2 (Biolegend), followed by flow cytometry analysis. For the in vitro cytotoxicity assay, 5,000 U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T-cells bearing the respective PD-1 chimeric cytokine receptor ectodomain variants were thawed and added to plated target cells at an Effector:Target (E:T) ratio of 1:4. FKBP chimeric cytokine receptor CAR-T-cells that do not activate cytokine signaling in response to PD-1 ligands were used as a control. Duplicate wells were set up for each condition. The number of live target cells at each timepoint was determined by enumerating the number of live nucGFP+ target cells using the IncuCyte Live Cell Analysis Imaging System.

Figure 9A:
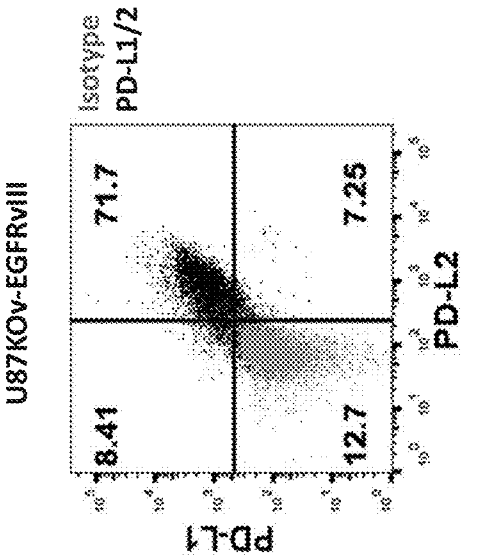
FIGS. 9A-9B show the cytotoxic response of the PD-1 chimeric cytokine receptor CAR-T-cells against target cells expressing PD-1 ligands.
Figure 9B:
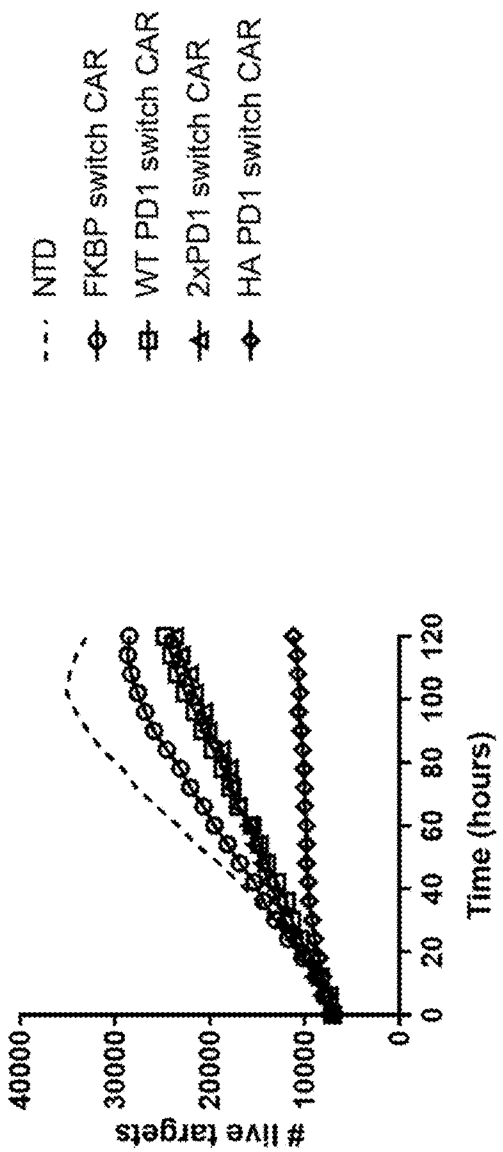

FIGS. 9A-B show the cytotoxic response of the PD-1 chimeric cytokine receptor CAR-T-cells against target cells expressing PD-1 ligands. FIG. 9A shows that U87KO-EGFRvIII-nucGFP cells express high levels of endogenous PD-L1 and PD-L2. FIG. 9B shows the results of the in vitro cytotoxic assay against U87KO-EGFRvIII-nucGFP target cells. Compared to FKBP chimeric cytokine receptor CAR-T-cells, WT PD-1 chimeric cytokine receptor CAR-T-cells showed marginally improved cytotoxic responses. While the 2×PD-1 chimeric cytokine receptor did not enhance cytotoxicity beyond that of the WT PD-1 chimeric cytokine receptor, the HA PD-1 chimeric cytokine receptor significantly enhanced CAR-T-cell cytotoxicity.

Example 3: Optimization of the HA PD-1 Chimeric Cytokine Receptor

The HA PD-1 ectodomain variant afforded a significant enhancement over the WT PD-1 chimeric cytokine receptor. The helical transmembrane (TM) region of TpoR is critical for ligand-induced receptor signaling by controlling JAK2 activation. It was analyzed whether in a chimeric cytokine receptor where a different ectodomain (e.g. PD-1) is fused with the TpoR TM/JAK2-activating domain, the optimal structural conformation for receptor activation is perturbed. The responsiveness of the HA PD-1 chimeric cytokine receptor was attempted to be increased by modifying the TpoR TM region. To this end, HA PD-1 chimeric cytokine receptor variants with either deletions or insertions in the TpoR TM region were generated and tested in the HEK293T-cell reporter assay.

Briefly, 20,000 HEK293T-cells were plated into each well of a poly-L-lysine-coated 96-well flat-bottom plate and allowed to adhere overnight. A PD-1 chimeric cytokine receptor (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a positive control, a FKBP chimeric cytokine receptor was usedwe, in which the WT PD-1 ectodomain was replaced with FKBP12(F36V), so that cytokine signaling could be inducible by the small molecule, AP1903. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 24 hours after transfection, cells were either left untreated, or treated with the indicated concentrations of anti-PD-1 (Nivolumab; Selleck Chemical), recombinant human PD-L1-Fc (Biolegend), anti-Human IgG Fc gamma secondary antibody (Thermo Fisher), or AP1903 (Apex Bio). As negative controls, hIgG4 and hIgG1 isotype controls were added in place of anti-PD-1 and PD-L1-Fc, respectively. All treatments were diluted in serum-free media. 24 hours after treatment, Stat reporter activity was evaluated using the Dual-Glo Luciferase Assay System (Promega). Fold induction of Stat5 reporter activity was normalized to that of HEK293T-cells transfected with all vectors except for the chimeric cytokine receptor and that were left untreated.

FIGS. 10A-B show the amino acid sequences for the wild type TpoR and the various TM deletion (FIG. 10A) or insertion (FIG. 10B) variants.

Figure 11A:
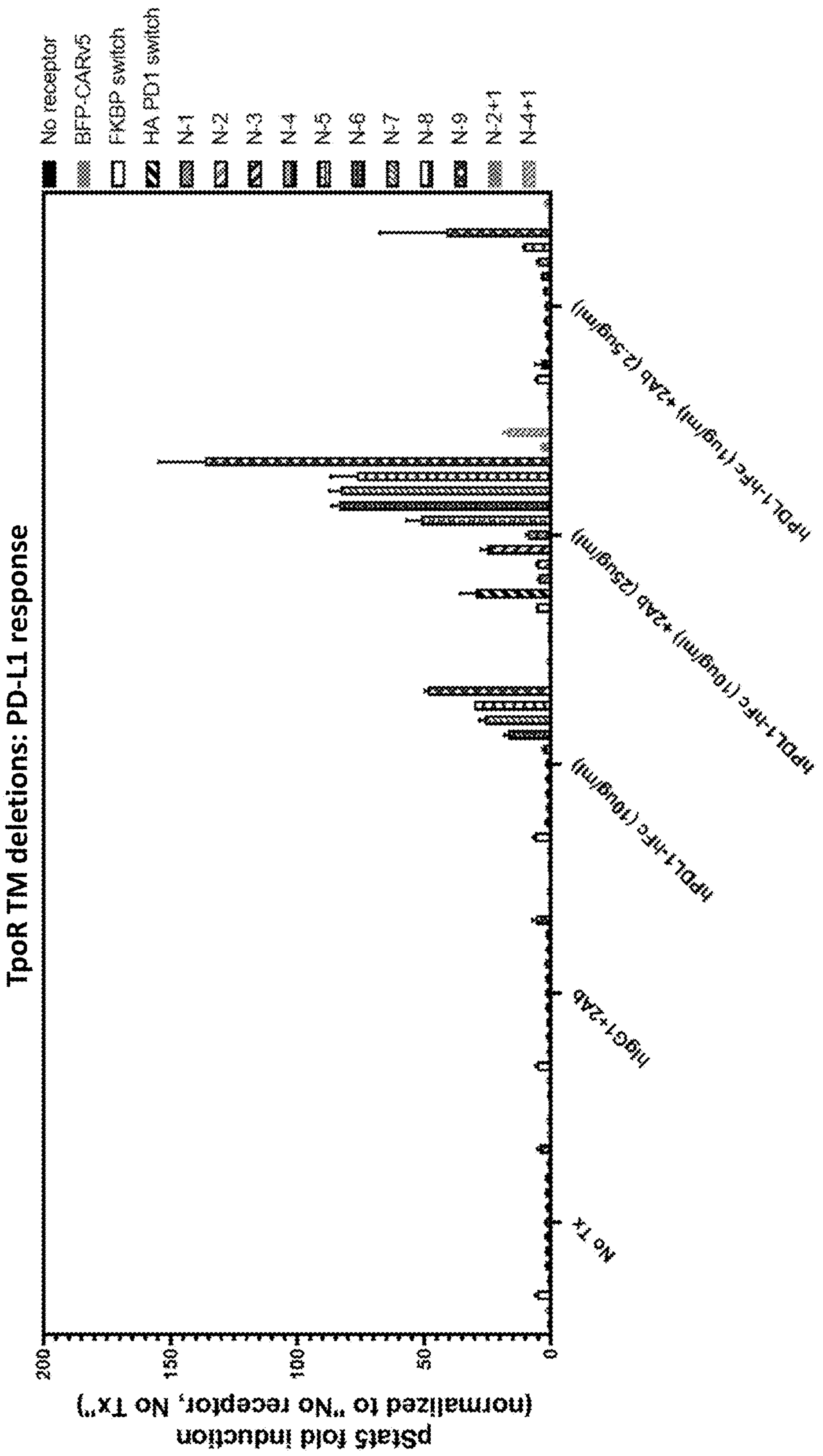
FIGS. 11A-11B show the response of a HA PD-1 chimeric cytokine receptor bearing TpoR TM deletions (FIG. 11A) and extensions (FIG. 11B) following treatment with PD-L1-Fc.
Figure 11B:
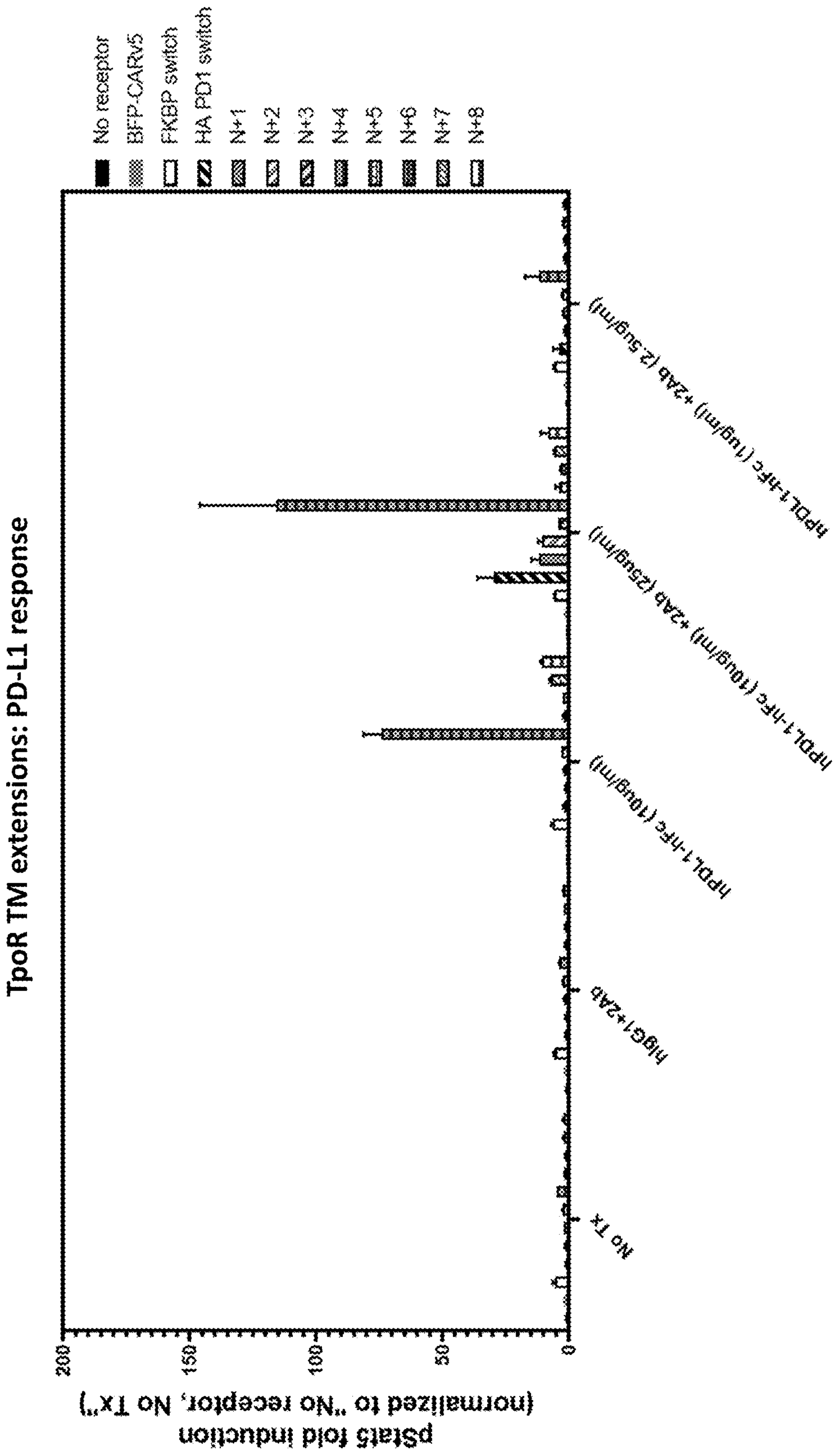

FIGS. 11A-B show the response of a HA PD-1 chimeric cytokine receptor bearing TpoR TM deletions (FIG. 11A) and extensions (FIG. 11B) following treatment with PD-L1-Fc. Unlike the HA PD-1 chimeric cytokine receptor that did not respond to PD-L1-Fc alone, the N−6, N−7, N−8, N−9 and N+4 TpoR TM variants were able to induce Stat5 activity in response to PD-L1 alone. Furthermore, compared to the HA PD-1 chimeric cytokine receptor, the N−5, N−6, N−7, N−8, N−9 and N+4 TpoR TM variants improved Stat5 activity in response to high concentrations of crosslinked PD-L1. The N−9 and N+4 TpoR TM variants retained the ability to respond to low concentrations of crosslinked PD-L1. These demonstrate that modulating the TpoR TM region enhanced the responsiveness and sensitivity of the HA PD-1 chimeric cytokine receptor to PD-1 ligands.

Figure 12A:
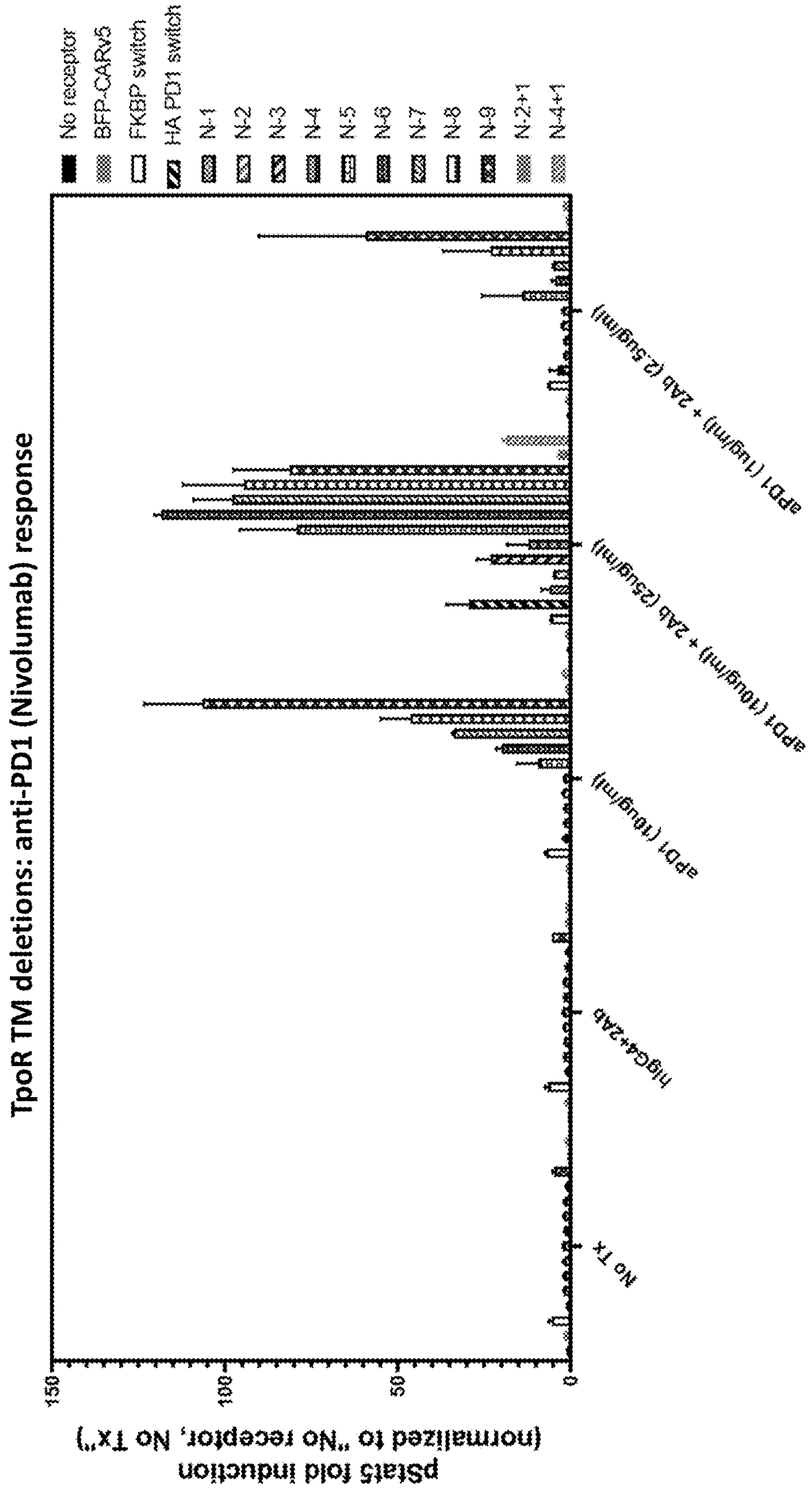
FIGS. 12A-12B shows the response of HA PD-1 chimeric cytokine receptor bearing TpoR TM deletions (FIG. 12A) and extensions (FIG. 12B) following treatment with anti-PD-1 (Nivolumab).
Figure 12B:
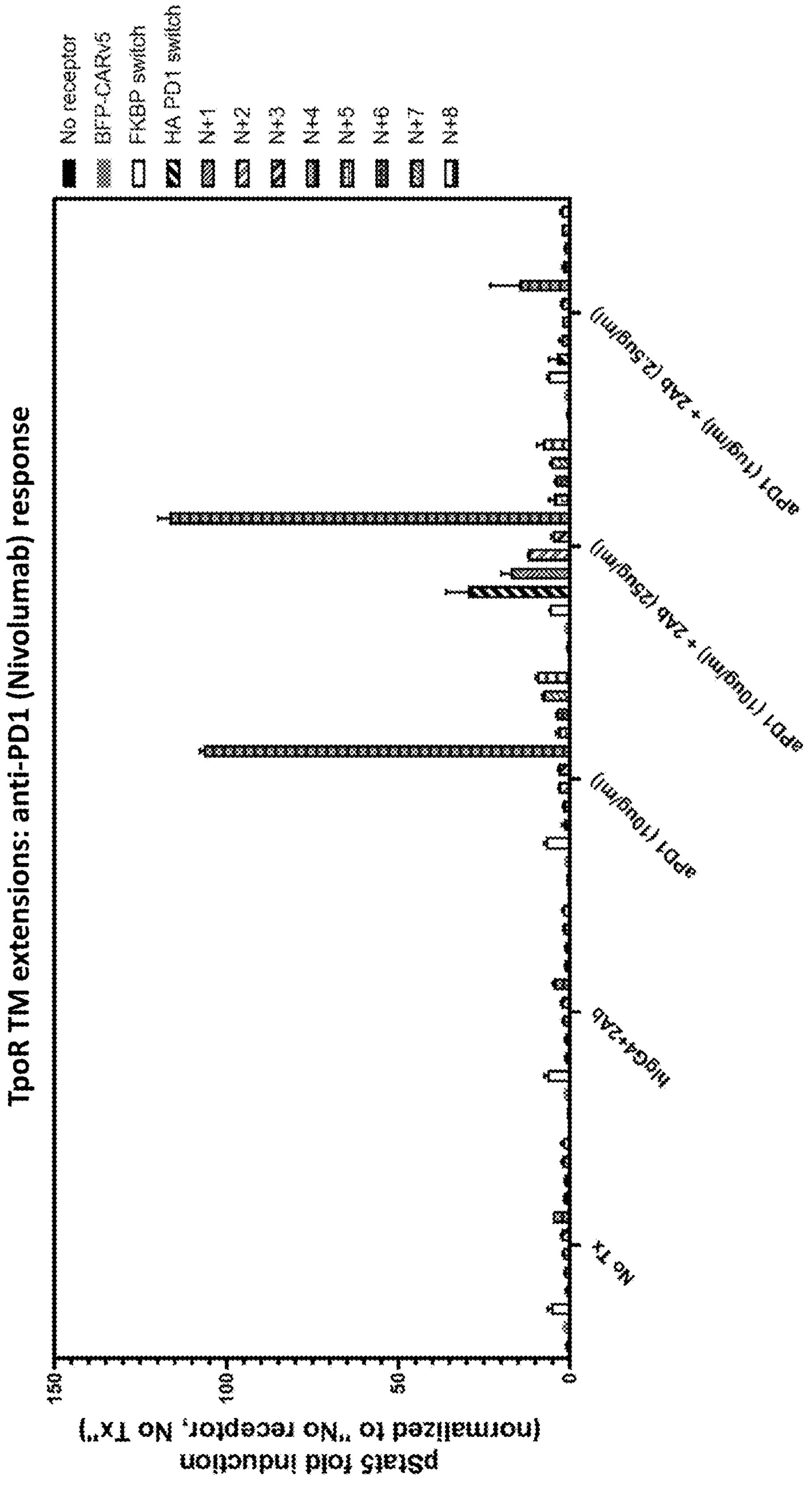

FIGS. 12A-B shows the response of HA PD-1 chimeric cytokine receptor bearing TpoR TM deletions (FIG. 12A) and extensions (FIG. 12B) following treatment with anti-PD-1 (Nivolumab). Unlike the HA PD-1 chimeric cytokine receptor that did not respond to anti-PD-1 alone, the N−5, N−6, N−7, N−8, N−9 and N+4 TpoR TM variants were able to induce Stat5 activity in response to anti-PD-1 alone, without the need for further crosslinking. These demonstrate that modulating the TpoR TM region enhanced the responsiveness and sensitivity of the HA PD-1 chimeric cytokine receptor to anti-PD-1.

Example 4: Effect of the HA PD-1 Chimeric Cytokine Receptor on CAR-T-Cell Cytotoxic Activity PD-1 blockade strategies, such as combination with anti-PD-1 or forced overexpression of a dominant-negative (DN) PD-1 decoy receptor, can ameliorate CAR-T-cell exhaustion. While PD-1 blockade prevents a negative signal from being transmitted into CAR-T-cells, it does not actively transmit any positive signals. It was therefore tested whether the HA PD-1 chimeric cytokine receptor, which couples PD-1 inhibition with simultaneous immune-potentiating cytokine signals, is more effective than PD-1 blockade alone. The cytotoxic activity of HA PD-1 chimeric cytokine receptor CAR-T-cells was compared against CAR-T-cells combined with Nivolumab, and against CAR-T-cells expressing a dominant-negative (DN) PD-1. (amino acid sequences in Table 9).

TABLE 9

| PD1 dominant negative (DN) sequences: | | |
|---|---|---|
| PD1 DN | Amino acid sequence | SEQ ID NO: |
| CD8SS-PD1(21-207) (Dominant negative wild type PD1) | MALPVTALLLPLALLLHAARP PGWFLDSPDRPWNPPTFSPALLVVTEGDNATFTCSFSNTSESF VLNWYRMSPSNQTDKLAAFPEDRSQPGQDCRFRVTQLPNGR DFHMSVVRARRNDSGTYLCGAISLAPKAQIKESLRAELRVTE RRAEVPTAHPSPSPRPAGQFQTLVVGVVGGLLGSLVLLVWV LAVICSRAARGTIGARRTGQ | 129 |
| CD8SS-HAPD1 (Dominant negative high affinity PD1) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLVVGVVGGLLGSLVLLVWVL AVICSRAARGTIGARRTGQ | 130 |

To assess in vitro cytotoxicity, 5,000 PD-L1+/PD-L2+ U87KO-EGFRvIII-nucGFP target cells were seeded and allowed to attach in 96-well plates with black walls and flat clear bottom in 50 uL RPMI containing 1000 FBS (Hyclone), non-essential amino acids, sodium pyruvate and 20-25 mM HEPES. EGFRvIII CAR (2173 scFv) T-cells bearing the respective PD-1 chimeric cytokine receptors or DN PD-1 were thawed and added to plated target cells at an Effector:Target (E:T) ratio of 1:4. FKBP chimeric cytokine receptor CAR-T-cells that do not activate cytokine signaling in response to PD-1 ligands were used as a control. Where indicated, anti-PD-1 (Nivolumab) or hIgG4 isotype control antibodies were added at a concentration of 10 ug/mL. Duplicate wells were set up for each condition. The number of live target cells at each timepoint was determined by enumerating the number of live nucGFP+ target cells using the IncuCyte Live Cell Analysis Imaging System.

Figure 13B:
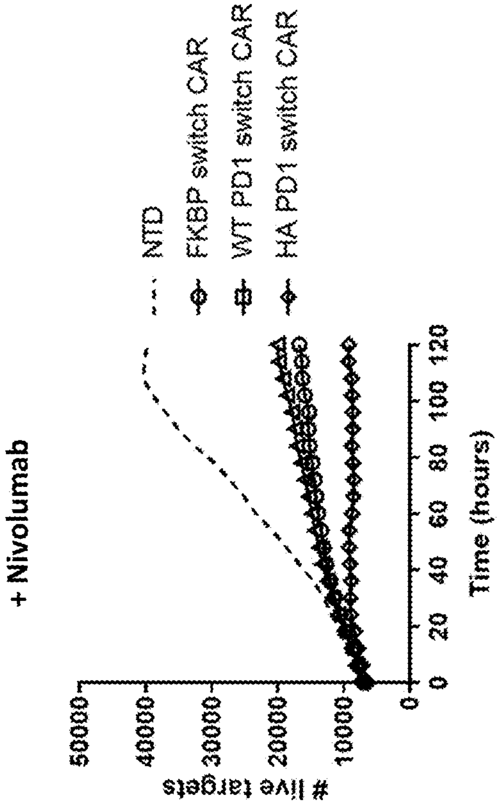
FIGS. 13A-13B show the cytotoxic response of PD-1 chimeric cytokine receptor CAR-T-cells in the absence (FIG. 13A) or presence (FIG. 13B) of anti-PD-1.
Figure 13A:
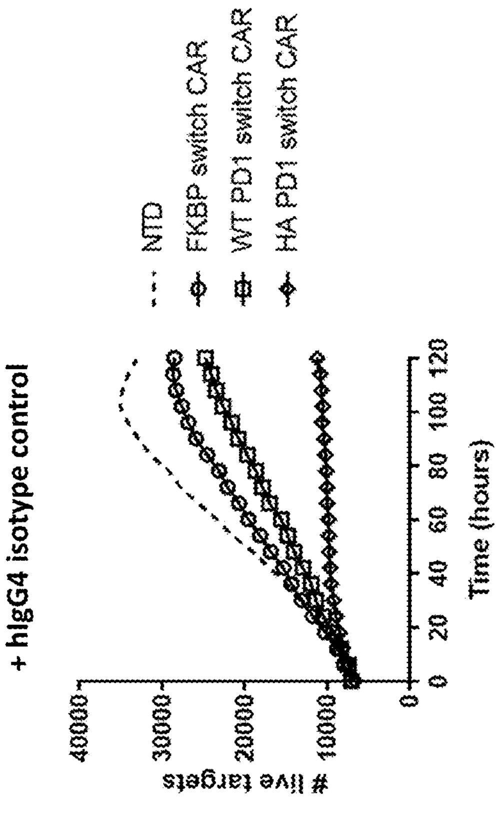

FIGS. 13A-B show the cytotoxic response of PD-1 chimeric cytokine receptor CAR-T-cells in the absence (FIG. 13A) or presence (FIG. 13B) of anti-PD-1. Although combination with anti-PD-1 did improve the activity of FKBP chimeric cytokine receptor CAR-T-cells and WT PD-1 CAR-T-cells, HA PD-1 chimeric cytokine receptor CAR-T-cells were more effective at target cell lysis. Combination with anti-PD-1 did not further improve the activity of HA PD-1 chimeric cytokine receptor CAR-T-cells, indicating that PD-1 ligands expressed on the target cells could bind to and activate the PD-1 chimeric cytokine receptor.

Figure 14:
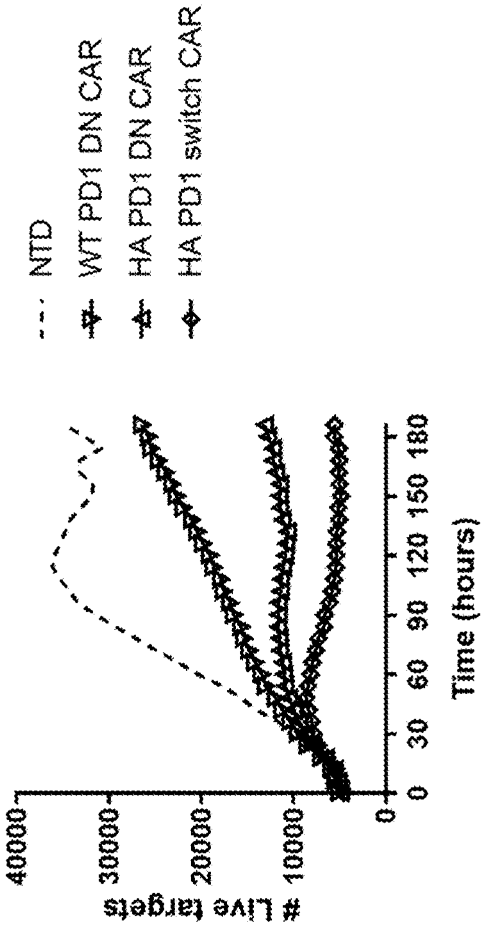
FIG. 14 shows the cytotoxic response of CAR-T-cells coexpressing either a DN WT PD-1, a DN HA PD-1 or the HA PD-1 chimeric cytokine receptor.

FIG. 14 shows the cytotoxic response of CAR-T-cells coexpressing either a DN WT PD-1, a DN HA PD-1 or the HA PD-1 chimeric cytokine receptor. HA PD-1 DN CAR-T-cells were more effective than WT PD-1 CAR-T-cells. Without being bound by any theory, this could be due to more effective sequestration and blockade of PD-1 ligands. However, HA PD-1 chimeric cytokine receptor CAR-T-cells were more cytotoxic than HA PD-1 DN CAR-T-cells. Without being bound by any theory, this could be due to the coupling of PD-1 blockade with simultaneous cytokine signaling.

Example 5: PD-1 Chimeric Cytokine Receptor that Delivers Constitutive Cytokine Signals in a Ligand-Independent Fashion The TM/JAK2-activating domain of PD1 chimeric cytokine receptors in some of the examples above is derived from TpoR, whose signaling activity can be modulated by key residues within the TpoR transmembrane (TM) domain. For instance, single point mutations within the TpoR TM domain, such as at S505 or W515, have been reported to cause constitutive TpoR signaling; on the other hand, mutating H499 in the TpoR TM domain dampens signaling from these activating mutations (Proc Natl Acad Sci USA. 2013 Feb. 12; 110(7):2540-5.; FASEB J. 2011 July; 25(7):2234-44.; J Biol Chem. 2016 Feb. 5; 291(6):2974-87.). It was analyzed whether a PD-1 chimeric cytokine receptor can be constitutively active by introducing the above-described single point mutations into the TpoR TM region of the receptor. To this end, HA PD-1 chimeric cytokine receptor variants with constitutively active single point mutations (S505 and/or W515) of the TpoR TM region and a single point mutation that reduces the activity of the TpoR TM region were generated. To mimic signaling from either IL-7 or IL-2/IL15, recruiting domains derived from the IL-7Ra and IL-2/IL15Rb receptors, respectively, were fused downstream of the TpoR TM/JAK2-activating domain. Exemplary amino acid sequences of the constructs are in Table 10.

TABLE 10

| PD1 chimeric cytokine receptor sequences: | | |
|---|---|---|
| Receptor | Amino acid sequence | SEQ ID NO: |
| CD8SS-HAPD1.TPOR/MPLR(478-582; H499L, S505N, W515K). IL7Ra(316-459) | MALPVTALLLPLALLLHAARP PGWFLDSPDRPWNPPTFSPALLVVTEGDNATFTCSFSNTSESF HVIWHRESPSGQTDTLAAFPEDRSQPGQDCRFRVTQLPNGRD FHMSVVRARRNDSGTYVCGVISLAPKIQIKESLRAELRVTER RAEVPTAHPSPSPRPAGQFQTLV SDPTRVETATETAWISLVTALLLVLGLNAVLGLLLLRKQFPA HYRRLRHALWPSLPDLHRVLGQYLRDTAALSPPKATVSDTC EEVEPSLLEILPKSSERTPLPL ARDEVEGFLQDTFPQQLEESEKQRLGGDVQSPNCPSEDVVIT | 141 |

TABLE 10-continued

PD1 chimeric cytokine receptor sequences:

| Receptor | Amino acid sequence | SEQ ID NO: |
|---|---|---|
| | PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ | |
| CD8SS-<br>HAPD1.TpoR<br>(478-582;<br>S505N, W515K).<br>IL2Rbsmall<br>(393-433, 518-<br>551) | MALPVTALLLPLALLLHAARP<br>PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLV<br>SDPTRVETATETAWISLVTALHLVLGLNAVLGLLLLRKQFPA<br>HYRRLRHALWPSLPDLHRVLGQYLRDTAALSPPKATVSDTC<br>EEVEPSLLEILPKSSERTPLPL<br>DEGVAGAPTGSSPQPLQPLSGEDDAYCTFPSRDDLLLFSPSG<br>QGEFRALNARLPLNTDAYLSLQELQGQDPTHLV | 142 |
| CD8SS-<br>HAPDIDN | MALPVTALLLPLALLLHAARP<br>PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLVVGVVGGLLGSLVLLVWVL<br>AVICSRAARGTIGARRTGQ | 143 |
| CD8SS-<br>HAPD1.TpoR<br>(478-582).<br>IL7Ra(316-459) | MALPVTALLLPLALLLHAARP<br>PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLV<br>SDPTRVETATETAWISLVTALHLVLGLSAVLGLLLLRWQFPA<br>HYRRLRHALWPSLPDLHRVLGQYLRDTAALSPPKATVSDTC<br>EEVEPSLLEILPKSSERTPLPL<br>ARDEVEGFLQDTFPQQLEESEKQRLGGDVQSPNCPSEDVVIT<br>PESFGRDSSLTCLAGNVSACDAPILSSSRSLDCRESGKNGPHV<br>YQDLLLSLGTTNSTLPPPFSLQSGILTLNPVAQGQPILTSLGSN<br>QEEAYVTMSSFYQNQ | 144 |
| CD8SS-<br>HAPD1.TpoR<br>(478-582).<br>IL2Rbsmall<br>(393-<br>433, 518-551) | MALPVTALLLPLALLLHAARP<br>PGWFLDSPDRPWNPPTFSPALLVVTEGDNATFTCSFSNTSESF<br>HVIWHRESPSGQTDTLAAFPEDRSQPGQDCRFRVTQLPNGRD<br>FHMSVVRARRNDSGTYVCGVISLAPKIQIKESLRAELRVTER<br>RAEVPTAHPSPSPRPAGQFQTLV<br>SDPTRVETATETAWISLVTALHLVLGLSAVLGLLLLRWQFPA<br>HYRRLRHALWPSLPDLHRVLGQYLRDTAALSPPKATVSDTC<br>EEVEPSLLEILPKSSERTPLPL<br>DEGVAGAPTGSSPQPLQPLSGEDDAYCTFPSRDDLLLFSPSG<br>QGEFRALNARLPLNTDAYLSLQELQGQDPTHLV | 145 |
| CD8SS-<br>HAPD1.TPOR/<br>MPLR(478-582;<br>H499L, S505N,<br>W515K).<br>IL7Ra(316-459) | MALPVTALLLPLALLLHAARPPGWFLDSPDRPWNPPTFSPAL<br>LVVTEGDNATFTCSFSNTSESFHVIWHRESPSGQTDTLAAFPE<br>DRSQPGQDCRFRVTQLPNGRDFHMSVVRARRNDSGTYVCG<br>VISLAPKIQIKESLRAELRVTERRAEVPTAHPSPSPRPAGQFQT<br>LVSDPTRVETATETAWISLVTALLLVLGLNAVLGLLLLRKQF<br>PAHYRRLRHALWPSLPDLHRVLGQYLRDTAALSPPKATVSD<br>TCEEVEPSLLEILPKSSERTPLPLLEARDEVEGFLQDTFPQQLE<br>ESEKQRLGGDVQSPNCPSEDVVITPESFGRDSSLTCLAGNVS<br>ACDAPILSSSRSLDCRESGKNGPHVYQDLLLSLGTTNSTLPPP<br>FSLQSGILTLNPVAQGQPILTSLGSNQEEAYVTMSSFYQNQ | 210 |
| CD8SS-<br>HAPD1.TpoR<br>(478-582;<br>S505N, W515K).<br>IL2Rbsmall<br>(393-433, 518-<br>551) | MALPVTALLLPLALLLHAARPPGWFLDSPDRPWNPPTFSPAL<br>LVVTEGDNATFTCSFSNTSESFHVIWHRESPSGQTDTLAAFPE<br>DRSQPGQDCRFRVTQLPNGRDFHMSVVRARRNDSGTYVCG<br>VISLAPKIQIKESLRAELRVTERRAEVPTAHPSPSPRPAGQFQT<br>LVSDPTRVETATETAWISLVTALHLVLGLNAVLGLLLLRKQF<br>PAHYRRLRHALWPSLPDLHRVLGQYLRDTAALSPPKATVSD<br>TCEEVEPSLLEILPKSSERTPLPLLEDEGVAGAPTGSSPQPLQP<br>LSGEDDAYCTFPSRDDLLLFSPSGQGEFRALNARLPLNTDAY<br>LSLQELQGQDPTHLV | 211 |
| CD8SS-<br>HAPD1.TpoR<br>(478-582).<br>IL7Ra(316-459) | MALPVTALLLPLALLLHAARPPGWFLDSPDRPWNPPTFSPAL<br>LVVTEGDNATFTCSFSNTSESFHVIWHRESPSGQTDTLAAFPE<br>DRSQPGQDCRFRVTQLPNGRDFHMSVVRARRNDSGTYVCG<br>VISLAPKIQIKESLRAELRVTERRAEVPTAHPSPSPRPAGQFQT<br>LVSDPTRVETATETAWISLVTALHLVLGLSAVLGLLLLRWQF<br>PAHYRRLRHALWPSLPDLHRVLGQYLRDTAALSPPKATVSD<br>TCEEVEPSLLEILPKSSERTPLPLLEARDEVEGFLQDTFPQQLE<br>ESEKQRLGGDVQSPNCPSEDVVITPESFGRDSSLTCLAGNVS | 212 |

TABLE 10-continued

PD1 chimeric cytokine receptor sequences:

| Receptor | Amino acid sequence | SEQ ID NO: |
|---|---|---|
| | ACDAPILSSSRSLDCRESGKNGPHVYQDLLLSLGTTNSTLPPP FSLQSGILTLNPVAQGQPILTSLGSNQEEAYVTMSSFYQNQ | |
| CD8SS-HAPD1.TpoR (478-582). IL2Rbsmall (393-433, 518-551) | MALPVTALLLPLALLLHAARPPGWFLDSPDRPWNPPTFSPAL LVVTEGDNATFTCSFSNTSESFHVIWHRESPSGQTDTLAAFPE DRSQPGQDCRFRVTQLPNGRDFHMSVVRARRNDSGTYVCG VISLAPKIQIKESLRAELRVTERRAEVPTAHPSPSPRPAGQFQT LVSDPTRVETATETAWISLVTALHLVLGLSAVLGLLLLRWQF PAHYRRLRHALWPSLPDLHRVLGQYLRDTAALSPPKATVSD TCEEVEPSLLEILPKSSERTPLPLLEDEGVAGAPTGSSPQPLQP LSGEDDAYCTFPSRDDLLLFSPSGQGEFRALNARLPLNTDAY LSLQELQGQDPTHLV | 213 |

A HEK293T cell reporter assay was used to test for constitutive cytokine signaling by PD1 chimeric cytokine receptors. Briefly, 20,000 HEK293T cells were plated into each well of a poly-L-lysine-coated 96-well flat-bottom plate and allowed to adhere overnight. A PD1 chimeric cytokine receptor-CAR construct (2.5 ng), a Stat5 response element that drives Firefly Luciferase (100 ng; Promega) and Renilla Luciferase control reporter vector (1 ng; Promega) were mixed in a final volume of 5 μL in Opti-MEM (Gibco) ("DNA mix"). As negative controls, cells were transfected with either a BFP CAR construct that expresses BFP instead of a PD1 chimeric cytokine receptor, or a dominant negative HA PD1 ectodomain CAR construct. As a comparison, cells were transfected with a vector encoding an inducible PD1 chimeric cytokine receptor (SEQ ID NOs: 213-214). As a positive control, cells were transfected with a vector encoding full-length human EpoR (in place of the cytokine receptor-CAR construct) so that Stat5 signaling could be induced by the addition of exogeneous recombinant human Epo. 0.3 μL Lipofectamine 2000 (Invitrogen) in 5 μL Opti-MEM was incubated at room temperature for 5 minutes and then added to the DNA mix. The mixture was incubated at room temperature for 20 minutes and the total volume of 10 μL was added to each well containing HEK-293T. 24 hours after transfection, human PD-L1 Fc, a secondary crosslinking antibody, or an isotype control antibody were added at the indicated final concentrations. 48 hours after transfection, Stat5 reporter activity was evaluated using the Dual-Glo Luciferase Assay System (Promega). Fold induction of Stat5 reporter activity was normalized to that of HEK293T cells transfected with all vectors except for the cytokine receptor and that were left untreated.

Figure 15:
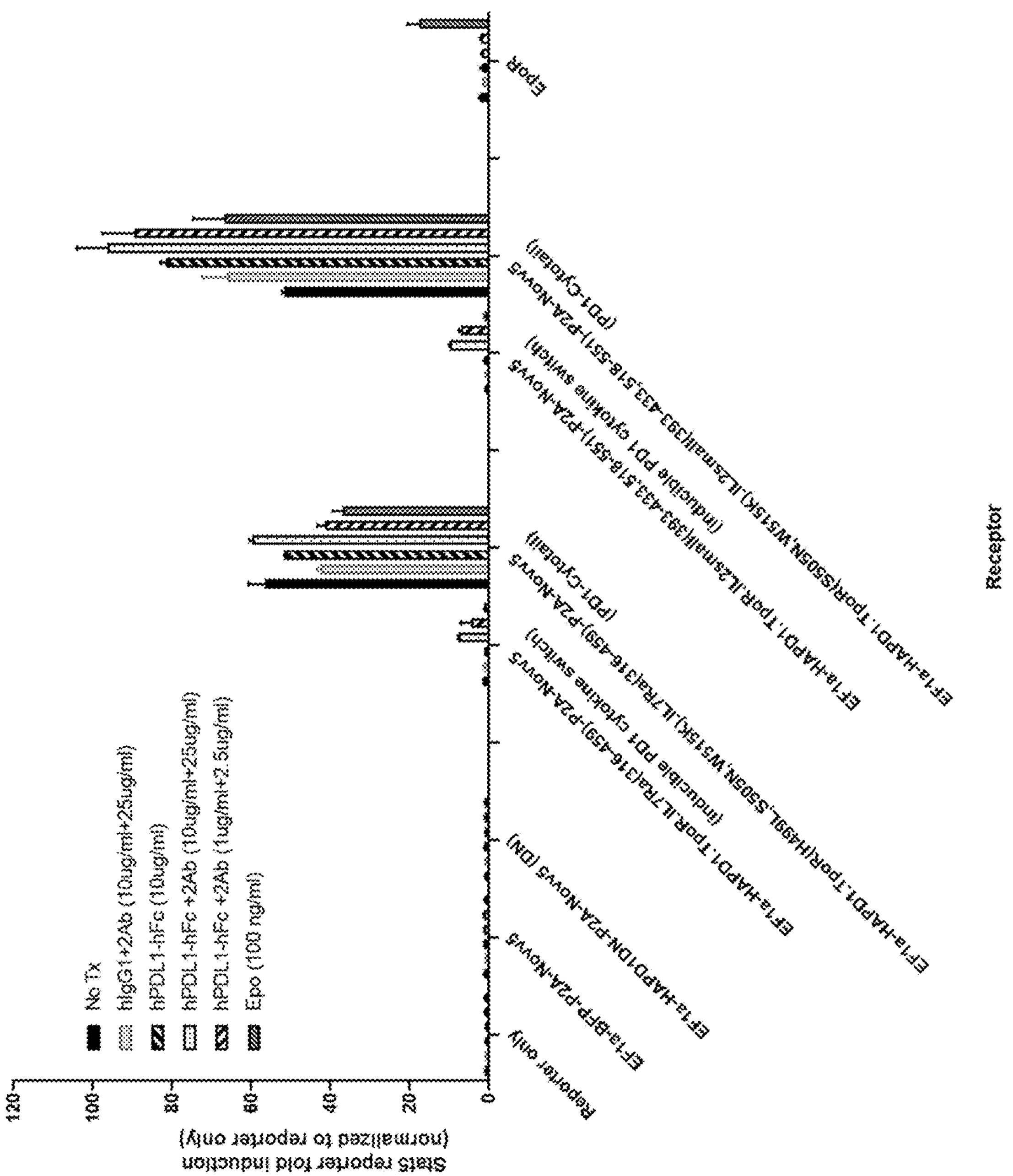
FIG. 15 shows a Stat reporter activity of the constitutively active, dominant negative, and inducible PD-1 chimeric cytokine receptors in response to PD-L1-Fc and crosslinked PD-L1-Fc.

FIG. 15 shows Stat5 reporter activity in the absence and presence of PD-L1. As expected, negative controls (i.e. BFP CAR and dominant negative HA PD1 ectodomain CAR constructs) did not induce Stat5 reporter activity. The inducible PD1 chimeric cytokine receptors bearing a TM/JAK2-activating domain derived from wild type TpoR ((SEQ ID NOs: 213-214) was active in the presence of crosslinked PD-L1, but was inactive in the absence of ligand. In contrast, strong, constitutive signaling was generated from PD1 chimeric cytokine receptors comprising a TM/JAK2-activating domain derived from a TpoR transmembrane domain with constitutively active point mutations (SEQ ID NOs.: 210-211) in a ligand-independent fashion. This ligand-independence is in contrast to an inducible PD1 chimeric cytokine receptor—bearing the wild type TpoR transmembrane domain—where the presence of PD1 ligands is required for cytokine signaling to occur. The constitutive activity of the PD1 chimeric cytokine receptor comprising the TM/JAK2-activating domain derived from a TpoR transmembrane domain with constitutively active point mutations (SEQ ID NO.: 2211) was increased in the presence of PD-L1 and crosslinked PD-L1. The activity of the PD1 chimeric cytokine receptor that comprises the constitutively active TpoR TM mutations and the inhibitor mutation (H499) (SEQ ID NO.: 210) showed a slight dampening of the constitutive activity in the presence of PD-L1 and crosslinked PD-L1.

Example 6 Increasing the Sensitivity and Responsiveness of the HA PD1 Switch Further Improves CAR T Cell Cytotoxicity As demonstrated above, the HA PD1 switch could be engineered for increased sensitivity and responsiveness towards PD-1 ligands and anti-PD-1 by modifying the TpoR TM helix. Specifically, in the HEK293T cell reporter assay, the N−5, N−6, N−7, N−8, N−9 and N+4 TpoR TM variants enhanced STAT5 activation in response to crosslinked PD-L1 (FIG. 11) and anti-PD-1 (FIG. 12). To evaluate if this translated into improved CAR T cell cytotoxicity in the presence of PD-1 ligands and anti-PD-1, we compared the killing activity of HA PD1 switch CAR T cells bearing either the wildtype (WT) or variant TpoR TM domains.

Briefly, 5,000 PD-L1+/PD-L2+ U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T cells coexpressing a HA PD1 switch with the indicated TpoR TM domain were thawed and added to plated target cells at an Effector:Target (E:T) ratio of 1:4 or 1:8. As a control, CAR T cells coexpressing BFP in place of a HA PD1 switch, and that do not activate cytokine signaling in response to PD-1 ligands, were used. Where indicated, anti-PD-1 (nivolumab) or hIgG4 isotype control antibodies were added at a concentration of 10 ug/mL. Duplicate wells were set up for each condition. The number of live target cells at each timepoint was determined by enumerating the number of live nucGFP+ target cells using the IncuCyte Live Cell Analysis Imaging System.

Figure 16:
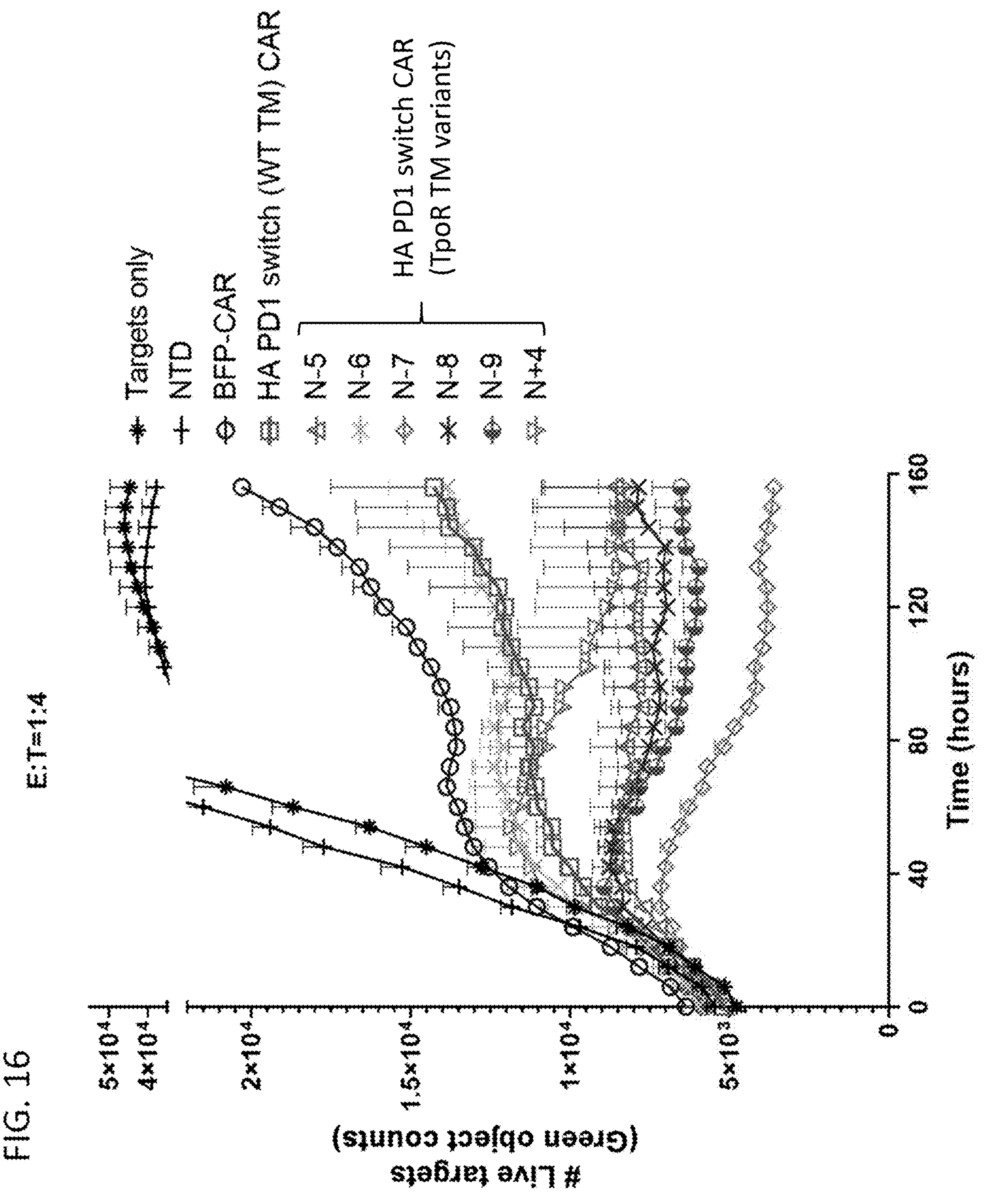
FIG. 16 shows the cytotoxic activity of HA PD1 switch CAR T cells with the indicated TpoR TM domains at an E:T ratio of 1:4 and in the absence of anti-PD-1.

FIG. 16 shows the cytotoxic activity of HA PD1 switch CAR T cells with the indicated TpoR TM domains at an E:T ratio of 1:4 and in the absence of anti-PD-1. As expected, compared to the control BFP-CAR T cells, HA PD1 switch CAR T cells with the WT TpoR TM domain showed improved target cell lysis in vitro. However, cytotoxic activity was further enhanced in HA PD1 switch CAR T cell variants bearing the N−5, N−7, N−8, N−9 or N+4 TpoR TM domains. Concordant with FIGS. 11 and 12, these data indicate that TpoR TM domain variants allow more effective cytotail activation in response to PD-1 ligands, thereby further enhancing the cytotoxic potency of HA PD1 switch CAR T cells.

Figure 17A:
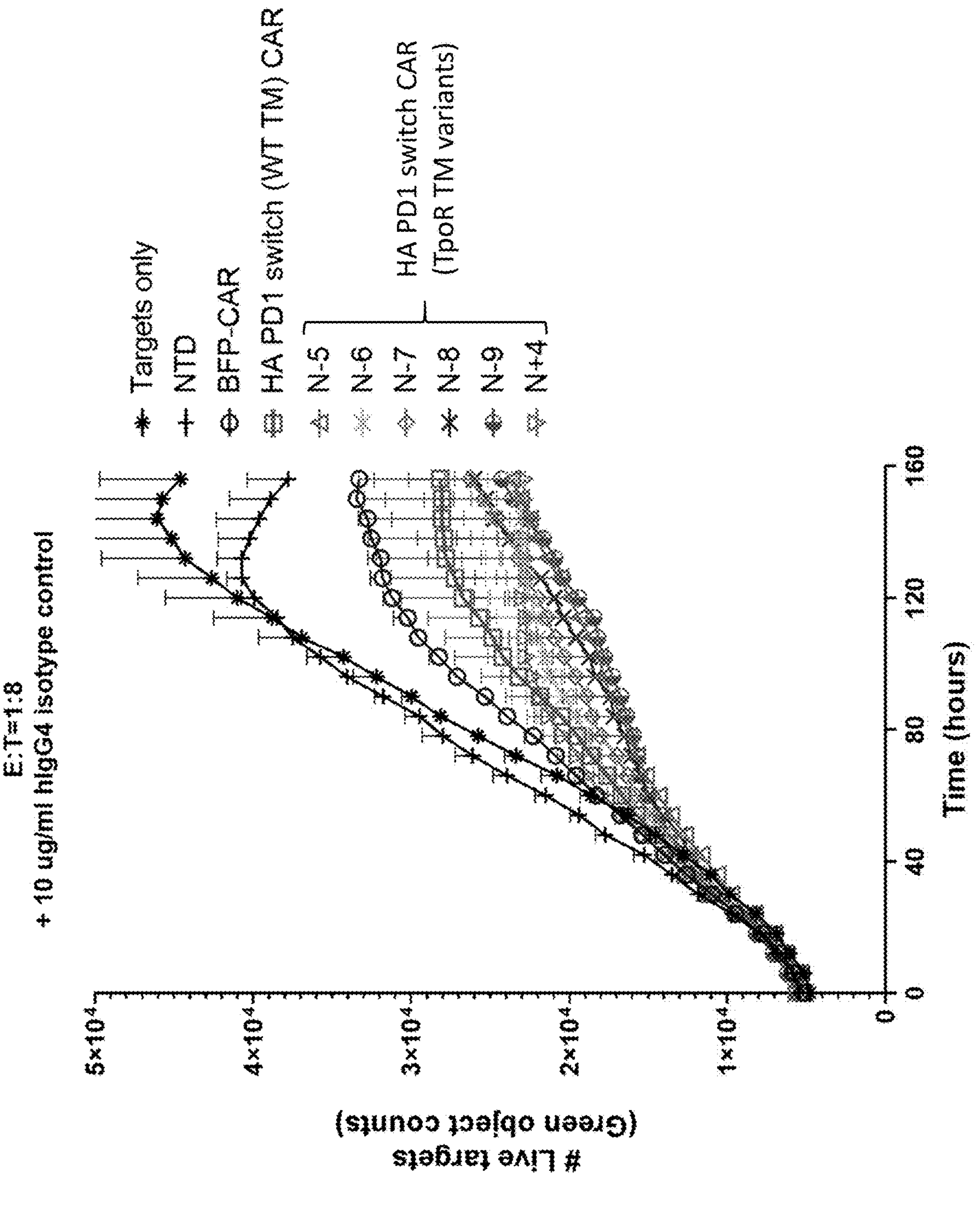
FIGS. 17A-17E show the cytotoxic activity of HA PD1 switch CAR T cells with the indicated TpoR TM domains at an E:T ratio of 1:8, and in the absence or presence of anti-PD-1.
Figure 17B:
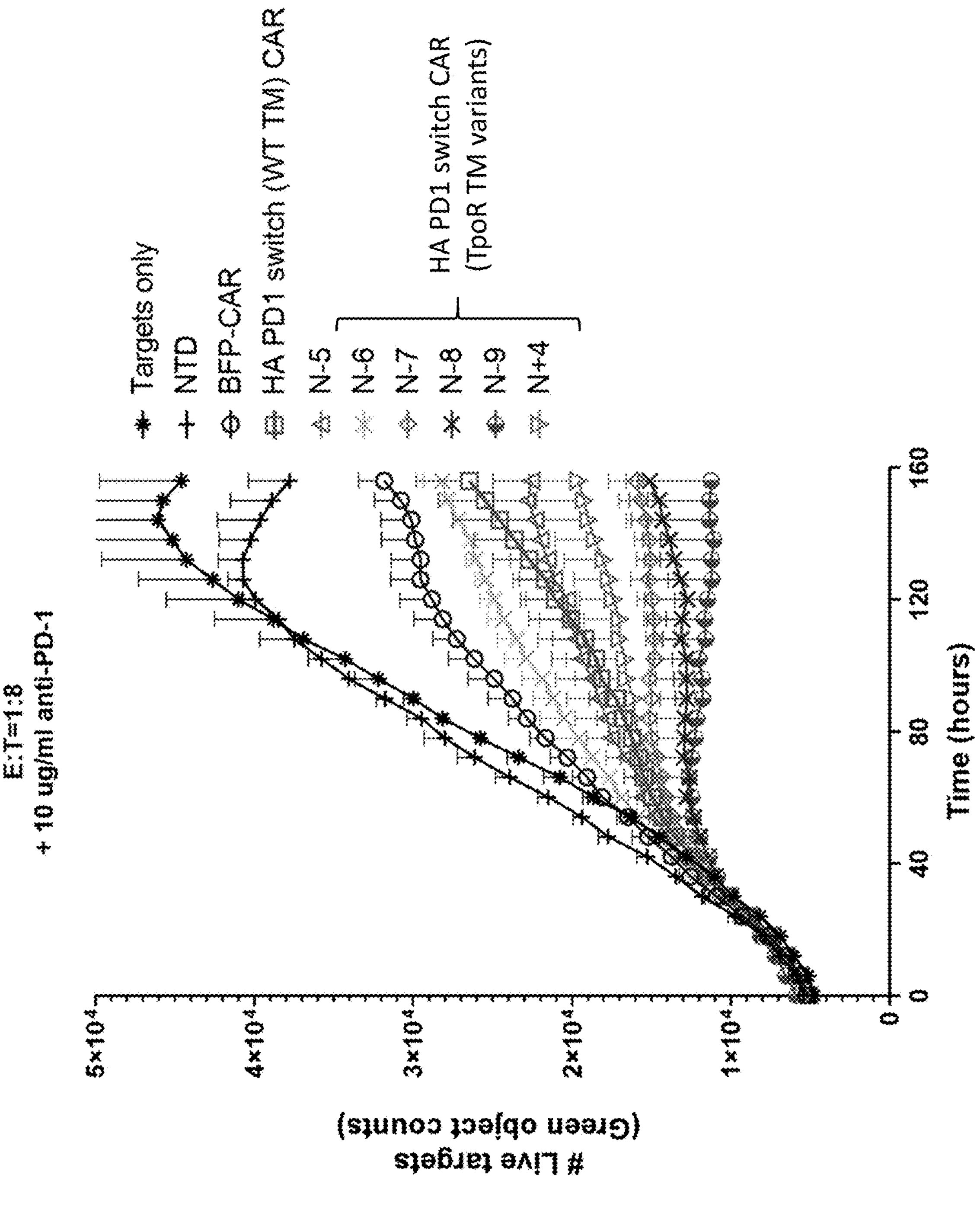
Figure 17C:
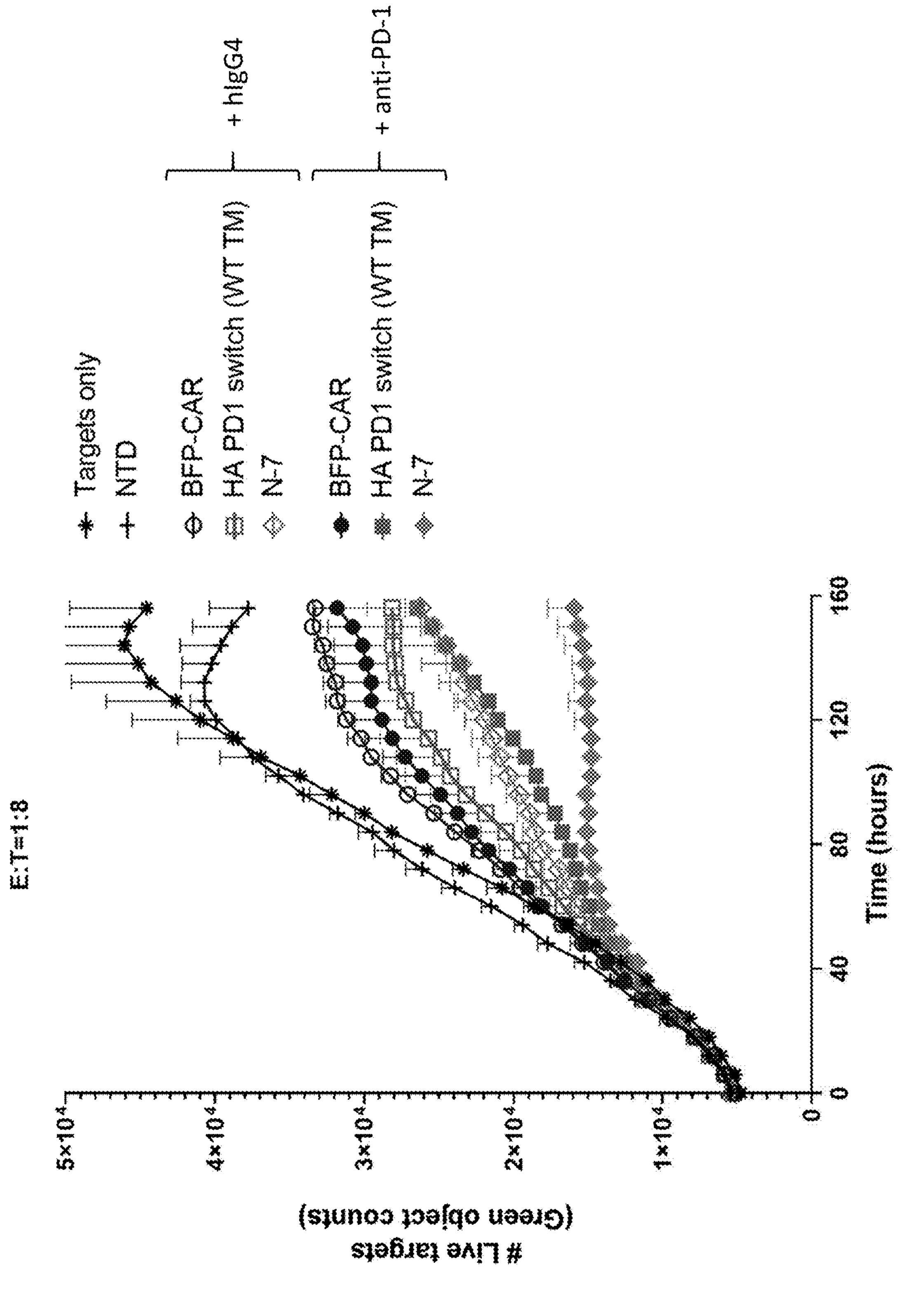
Figure 17D:
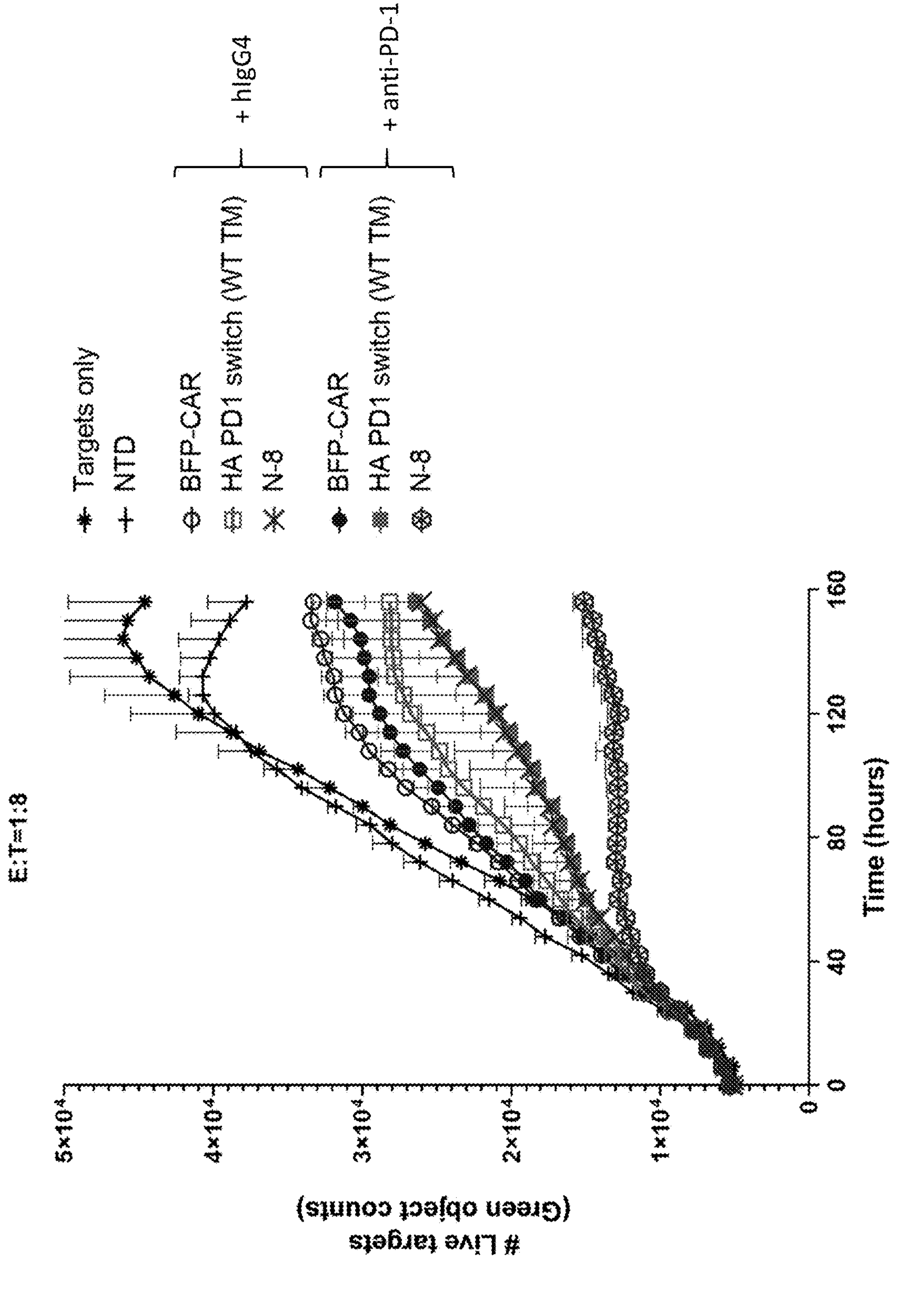
Figure 17E:
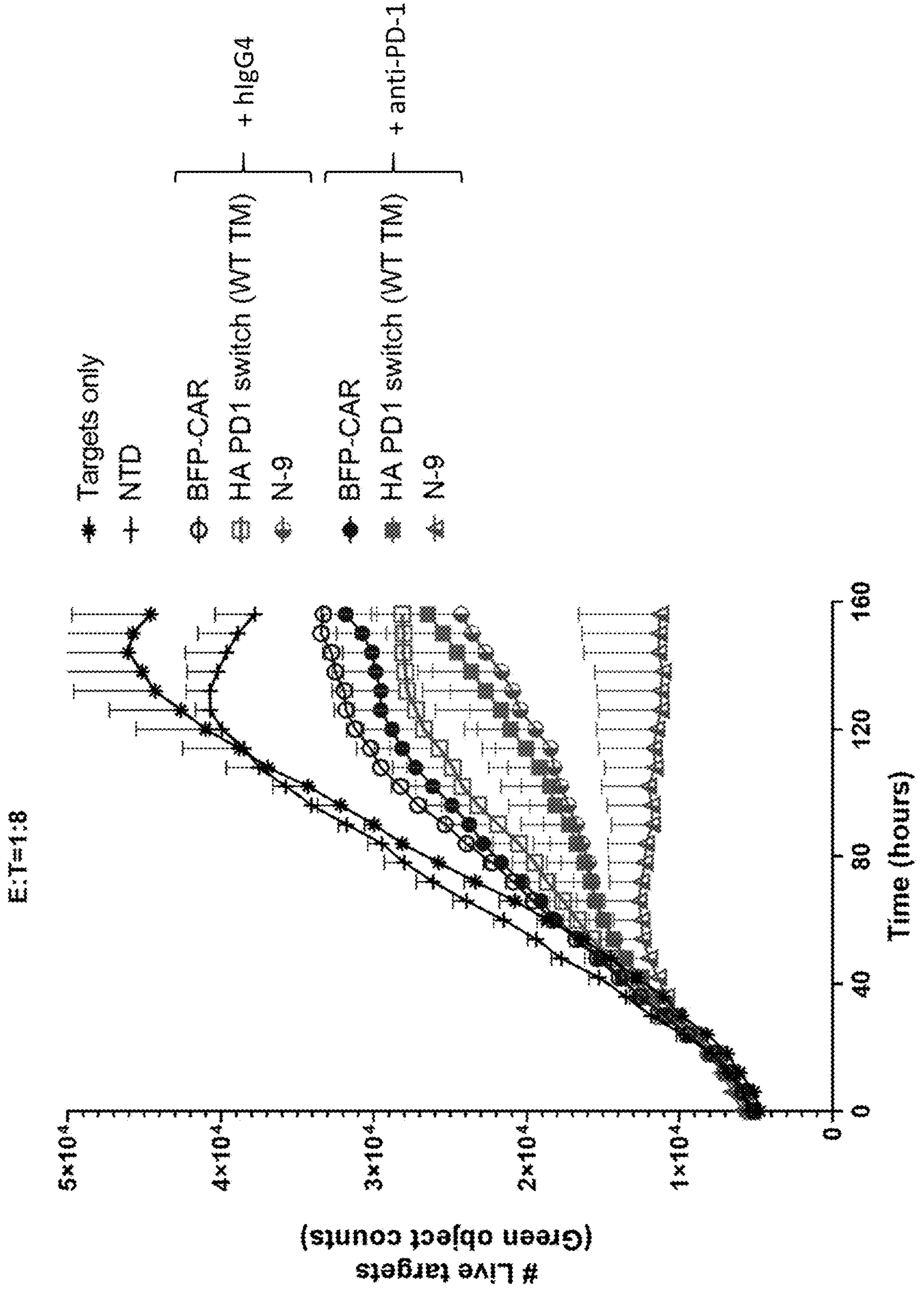

FIGS. 17A-B show the cytotoxic activity of HA PD1 switch CAR T cells with the indicated TpoR TM domains at an E:T ratio of 1:8, and in the absence or presence of anti-PD-1. FIG. 17A shows HA PD1 switch CAR T cell cytotoxicity in the absence of anti-PD-1. As expected, target cell lysis was less efficient at this lower E:T ratio as compared to the 1:4 ratio. Compared to the control BFP-CAR T cells, co-expression of a HA PD1 switch improved CAR T cell cytotoxicity, with the TpoR TM variants showing better activity than their WT TpoR TM counterpart. FIG. 17B shows HA PD1 switch CAR T cell cytotoxicity in the presence of anti-PD-1. Cytotoxic activity of control BFP-CAR T cells was not markedly improved even when combined with anti-PD-1. Additional dimerization and activation by anti-PD-1 improved the activity of HA PD1 switch with WT TpoR TM domain, and this was further enhanced in the N−7, N−8 and N−9 TpoR TM variants. FIGS. 17C-E show a comparison of the N−7 (FIG. 17C), N−8 (FIG. 17D) and N−9 (FIG. 17E) TpoR TM variants in the absence or presence of anti-PD-1. Without being limited to any specific mechanisms, the engagement of the PD-1 ectodomain with monomeric PD-L1/2 expressed on tumor cells or with a dimeric anti-PD-1 antibody may affect the conformation of the TpoR TM helix and different strength of signal transduction. Taken together, increasing the sensitivity and responsiveness of the HA PD1 switch via TpoR TM modifications can markedly improve the efficiency of cytotail signaling and enhance CAR T cell cytotoxic potency.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A polynucleotide encoding a PD-1 chimeric cytokine receptor comprising:

a. a PD-1 ectodomain or an antigen binding domain of an anti-PD-L1 or an anti-PD-L2 antibody;

b. a transmembrane domain;

c. a Janus Kinase (JAK)-binding domain; and d. a recruiting domain comprising a STAT-recruiting domain from IL2Rb, wherein the transmembrane domain and JAK-binding domain comprise SEQ ID NO: 40, SEQ ID NO: 23, SEQ ID NO: 24, SEQ ID NO: 25, SEQ ID NO: 26, or SEQ ID NO: 27.

2. The polynucleotide of claim 1, wherein the PD-1 chimeric cytokine receptor is dimerized, and each monomer comprises: a. the PD-1 ectodomain; b. the transmembrane domain; c. the Janus Kinase (JAK)-binding domain; and d. the recruiting domain.

3. The polynucleotide of claim 1, wherein the PD-1 ectodomain comprises a wild type PD-1 ectodomain sequence.

4. The polynucleotide of claim 1, wherein the PD-1 ectodomain comprises one or more mutations to the wild type PD-1 ectodomain sequence.

5. The polynucleotide of claim 4, wherein the PD-1 ectodomain comprising one or more mutations has a higher binding affinity for its ligand than a wild type PD-1 ectodomain.

6. The polynucleotide of claim 1, wherein the antigen binding domain is a scFv.

7. The polynucleotide of claim 1, wherein the JAK-binding domain is a JAK2-binding domain.

8. The polynucleotide of claim 1, wherein the STAT-recruiting domain from IL2Rb comprises SEQ ID NO: 76 or 77.

9. The polynucleotide of claim 1, wherein the transmembrane domain and JAK-binding domain comprise SEQ ID NO: 40.

10. The polynucleotide of claim 9, wherein the STAT-recruiting domain from IL2Rb comprises SEQ ID NO: 76 or 77.

11. The polynucleotide of claim 1, wherein the transmembrane domain and JAK-binding domain comprise SEQ ID NO: 23.

12. The polynucleotide of claim 11, wherein the STAT-recruiting domain from IL2Rb comprises SEQ ID NO: 76 or 77.

13. The polynucleotide of claim 1, wherein the transmembrane domain and JAK-binding domain comprise SEQ ID NO: 24.

14. The polynucleotide of claim 13, wherein the STAT-recruiting domain from IL2Rb comprises SEQ ID NO: 76 or 77.

15. The polynucleotide of claim 1, wherein the transmembrane domain and JAK-binding domain comprise SEQ ID NO: 25.

16. The polynucleotide of claim 15, wherein the STAT-recruiting domain from IL2Rb comprises SEQ ID NO: 76 or 77.

17. The polynucleotide of claim 1, wherein the transmembrane domain and JAK-binding domain comprise SEQ ID NO: 26.

18. The polynucleotide of claim 17, wherein the STAT-recruiting domain from IL2Rb comprises SEQ ID NO: 76 or 77.

19. The polynucleotide of claim 1, wherein the transmembrane domain and JAK-binding domain comprise SEQ ID NO: 27.

20. The polynucleotide of claim 19, wherein the STAT-recruiting domain from IL2Rb comprises SEQ ID NO: 76 or 77.

21. An expression vector comprising the polynucleotide of claim 1.

22. An engineered immune cell comprising the expression vector of claim 21.

23. A pharmaceutical composition comprising the immune cell of claim 22.

24. A kit comprising the immune cell of claim 22.

25. A method of preparing an engineered immune cell, the method comprising introducing the polynucleotide of claim 1 into an immune cell.

* * * * *